(12) United States Patent
Bourang

(10) Patent No.: US 11,717,428 B2
(45) Date of Patent: Aug. 8, 2023

(54) SYSTEM AND METHODS FOR TREATING A BIFURCATION WITH A FULLY CRIMPED STENT

(71) Applicant: ADVANCED BIFURCATION SYSTEMS INC., Los Angeles, CA (US)

(72) Inventor: Henry Bourang, Turlock, CA (US)

(73) Assignee: Advanced Bifurcation Systems Inc., Livermore, CA (US)

(*) Notice: Subject to any disclaimer, the term of this patent is extended or adjusted under 35 U.S.C. 154(b) by 286 days.

(21) Appl. No.: 17/225,354

(22) Filed: Apr. 8, 2021

(65) Prior Publication Data

US 2021/0220157 A1 Jul. 22, 2021

Related U.S. Application Data

(60) Continuation of application No. 16/261,066, filed on Jan. 29, 2019, now Pat. No. 11,000,393, which is a
(Continued)

(51) Int. Cl.
*A61F 2/954* (2013.01)
*A61F 2/856* (2013.01)
(Continued)

(52) U.S. Cl.
CPC .............. *A61F 2/954* (2013.01); *A61F 2/844* (2013.01); *A61F 2/856* (2013.01); *A61F 2/915* (2013.01);
(Continued)

(58) Field of Classification Search
CPC .......... A61F 2/954; A61F 2/856; A61F 2/915; A61F 2/958; A61F 2002/826; A61M 2025/1013; A61M 2025/1059
See application file for complete search history.

(56) References Cited

U.S. PATENT DOCUMENTS

| 4,069,825 A | 1/1978 | Akiyama |
| 4,468,224 A | 8/1984 | Enzmann et al. |
| | (Continued) | |

FOREIGN PATENT DOCUMENTS

| CA | 2826769 A1 | 8/2012 |
| CN | 1441654 A | 9/2003 |
| | (Continued) | |

OTHER PUBLICATIONS

"European Application Serial No. 20190983.5, Response filed Aug. 12, 2021 to Extended European Search Report dated Nov. 26, 2020", 20 pgs.

(Continued)

*Primary Examiner* — Katherine M Rodjom
(74) *Attorney, Agent, or Firm* — Schwegman Lundberg & Woessner, P.A.

(57) ABSTRACT

A system for treating a bifurcation includes first and second delivery catheters. The first catheter has a first shaft, a first expandable member adjacent the distal end of the first shaft, an auxiliary expandable member disposed under the first expandable member, and a first radially expandable stent disposed over both the first expandable member and the auxiliary expandable member. The second delivery catheter has a second shaft, and a second expandable member adjacent the distal end of the second shaft. A portion of the second catheter is disposed under a portion of the first stent, and a portion of the second delivery catheter passes through a side hole in the first stent. The first stent is crimped over the first and second catheters such that the first stent remains attached to the first and the second catheters during advancement of the catheters through a blood vessel.

16 Claims, 56 Drawing Sheets

Related U.S. Application Data continuation of application No. 15/157,321, filed on May 17, 2016, now Pat. No. 10,285,832, which is a division of application No. 13/796,424, filed on Mar. 12, 2013, now Pat. No. 9,364,356, which is a continuation of application No. PCT/US2012/024347, filed on Feb. 8, 2012.

(60) Provisional application No. 61/440,737, filed on Feb. 8, 2011.

(51) Int. Cl.
  *A61F 2/915* (2013.01)
  *A61F 2/958* (2013.01)
  *A61F 2/844* (2013.01)
  *A61M 25/10* (2013.01)
  *A61F 2/82* (2013.01)

(52) U.S. Cl.
  CPC ........ *A61F 2/958* (2013.01); *A61F 2002/826* (2013.01); *A61F 2002/91525* (2013.01); *A61F 2230/001* (2013.01); *A61F 2250/006* (2013.01); *A61M 2025/1013* (2013.01); *A61M 2025/1059* (2013.01)

(56) References Cited

U.S. PATENT DOCUMENTS

| | | |
|---|---|---|
| 4,512,338 A | 4/1985 | Balko et al. |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | Mcgreevy et al. |
| 4,733,665 A | 3/1988 | Palmar |
| 4,739,762 A | 4/1988 | Palmaz |
| 4,762,129 A | 8/1988 | Bonzel |
| 4,770,176 A | 9/1988 | Mcgreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,040,548 A | 8/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,171,222 A | 12/1992 | Euteneuer et al. |
| 5,195,984 A | 3/1993 | Schatz |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,403,341 A | 4/1995 | Solar |
| 5,421,955 A | 6/1995 | Lau et al. |
| 5,456,694 A | 10/1995 | Marin et al. |
| 5,456,713 A | 10/1995 | Chuter |
| 5,458,615 A | 10/1995 | Klemm et al. |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,228 A | 1/1997 | Edoga |
| 5,593,412 A | 1/1997 | Martinez et al. |
| 5,607,444 A | 3/1997 | Lam |
| 5,607,463 A | 3/1997 | Schwartz et al. |
| 5,609,627 A | 3/1997 | Goicoechea et al. |
| 5,609,629 A | 3/1997 | Fearnot et al. |
| 5,628,775 A | 5/1997 | Jackson et al. |
| 5,632,763 A | 5/1997 | Glastra |
| 5,632,772 A | 5/1997 | Alcime et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,669,924 A | 9/1997 | Shaknovich |
| 5,670,161 A | 9/1997 | Healy |
| 5,676,654 A | 10/1997 | Ellis et al. |
| 5,679,400 A | 10/1997 | Tuch |
| 5,683,451 A | 11/1997 | Lenker et al. |
| 5,697,948 A | 12/1997 | Marin et al. |
| 5,697,967 A | 12/1997 | Dinh et al. |
| 5,702,418 A | 12/1997 | Ravenscroft |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,921 A | 5/1998 | Lenker et al. |
| 5,755,735 A | 5/1998 | Richter et al. |
| 5,755,771 A | 5/1998 | Penn et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,797,951 A | 8/1998 | Mueller |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,824,048 A | 10/1998 | Tuch |
| 5,827,320 A | 10/1998 | Richter et al. |
| 5,833,694 A | 11/1998 | Poncet |
| 5,836,964 A | 11/1998 | Richter et al. |
| 5,837,008 A | 11/1998 | Berg et al. |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,893,887 A | 4/1999 | Jayaraman |
| 5,895,398 A | 4/1999 | Wensel et al. |
| 5,899,935 A | 5/1999 | Ding |
| 5,902,332 A | 5/1999 | Schatz |
| 5,911,754 A | 6/1999 | Kanesaka et al. |
| 5,919,175 A | 7/1999 | Sirhan |
| 5,922,020 A | 7/1999 | Klein et al. |
| 5,961,536 A | 10/1999 | Mickley et al. |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Lapewicz, Jr. et al. |
| 5,997,563 A | 12/1999 | Kretzers |

(56) References Cited

U.S. PATENT DOCUMENTS

| | | | |
|---|---|---|---|
| 6,004,328 A | 12/1999 | Solar et al. |
| 6,007,517 A | 12/1999 | Anderson |
| 6,017,363 A | 1/2000 | Hojeibane |
| 6,022,359 A | 2/2000 | Frantzen |
| 6,022,374 A | 2/2000 | Imran |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,048,361 A | 4/2000 | Von Oepen |
| 6,056,722 A | 5/2000 | Jayaraman |
| 6,056,775 A | 5/2000 | Borghi et al. |
| 6,059,811 A | 5/2000 | Pinchasik et al. |
| 6,059,824 A | 5/2000 | Taheri |
| 6,066,155 A | 5/2000 | Amann et al. |
| 6,068,655 A | 5/2000 | Seguin et al. |
| 6,070,589 A | 6/2000 | Keith et al. |
| 6,086,604 A | 7/2000 | Fischell et al. |
| 6,090,063 A | 7/2000 | Makower et al. |
| 6,090,136 A | 7/2000 | Mcdonald et al. |
| 6,096,071 A | 8/2000 | Yadav |
| 6,096,073 A | 8/2000 | Webster et al. |
| 6,099,497 A | 8/2000 | Adams et al. |
| 6,102,942 A | 8/2000 | Ahari |
| 6,106,530 A | 8/2000 | Harada |
| RE36,857 E | 9/2000 | Euteneuer et al. |
| 6,117,117 A | 9/2000 | Mauch |
| 6,120,522 A | 9/2000 | Vrba et al. |
| 6,123,712 A | 9/2000 | Di Caprio et al. |
| 6,123,723 A | 9/2000 | Konya |
| 6,126,685 A | 10/2000 | Lenker et al. |
| 6,129,738 A | 10/2000 | Lashinski et al. |
| 6,129,756 A | 10/2000 | Kugler et al. |
| 6,132,460 A | 10/2000 | Thompson |
| 6,136,011 A | 10/2000 | Stambaugh |
| 6,142,973 A | 11/2000 | Carleton et al. |
| 6,143,016 A | 11/2000 | Bleam et al. |
| 6,165,167 A | 12/2000 | Delaloye |
| 6,165,210 A | 12/2000 | Lau et al. |
| 6,179,878 B1 | 1/2001 | Duerig et al. |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,210,429 B1 | 4/2001 | Vardi et al. |
| 6,231,600 B1 | 5/2001 | Zhong |
| 6,238,991 B1 | 5/2001 | Suzuki |
| 6,241,691 B1 | 6/2001 | Ferrera et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,258,121 B1 | 7/2001 | Yang et al. |
| 6,264,682 B1 | 7/2001 | Wilson et al. |
| 6,264,688 B1 | 7/2001 | Herklotz et al. |
| 6,267,783 B1 | 7/2001 | Letendre et al. |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,325,826 B1* | 12/2001 | Vardi ................ A61F 2/82 |
| | | 623/1.35 |
| 6,326,826 B1 | 12/2001 | Lee et al. |
| 6,334,871 B1 | 1/2002 | Dor et al. |
| 6,344,053 B1 | 2/2002 | Boneau |
| 6,344,056 B1 | 2/2002 | Dehdashtian |
| 6,344,272 B1 | 2/2002 | Oldenburg et al. |
| 6,357,104 B1 | 3/2002 | Myers |
| 6,361,555 B1 | 3/2002 | Wilson |
| 6,375,676 B1 | 4/2002 | Cox |
| 6,379,365 B1 | 4/2002 | Diaz |
| 6,383,171 B1 | 5/2002 | Gifford et al. |
| 6,383,215 B1 | 5/2002 | Sass |
| 6,398,807 B1 | 6/2002 | Chouinard et al. |
| 6,409,753 B1 | 6/2002 | Brown et al. |
| 6,415,696 B1 | 7/2002 | Erickson et al. |
| 6,419,693 B1 | 7/2002 | Fariabi |
| 6,428,811 B1 | 8/2002 | West et al. |
| 6,443,982 B1 | 9/2002 | Israel et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,485,511 B2 | 11/2002 | Lau et al. |
| 6,488,694 B1 | 12/2002 | Lau et al. |
| 6,488,702 B1 | 12/2002 | Besselink |
| 6,488,703 B1 | 12/2002 | Kveen et al. |
| 6,511,468 B1 | 1/2003 | Cragg et al. |
| 6,514,281 B1 | 2/2003 | Blaeser et al. |
| 6,520,986 B2 | 2/2003 | Martin et al. |
| 6,520,987 B1 | 2/2003 | Plante |
| 6,520,988 B1 | 2/2003 | Colombo et al. |
| 6,527,789 B1 | 3/2003 | Lau et al. |
| 6,527,799 B2 | 3/2003 | Shanley |
| 6,529,549 B1 | 3/2003 | Norrell et al. |
| 6,530,944 B2 | 3/2003 | West et al. |
| 6,540,777 B2 | 4/2003 | Stenzel |
| 6,540,779 B2 | 4/2003 | Richter et al. |
| 6,551,350 B1 | 4/2003 | Thornton et al. |
| 6,555,157 B1 | 4/2003 | Hossainy |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,592,549 B2 | 7/2003 | Gerdts et al. |
| 6,592,568 B2 | 7/2003 | Campbell |
| 6,596,020 B2 | 7/2003 | Vardi et al. |
| 6,596,022 B2 | 7/2003 | Lau et al. |
| 6,599,296 B1 | 7/2003 | Gillick et al. |
| 6,599,314 B2 | 7/2003 | Mathis |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,645,517 B2 | 11/2003 | West et al. |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,666,883 B1 | 12/2003 | Seguin et al. |
| 6,676,695 B2 | 1/2004 | Solem |
| 6,679,909 B2 | 1/2004 | Mcintosh et al. |
| 6,685,721 B1 | 2/2004 | Kramer |
| 6,685,730 B2 | 2/2004 | West et al. |
| 6,689,156 B1 | 2/2004 | Davidson et al. |
| 6,692,465 B2 | 2/2004 | Kramer |
| 6,692,483 B2 | 2/2004 | Vardi et al. |
| 6,699,280 B2 | 3/2004 | Camrud et al. |
| 6,699,724 B1 | 3/2004 | West |
| 6,702,843 B1 | 3/2004 | Brown et al. |
| 6,706,062 B2 | 3/2004 | Vardi et al. |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,251 B1 | 6/2004 | Eder |
| 6,749,628 B1 | 6/2004 | Callol et al. |
| 6,761,734 B2 | 7/2004 | Suhr |
| 6,770,091 B2 | 8/2004 | Richter et al. |
| 6,778,316 B2 | 8/2004 | Halas et al. |
| 6,800,065 B2 | 10/2004 | Duane et al. |

(56) References Cited

U.S. PATENT DOCUMENTS

| | | |
|---|---|---|
| 6,811,566 B1 | 11/2004 | Penn et al. |
| 6,825,203 B2 | 11/2004 | Pasternak et al. |
| 6,835,203 B1 | 12/2004 | Vardi et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,875,228 B2 | 4/2005 | Pinchasik et al. |
| 6,878,161 B2 | 4/2005 | Lenker |
| 6,879,370 B2 | 4/2005 | Yokoue et al. |
| 6,884,258 B2 | 4/2005 | Vardi et al. |
| 6,893,417 B2 | 5/2005 | Gribbons et al. |
| 6,896,695 B2 | 5/2005 | Mueller et al. |
| 6,908,477 B2 | 6/2005 | Mcguckin, Jr. et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,949,120 B2 | 9/2005 | Kveen et al. |
| 6,951,053 B2 | 10/2005 | Padilla et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,026 B2 | 1/2006 | Richter et al. |
| 7,005,454 B2 | 2/2006 | Brocchini et al. |
| 7,037,327 B2 | 5/2006 | Salmon et al. |
| 7,052,510 B1 | 5/2006 | Richter |
| 7,090,694 B1 | 8/2006 | Morris et al. |
| 7,101,840 B2 | 9/2006 | Brocchini et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,182,779 B2 | 2/2007 | Acosta et al. |
| 7,192,440 B2 | 3/2007 | Andreas et al. |
| 7,220,275 B2 | 5/2007 | Davidson et al. |
| 7,241,308 B2 | 7/2007 | Andreas et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,323,009 B2 | 1/2008 | Suhr et al. |
| 7,326,236 B2 | 2/2008 | Andreas et al. |
| 7,326,242 B2 | 2/2008 | Eidenschink |
| 7,341,598 B2 | 3/2008 | Davidson et al. |
| 7,344,556 B2 | 3/2008 | Seguin et al. |
| 7,387,639 B2 | 6/2008 | Bourang et al. |
| 7,445,688 B2 | 11/2008 | Suzuki et al. |
| 7,476,243 B2 | 1/2009 | Eidenschink |
| 7,520,895 B2 | 4/2009 | Douglas et al. |
| 7,537,609 B2 | 5/2009 | Davidson et al. |
| 7,540,881 B2 | 6/2009 | Meyer et al. |
| 7,635,383 B2 | 12/2009 | Gumm |
| 7,641,684 B2 | 1/2010 | Hilaire et al. |
| 7,641,685 B2 | 1/2010 | Richter |
| 7,695,508 B2 | 4/2010 | Der Leest |
| 8,016,870 B2 | 9/2011 | Chew et al. |
| 8,070,789 B2 | 12/2011 | Will et al. |
| 8,769,796 B2 | 7/2014 | Bourang et al. |
| 8,795,347 B2 | 8/2014 | Bourang et al. |
| 8,808,347 B2 | 8/2014 | Bourang et al. |
| 8,821,562 B2 | 9/2014 | Bourang et al. |
| 8,828,071 B2 | 9/2014 | Bourang et al. |
| 8,979,917 B2 | 3/2015 | Bourang et al. |
| 9,254,210 B2 | 2/2016 | Bourang |
| 9,364,356 B2 | 6/2016 | Bourang |
| 9,724,218 B2 | 8/2017 | Bourang et al. |
| 9,730,821 B2 | 8/2017 | Bourang et al. |
| 9,737,424 B2 | 8/2017 | Bourang et al. |
| 9,855,158 B2 | 1/2018 | Bourang et al. |
| 10,285,832 B2 | 5/2019 | Bourang |
| 11,000,393 B2 | 5/2021 | Bourang |
| 2001/0003161 A1 | 6/2001 | Vardi et al. |
| 2001/0020154 A1 | 9/2001 | Bigus et al. |
| 2001/0020181 A1 | 9/2001 | Layne |
| 2001/0039395 A1 | 11/2001 | Mareiro et al. |
| 2001/0044595 A1 | 11/2001 | Reydel et al. |
| 2001/0044622 A1 | 11/2001 | Vardi et al. |
| 2001/0044632 A1 | 11/2001 | Daniel et al. |
| 2001/0049547 A1 | 12/2001 | Moore |
| 2002/0037358 A1 | 3/2002 | Barry et al. |
| 2002/0091439 A1 | 7/2002 | Baker et al. |
| 2002/0107560 A1 | 8/2002 | Richter |
| 2002/0111671 A1 | 8/2002 | Stenzel |
| 2002/0128706 A1 | 9/2002 | Osypka |
| 2002/0138132 A1 | 9/2002 | Brown |
| 2002/0143382 A1 | 10/2002 | Hijlkema et al. |
| 2002/0151924 A1 | 10/2002 | Shiber |
| 2002/0151955 A1 | 10/2002 | Tran et al. |
| 2002/0156496 A1 | 10/2002 | Chermoni |
| 2002/0173835 A1 | 11/2002 | Bourang et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0028233 A1 | 2/2003 | Vardi et al. |
| 2003/0029039 A1 | 2/2003 | Richter et al. |
| 2003/0045923 A1 | 3/2003 | Bashiri |
| 2003/0093143 A1 | 5/2003 | Zhao et al. |
| 2003/0097169 A1 | 5/2003 | Brucker et al. |
| 2003/0105922 A1 | 6/2003 | Tomita |
| 2003/0114912 A1 | 6/2003 | Sequin et al. |
| 2003/0114919 A1 | 6/2003 | Mcquiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0176909 A1 | 9/2003 | Kusleika |
| 2003/0191516 A1 | 10/2003 | Weldon et al. |
| 2003/0192164 A1 | 10/2003 | Austin |
| 2003/0195609 A1 | 10/2003 | Berenstein et al. |
| 2003/0199821 A1 | 10/2003 | Gerdts et al. |
| 2003/0204238 A1 | 10/2003 | Tedeschi |
| 2003/0212447 A1 | 11/2003 | Euteneuer et al. |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0044398 A1 | 3/2004 | Nicholas |
| 2004/0085845 A1 | 5/2004 | Ooishi |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea et al. |
| 2004/0111145 A1 | 6/2004 | Serino et al. |
| 2004/0117008 A1 | 6/2004 | Wnendt et al. |
| 2004/0176832 A1 | 9/2004 | Hartley et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2005/0010276 A1 | 1/2005 | Acosta et al. |
| 2005/0038505 A1 | 2/2005 | Shulze et al. |
| 2005/0049673 A1 | 3/2005 | Andreas et al. |
| 2005/0049680 A1 | 3/2005 | Fischell et al. |
| 2005/0080474 A1 | 4/2005 | Andreas et al. |
| 2005/0080475 A1 | 4/2005 | Andreas et al. |
| 2005/0085845 A1* | 4/2005 | Hilaire .......... A61F 2/958 623/1.11 |

(56) References Cited

U.S. PATENT DOCUMENTS

| | | |
|---|---|---|
| 2005/0090846 A1 | 4/2005 | Pedersen et al. |
| 2005/0101624 A1 | 5/2005 | Betts et al. |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0143827 A1 | 6/2005 | Globerman et al. |
| 2005/0149159 A1 | 7/2005 | Andreas et al. |
| 2005/0165378 A1 | 7/2005 | Heinrich et al. |
| 2005/0182473 A1 | 8/2005 | Eidenschink et al. |
| 2005/0183259 A1 | 8/2005 | Eidenschink et al. |
| 2005/0197688 A1 | 9/2005 | Theron et al. |
| 2005/0209674 A1 | 9/2005 | Kutscher et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0100694 A1 | 5/2006 | Globerman |
| 2006/0116748 A1 | 6/2006 | Kaplan et al. |
| 2006/0123874 A1 | 6/2006 | Motsenbocker |
| 2006/0155362 A1 | 7/2006 | Israel |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271090 A1 | 11/2006 | Shaked et al. |
| 2006/0271150 A1 | 11/2006 | Andreas et al. |
| 2006/0271151 A1 | 11/2006 | Mcgarry et al. |
| 2006/0282147 A1 | 12/2006 | Andreas |
| 2006/0282149 A1 | 12/2006 | Kao |
| 2006/0282150 A1 | 12/2006 | Olson et al. |
| 2006/0287726 A1 | 12/2006 | Segal et al. |
| 2007/0027521 A1 | 2/2007 | Andreas et al. |
| 2007/0027524 A1 | 2/2007 | Johnson et al. |
| 2007/0055351 A1 | 3/2007 | Eidenschink et al. |
| 2007/0061003 A1 | 3/2007 | Shmulewitz et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0123970 A1 | 5/2007 | Lenz |
| 2007/0129733 A1 | 6/2007 | Will et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0203571 A1 | 8/2007 | Kaplan et al. |
| 2007/0219611 A1* | 9/2007 | Krever ................ A61F 2/954 623/1.11 |
| 2007/0219612 A1 | 9/2007 | Andreas et al. |
| 2007/0219613 A1 | 9/2007 | Kao et al. |
| 2007/0219625 A1 | 9/2007 | Venturelli et al. |
| 2007/0264305 A1 | 11/2007 | Von et al. |
| 2007/0265637 A1 | 11/2007 | Andreas et al. |
| 2007/0270936 A1 | 11/2007 | Andreas et al. |
| 2007/0276460 A1 | 11/2007 | Davis et al. |
| 2007/0276461 A1 | 11/2007 | Andreas et al. |
| 2007/0281117 A1 | 12/2007 | Kaplan et al. |
| 2007/0282419 A1 | 12/2007 | Hilaire et al. |
| 2007/0292518 A1 | 12/2007 | Ludwig |
| 2008/0009932 A1 | 1/2008 | Ta et al. |
| 2008/0009933 A1 | 1/2008 | Ta et al. |
| 2008/0051869 A1 | 2/2008 | Yribarren |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0132989 A1 | 6/2008 | Snow et al. |
| 2008/0147162 A1 | 6/2008 | Andreas et al. |
| 2008/0199510 A1 | 8/2008 | Ruane et al. |
| 2008/0208309 A1 | 8/2008 | Saeed |
| 2008/0208311 A1 | 8/2008 | Kao et al. |
| 2008/0208318 A1 | 8/2008 | Kao et al. |
| 2008/0221655 A1 | 9/2008 | Miller |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0269865 A1 | 10/2008 | Snow et al. |
| 2009/0076584 A1 | 3/2009 | Mao et al. |
| 2009/0105686 A1 | 4/2009 | Snow et al. |
| 2009/0132019 A1 | 5/2009 | Duffy et al. |
| 2009/0143854 A1 | 6/2009 | Adams et al. |
| 2009/0171430 A1 | 7/2009 | Baim et al. |
| 2009/0182270 A1 | 7/2009 | Nanavati |
| 2009/0182409 A1 | 7/2009 | Feld et al. |
| 2009/0228088 A1 | 9/2009 | Lowe et al. |
| 2009/0240321 A1 | 9/2009 | Davidson et al. |
| 2009/0254167 A1 | 10/2009 | Ricci et al. |
| 2009/0259285 A1 | 10/2009 | Duane et al. |
| 2009/0287289 A1 | 11/2009 | Sagedahl et al. |
| 2009/0299454 A1* | 12/2009 | Jennings ................ A61F 2/954 623/1.11 |
| 2009/0319030 A1 | 12/2009 | Yadin et al. |
| 2009/0326641 A1 | 12/2009 | Davis et al. |
| 2010/0004737 A1 | 1/2010 | Eidenschink |
| 2010/0030183 A1 | 2/2010 | Toner et al. |
| 2010/0036477 A1 | 2/2010 | Bronson et al. |
| 2010/0042199 A1 | 2/2010 | Burton |
| 2010/0049298 A1 | 2/2010 | Hamer et al. |
| 2010/0057020 A1 | 3/2010 | Uretsky |
| 2010/0063571 A1 | 3/2010 | Roach et al. |
| 2010/0106238 A1 | 4/2010 | Hilaire et al. |
| 2010/0222861 A1* | 9/2010 | Dibie ..................... A61F 2/856 623/1.11 |
| 2011/0029061 A1 | 2/2011 | Ahn et al. |
| 2011/0282427 A1 | 11/2011 | Bourang et al. |
| 2011/0307044 A1 | 12/2011 | Bourang et al. |
| 2011/0307045 A1 | 12/2011 | Bourang et al. |
| 2011/0307046 A1 | 12/2011 | Bourang et al. |
| 2011/0307047 A1 | 12/2011 | Bourang et al. |
| 2011/0307052 A1 | 12/2011 | Bourang et al. |
| 2013/0268047 A1 | 10/2013 | Bourang |
| 2014/0100647 A1 | 4/2014 | Bourang |
| 2015/0032196 A1 | 1/2015 | Bourang et al. |
| 2015/0073521 A1 | 3/2015 | Bourang et al. |
| 2015/0073527 A1 | 3/2015 | Bourang et al. |
| 2015/0081001 A1 | 3/2015 | Bourang et al. |
| 2015/0081002 A1 | 3/2015 | Bourang et al. |
| 2015/0216690 A1 | 8/2015 | Bourang et al. |
| 2016/0100966 A1 | 4/2016 | Bourang |
| 2016/0256303 A1 | 9/2016 | Bourang |
| 2017/0319366 A1 | 11/2017 | Bourang et al. |
| 2019/0159918 A1 | 5/2019 | Bourang |

FOREIGN PATENT DOCUMENTS

| | | |
|---|---|---|
| CN | 1788977 A | 6/2006 |
| CN | 1867374 A | 11/2006 |
| CN | 101035488 A | 9/2007 |
| CN | 102215780 A | 10/2011 |
| CN | 103037813 A | 4/2013 |
| CN | 103037815 A | 4/2013 |
| CN | 103037816 A | 4/2013 |
| CN | 103037817 A | 4/2013 |
| CN | 103068345 A | 4/2013 |
| EP | 0203945 A1 | 12/1986 |
| EP | 0274129 A2 | 7/1988 |
| EP | 0282143 A1 | 9/1988 |
| EP | 0274129 B1 | 5/1992 |
| EP | 0505686 A1 | 9/1992 |
| EP | 0533960 A1 | 3/1993 |
| EP | 0596145 A1 | 5/1994 |
| EP | 0714640 A1 | 6/1996 |
| EP | 0203945 B2 | 6/1998 |
| EP | 0897700 A1 | 2/1999 |
| EP | 0947180 A2 | 10/1999 |

(56) References Cited

FOREIGN PATENT DOCUMENTS

| | | |
|---|---|---|
| EP | 1074227 A2 | 2/2001 |
| EP | 1258230 A2 | 11/2002 |
| EP | 1266638 A2 | 12/2002 |
| EP | 1277449 A1 | 1/2003 |
| EP | 1523959 A2 | 4/2005 |
| EP | 1523960 A2 | 4/2005 |
| EP | 1266638 B1 | 10/2005 |
| EP | 1788977 A1 | 5/2007 |
| EP | 1788977 B1 | 3/2008 |
| EP | 1905398 A2 | 4/2008 |
| EP | 2036519 A1 | 3/2009 |
| EP | 2344068 A1 | 7/2011 |
| EP | 2549949 A1 | 1/2013 |
| EP | 2549950 A1 | 1/2013 |
| EP | 2549951 A1 | 1/2013 |
| EP | 2549952 A1 | 1/2013 |
| EP | 2549958 A1 | 1/2013 |
| EP | 2672925 A2 | 12/2013 |
| EP | 2672932 A1 | 12/2013 |
| EP | 2549951 B1 | 5/2017 |
| EP | 2672932 B1 | 9/2018 |
| EP | 3449879 B1 | 9/2020 |
| FR | 2733689 A1 | 11/1996 |
| JP | 1043313 A | 2/1998 |
| JP | 2003532437 A | 11/2003 |
| JP | 2004052887 A | 2/2004 |
| JP | 2004528877 A | 9/2004 |
| JP | 2007508082 A | 4/2007 |
| JP | 2010503465 A | 2/2010 |
| JP | 2012503534 A | 2/2012 |
| JP | 2013523215 A | 6/2013 |
| WO | WO-9013332 A1 | 11/1990 |
| WO | WO-9112779 A1 | 9/1991 |
| WO | WO-9626689 A1 | 9/1996 |
| WO | WO-9633677 A1 | 10/1996 |
| WO | WO-9746174 A1 | 12/1997 |
| WO | WO-9748351 A1 | 12/1997 |
| WO | WO-9820810 A1 | 5/1998 |
| WO | WO-9837833 A1 | 9/1998 |
| WO | WO-9858600 A1 | 12/1998 |
| WO | WO-9901087 A1 | 1/1999 |
| WO | WO-0012832 A2 | 3/2000 |
| WO | WO-0015151 A1 | 3/2000 |
| WO | WO-0025841 A1 | 5/2000 |
| WO | WO-0032136 A1 | 6/2000 |
| WO | WO-0041649 A1 | 7/2000 |
| WO | WO-0050116 A1 | 8/2000 |
| WO | WO-0062708 A1 | 10/2000 |
| WO | WO-0072780 A1 | 12/2000 |
| WO | WO-0074595 A1 | 12/2000 |
| WO | WO-0170297 A2 | 9/2001 |
| WO | WO-0191918 A1 | 12/2001 |
| WO | WO-02060344 A2 | 8/2002 |
| WO | WO-02085253 A1 | 10/2002 |
| WO | WO-03022178 A1 | 3/2003 |
| WO | WO-03047651 A2 | 6/2003 |
| WO | WO-03051425 A2 | 6/2003 |
| WO | WO-03055414 A1 | 7/2003 |
| WO | WO-03105922 A2 | 12/2003 |
| WO | WO-2004017865 A1 | 3/2004 |
| WO | WO-2004043299 A1 | 5/2004 |
| WO | WO-2004043301 A1 | 5/2004 |
| WO | WO-2004043510 A1 | 5/2004 |
| WO | WO-2004052237 A2 | 6/2004 |
| WO | WO-2005013853 A2 | 2/2005 |
| WO | WO-2005039681 A1 | 5/2005 |
| WO | WO-2006036939 A2 | 4/2006 |
| WO | WO-2006047520 A2 | 5/2006 |
| WO | WO-2007035805 A2 | 3/2007 |
| WO | WO-2007053187 A2 | 5/2007 |
| WO | WO-2007146411 A2 | 12/2007 |
| WO | WO-2008005111 A1 | 1/2008 |
| WO | WO-2008033621 A1 | 3/2008 |
| WO | WO-2008130503 A2 | 10/2008 |
| WO | WO-2009148594 A1 | 12/2009 |
| WO | WO-2009148997 A1 | 12/2009 |
| WO | WO-2010022516 A1 | 3/2010 |
| WO | WO-2010036982 A1 | 4/2010 |
| WO | WO-2011119879 A1 | 9/2011 |
| WO | WO-2011119880 A1 | 9/2011 |
| WO | WO-2011119882 A1 | 9/2011 |
| WO | WO-2011119883 A1 | 9/2011 |
| WO | WO-2011119884 A1 | 9/2011 |
| WO | WO-2012109365 A1 | 8/2012 |
| WO | WO-2012109382 A2 | 8/2012 |
| WO | WO-2012109382 A3 | 1/2013 |

OTHER PUBLICATIONS

"U.S. Appl. No. 13/071,149, Final Office Action dated Nov. 5, 2013", 20 pgs.

"U.S. Appl. No. 13/071,149, Non Final Office Action dated Apr. 11, 2013", 16 pgs.

"U.S. Appl. No. 13/071,149, Notice of Allowance dated Mar. 26, 2014", 11 pgs.

"U.S. Appl. No. 13/071,162, Non Final Office Action dated Aug. 30, 2013", 17 pgs.

"U.S. Appl. No. 13/071,162, Notice of Allowance dated Mar. 31, 2014", 12 pgs.

"U.S. Appl. No. 13/071,183, Final Office Action dated Nov. 5, 2013", 35 pgs.

"U.S. Appl. No. 13/071,183, Non Final Office Action dated Mar. 29, 2013", 23 pgs.

"U.S. Appl. No. 13/071,183, Notice of Allowance dated Mar. 20, 2014", 13 pgs.

"U.S. Appl. No. 13/071,198, Final Office Action dated Nov. 6, 2013", 20 pgs.

"U.S. Appl. No. 13/071,198, Non Final Office Action dated Apr. 11, 2013", 17 pgs.

"U.S. Appl. No. 13/071,198, Notice of Allowance dated Mar. 24, 2014", 11 pgs.

"U.S. Appl. No. 13/071,239, Final Office Action dated Nov. 26, 2013", 18 pgs.

"U.S. Appl. No. 13/071,239, Non Final Office Action dated Mar. 14, 2013", 17 pgs.

"U.S. Appl. No. 13/071,239, Notice of Allowance dated Mar. 4, 2014", 10 pgs.

"U.S. Appl. No. 13/071,251, Non Final Office Action dated Sep. 10, 2013", 15 pgs.

"U.S. Appl. No. 13/071,251, Notice of Allowance dated May 28, 2014", 15 pgs.

"U.S. Appl. No. 13/071,251, Notice of Allowance dated Aug. 13, 2014", 12 pgs.

"U.S. Appl. No. 13/796,424, Notice of Allowance dated Feb. 16, 2016", 13 pgs.

"U.S. Appl. No. 13/796,424, Response filed Nov. 10, 2015 to Restriction Requirement dated Sep. 11, 2015", 1 pg.

"U.S. Appl. No. 13/796,424, Restriction Requirement dated Sep. 11, 2015", 8 pgs.

"U.S. Appl. No. 13/796,466, Non Final Office Action dated Apr. 3, 2015", 19 pgs.

"U.S. Appl. No. 13/796,466, Notice of Allowance dated Oct. 7, 2015", 16 pgs.

"U.S. Appl. No. 13/796,466, Notice of Allowance dated Nov. 18, 2015", 2 pgs.

"U.S. Appl. No. 14/294,631, Final Office Action dated Mar. 24, 2017", 15 pgs.

"U.S. Appl. No. 14/294,631, Non Final Office Action dated Sep. 22, 2017", 16 pgs.

"U.S. Appl. No. 14/294,631, Non Final Office Action dated Oct. 7, 2016", 15 pgs.

"U.S. Appl. No. 14/313,742, Final Office Action dated Aug. 12, 2016", 19 pgs.

"U.S. Appl. No. 14/313,742, Non Final Office Action dated Jan. 29, 2016", 17 pgs.

"U.S. Appl. No. 14/313,742, Non Final Office Action dated Mar. 24, 2017", 20 pgs.

(56) References Cited

OTHER PUBLICATIONS

"U.S. Appl. No. 14/313,742, Notice of Allowance dated Oct. 20, 2017", 8 pgs.
"U.S. Appl. No. 14/314,361, Non Final Office Action dated Oct. 6, 2016", 33 pgs.
"U.S. Appl. No. 14/314,361, Notice of Allowance dated Apr. 12, 2017", 11 pgs.
"U.S. Appl. No. 14/317,387, Non Final Office Action dated Oct. 6, 2016", 15 pgs.
"U.S. Appl. No. 14/317,387, Notice of Allowance dated Apr. 17, 2017", 10 pgs.
"U.S. Appl. No. 14/321,506, Non Final Office Action dated Oct. 6, 2016", 15 pgs.
"U.S. Appl. No. 14/321,506, Notice of Allowance dated Apr. 4, 2017", 10 pgs.
"U.S. Appl. No. 14/621,231, Final Office Action dated Oct. 20, 2017", 19 pgs.
"U.S. Appl. No. 14/621,231, Non Final Office Action dated Jun. 15, 2017", 17 pgs.
"U.S. Appl. No. 15/157,321, Applicant's Summary of Examiner Interview filed Feb. 14, 2018", 1 pg.
"U.S. Appl. No. 15/157,321, Examiner Interview Summary dated Feb. 22, 2018", 3 pgs.
"U.S. Appl. No. 15/157,321, Final Office Action dated Aug. 1, 2018", 10 pgs.
"U.S. Appl. No. 15/157,321, Non Final Office Action dated Aug. 11, 2017", 10 pgs.
"U.S. Appl. No. 15/157,321, Notice of Allowance dated Jan. 2, 2019", 7 pgs.
"U.S. Appl. No. 15/157,321, Response filed Feb. 7, 2018 to Non Final Office Action dated Aug. 11, 2017", 9 pgs.
"U.S. Appl. No. 15/157,321, Response filed Aug. 1, 2017 to Restriction Requirement dated Jun. 1, 2017", 1 pg.
"U.S. Appl. No. 15/157,321, Response filed Oct. 31, 2018 to Final Office Action dated Aug. 1, 2018", 10 pgs.
"U.S. Appl. No. 15/157,321, Restriction Requirement dated Jun. 1, 2017", 6 pgs.
"U.S. Appl. No. 16/261,066, Corrected Notice of Allowability dated Apr. 14, 2021", 2 pgs.
"U.S. Appl. No. 16/261,066, Non Final Office Action dated Dec. 23, 2020", 9 pgs.
"U.S. Appl. No. 16/261,066, Notice of Allowance dated Mar. 31, 2021", 9 pgs.
"U.S. Appl. No. 16/261,066, Preliminary Amendment filed Jan. 30, 2019", 3 pgs.
"U.S. Appl. No. 16/261,066, Response filed Mar. 9, 2021 to Non Final Office Action dated Dec. 23, 2020", 9 pgs.
"Australian Application Serial No. 2011232357, First Examination Report dated Dec. 3, 2014", 2 pgs.
"Australian Application Serial No. 2011232358, First Examination Report dated Dec. 5, 2014", 2 pgs.
"Australian Application Serial No. 2011232360, First Examination Report dated Dec. 9, 2014", 2 pgs.
"Australian Application Serial No. 2011232361, First Examination Report dated Dec. 12, 2014", 3 pgs.
"Australian Application Serial No. 2011232362, First Examination Report dated Jan. 11, 2015", 2 pgs.
"Canadian Application Serial No. 2,826,769, Voluntary Amendment filed Aug. 7, 2013", 7 pgs.
"Chinese Application Serial No. 200980143592.X, Final Office Action dated Jun. 4, 2013", 10 pgs.
"Chinese Application Serial No. 200980143592.X, Office Action dated Apr. 21, 2014", 26 pgs.
"Chinese Application Serial No. 200980143592.X, Office Action dated Jun. 4, 2013", 10 pgs.
"Chinese Application Serial No. 2009801473592.X, Office Action dated Nov. 24, 2014", 16 pgs.
"Chinese Application Serial No. 201180025662.9, Office Action dated Aug. 21, 2014", 25 pgs.
"Chinese Application Serial No. 201180025670.3, Office Action dated Aug. 20, 2014", 24 pgs.
"Chinese Application Serial No. 201180025716.1, Office Action dated Aug. 22, 2014", 28 pgs.
"Chinese Application Serial No. 201180025742.4, Office Action dated Oct. 29, 2014", 12 pgs.
"Chinese Application Serial No. 201180025746.2, Office Action dated Sep. 28, 2014", 21 pgs.
"Drug Delivery Stent With Holes Located on Neutral Axis", No. 429007; Research Disclosure, Kenneth Mason Publications, Hampshire, CB vol. 2266, (Jan. 2000), 13 pgs.
"European Application Serial No. 05727731.1, Supplementary European Search Report dated Apr. 8, 2008", 3 pgs.
"European Application Serial No. 05744136.2, Supplementary European Search Report dated Apr. 9, 2008", 3 pgs.
"European Application Serial No. 09816963.4, Extended European Search Report dated Aug. 21, 2015", 5 pgs.
"European Application Serial No. 11760253.2, Extended European Search Report dated Feb. 22, 2017", 7 pgs.
"European Application Serial No. 11760254.0, Extended European Search Report dated Apr. 12, 2017", 6 pgs.
"European Application Serial No. 11760256.5, Extended European Search Report dated Aug. 12, 2016", 8 pgs.
"European Application Serial No. 11760257.3, Extended European Search Report dated Sep. 29, 2015", 7 pgs.
"European Application Serial No. 11760258.1, Extended European Search Report dated Dec. 5, 2016", 8 pgs.
"European Application Serial No. 12744749.8, Communication Pursuant to Article 94(3) EPC dated Feb. 14, 2017", 5 pgs.
"European Application Serial No. 12744749.8, Decision to grant dated Aug. 23, 2018", 2 pgs.
"European Application Serial No. 12744749.8, Extended European Search Report dated Apr. 7, 2016", 10 pgs.
"European Application Serial No. 12744749.8, Intention to Grant dated Mar. 28, 2018", 6 pgs.
"European Application Serial No. 12744749.8, Intention to Grant dated Aug. 13, 2018", 4 pgs.
"European Application Serial No. 12744749.8, Response filed Aug. 23, 2017 to Communication Pursuant to Article 94(3) EPC dated Feb. 14, 2017", 13 pgs.
"European Application Serial No. 12744749.8, Response filed Oct. 21, 2016 to Extended European Search Report dated Apr. 7, 2016", 24 pgs.
"European Application Serial No. 12744813.2, Extended European Search Report dated Nov. 25, 2015", 9 pgs.
"European Application Serial No. 18194894.4, Extended European Search Report dated Nov. 28, 2018", 9 pgs.
"European Application Serial No. 20190983.5, Extended European Search Report dated Nov. 26, 2020", 8 pgs.
"Functional Sites on Non-polymeric Materials: Gas Plasma Treatment and Surface Analysis", Evans Analytical Group, [Online] Retrieved from the internet: <http://www.eaglabs.com>, (2003), 2 pgs.
"International Application Serial No. PCT/US2009/058505, International Preliminary Report on Patentability dated Oct. 28, 2010", 11 pgs.
"International Application Serial No. PCT/US2009/058505, International Search Report dated Nov. 25, 2009", 2 pgs.
"International Application Serial No. PCT/US2009/058505, Written Opinion dated Nov. 25, 2009", 9 pgs.
"International Application Serial No. PCT/US2011/029858, International Search Report dated May 25, 2011", 2 pgs.
"International Application Serial No. PCT/US2011/029858, Written Opinion dated May 25, 2011", 7 pgs.
"International Application Serial No. PCT/US2011/029859, International Preliminary Report on Patentability dated Oct. 4, 2012", 8 pgs.
"International Application Serial No. PCT/US2011/029859, International Search Report dated May 23, 2011", 2 pgs.
"International Application Serial No. PCT/US2011/029859, Written Opinion dated May 23, 2011", 6 pgs.

(56) References Cited

OTHER PUBLICATIONS

"International Application Serial No. PCT/US2011/029861, International Preliminary Report on Patentability dated Oct. 4, 2012", 9 pgs.
"International Application Serial No. PCT/US2011/029861, International Search Report dated May 20, 2011", 2 pgs.
"International Application Serial No. PCT/US2011/029861, Written Opinion dated May 20, 2011", 7 pgs.
"International Application Serial No. PCT/US2011/029862, International Preliminary Report on Patentability dated Oct. 4, 2012", 11 pgs.
"International Application Serial No. PCT/US2011/029862, International Search Report dated May 25, 2011", 2 pgs.
"International Application Serial No. PCT/US2011/029862, Written Opinion dated May 25, 2011", 9 pgs.
"International Application Serial No. PCT/US2011/029863, International Preliminary Report on Patentability dated Oct. 4, 2012", 13 pgs.
"International Application Serial No. PCT/US2011/029863, International Search Report dated May 27, 2011", 2 pgs.
"International Application Serial No. PCT/US2011/029863, Written Opinion dated May 27, 2011", 11 pgs.
"International Application Serial No. PCT/US2012/024347, International Preliminary Report on Patentability dated Aug. 22, 2013", 9 pgs.
"International Application Serial No. PCT/US2012/024347, International Search Report dated Jun. 29, 2012", 2 pgs.
"International Application Serial No. PCT/US2012/024347, Written Opinion dated Jun. 29, 2012", 7 pgs.
"International Application Serial No. PCT/US2012/024366, International Preliminary Report on Patentability dated Aug. 22, 2013", 20 pgs.
"International Application Serial No. PCT/US2012/024366, International Search Report dated Sep. 7, 2012", 3 pgs.
"International Application Serial No. PCT/US2012/024366, Invitation to Pay Additional Fees and Partial Search Report dated Jun. 1, 2012", 3 pgs.
"International Application Serial No. PCT/US2012/024366, Written Opinion dated Sep. 7, 2012", 18 pgs.
"Japanese Application Serial No. 2011-529290, Office Action dated Sep. 25, 2013", 5 pgs.
"Japanese Application Serial No. 2013-501497, Office Action dated Nov. 5, 2014", 7 pgs.
"Stent", Unabridged (v1.01 ), [Online]. Retrieved from the Internet: <http://dictionary.reference.com/search?q=stent>, (Sep. 22, 2006), 1 pg.
Aaron, Kaplan V, "U.S. Appl. No. 09/225,364, filed Jan. 4, 2099", (Jan. 4, 1999).
Bernard, Andreas, "U.S. Appl. No. 60/336,607, filed Dec. 3, 2001".
Bernard, Andreas, "U.S. Appl. No. 60/336,767, filed Dec. 3, 2001".
Bernard, Andreas, "U.S. Appl. No. 60/440,839, filed Jan. 17, 2003".
Bernard, Andreas, "U.S. Appl. No. 60/784,309, filed Mar. 20, 2006".
Bourang, et al., "U.S. Appl. No. 14/294,631 filed Jun. 3, 2014", 151 pgs.
Bourang, et al., "U.S. Appl. No. 14/313,742 filed Jun. 24, 2014", 142 pgs.
Bourang, et al., "U.S. Appl. No. 14/314,361 filed Jun. 25, 2014", 132 pgs.
Bourang, et al., "U.S. Appl. No. 14/317,387 filed Jun. 27, 2014", (Jun. 27, 2014), 39 pgs.
Bourang, et al., "U.S. Appl. No. 14/321,506 filed Jul. 1, 2014", 131 pgs.
Bourang, et al., "U.S. Appl. No. 14/621,231 filed Feb. 12, 2015", 138 pgs.
Bourang, Henry, et al., "U.S. Appl. No. 15/831,110, filed Dec. 1, 2017", 130 pgs.
Colombo, "The Invatec Bifurcation Stent Solution", Colombo Bifurcation Stents: Novel Solutions, TCT Washington, (Sep. 15-19, 2003), 24 pgs.
Cooley, Patrick, et al., "Applications of Ink-Jet Printing Technology to BioMEMs and Microfluidic Systems", Proceedings, SPIE Conference on Microfluidics and BioMEMs, (Oct. 2001), 12 pgs.
Dichek, et al., "Seeding of intravascular stents with genetically engineered endothelial cells", Circulation, vol. 80, No. 5, (1989), 7 pgs.
Enrique, Klein J, "U.S. Appl. No. 09/097,855, filed Jun. 15, 1998".
Jeffry, Grainger, "U.S. Appl. No. 60/561,041, filed Apr. 9, 2004".
Joung, Yoon Ki, et al., "Estrogen Release from Metallic Stent Surface for the Prevention of Restenosis", Journal of Controlled Release vol. 92, (2003), 83-91.
Lefevre, Thierry, et al., "Approach to Coronary Bifurcation Stenting in 2003", Euro PCR, (May 2003), 127-154.
Pablo, Acosta, et al., "U.S. Appl. No. 10/874,859, filed Jun. 22, 2004".
Patrick, Ruane, "U.S. Appl. No. 60/890,703, filed Feb. 20, 2007".
Patrick, Ruane, "U.S. Appl. No. 61/012,317, filed Dec. 7, 2007".
Stephen, Kaplan, "U.S. Appl. No. 60/810,522, filed Jun. 2, 2006".
Stimpson, Donald I et al., "Parallel Production of Oligonucleotide Arrays Using Membranes and Reagent Jet Printing", Bio Techniques; vol. 25, (Nov. 1998), 886-890.
Sunmi, Chew, "U.S. Appl. No. 60/336,967, filed Dec. 3, 2001".
Sunmi, Chew, "U.S. Appl. No. 60/364,389, filed Mar. 13, 2002".

\* cited by examiner

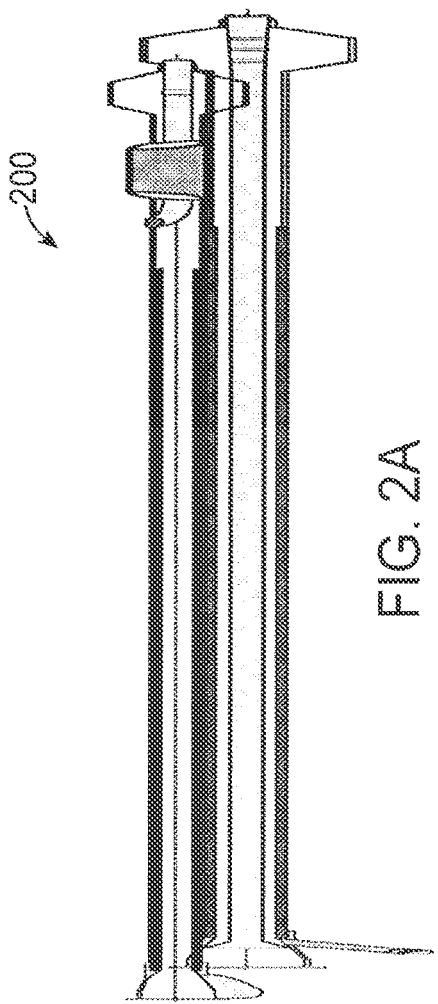
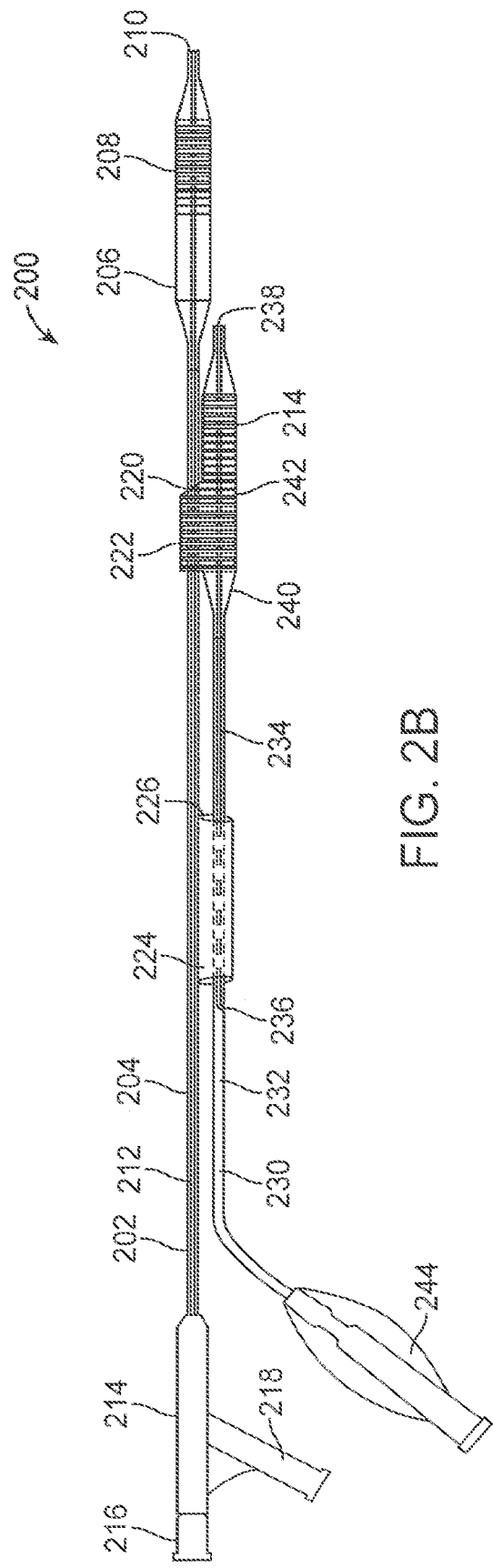
FIG. 2A
FIG. 2B

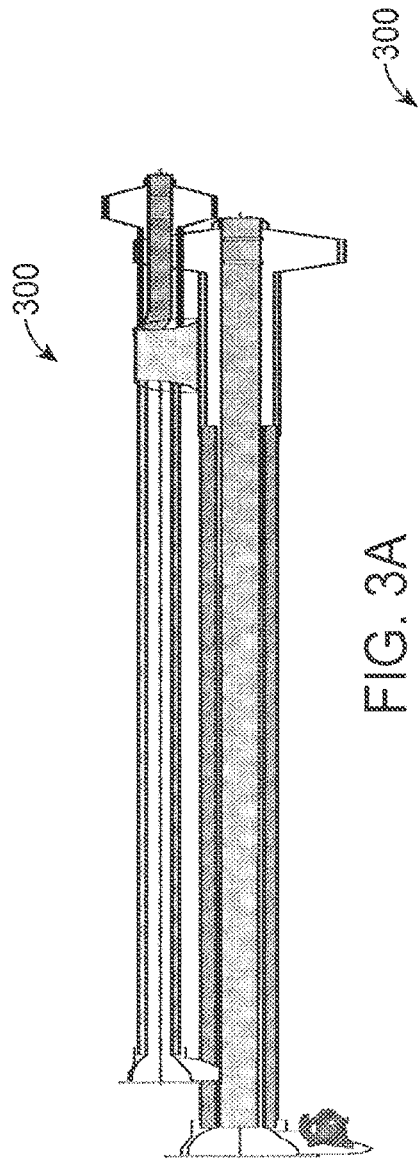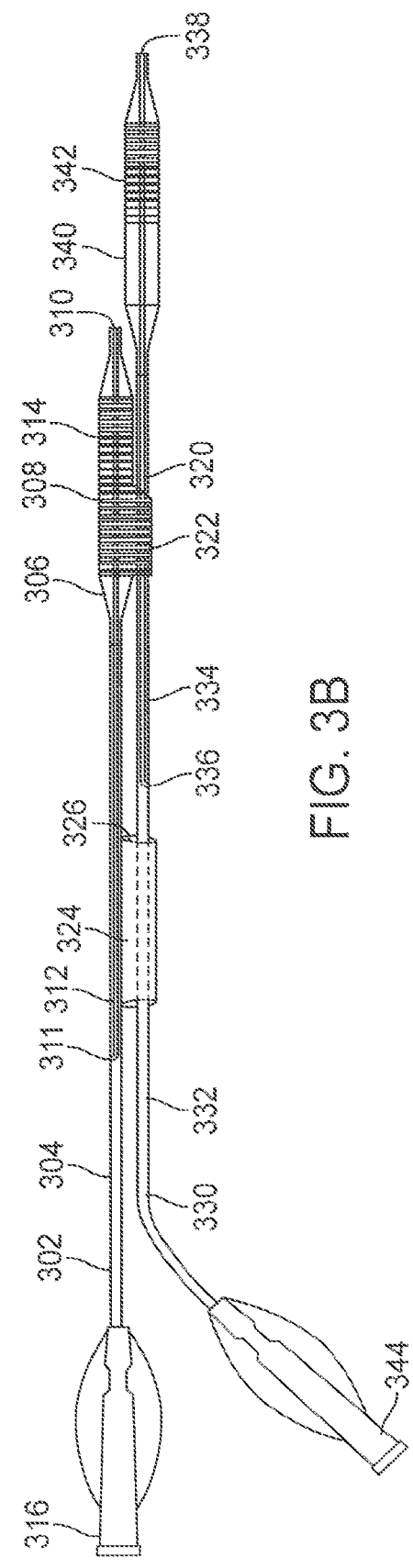
FIG. 3A
FIG. 3B

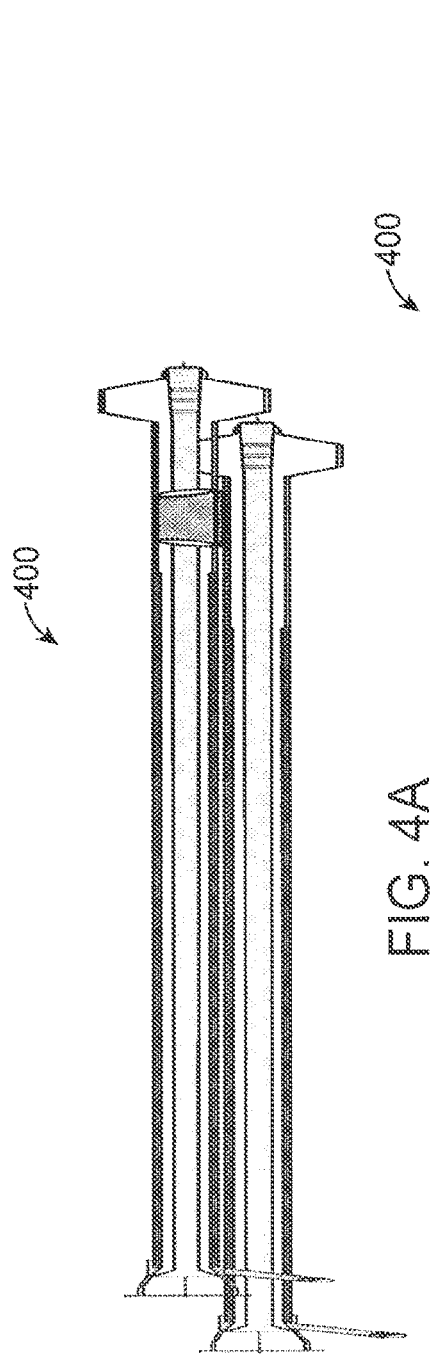
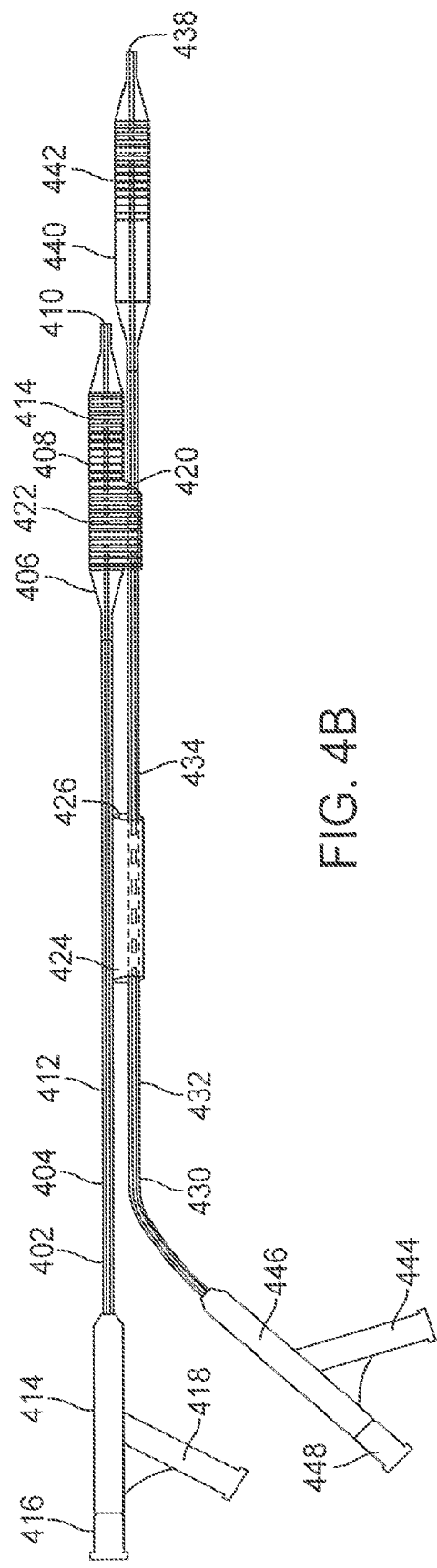
FIG. 4A
FIG. 4B

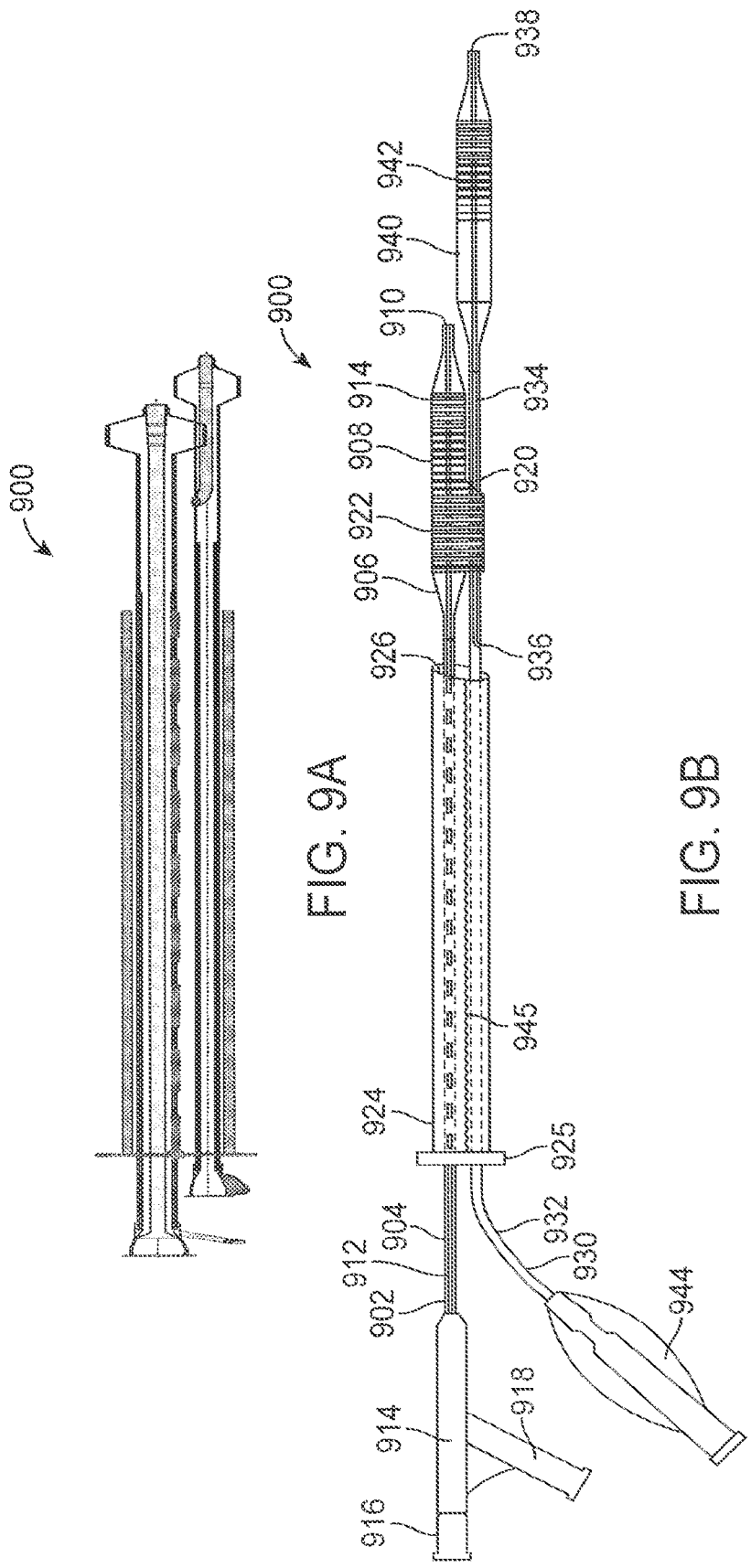

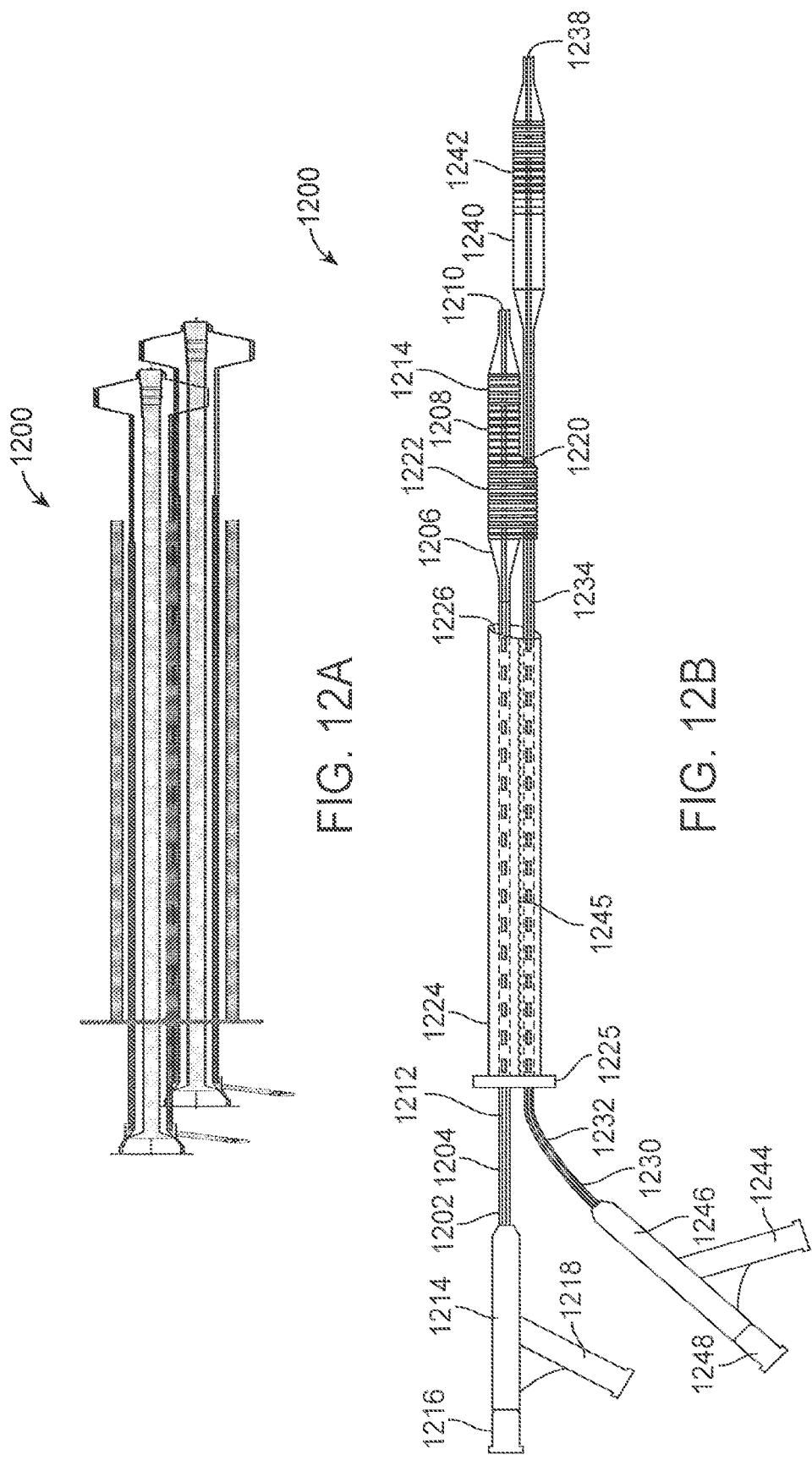

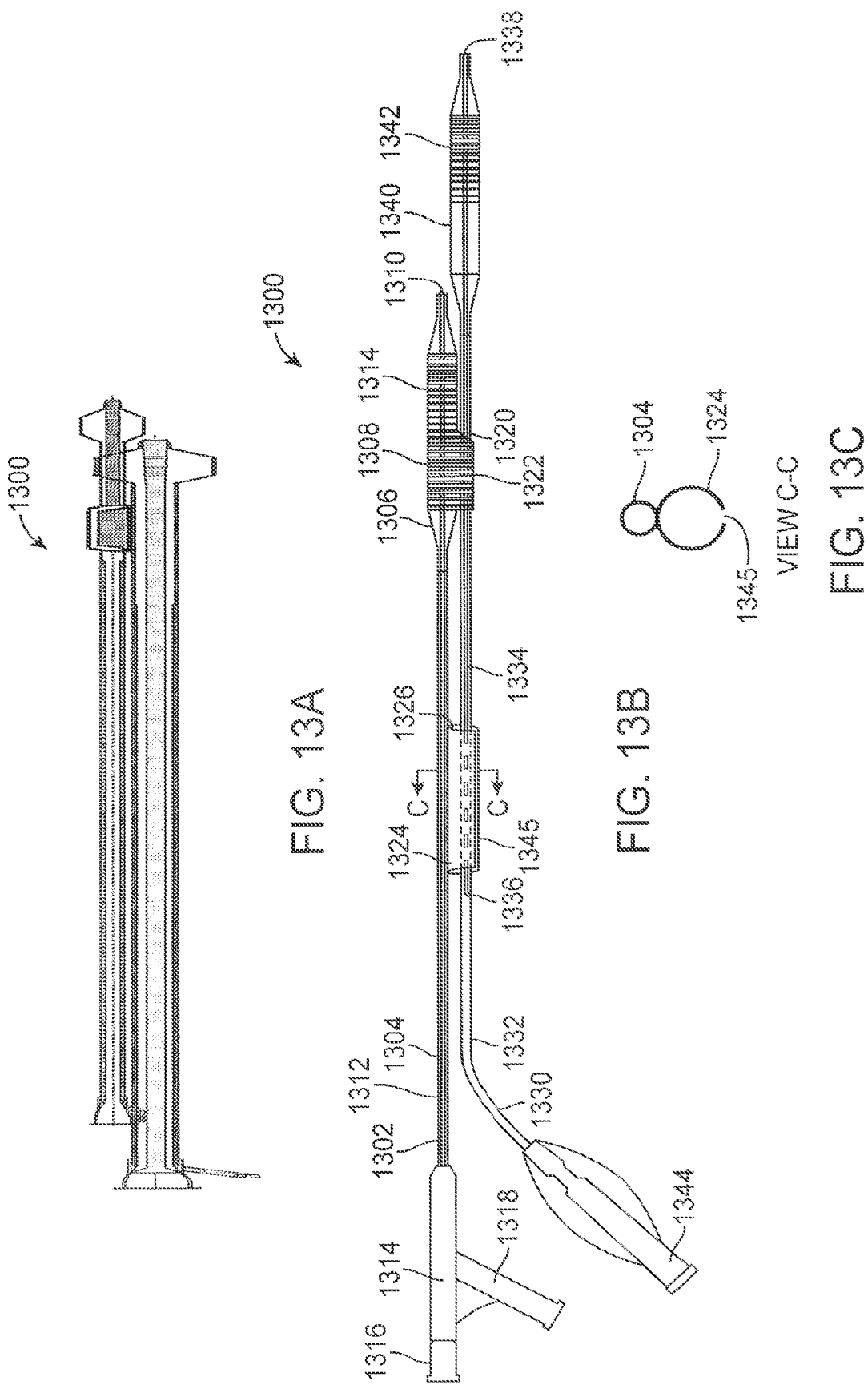

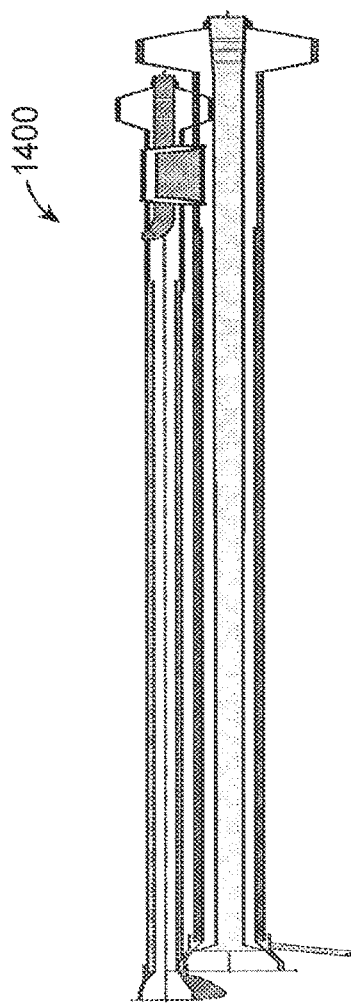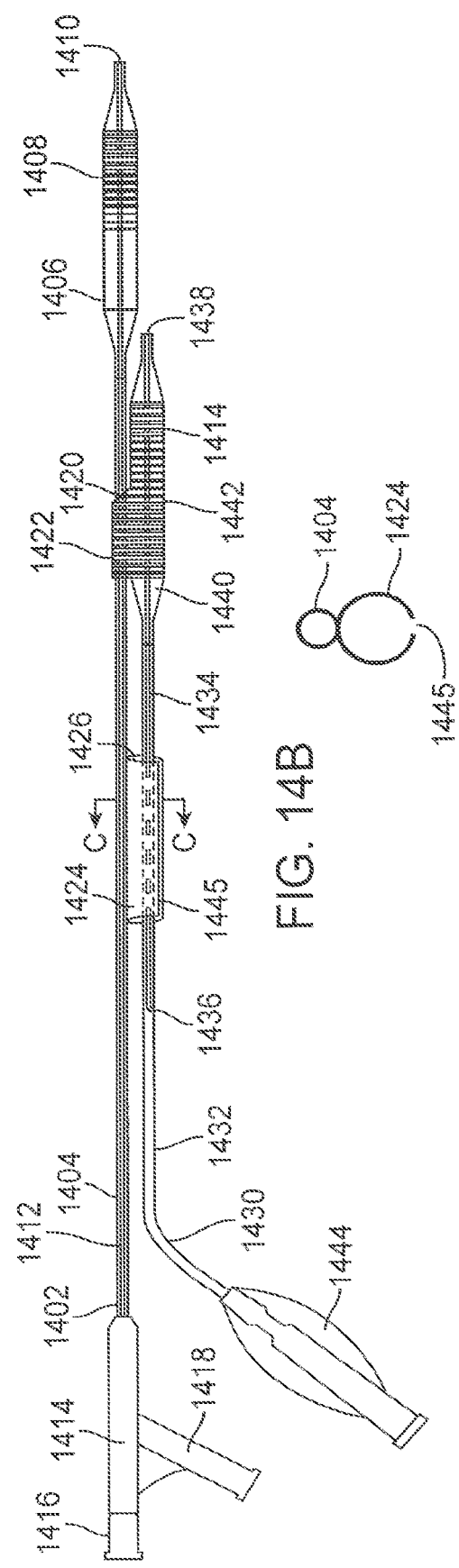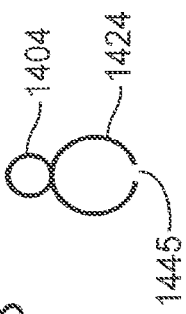

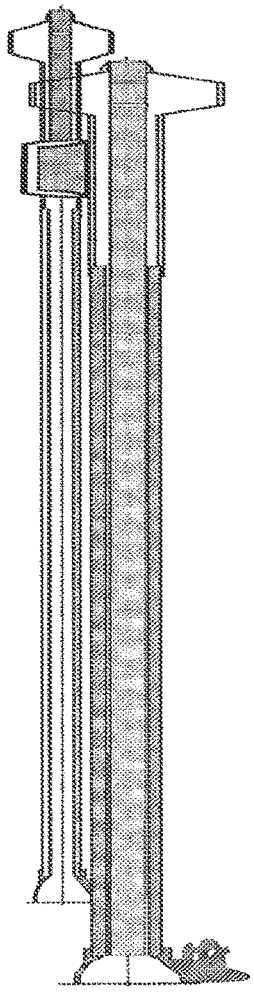
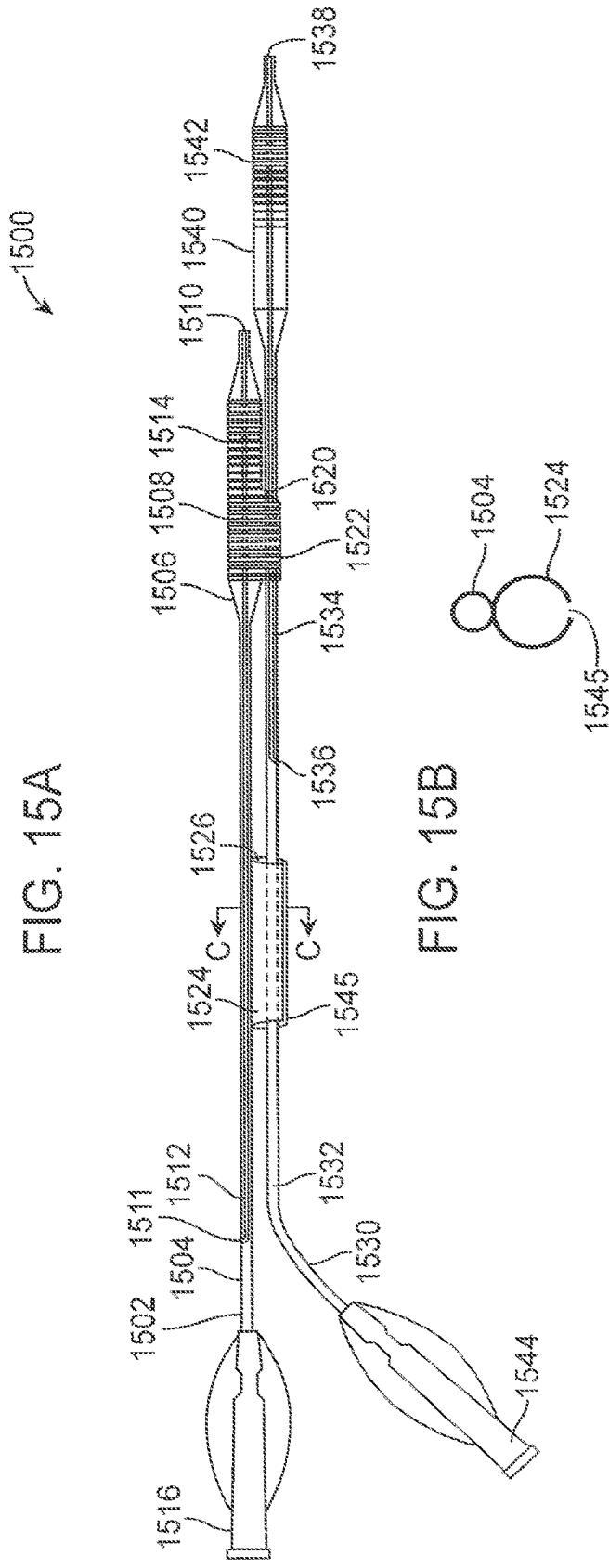
FIG. 15A
FIG. 15B
FIG. 15C

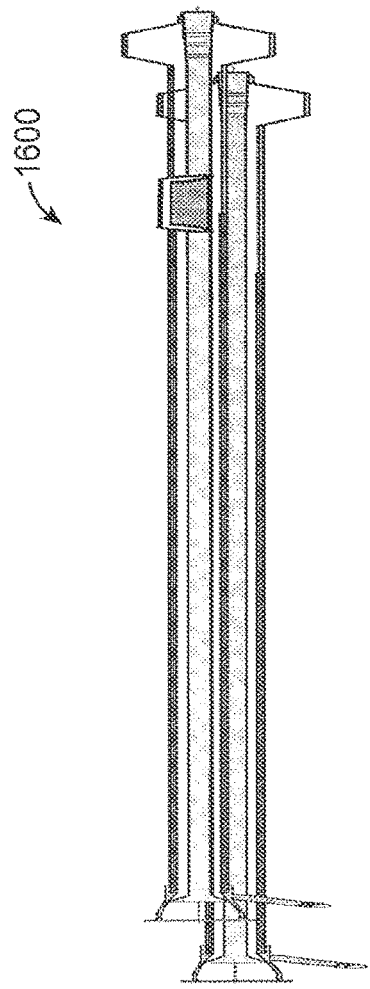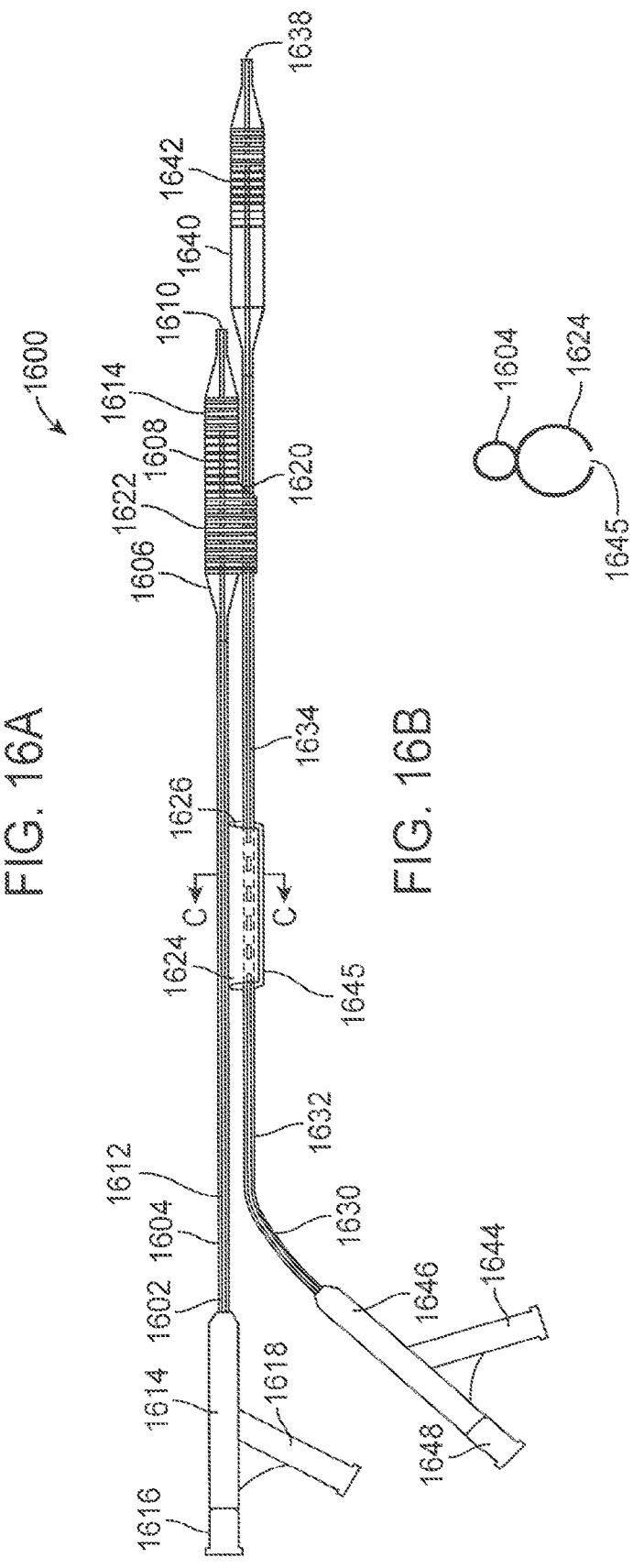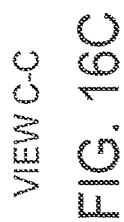

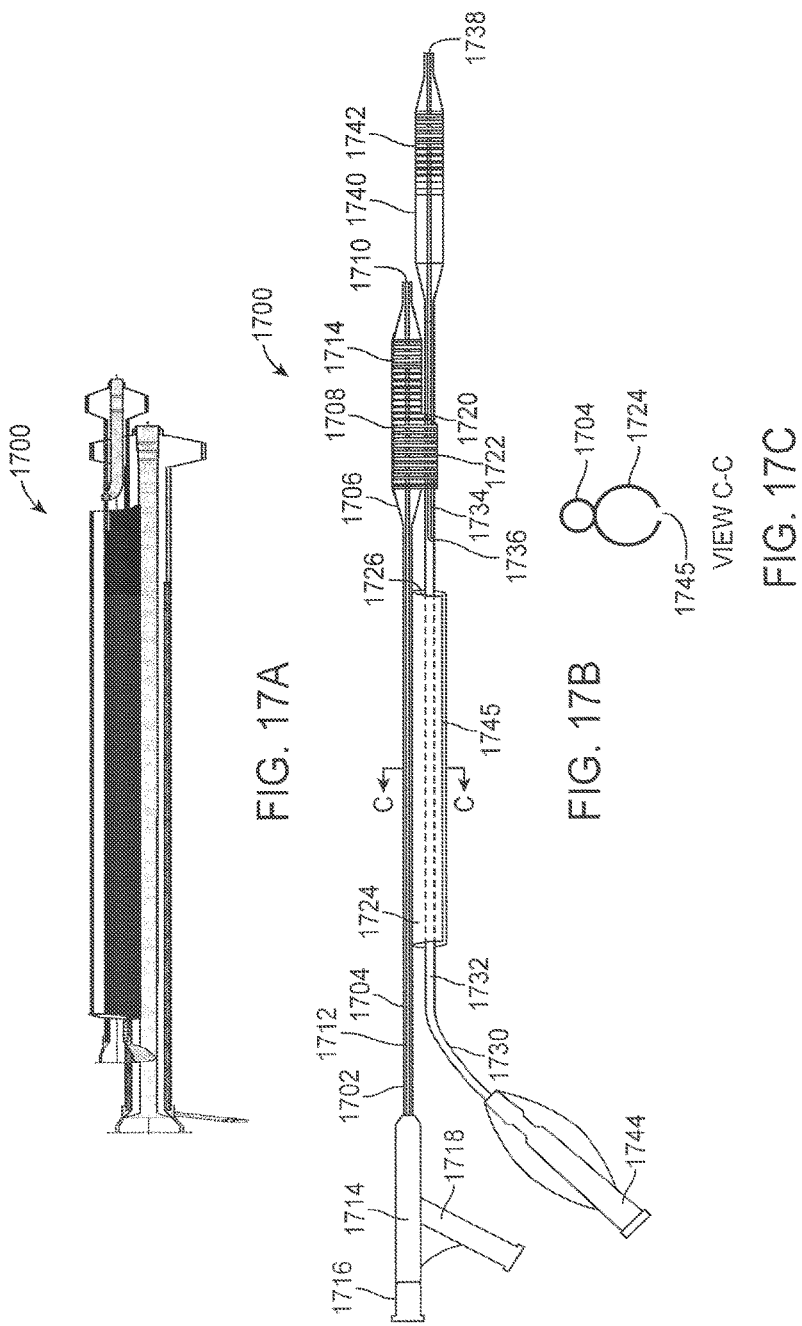

VIEW C-C

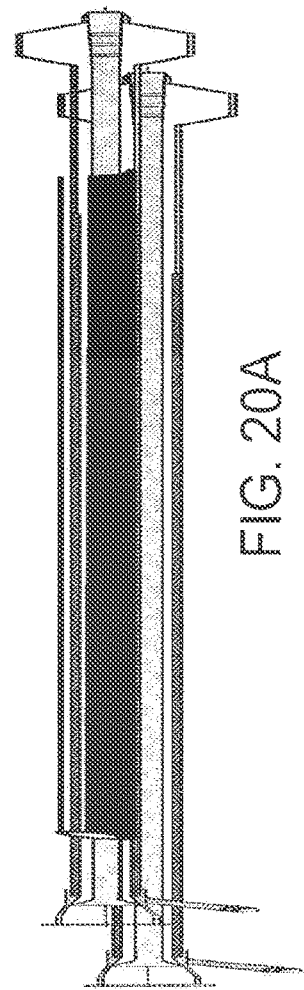
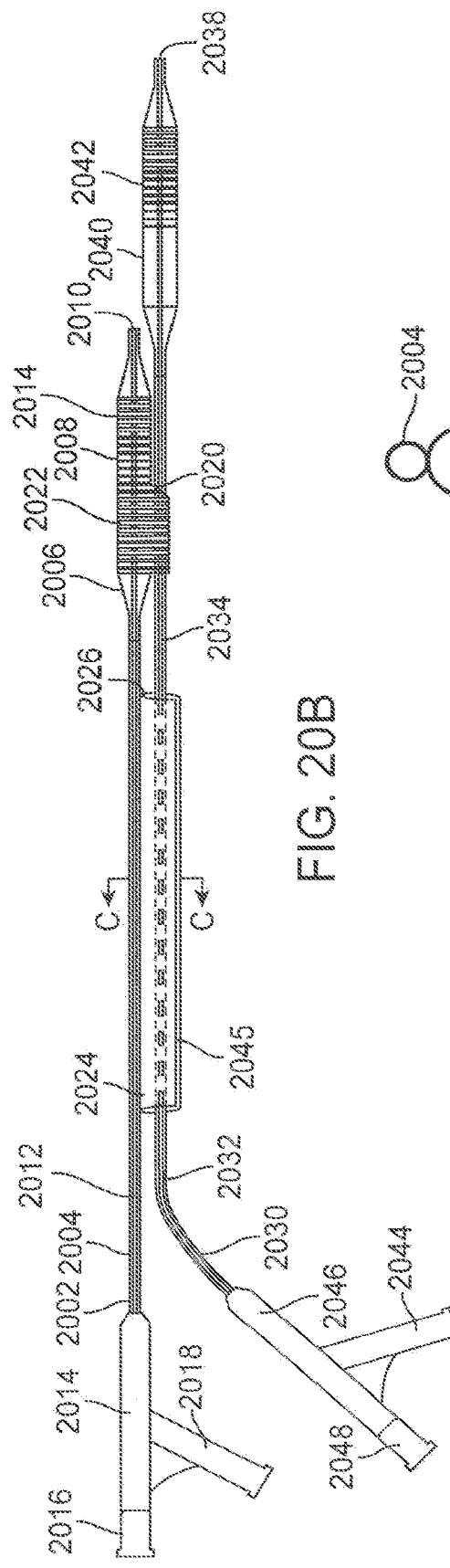
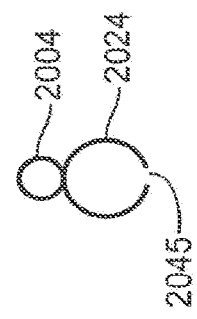

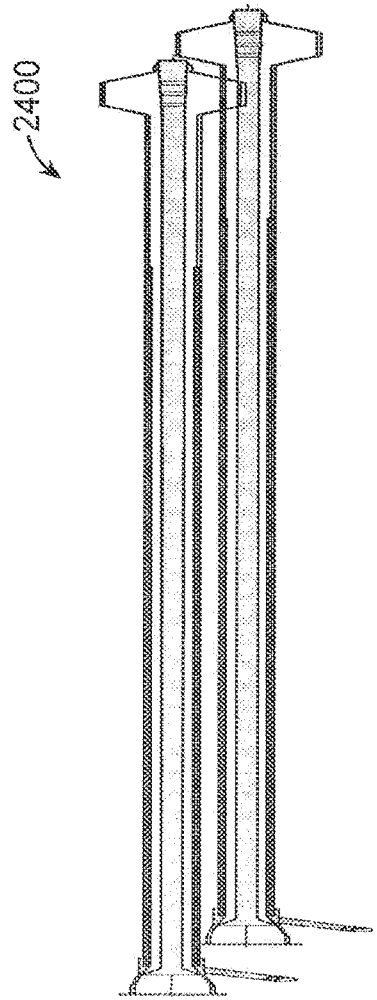
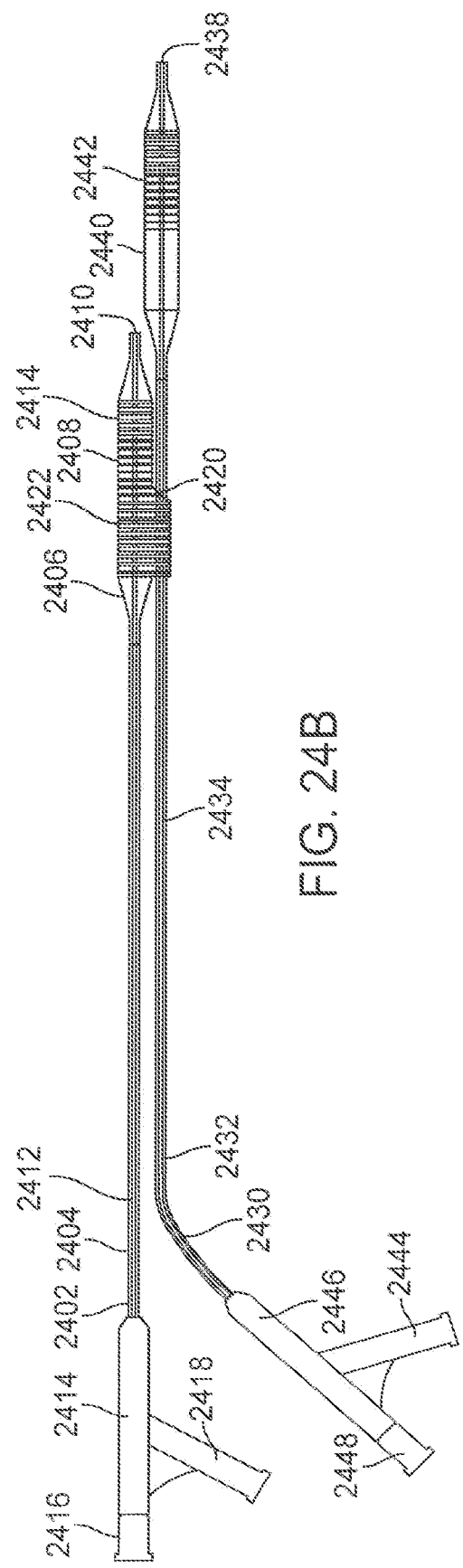
FIG. 24A
FIG. 24B

SYSTEM AND METHODS FOR TREATING A BIFURCATION WITH A FULLY CRIMPED STENT

CROSS REFERENCE TO RELATED APPLICATION DATA

The present application is a continuation of U.S. Ser. No. 16/261,066 filed Jan. 29, 2019, which is a continuation of U.S. Ser. No. 15/157,321 filed May 17, 2016, now issued as U.S. Pat. No. 10,285,832, which application is a Divisional of U.S. Ser. No. 13/796,424 filed Mar. 12, 2013, now issued as U.S. Pat. No. 9,364,356, which is a Continuation of PCT/US2012/024347 filed Feb. 8, 2012 (published as WO 2012/109365 on Aug. 16, 2012); which claims the benefit of U.S. Provisional Application No. 61/440,737 filed Feb. 8, 2011; the full disclosures which are incorporated herein by reference in their entirety for all purposes.

BACKGROUND OF THE INVENTION

The present invention relates to medical devices, and more particularly to stenting and treatment of bifurcated vessels. A stent is an implantable scaffold that is typically delivered percutaneously and deployed in a vein, artery, or other tubular body organ for treating an occlusion, stenosis, aneurysm, collapse, dissection, or weakened, diseased, or abnormally dilated vessel or vessel wall. The stent is radially expanded in situ thereby expanding and/or supporting the vessel wall or body organ wall. In particular, stents are quite commonly implanted in the coronary, cardiac, pulmonary, neurovascular, peripheral vascular, renal, gastrointestinal and reproductive systems, and have been successfully implanted in the urinary tract, the bile duct, the esophagus, the tracheo-bronchial tree and the brain, to reinforce these body organs.

Stents are often used for improving angioplasty results by preventing elastic recoil and remodeling of the vessel wall and for treating dissections in blood vessel walls caused by balloon angioplasty of coronary arteries, as well as peripheral arteries, by pressing together the intimal flaps in the lumen at the site of the dissection. Conventional stents have been used for treating more complex vascular problems, such as lesions at or near bifurcation points in the vascular system, where a secondary artery branches out of a typically larger, main artery, with limited success rates.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or pattern has strut and connecting balloon catheter portions that can impede blood flow at vessel bifurcations.

Furthermore, the configuration of struts and connecting balloon catheter portions may obstruct the use of post-operative devices to treat a daughter vessel in the region of a vessel bifurcation. For example, deployment of a first stent in the mother lumen may prevent a physician from inserting a daughter stent through the ostium of a daughter vessel of a vessel bifurcation in cases where treatment of the mother vessel is suboptimal because of displaced diseased tissue (for example, due to plaque shifting or "snow plowing"), occlusion, vessel spasm, dissection with or without intimal flaps, thrombosis, embolism, and/or other vascular diseases. A regular stent is designed in view of conflicting considerations of coverage versus access. For example, to promote coverage, the cell structure size of the stent may be minimized for optimally supporting a vessel wall, thereby preventing or reducing tissue prolapse. To promote access, the cell size may be maximized for providing accessibility of blood flow and of a potentially future implanted daughter stent to daughter vessels, thereby preventing "stent jailing," and minimizing the amount of implanted material. Regular stent design has typically compromised one consideration for the other in an attempt to address both. Problems the present inventors observed involving daughter jailing, fear of plaque shifting, total occlusion, and difficulty of the procedure are continuing to drive the present inventors' into the development of novel, delivery systems, which are easier, safer, and more reliable to use for treating the above-indicated variety of vascular disorders. Although conventional stents are routinely used in clinical procedures, clinical data shows that these stents are not capable of completely preventing in-stent restenosis (ISR) or restenosis caused by intimal hyperplasia. In-stent restenosis is the reoccurrence of the narrowing or blockage of an artery in the area covered by the stent following stent implantation. Patients treated with coronary stents can suffer from in-stent restenosis.

Many pharmacological attempts have been made to reduce the amount of restenosis caused by intimal hyperplasia. Many of these attempts have dealt with the systemic delivery of drugs via oral or intravascular introduction. However, success with the systemic approach has been limited.

Systemic delivery of drugs is inherently limited since it is difficult to achieve constant drug delivery to the afflicted region and since systemically administered drugs often cycle through concentration peaks and valleys, resulting in time periods of toxicity and ineffectiveness. Therefore, to be effective, anti-restenosis drugs should be delivered in a localized manner. One approach for localized drug delivery utilizes stents as delivery vehicles. For example, stents seeded with transfected endothelial cells expressing bacterial betagalactosidase or human tissue-type plasminogen activator were utilized as therapeutic protein delivery vehicles. See, e.g., Dichek, D. A. et al., "Seeding of Intravascular Stents With Genetically Engineered Endothelial Cells," Circulation, 80:1347-1353 (1989). U.S. Pat. No. 5,679,400, International Patent Publication No. WO 91/12779, entitled "Intraluminal Drug Eluting Prosthesis," and International Patent Publication No. WO 90/13332, entitled "Stent With Sustained Drug Delivery" disclose stent devices capable of delivering antiplatelet agents, anticoagulant agents, antimigratory agents, antimetabolic agents, and other anti-restenosis drugs. U.S. Pat. Nos. 6,273,913; 6,383,215; 6,258,121:6,231,600; 5,837,008, 5,824,048; 5,679,400; and 5,609,629 teach stents coated with various pharmaceutical agents such as Rapamycin, 17-beta-estradiol, Taxol and Dexamethasone. This and all other referenced patents are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

Therefore, given the challenges of current stent technology, a need exists for improved stent delivery systems and methods, particularly for treating bifurcated vessels. At least some of these objectives will be met by the present invention.

BRIEF SUMMARY OF THE INVENTION

The present invention relates to methods and delivery systems used to deliver stents in a bifurcated vessel.

Embodiments may be configured to stent at least a portion of a mother vessel and a portion of a daughter vessel.

In a first aspect of the present invention, a system for treating a bifurcated vessel comprises a first delivery catheter comprising a first elongate shaft with a proximal end and a distal end, a first expandable member adjacent the distal end of the first elongate shaft, an auxiliary expandable member disposed under the first expandable member, and a first radially expandable stent disposed over the first expandable member and over the auxiliary expandable member. The first stent comprises a sidewall having a side hole therethrough, and the first stent has a crimped configuration and an expanded configuration. In the crimped configuration the first stent is coupled with the first expandable member, and in the expanded configuration the first stent supports a vessel wall. The system also has a second delivery catheter which comprises a second elongate shaft with a proximal end and a distal end, and a second expandable member is adjacent the distal end of the second elongate shaft. A portion of the second delivery catheter is disposed under a portion of the first radially expandable stent. Also, a portion of the second delivery catheter passes through the side hole in the first radially expandable stent. In the crimped configuration, the first stent is crimped over the first and second delivery catheters such that the first stent remains attached to the first and the second delivery catheters during advancement of the delivery catheters through a blood vessel.

In the crimped configuration, the first stent may be crimped to the first and the second delivery catheters thereby preventing axial movement of the first elongate shaft relative to the second elongate shaft during advancement through the blood vessel. The stent may be crimped over the first and the second shafts. The auxiliary expandable member may have a collapsed configuration and a radially expanded configuration, and when the auxiliary expandable member is in the collapsed configuration, the first delivery catheter may be sized to be advanced through the blood vessel. In the radially expanded configuration, the auxiliary expandable member may engage and partially expand a portion of the first expandable member as well as expanding a portion of the first stent. The expanded portion of the first stent may comprise a proximal portion of the first stent. The expanded portion of the first expandable member may comprise a proximal portion of the first expandable member. The first stent may be expanded such that only the proximal portion is partially expanded to a size less than the stent's maximum rated expansion size while a distal portion of the first stent remains unexpanded in its crimped configuration.

In the collapsed configuration, after radial expansion of the auxiliary expandable member into the radially expanded configuration, the second elongate shaft may be axially movable relative to the first elongate shaft. The second elongate shaft may be slidably movable under the first stent and out the side hole. The second elongate shaft may be slidable under a proximal portion of the first stent, and over a distal portion of the first stent. The first stent may comprise a balloon expandable stent.

The system may further comprise a second radially expandable stent disposed over the second expandable member. The second stent may have a collapsed configuration and an expanded configuration. In the collapsed configuration the second stent may be coupled with the second expandable member, and in the expanded configuration the second stent may support a vessel wall. The second stent may comprise a balloon expandable stent.

The first expandable member and the second expandable member may be independently expandable of one another.

The first expandable member or the second expandable member may comprises a balloon.

The first or the second delivery catheter may have rapid exchange guidewire features. Thus, each of the first delivery catheter and the second delivery catheter may comprise a guidewire lumen. The first delivery catheter may comprise a distal guidewire opening in the distal end of the first elongate shaft, and a proximal guidewire opening, the proximal guidewire opening may be spaced closer to the distal guidewire opening than the proximal end of the first elongate shaft. The guidewire lumen in the first delivery catheter may be configured to slidably receive a guidewire, and the guidewire lumen may extend from the distal guidewire opening to the proximal guidewire opening. The second delivery catheter may similarly comprise a distal guidewire opening in the distal end of the second elongate shaft, and a proximal guidewire opening. The proximal guidewire opening may be spaced closer to the distal guidewire opening than the proximal end of the second elongate shaft. The guidewire lumen in the second delivery catheter may be configured to slidably receive a guidewire, and the guidewire lumen may extend from the distal guidewire opening to the proximal guidewire opening.

The first or the second delivery catheter may have over the wire guidewire features. Thus, each of the first delivery catheter and the second delivery catheter may comprise a guidewire lumen. The first delivery catheter may comprise a distal guidewire opening in the distal end of the first elongate shaft, and a proximal guidewire opening in the proximal end of the first elongate shaft. The proximal guidewire opening may be closer to the proximal end of the first elongate shaft than the distal guidewire opening. The guidewire lumen in the first delivery catheter may be configured to slidably receive a guidewire, and the guidewire lumen may extend from the distal guidewire opening to the proximal guidewire opening. Similarly, the second delivery catheter may comprise a distal guidewire opening in the distal end of the second elongate shaft, and a proximal guidewire opening in the proximal end of the second elongate shaft. The proximal guidewire opening may be closer to the proximal end of the second elongate shaft than the distal guidewire opening. The guidewire lumen in the second delivery catheter may be configured to slidably receive a guidewire, and the guidewire lumen may extend from the distal guidewire opening to the proximal guidewire opening.

Various combinations of rapid exchange and over the wire guidewire features may be used with the two delivery catheters. For example, both delivery catheters may be rapid exchange, or both may be over the wire. Similarly, one delivery catheter may be rapid exchange while the other is over the wire.

The system may further comprise a therapeutic agent disposed on the first radially expandable stent, or one of the expandable members. The therapeutic agent may be adapted to be eluted therefrom. The therapeutic agent may comprise an anti-restenosis agent.

In another aspect of the present invention, a method for treating a bifurcated vessel comprises providing a first delivery catheter and a second delivery catheter. The first delivery catheter comprises a first elongate shaft, a first expandable member, an auxiliary expandable member disposed under the first expandable member, and a first stent disposed over both the first expandable member and the auxiliary expandable member. The second delivery catheter comprises a second elongate shaft, and a second expandable member. A portion of the second elongate shaft is disposed under the first stent and the second elongate shaft exits a side hole in the first stent. The method also includes advancing both the first delivery catheter and the second delivery catheter through a main branch vessel to a bifurcation in the main branch. The bifurcation comprises a side branch vessel. Radially expanding the auxiliary expandable member expands it to an expanded configuration wherein the expanded auxiliary expandable member engages and expands the first expandable member. Also, in the expanded configuration, the expanded auxiliary expandable member also radially expands to expand a portion of the first stent from a crimped configuration to a partially expanded configuration. Radially contracting the auxiliary expandable member changes the expandable member from the expanded configuration to a collapsed configuration, thereby radially contracting the first expandable member. This also forms an annular gap between an inside surface of the first stent and an outer surface of the first elongate shaft and an outer surface of the second elongate shaft. The second elongate shaft may then be slidably moved relative to the first elongate shaft. The second elongate shaft slides under a portion of the first stent and extends from a side hole in the first stent while a portion of the stent is crimped to the first delivery catheter thereby preventing movement of the stent relative thereto.

Advancing may comprise advancing both the first and the second delivery catheters through a patient's vasculature toward the bifurcation until resistance against further advancement is felt by an operator. The resistance may be provided by one or more of the first and the second delivery catheters engaging a carina of the bifurcation. The auxiliary expandable member may comprise a balloon, and radially expanding the auxiliary member may comprise inflating the balloon. Radially contracting the auxiliary member may comprise deflating the balloon. Slidably moving the second elongate shaft may comprise proximally retracting the second elongate shaft under a portion of the first stent until a portion of the second expandable member enters the side hole of the first stent and is disposed under the first stent.

The method may further comprise radially expanding the first expandable member, thereby expanding the first stent into engagement with a portion of the bifurcated vessel. The second delivery catheter may further comprise a second stent disposed over the second expandable member, and the method may further comprise radially expanding the second expandable member which may be expanded into engagement with another portion of the bifurcated vessel or which may expand the second stent into engagement with a vessel wall. The method may also further comprise eluting a therapeutic agent from the first stent, or one of the expandable members into the bifurcated vessel. The therapeutic agent may comprise an anti-restenosis agent.

In still another aspect of the present invention, a system for treating a bifurcated vessel comprises a first delivery catheter and a second delivery catheter. The first delivery catheter comprises a first elongate shaft with a proximal end and a distal end, a first expandable member adjacent the distal end of the first elongate shaft, and a first radially expandable stent disposed over the first expandable member. The first stent comprises a sidewall having a side hole therethrough. The first stent has a crimped configuration and an expanded configuration. In the crimped configuration the first stent is coupled with the first expandable member, and in the expanded configuration the first stent supports a vessel wall. The second delivery catheter comprises a second elongate shaft with a proximal end and a distal end, a second expandable member adjacent the distal end of the second elongate shaft, and a second stent. The second expandable member is disposed under a portion of the second stent and also is disposed under a portion of the first stent. A portion of the second delivery catheter passes through the side hole in the first radially expandable stent. In the crimped configuration, the first stent is crimped over the first and the second delivery catheters such that the first stent remains attached to the first and the second delivery catheters during advancement of the delivery catheters through a blood vessel.

In another aspect of the present invention, a system for treating a bifurcated vessel comprises a first delivery catheter and a second delivery catheter. The first delivery catheter comprises a first elongate shaft with a proximal end and a distal end, a first expandable member adjacent the distal end of the first elongate shaft, and a first radially expandable stent disposed over the first expandable member. The first stent has a sidewall having a side hole therethrough. The first stent has a crimped configuration and an expanded configuration. In the crimped configuration the first stent is coupled with the first expandable member, and in the expanded configuration the first stent supports a vessel wall. The second delivery catheter comprises a second elongate shaft with a proximal end and a distal end, a distal expandable member adjacent the distal end of the second elongate shaft, a proximal expandable member proximal to the distal expandable member, and a second stent disposed over the distal expandable member. The proximal and distal expandable members are independently expandable of one another. The proximal expandable member is disposed under a portion of the first stent, and the second elongate shaft passes through the side hole. In the crimped configuration the first stent is crimped over the first expandable member and the proximal expandable member such that the first stent remains attached to the first and the second delivery catheters during advancement of the delivery catheters through a blood vessel. Radial expansion of the proximal expandable member partially expands the first stent thereby allowing axial movement of the second delivery catheter relative to the first delivery catheter.

These and other embodiments are described in further detail in the following description related to the appended drawing figures.

BRIEF DESCRIPTION OF THE DRAWINGS

FIGS. 2A-2B illustrate an exemplary embodiment of a system having an over-the-wire daughter catheter and a rapid exchange mother catheter.

FIGS. 3A-3B illustrate an exemplary embodiment of a system having a rapid exchange mother catheter and a rapid exchange daughter catheter.

FIGS. 4A-4B illustrate an exemplary embodiment of a system having an over-the-wire mother catheter and an over-the-wire daughter catheter.

FIGS. 9A-9B illustrate yet another exemplary embodiment of a system having a removable capture tube, an over-the-wire mother catheter and a rapid exchange daughter catheter.

FIGS. 12A-12B illustrate yet another exemplary embodiment of a system having a removable capture tube, an over-the-wire mother catheter and an over-the-wire daughter catheter.

FIGS. 13A-13C illustrate still another exemplary embodiment of a system having a snap fitting, an over-the-wire mother catheter and a rapid exchange daughter catheter.

FIGS. 14A-14C illustrate still another exemplary embodiment of a system having a snap fitting, an over-the-wire daughter catheter and a rapid exchange mother catheter.

FIGS. 15A-15C illustrate still another exemplary embodiment of a system having a snap fitting, a rapid exchange mother catheter and a rapid exchange daughter catheter.

FIGS. 16A-16C illustrate still another exemplary embodiment of a system having a snap fitting, an over-the-wire mother catheter and an over-the-wire daughter catheter.

FIGS. 17A-17C illustrate another exemplary embodiment of a system having a snap fitting, an over-the-wire mother catheter and a rapid exchange daughter catheter.

FIGS. 20A-20C illustrate another exemplary embodiment of a system having a snap fitting, an over-the-wire mother catheter and an over-the-wire daughter catheter.

FIGS. 24A-24B illustrate yet another exemplary embodiment of a system having an over-the-wire mother catheter and an over-the-wire daughter catheter.

DETAILED DESCRIPTION OF THE INVENTION

Figures 1A, 1B:
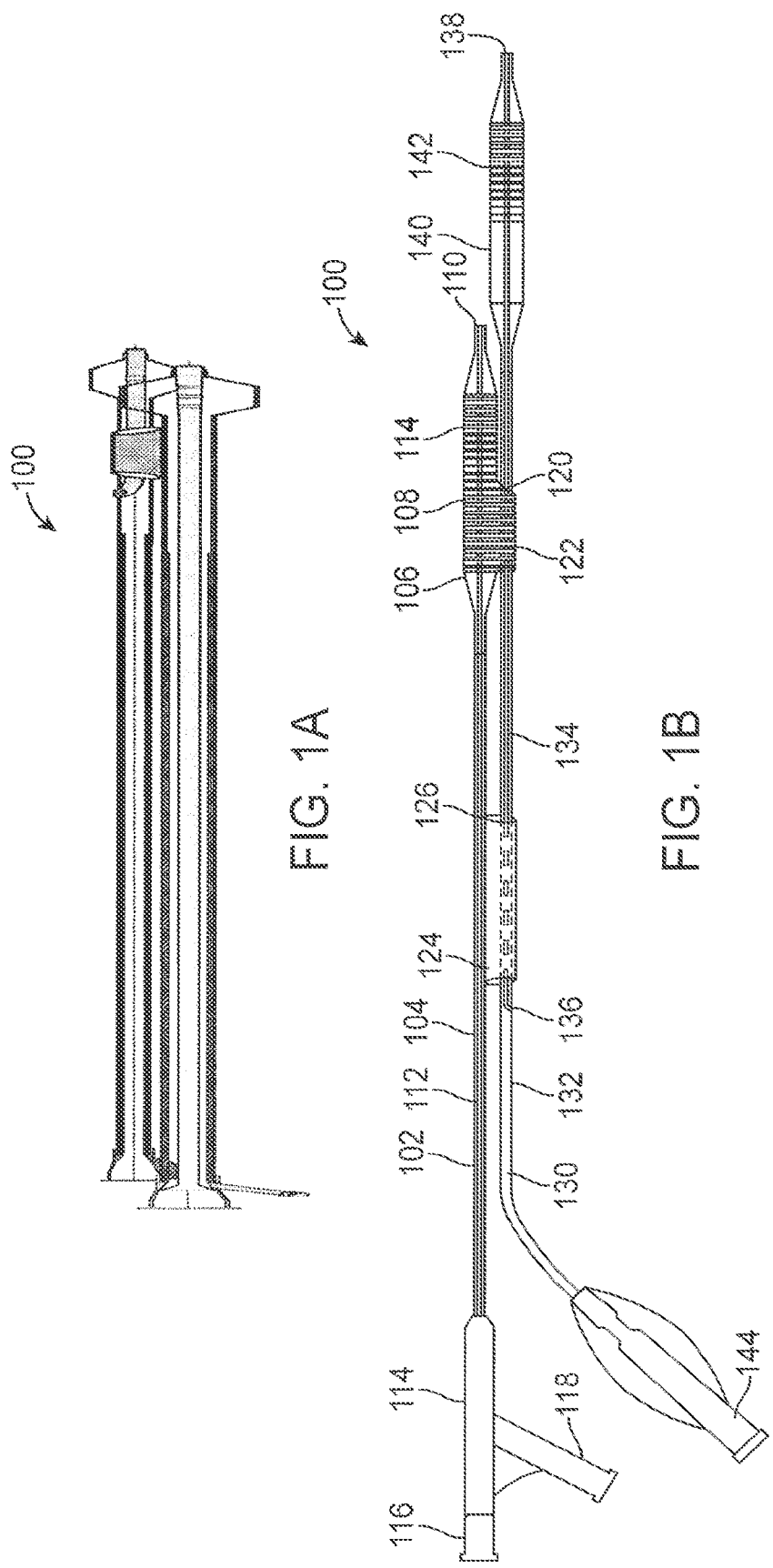
FIGS. 1A-1B illustrate an exemplary embodiment of a system having an over-the-wire mother catheter and a rapid exchange daughter catheter.

The present invention relates to delivery systems for delivery of stents to vessel bifurcations having a main branch and a side branch, and is generally configured to at least partially cover a portion of a the side branch as well as a portion of the main branch. However, this is not intended to be limiting, and one of skill in the art will appreciate that the devices and methods described herein may be used for treating other regions of the body.

The scientific community is slowly moving away from a main branch vs. side branch model and nomenclature. It is now well accepted that a "mother" vessel bifurcates into two "daughter vessels," the two vessels that are anatomically after the carina. The vessel that appears to be the continuation of the mother vessel is usually less angulated. The other vessel may be commonly referred to as the side branch, or a daughter vessel. Therefore, in this specification, the terms "main branch," "trunk," or "mother vessel" may be used interchangeably. Also in this specification, the terms "side branch vessel" and "daughter vessel" may also be used interchangeably. The terms "main branch stent," "trunk stent," or "mother stent" are interchangeable, and the term "side branch stent" is also interchangeable with the term "daughter stent." In the case where a main branch vessel bifurcates into two equally sized branches, one of the branches may still be considered to be the main branch or mother vessel, and the other branch may be considered a side branch or daughter vessel.

A variety of catheter designs may be employed to deploy and position the mother and daughter stents. Such catheters may be used in connection with multiple guidewires that terminate in the mother and daughter vessels. These guidewires may be used to facilitate introduction of the catheter, any angioplasty balloons, any stents, and/or to properly orient the stent or balloon within the vessel.

In general, the methods disclosed herein may utilize a catheter system comprising a catheter body having a mother vessel guidewire lumen and a daughter vessel balloon that is independently operable and coupled to the catheter body. The daughter balloon catheter portion has a daughter vessel guidewire lumen. The catheter system further includes a mother catheter balloon, and a stent is disposed over the balloon. The daughter catheter portion extends into the proximal opening of the mother stent and exits the mother stent through a side passage of the mother stent.

According to one method, a mother vessel guidewire is inserted into the mother vessel until a distal end of the mother vessel guidewire passes beyond the ostium of the daughter vessel, and a daughter vessel guidewire is inserted into the mother vessel until a distal end of the daughter vessel guidewire passes into the daughter vessel. To prevent the crossing of guidewires, the two vessels are wired through a guidewire catheter with two lumens to keep the guidewires separate and untangled.

The guidewire catheter is then removed and a wire separator is placed on the wires to keep the guidewires unwrapped. The catheter system is then advanced over the mother and daughter vessel guidewires, with the mother and daughter vessel catheters passing over the mother vessel guidewire and the daughter vessel guidewire. The catheter system is advanced on both wires with the daughter vessel balloon catheter portion distal to the mother balloon catheter portion, leading the system. As the catheter system advances over the wires, the daughter vessel balloon will enter the daughter vessel and may be positioned after or simultaneously with placement of the mother vessel balloon. The mother balloon catheter portion of the catheter system is then advanced distally as far as it can be advanced where it is stopped by the bifurcation. It cannot be advanced beyond the bifurcation site because the tension of the daughter catheter on the mother stent will prevent the mother catheter from moving distally. At this time the distal portion of the mother stent is beyond the carina in the mother vessel and cannot be advanced any further. This method facilitates advancement of the catheter system to the bifurcation, which may be necessary for tortuous or calcified coronaries. Once the catheter system is in place the daughter vessel balloon catheter portion is then pulled back relative to the mother catheter so that the proximal part of the daughter balloon is partially within the mother stent. Alignment can be performed with radiopaque markers, in that the proximal markers on the two balloons are next to each other. The operator can then gently push the catheter system distal to maximize apposition to the carina. The daughter balloon which is now partially under the mother stent is then inflated to ensure proper alignment of the mother stent. The daughter balloon may also have a stent on its distal portion, which would result in the proximal portion of the mother stent and the daughter stent to expand simultaneously. The daughter balloon is then deflated.

The mother balloon is then inflated which deploys the mother stent. Kissing, reinflation, of the two balloons is performed if necessary or for shifting plaque. The catheter system may be removed while the wires remain in place. In this embodiment, or any of the other embodiments disclosed herein, an angioplasty catheter may be used to predilate the vessel and lesion prior to stenting. In some embodiments, primary stenting is employed where the stent is deployed without the predilation. The two vessels may be angioplastied separately if predilatation is indicated on occasion.

In an alternative method, the mother catheter can be mounted on the daughter vessel guidewire and the daughter catheter can be mounted on the mother vessel guidewire. In daughter vessels with a high degree of angularity, for example, when the bifurcation angle is greater than about 60-70°, the friction between catheters is lower when the operator needs to draw the daughter stent proximally along the main branch and into the mother stent, as opposed to the prior configuration where the daughter stent is drawn along the side branch into the mother stent. The catheter system is advanced so the daughter balloon catheter leads the system and passes the ostium of the daughter vessel, while remaining in the mother vessel. As the catheter system is advanced further, the mother balloon catheter will enter the daughter vessel. The catheter system can only be advanced a certain distance toward the bifurcation, until it is stopped by the bifurcation. It cannot be advanced beyond the bifurcation site because the tension of the daughter catheter on the mother stent will prevent the mother catheter from moving distally. At this time the distal portion of the mother stent is beyond the ostium of the daughter vessel and cannot be advanced any further. While the mother catheter is held in place, the daughter catheter is drawn back such that the proximal portion of the daughter balloon is partially in the mother stent. Alignment can be performed with radiopaque markers, in that the proximal markers on the two balloons are next to each other. The operator can then gently push the catheter system distally to maximize apposition to the carina. A stent on the daughter balloon (which is now partially under the mother stent) is aligned so that when the daughter balloon is inflated the daughter stent and the proximal portion of the mother stent expand simultaneously and give complete coverage of the mother vessel. The daughter vessel balloon is then deflated. The mother vessel balloon is then inflated and the distal portion of the mother stent is expanded. A kissing procedure can also be performed if required.

The mother vessel can be stented if necessary with any commercially available stent. A balloon on a wire could be used as an alternative to the daughter catheter. In an alternative embodiment, the catheter system can be arranged with the daughter balloon portion proximal to the mother balloon portion and advanced over the guidewires to the bifurcation. In the case of the mother catheter on the mother guidewire, the alignment of the mother stent with the ostium of the daughter vessel occurs because tension between the daughter guidewire and mother stent on the mother catheter prevents further advancement of the mother catheter. In the alternative case of the mother catheter on the daughter guidewire, the alignment of the mother stent with the ostium of the mother vessel occurs because tension between the mother guidewire and mother stent on the mother catheter (on the daughter guidewire) prevents further advancement of the mother catheter. In both cases the daughter stent is advanced into alignment with the mother stent and expanded. In preferred embodiments, the mother catheter is an over-the-wire (OTW) design and the daughter catheter is a rapid-exchange (RX) design with daughter catheter portion preferably distal thereto. The daughter balloon is placed just distal to the tip of the mother catheter, this arrangement minimizes the overall profile of the catheter system and allows maximal tracking of the arteries. The system may additionally have stents crimped over the balloons. The daughter stent may be any length, but in preferred embodiments is approximately half the length of the daughter balloon or mother stent. The proximal end of the mother stent may be crimped only slightly to allow the daughter catheter balloon portion to operate independently so that it may be pushed or pulled without dislodging the mother stent.

An exemplary method comprises the following steps:
1. Advance the catheter system to bifurcation, daughter balloon catheter portion and mother balloon catheter portion in their respective vessels.
2. The mother catheter is no longer able to advance because of the tension between the mother stent and daughter catheter.
3. The daughter balloon proximal portion is drawn back into the mother stent and aligned with radiopaque markers.
4. While holding both the mother and daughter catheters tightly, the operator pushes forward lightly.
5. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.
6. Once the daughter stent is fully deployed, then the mother balloon can be fully expanded to deploy the distal portion of the mother stent.
7. A conventional kissing procedure may be utilized to ensure full apposition. In one particular aspect, the daughter balloon catheter portion may be used without a stent. This allows perfect alignment of the mother stent around the ostium of the daughter vessel. The daughter balloon would be used for the alignment as outlined in step three above, and expands the proximal portion of the mother stent.

In an alternative embodiment, the mother catheter is an over-the-wire (OTW) design and the daughter catheter is a rapid-exchange (RX) design with daughter catheter portion distal thereto. The system may additionally have stents crimped over the balloons. The daughter stent is preferably less than the length of the mother balloon or stent, although this is not intended to be limiting, and the daughter stent may be any length. The proximal end of the mother stent may be partially crimped to allow the daughter catheter balloon portion to operate independently, so that it may be pushed or pulled without restriction and minimum friction, and without dislodging or affecting the mother stent. An exemplary method comprises the following steps:
1. Looping the OTW so that one operator can hold both guide wires with one hand and then push both catheters with the other.
2. Advance the catheter system to bifurcation, daughter balloon catheter portion and mother balloon catheter portion aligned in their respective vessels, as disclosed in steps two through three in the above embodiment.
3. While holding both the mother and daughter catheters tightly, push the catheter system forward until the mother balloon catheter portion is stopped at the carina.
4. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.
5. Once the daughter stent is fully deployed, then the mother balloon can be fully expanded to deploy the distal portion of the mother stent.
6. A conventional kissing procedure may be utilized to ensure full apposition.

In one particular aspect, the daughter balloon catheter portion may be used without a stent. This would allow perfect alignment of the mother stent around the ostium of the daughter vessel. The daughter balloon would be used for the alignment as outlined in step three above, and expand the proximal portion of the mother stent.

In an alternative embodiment, the mother catheter is an over-the-wire design and the daughter catheter is a rapid-exchange design with daughter catheter portion distal thereto. The system may additionally have stents crimped over the balloons. The daughter stent may be approximately half the length of the mother balloon or stent, but this is not intended to be limiting, and the daughter stent may be any length. The proximal end of the mother stent may be partially crimped to allow the daughter catheter balloon portion to operate independently, so that it may be pushed or pulled without dislodging the mother stent. An exemplary method comprises the following steps:
1. Place the daughter catheter over the guidewire in the daughter vessel and slide the system into the guide catheter without placing the mother balloon over a guidewire at this time. After the leading daughter catheter enters the coronary artery and just before the mother catheter exits the guide catheter, insert the mother guidewire through the mother catheter and into the mother vessel, then push the system out of the guide catheter over the two guidewires. This method mitigates wire wrap.
2. Advance the catheter system to the bifurcation, daughter balloon catheter portion and mother balloon catheter portion aligned in their respective vessels.
3. Advance the catheter system to bifurcation, daughter balloon catheter portion and mother balloon catheter portion aligned in their respective vessels, as disclosed in step two in the above embodiment. Pull the daughter catheter back until the proximal markers on both balloons are aligned.
4. Inflate the daughter balloon and expand the daughter stent, approximately half of the daughter balloon distal portion will expand the "half-stent," and half of the daughter balloon proximal portion will expand inside the mother vessel and partially expand the proximal portion of the mother stent.
5. Once the daughter stent is fully deployed, then the mother balloon can be fully expanded to deploy the distal portion of the mother stent.
6. A conventional kissing procedure may be utilized to ensure full apposition. In one particular aspect, the daughter balloon catheter portion may be used without a stent. This would allow perfect alignment of mother stent around the ostium of the daughter vessel. The daughter balloon would be used for the alignment as outlined in step three above, and expand the proximal portion of the mother stent.

In an alternative embodiment the mother and daughter systems balloons are aligned. This embodiment could include the mother stent and daughter stent or either stent. When there is both a mother stent and a daughter stent, the daughter stent is preferably shorter than the mother stent, although it may be any length, and in preferred embodiments is approximately half the length of the mother stent so that the daughter stent could be mounted on the distal half of the daughter balloon. Furthermore, the proximal portion of the daughter catheter shaft is positioned under the non-uniformly crimped mother stent. The dual stent arrangement reduces the profile compared to a full length stent that covers the entire length of the daughter balloon.

The methods described herein could alternatively include the step of flushing the catheters and the guidewire port to assist with maneuverability. The methods described herein could alternatively include the step of a couple of snap-on couplers that lock the two catheters together. In another particular aspect, each balloon catheter portion may include at least one radiopaque marker. With such a configuration, separation of the markers may be conveniently observed using fluoroscopy to indicate that the balloon catheter portions have passed beyond the ostium and the daughter balloon catheter portion has passed into the daughter vessel, thus aligning the passage of the stent with the ostium of the daughter vessel. In another particular aspect, the catheter systems design is contemplated to cover combinations of rapid exchange and over the wire; for visualization purposes the hybrid versions are preferred because they are easier to distinguish while using fluoroscopy.

In another particular aspect, the proximal balloon may be differentially expandable, such that one end of the balloon may expand prior to the other end. In another particular aspect, the proximal balloon catheter portion may receive a stent that can be crimped under variable pressure to allow the distal balloon catheter portion freedom of movement.

In another particular aspect, a stent may be crimped over the proximal balloon catheter portion and the stent may be designed to deploy with variable profile to better oppose the patient anatomy.

In another particular aspect, the distal balloon catheter portion may be delivered via a pull away or peel away capture tube. All of the above embodiments may utilize mother vessel stents having any diameter, with diameter preferably ranging from about 2.5 to about 5 millimeters, and daughter vessel stent having any diameter, preferably ranging from about 2 to about 5 millimeters. The length of the stents may be any length, preferably in the range of about 4 to about 40 millimeters. The position of a stent on a catheter need not be fixed and may be positioned on either or both catheters.

Catheter Configurations:

FIG. 1A illustrates an exemplary embodiment of the catheter system 100 with a distal daughter balloon catheter portion comprising a balloon with a daughter stent crimped thereon. The daughter stent may be shorter than the mother stent. In a particular embodiment the daughter stent is preferably about half the length of the mother stent. The distal daughter stent is crimped under standard conditions known in the art. The proximal mother balloon catheter portion comprises a mother balloon and a mother stent. The mother stent is crimped differentially along the longitudinal direction and circumferentially. In this exemplary embodiment, the distal half of the mother stent is crimped under typical conditions to ensure that the mother stent is not dislodged during the alignment with the distal daughter balloon. Further, the proximal portion of the mother stent is crimped under non-standard, relatively loose, conditions to allow the distal daughter balloon catheter portion freedom of movement even though a portion of the daughter balloon catheter portion is circumferentially enclosed. The mother and daughter catheters are slidably attached to each other via a hollow exchange port. The exchange port is embedded in the side of the mother over the wire catheter and has an inner diameter just large enough to allow the insertion of the rapid exchange daughter catheter and balloon. The exchange port may be any length that extends between a proximal portion of the balloons and a distal portion of the catheter connectors, and in this embodiment is about 10 centimeters long, but in preferred embodiments varies from about 1 centimeter to about 30 centimeters, and in more preferred embodiments is about 5 cm to about 10 cm long. The entry for the daughter catheter on the exchange port is proximal and the exit for the daughter catheter is on the distal end of the exchange port. The daughter catheter is loaded through the exchange port and the daughter balloon extends distally from the exit of the exchange port, preferably about 5 centimeters. However, it is possible to have the exchange port any distance from the mother balloon, but preferably about 1 to about 30 centimeters proximal to the mother balloon. The daughter stent can be crimped on to the balloon after it has been loaded through the exchange port. The exchange port preferably has a tight fit to reduce catheter profile and preferably has low friction to allow the operator to easily slide the catheters relative to each other.

FIG. 1B more clearly illustrates the features of the catheter system 100 in FIG. 1A. The stent delivery system 100 includes a first catheter 102, and a second catheter 130. The first catheter 102 includes an elongate shaft 104 with a radially expandable balloon 106 disposed near a distal end of the elongate shaft 104. A stent 108 having a proximal portion 122, a distal portion 114 and a side hole 120 is disposed over the balloon 106. The distal portion 114 is crimped to the balloon 106 to prevent ejection during delivery, while the proximal portion 122 is partially crimped to the balloon 106 so the second catheter 130 may be slidably advanced or retracted under the proximal portion 122 of stent 108. The first catheter is an over-the-wire (OTW) catheter having a guidewire lumen 112 extending from the distal guidewire port 110 at the distal end of the elongate shaft 104 to the proximal end of the elongate shaft 104 into Y-adapter 114 having a connector 116. The connector 116 is preferably a Luer connector and this allows easy coupling with a syringe or other device for lumen flushing or injecting contrast media. When unconnected, the guidewire lumen 112 exits via connector 116. A second connector 118, also preferably a Luer connector allows attachment of an Indeflator or other device to the catheter for inflation of the balloon 106 via an inflation lumen (not shown) in the elongate shaft 104. The first catheter 102 also includes a hollow exchange port tube 124 coupled to the elongate shaft 104. The hollow exchange port tube 124 may be coextruded with the first shaft 104, or it may be bonded or otherwise attached thereto using techniques known to those skilled in the art. The hollow exchange port may alternatively be coupled with the other shaft 132. The hollow exchange port tube 124 includes a central channel 126 extending therethrough and is sized to slidably receive a portion of the second catheter 130. Radiopaque markers may be placed at different locations along the shaft 104, often near the balloon 106 and/or stent 108, to help mark the proximal and distal ends of the stent or balloon, as well to facilitate alignment of the two catheters during stent deployment, as discussed elsewhere in this specification.

The second catheter 130 includes an elongate shaft 132 with a radially expandable balloon 140 disposed near a distal end of the elongate shaft 132. A stent 142 is disposed over balloon 140. The stent may have a length that matches the working length of the balloon, or the stent length may be shorter than the balloon working length. In preferred embodiments, the stent 142 is shorter than the working length of the balloon 140 so that a proximal portion of the balloon 140 is unconstrained by the stent 142 and this unconstrained portion of the balloon 140 may be slidably advanced or retracted through side hole 120 and under proximal portion 122 of stent 108 as will be discussed below. Stent 142 is crimped to balloon 140 to prevent ejection during delivery. At least a portion of balloon 140, and stent 142 are distally offset relative to balloon 106 and stent 108 so as to minimize profile of the device. In this embodiment the distal stent 142 may be deployed in a main branch of the vessel and the other stent 108 may be deployed in a side branch of the vessel. Alternatively, the distal stent 142 may be deployed in a side branch of a vessel and the other stent 108 may be deployed in the main branch of a vessel. The second catheter 130 is a rapid exchange catheter (RX) having a guidewire lumen 134 extending from the distal guidewire port 138 at the distal end of the elongate shaft 132 to a proximal guidewire port 136 which is closer to the distal port 138 than the proximal end of the catheter shaft 132. The proximal guidewire port 136 is also unobstructed by the hollow exchange tube 124 and preferably proximal thereto. A connector 144, preferably a Luer connector is connected to the proximal end of the elongate shaft 132 and allows an Indeflator or other device to be coupled with an inflation lumen (not shown) in elongate shaft 132 for inflation of balloon 140. A portion of shaft 132 is disposed in the central channel 126 of the hollow exchange tube 124 and this helps keep the two catheter shafts 104, 132 parallel and prevents tangling during delivery and as shaft 132 is slidably advanced or retracted relative to shaft 104. Also, another portion of shaft 132 is disposed under proximal portion 122 of stent 108. The second catheter 130 may also be slidably advanced or retracted under the proximal portion 122 of stent 108 so that the shaft 132 passes through the side hole 120 in stent 108. Radiopaque markers may be placed at different locations on the shaft 132, often near the balloon 140 or stent 142, to help mark the proximal and distal ends of the stent or balloon, as well to facilitate alignment of the two catheters during stent deployment, as discussed elsewhere in this specification.

FIG. 2A illustrates a cross sectional view of one embodiment of a catheter system 200 with the daughter catheter balloon portion distal to the mother balloon portion utilizing the same exchange port as described in FIG. 1A. The mother balloon is preferably at least about 5 centimeters distal from the exit of the exchange port. As disclosed above the mother balloon could be distal from the exchange port from about 1 cm to about 30 centimeters.

FIG. 2B more clearly illustrates the features of the catheter system 200 in FIG. 2A. The stent delivery system 20 includes a first catheter 202, and a second catheter 230. The first catheter 202 includes an elongate shaft 204 with a radially expandable balloon 206 disposed near a distal end of the elongate shaft 204, and a stent 208 disposed over the balloon 206. The stent 208 may be the same length as the working length of the balloon 208, or it may be shorter. In preferred embodiments, the stent 208 is shorter than the working length of balloon 206 such that a proximal portion of balloon 206 remains unconstrained by stent 208. The proximal portion of balloon 206 may be slidably advanced and retracted under stent 242 via side hole 220. Stent 208 is crimped to the balloon 206 to prevent ejection during delivery. The first catheter is an over-the-wire (OTW) catheter having a guidewire lumen 212 extending from the distal guidewire port 210 at the distal end of the elongate shaft 204 to the proximal end of the elongate shaft 204 into Y-adapter 214 having a connector 216. The connector 216 is preferably a Luer connector and this allows easy coupling with a syringe or other device for lumen flushing or injecting contrast media. When unconnected, the guidewire lumen 212 exits via connector 216. A second connector 218, also preferably a Luer connector allows attachment of an Indeflator or other device to the catheter for inflation of the balloon 206 via an inflation lumen (not shown) in the elongate shaft 204. The first catheter 202 also includes a hollow exchange port tube 224 coupled to the elongate shaft 204. The hollow exchange port tube 224 may be coextruded with the first shaft 204, or it may be bonded or otherwise attached thereto using techniques known to those skilled in the art. The hollow exchange port may alternatively be coupled with the other shaft 232. The hollow exchange port tube 224 includes a central channel 226 extending therethrough and is sized to slidably receive a portion of the second catheter 230. Radiopaque markers may be placed at different locations along the shaft 204, often near the balloon 206 and/or stent 208, to help mark the proximal and distal ends of the stent or balloon, as well to facilitate alignment of the two catheters during stent deployment, as discussed elsewhere in this specification.

The second catheter 230 includes an elongate shaft 232 with a radially expandable balloon 240 disposed near a distal end of the elongate shaft 232. A stent 242 having a proximal portion 222, a distal portion 214, and a side hole 220 is disposed over balloon 240. The distal portion 214 is crimped to balloon 240 to prevent ejection during delivery, while the proximal portion 222 is partially crimped to balloon 240 so elongate shaft 204 may be slidably advanced or retracted under the proximal portion 222 of stent 242. The stent may preferably have a length that matches the working length of the balloon, or the stent length may be shorter than the balloon working length. At least a portion of balloon 206, and stent 208 are distally offset relative to balloon 240 and stent 242 so as to minimize profile of the device. In this embodiment the distal stent 208 may be deployed in a main branch of the vessel and the other stent 242 may be deployed in a side branch of the vessel. Alternatively, the distal stent 208 may be deployed in a side branch of a vessel and the other stent 242 may be deployed in the main branch of a vessel. The second catheter 230 is a rapid exchange catheter (RX) having a guidewire lumen 234 extending from the distal guidewire port 238 at the distal end of the elongate shaft 232 to a proximal guidewire port 236 which is closer to the distal port 238 than the proximal end of the catheter shaft 232. The proximal guidewire port 236 is also unobstructed by the hollow exchange tube 224 and preferably proximal thereto. A connector 244, preferably a Luer connector is connected to the proximal end of the elongate shaft 232 and allows an Indeflator or other device to be coupled with an inflation lumen (not shown) in elongate shaft 232 for inflation of balloon 240. A portion of shaft 232 is disposed in the central channel 226 of the hollow exchange tube 224 and this helps keep the two catheter shafts 204, 232 parallel and prevents tangling during delivery and as shaft 232 is slidably advanced or retracted relative to shaft 204. Also, a portion of shaft 204 is disposed under proximal portion 222 of stent 242. The first catheter 202 may be slidably advanced or retracted under the proximal portion 222 of stent 242 so that the shaft 204 passes through the side hole 220 in stent 242. Radiopaque markers may be placed at different locations on the shaft 232, often near the balloon 240 or stent 242, to help mark the proximal and distal ends of the stent or balloon, as well to facilitate alignment of the two catheters during stent deployment, as discussed elsewhere in this specification.

FIG. 3A illustrates a cross sectional view of one embodiment of a catheter system 300 with the mother and daughter catheters both having a rapid exchange design. In this particular embodiment one of the catheters has a hollow exchange port embedded in its side and the other catheter is loaded through the exchange port. Typically, the catheter is loaded prior to having a stent crimped over the balloon portion.

FIG. 3B more clearly illustrates the features of the catheter system 300 in FIG. 3A. The stent delivery system 300 includes a first catheter 302, and a second catheter 330. The first catheter 302 includes an elongate shaft 304 with a radially expandable balloon 306 disposed near a distal end of the elongate shaft 304. A stent 308 having a proximal portion 322, a distal portion 314 and a side hole 320 is disposed over the balloon 306. The distal portion 314 is crimped to the balloon 306 to prevent ejection during delivery, while the proximal portion 322 is partially crimped to the balloon 306 so the second catheter 330 may be slidably advanced under the proximal portion 322 of stent 308. The first catheter is a rapid exchange catheter (RX) having a guidewire lumen 312 extending from the distal guidewire port 310 at the distal end of the elongate shaft 304 to a proximal guidewire port 311 which is closer to the distal port 310 than the proximal end of the catheter shaft 304. A connector 316 is coupled with the proximal end of the elongate shaft 304. The connector 316 is preferably a Luer connector and this allows easy coupling with an Indeflator or other device for inflation of the balloon 306. The first catheter 302 also includes a hollow exchange port tube 324 coupled to the elongate shaft 304. The hollow exchange port tube 324 may be coextruded with the first shaft 304, or it may be bonded or otherwise attached thereto using techniques known to those skilled in the art. The hollow exchange port may alternatively be coupled with the other shaft 332. The hollow exchange port tube 324 includes a central channel 326 extending therethrough and is sized to slidably receive a portion of the second catheter 330. Radiopaque markers may be placed at different locations along the shaft 304, often near the balloon 306 and/or stent 308, to help mark the proximal and distal ends of the stent or balloon, as well to facilitate alignment of the two catheters during stent deployment, as discussed elsewhere in this specification.

The second catheter 330 includes an elongate shaft 332 with a radially expandable balloon 340 disposed near a distal end of the elongate shaft 332. A stent 342 is disposed over balloon 340. The stent may have a length that matches the working length of the balloon, or the stent length may be shorter than the balloon working length. In preferred embodiments, the stent 342 is shorter than the working length of the balloon 340 so that a proximal portion of the balloon 340 is unconstrained by the stent 342 and this unconstrained portion of the balloon 340 may be slidably advanced or retracted through side hole 320 and under proximal portion 322 of stent 308 as will be discussed below. Stent 342 is crimped to balloon 340 to prevent ejection during delivery. At least a portion of balloon 340, and stent 342 are distally offset relative to balloon 306 and stent 308 so as to minimize profile of the device. In this embodiment the distal stent 342 may be deployed in a main branch of the vessel and the other stent 308 may be deployed in a side branch of the vessel. Alternatively, the distal stent 342 may be deployed in a side branch of a vessel and the other stent 308 may be deployed in the main branch of a vessel. The second catheter 330 is a rapid exchange catheter (RX) having a guidewire lumen 334 extending from the distal guidewire port 338 at the distal end of the elongate shaft 332 to a proximal guidewire port 336 which is closer to the distal port 338 than the proximal end of the catheter shaft 332. The proximal guidewire port 336 is also unobstructed by the hollow exchange tube 324 and may be distal thereto. A connector 344, preferably a Luer connector is connected to the proximal end of the elongate shaft 332 and allows an Indeflator or other device to be coupled with an inflation lumen (not shown) in elongate shaft 332 for inflation of balloon 340. A portion of shaft 332 is disposed in the central channel 326 of the hollow exchange tube 324 and this helps keep the two catheter shafts 304, 332 parallel and prevents tangling during delivery and as shaft 332 is slidably advanced or retracted relative to shaft 304. Also, another portion of shaft 332 is disposed under proximal portion 322 of stent 308. The second catheter 330 may also be slidably advanced or retracted under the proximal portion 122 of stent 108 so that the shaft 132 passes through the side hole 320 in stent 308. Radiopaque markers may be placed at different locations on the shaft 332, often near the balloon 340 or stent 342, to help mark the proximal and distal ends of the stent or balloon, as well to facilitate alignment of the two catheters during stent deployment, as discussed elsewhere in this specification.

FIG. 4A illustrates a cross sectional view of one embodiment of a catheter system 400 with the mother and daughter catheters both having an over the wire design. In this particular embodiment one of the catheters has a hollow exchange port embedded in its side and the other catheter does not have a hollow exchange port. The catheter without the exchange port is loaded onto the catheter with an exchange port. Typically, the catheter would have to be loaded prior to having a stent crimped over the balloon portion.

FIG. 4B more clearly illustrates the features of the catheter system 400 in FIG. 4A. The stent delivery system 400 includes a first catheter 402, and a second catheter 430. The first catheter 402 includes an elongate shaft 404 with a radially expandable balloon 406 disposed near a distal end of the elongate shaft 404. A stent 408 having a proximal portion 422, a distal portion 414 and a side hole 420 is disposed over the balloon 406. The distal portion 414 is crimped to the balloon 406 to prevent ejection during delivery, while the proximal portion 422 is partially crimped to the balloon 406 so the second catheter 430 may be slidably advanced under the proximal portion 422 of stent 408. The first catheter is an over-the-wire (OTW) catheter having a guidewire lumen 412 extending from the distal guidewire port 410 at the distal end of the elongate shaft 404 to the proximal end of the elongate shaft 404 into Y-adapter 414 having a connector 416. The connector 416 is preferably a Luer connector and this allows easy coupling with a syringe or other device for lumen flushing or injecting contrast media. When unconnected, the guidewire lumen 412 exits via connector 416. A second connector 418, also preferably a Luer connector allows attachment of an Indeflator or other device to the catheter for inflation of the balloon 406 via an inflation lumen (not shown) in the elongate shaft 404. The first catheter 402 also includes a hollow exchange port tube 424 coupled to the elongate shaft 404. The hollow exchange port tube 424 may be coextruded with the first shaft 404, or it may be bonded or otherwise attached thereto using techniques known to those skilled in the art. The hollow exchange port may alternatively be coupled with the other shaft 432. The hollow exchange port tube 424 includes a central channel 426 extending therethrough and is sized to slidably receive a portion of the second catheter 430. Radiopaque markers may be placed at different locations along the shaft 404, often near the balloon 406 and/or stent 408, to help mark the proximal and distal ends of the stent or balloon, as well to facilitate alignment of the two catheters during stent deployment, as discussed elsewhere in this specification.

The second catheter 430 includes an elongate shaft 432 with a radially expandable balloon 440 disposed near a distal end of the elongate shaft 432. A stent 442 is disposed over balloon 440. The stent may have a length that matches the working length of the balloon, or the stent length may be shorter than the balloon working length. In preferred embodiments, the stent 442 is shorter than the working length of the balloon 440 so that a proximal portion of the balloon 440 is unconstrained by the stent 442 and this unconstrained portion of the balloon 440 may be slidably advanced or retracted through side hole 420 and under proximal portion 422 of stent 408 as will be discussed below. Stent 442 is crimped to balloon 440 to prevent ejection during delivery. At least a portion of balloon 440, and stent 442 are distally offset relative to balloon 406 and stent 408 so as to minimize profile of the device. In this embodiment the distal stent 442 may be deployed in a main branch of the vessel and the other stent 408 may be deployed in a side branch of the vessel. Alternatively, the distal stent 442 may be deployed in a side branch of a vessel and the other stent 408 may be deployed in the main branch of a vessel. The second catheter 430 is an over-the-wire (OTW) catheter having a guidewire lumen 434 extending from the distal guidewire port 438 at the distal end of the elongate shaft 432 to the proximal end of the elongate shaft 432 into Y-adapter 446 having a connector 448. The connector 448 is preferably a Luer connector and this allows easy coupling with a syringe or other device for lumen flushing or injecting contrast media. When unconnected, the guidewire lumen 434 exits via connector 448. A second connector 444, also preferably a Luer connector allows attachment of an Indeflator or other device to the catheter for inflation of the balloon 440 via an inflation lumen (not shown) in the elongate shaft 432. A portion of shaft 432 is disposed in the central channel 426 of the hollow exchange tube 424 and this helps keep the two catheter shafts 404, 432 parallel and prevents tangling during delivery and as shaft 432 is slidably advanced or retracted relative to shaft 404. Also, another portion of shaft 432 is disposed under proximal portion 422 of stent 408. The second catheter 430 may also be slidably advanced or retracted under the proximal portion 422 of stent 408 so that the shaft 432 passes through the side hole 420 in stent 408. Radiopaque markers may be placed at different locations on the shaft 432, often near the balloon 440 or stent 442, to help mark the proximal and distal ends of the stent or balloon, as well to facilitate alignment of the two catheters during stent deployment, as discussed elsewhere in this specification.

FIGS. 5A, 6A, 7A, and 8A illustrate an end to end capture tube that connects the catheters together. The capture tube keeps the catheters from tangling. The capture tube preferably remains in place during the entire clinical procedure. In these exemplary embodiments, the capture tube is a thin polymer hollow straw that covers the mother and daughter catheters from a point about 10 centimeters distal to the Indeflator attachment to a distal point that is about 10 centimeters proximal from the rapid exchange catheter's proximal rapid exchange port.

Figure 5A:
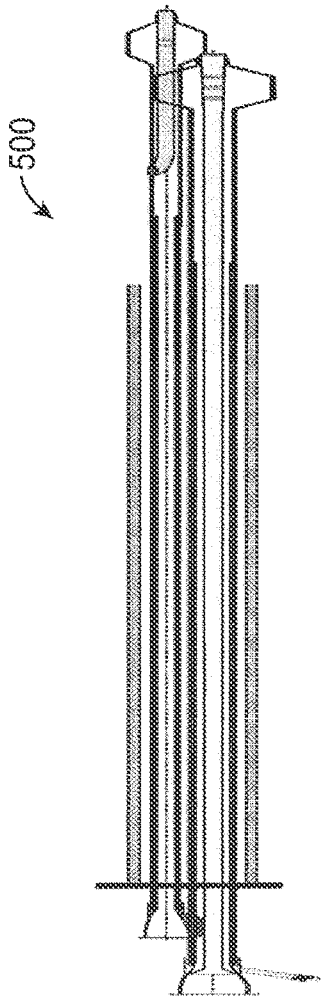
FIGS. 5A-5B illustrate another exemplary embodiment of a system having a capture tube, an over-the-wire mother catheter, and a rapid exchange daughter catheter.
Figure 5B:
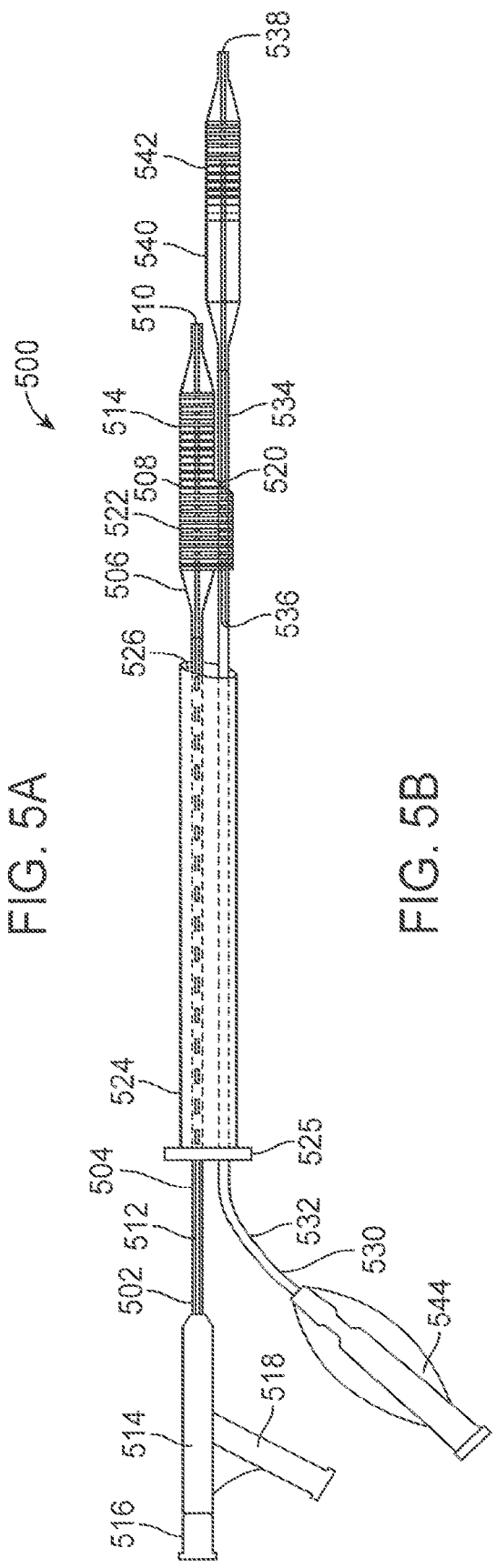

FIG. 5A illustrates a catheter system 500 having a distal daughter catheter with a rapid exchange configuration and a proximal mother catheter with an over-the-wire configuration. FIG. 5B more clearly illustrates the features of the catheter system 500 seen in FIG. 5A. The stent delivery system 500 includes a first catheter 502, and a second catheter 530. The first catheter 502 includes an elongate shaft 504 with a radially expandable balloon 506 disposed near a distal end of the elongate shaft 504. A stent 508 having a proximal portion 522, a distal portion 514 and a side hole 220 is disposed over the balloon 506. The distal portion 514 is crimped to the balloon 506 to prevent ejection during delivery, while the proximal portion 522 is partially crimped to the balloon 506 so the second catheter 530 may be slidably advanced under the proximal portion 522 of stent 508. The first catheter is an over-the-wire (OTW) catheter having a guidewire lumen 512 extending from the distal guidewire port 510 at the distal end of the elongate shaft 504 to the proximal end of the elongate shaft 504 into Y-adapter 514 having a connector 516. The connector 516 is preferably a Luer connector and this allows easy coupling with a syringe or other device for lumen flushing or injecting contrast media. When unconnected, the guidewire lumen 512 exits via connector 516. A second connector 518, also preferably a Luer connector allows attachment of an Indeflator or other device to the catheter for inflation of the balloon 506 via an inflation lumen (not shown) in the elongate shaft 504. The first catheter 502 is disposed in the central channel 526 of a capture tube 524. Central channel 526 is sized to fit both shafts 504, 532 and allow slidable movement thereof. Shaft 504 is slidable in the central channel 526, or it may be locked with a locking collar 525 such as a Tuohy-Borst compression fitting. Radiopaque markers may be placed at different locations along the shaft 504, often near the balloon 506 and/or stent 508, to help mark the proximal and distal ends of the stent or balloon, as well to facilitate alignment of the two catheters during stent deployment, as discussed elsewhere in this specification.

The second catheter 530 includes an elongate shaft 532 with a radially expandable balloon 540 disposed near a distal end of the elongate shaft 532. A stent 542 is disposed over balloon 540. The stent may have a length that matches the working length of the balloon, or the stent length may be shorter than the balloon working length. In preferred embodiments, the stent 542 is shorter than the working length of the balloon 540 so that a proximal portion of the balloon 540 is unconstrained by the stent 542 and this unconstrained portion of the balloon 540 may be slidably advanced or retracted through side hole 520 and under proximal portion 522 of stent 508 as will be discussed below. Stent 542 is crimped to balloon 540 to prevent ejection during delivery. At least a portion of balloon 540, and stent 542 are distally offset relative to balloon 506 and stent 508 so as to minimize profile of the device. In this embodiment the distal stent 542 may be deployed in a main branch of the vessel and the other stent 508 may be deployed in aside branch of the vessel. Alternatively, the distal stent 542 may be deployed in a side branch of a vessel and the other stent 508 may be deployed in the main branch of a vessel. The second catheter 530 is a rapid exchange catheter (RX) having a guidewire lumen 534 extending from the distal guidewire port 538 at the distal end of the elongate shaft 532 to a proximal guidewire port 536 which is closer to the distal port 538 than the proximal end of the catheter shaft 532. The proximal guidewire port 536 is also unobstructed by the capture tube 524 and may be distal thereto. A connector 544, preferably a Luer connector is connected to the proximal end of the elongate shaft 532 and allows an Indeflator or other device to be coupled with an inflation lumen (not shown) in elongate shaft 532 for inflation of balloon 540. A portion of shaft 532 is disposed in the central channel 526 of the capture tube 524 and this helps keep the two catheter shafts 504, 532 parallel and prevents tangling during delivery and as shaft 532 is slidably advanced in the central channel 526. Compression fitting 525 may be used to lock elongate shafts 504, 532 in the capture tube 524 to prevent axial movement. The compression fitting may be a Tuohy-Borst fitting. Also, another portion of shaft 532 is disposed under proximal portion 522 of stent 508. The second catheter 530 may also be slidably advanced or retracted under the proximal portion 522 of stent 508 so that the shaft 532 passes through the side hole 520 in stent 508. Radiopaque markers may be placed at different locations on the shaft 532, often near the balloon 540 or stent 542, to help mark the proximal and distal ends of the stent or balloon, as well to facilitate alignment of the two catheters during stent deployment, as discussed elsewhere in this specification.

Figure 6A:
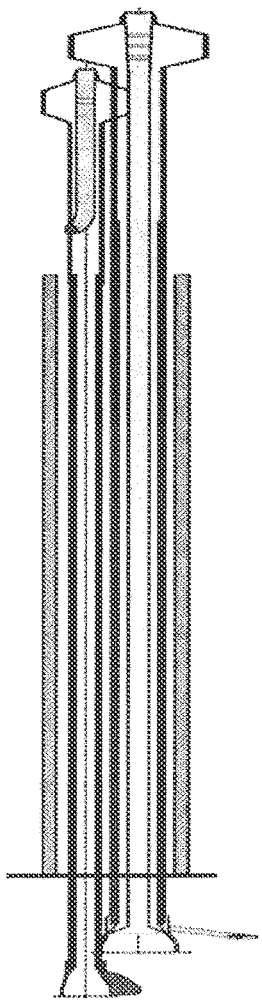
FIGS. 6A-6B illustrate another exemplary embodiment of a system having a capture tube, an over-the-wire daughter catheter, and a rapid exchange mother catheter.
Figure 6B:
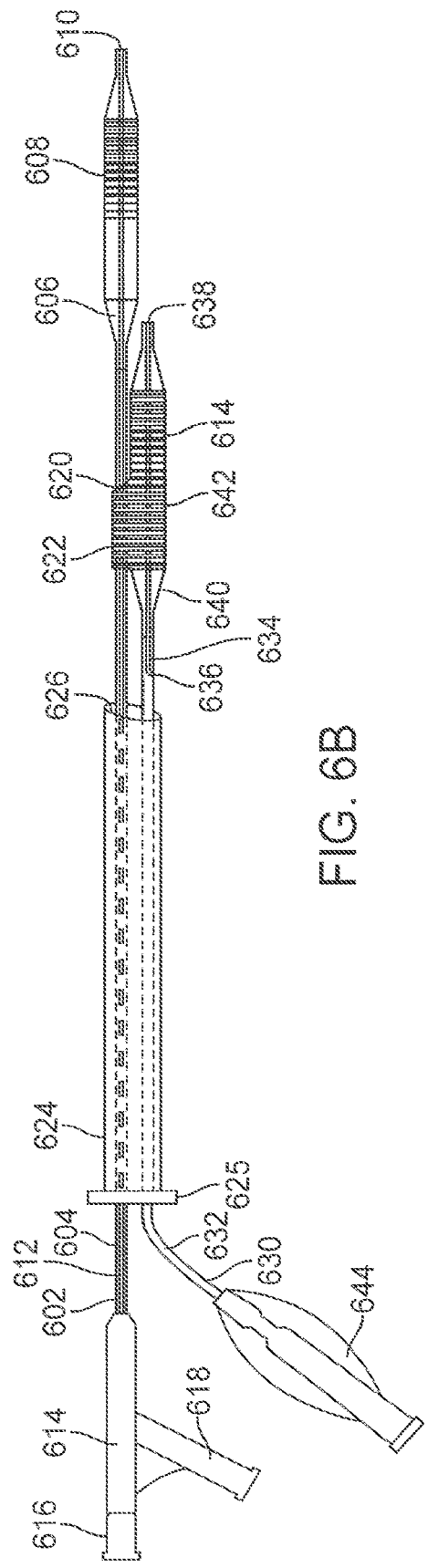

FIG. 6A illustrates a catheter system 600 having a distal daughter catheter with an over the wire design and a proximal mother catheter with a rapid exchange design. FIG. 6B more clearly illustrates the features of the catheter system 600 in FIG. 6A. The stent delivery system 600 includes a first catheter 602, and a second catheter 630. The first catheter 602 includes an elongate shaft 604 with a radially expandable balloon 606 disposed near a distal end of the elongate shaft 604, and a stent 608 disposed over the balloon 606. The stent 608 may be the same length as the working length of the balloon 608, or it may be shorter. In preferred embodiments, the stent 608 is shorter than the working length of balloon 606 such that a proximal portion of balloon 606 remains unconstrained by stent 608. The proximal portion of balloon 606 may be slidably advanced and retracted under stent 642 via side hole 620. Stent 608 is crimped to the balloon 606 to prevent ejection during delivery. The first catheter is an over-the-wire (OTW) catheter having a guidewire lumen 612 extending from the distal guidewire port 610 at the distal end of the elongate shaft 604 to the proximal end of the elongate shaft 604 into Y-adapter 614 having a connector 616. The connector 616 is preferably a Luer connector and this allows easy coupling with a syringe or other device for lumen flushing or injecting contrast media. When unconnected, the guidewire lumen 612 exits via connector 616. A second connector 618, also preferably a Luer connector allows attachment of an Indeflator or other device to the catheter for inflation of the balloon 606 via an inflation lumen (not shown) in the elongate shaft 604. The first catheter 602 is disposed in the central channel 626 of a capture tube 624. Central channel 626 is sized to fit both shafts 604, 632 and allow slidable movement thereof. Shaft 604 is slidable in the central channel 626, or it may be locked with a locking collar 625 such as a Tuohy-Borst compression fitting. Radiopaque markers may be placed at different locations along the shaft 604, often near the balloon 606 and/or stent 608, to help mark the proximal and distal ends of the stent or balloon, as well to facilitate alignment of the two catheters during stent deployment, as discussed elsewhere in this specification.

The second catheter 630 includes an elongate shaft 632 with a radially expandable balloon 640 disposed near a distal end of the elongate shaft 632. A stent 642 having a proximal portion 622, a distal portion 614, and a side hole 620 is disposed over balloon 640. The distal portion 614 is crimped to balloon 640 to prevent ejection during delivery, while the proximal portion 622 is partially crimped to balloon 640 so elongate shaft 604 may be slidably advanced or retracted under the proximal portion 622 of stent 642. The stent may preferably have a length that matches the working length of the balloon, or the stent length may be shorter than the balloon working length. At least a portion of balloon 606, and stent 608 are distally offset relative to balloon 640 and stent 642 so as to minimize profile of the device. In this embodiment the distal stent 608 may be deployed in a main branch of the vessel and the other stent 642 may be deployed in a side branch of the vessel. Alternatively, the distal stent 608 may be deployed in a side branch of a vessel and the other stent 642 may be deployed in the main branch of a vessel. The second catheter 630 is a rapid exchange catheter (RX) having a guidewire lumen 634 extending from the distal guidewire port 638 at the distal end of the elongate shaft 632 to a proximal guidewire port 636 which is closer to the distal port 638 than the proximal end of the catheter shaft 632. The proximal guidewire port 636 is also unobstructed by the capture tube 624 and may be distal thereto. A connector 644, preferably a Luer connector is connected to the proximal end of the elongate shaft 632 and allows an Indeflator or other device to be coupled with an inflation lumen (not shown) in elongate shaft 632 for inflation of balloon 640. A portion of shaft 632 is disposed in the central channel 626 of the capture tube 624 and this helps keep the two catheter shafts 604, 632 parallel and prevents tangling during delivery and as shaft 604 is slidably advanced in the central channel 626. Compression fitting 625 may be used to lock elongate shafts 604, 632 in the capture tube 624 to prevent axial movement. The compression fitting may be a Tuohy-Borst fitting. Also, a portion of shaft 604 is disposed under proximal portion 622 of stent 642. The first catheter 602 may be slidably advanced or retracted under the proximal portion 622 of stent 642 so that the shaft 604 passes through the side hole 620 in stent 642. Radiopaque markers may be placed at different locations on the shaft 632, often near the balloon 640 or stent 642, to help mark the proximal and distal ends of the stent or balloon, as well as to facilitate alignment of the two catheters during stent deployment, as discussed elsewhere in this specification.

Figure 7A:
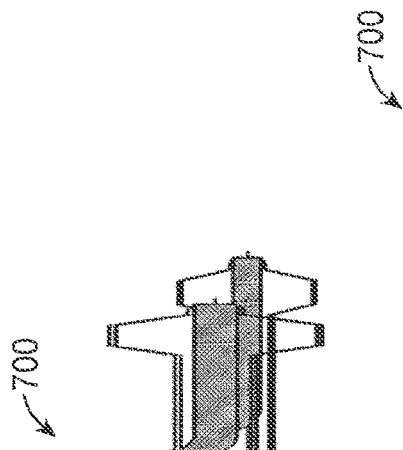
FIGS. 7A-7B illustrate another exemplary embodiment of a system having a capture tube, a rapid exchange mother catheter, and a rapid exchange daughter catheter.
Figure 7B:
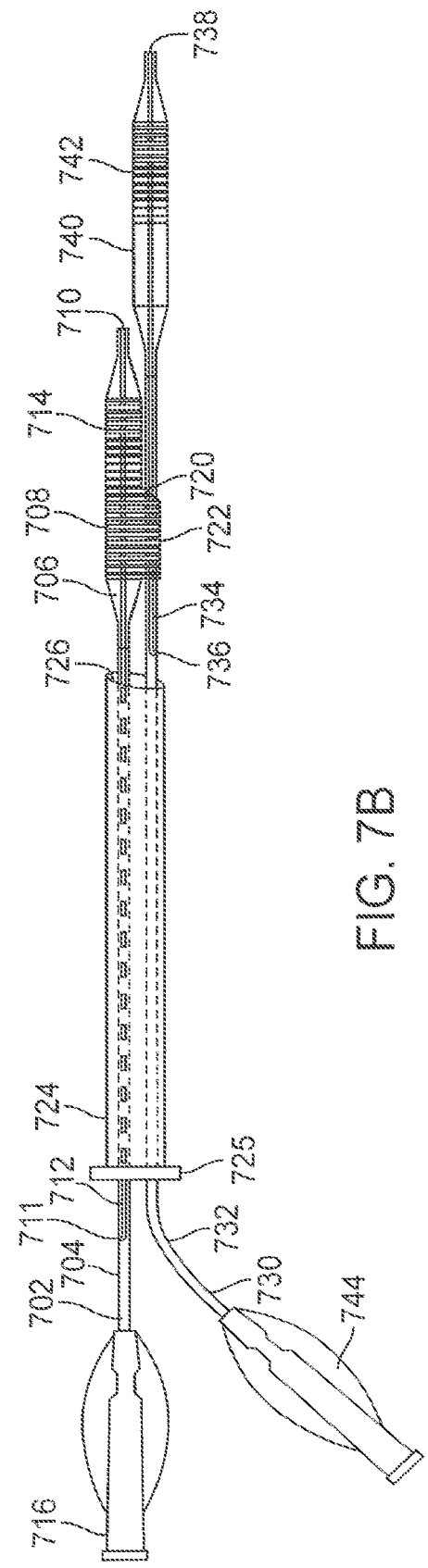

FIG. 7A shows a catheter system 700 having dual rapid exchange mother and daughter catheters so the end point of the capture tube is preferably about 10 centimeters proximal from the rapid exchange port on the distal most catheter. FIG. 7B more clearly illustrates the features of the catheter system 700 in FIG. 7A. The stent delivery system 700 includes a first catheter 702, and a second catheter 730. The first catheter 702 includes an elongate shaft 704 with a radially expandable balloon 706 disposed near a distal end of the elongate shaft 704. A stent 708 having a proximal portion 722, a distal portion 714 and a side hole 720 is disposed over the balloon 706. The distal portion 714 is crimped to the balloon 706 to prevent ejection during delivery, while the proximal portion 722 is partially crimped to the balloon 706 so the second catheter 730 may be slidably advanced under the proximal portion 722 of stent 708. The first catheter is a rapid exchange catheter (RX) having a guidewire lumen 712 extending from the distal guidewire port 710 at the distal end of the elongate shaft 704 to a proximal guidewire port 711 which is closer to the distal port 710 than the proximal end of the catheter shaft 704. A connector 716 is coupled with the proximal end of the elongate shaft 704. The connector 716 is preferably a Luer connector and this allows easy coupling with an Indeflator or other device for inflation of the balloon 706. The first catheter 702 is disposed in the central channel 726 of a capture tube 724. Central channel 726 is sized to fit both shafts 704, 732 and allow slidable movement thereof. Shaft 704 is slidable in the central channel 726, or it may be locked with a locking collar 725 such as a Tuohy-Borst compression fitting. Radiopaque markers may be placed at different locations along the shaft 704, often near the balloon 706 and/or stent 708, to help mark the proximal and distal ends of the stent or balloon, as well to facilitate alignment of the two catheters during stent deployment, as discussed elsewhere in this specification.

The second catheter 730 includes an elongate shaft 732 with a radially expandable balloon 740 disposed near a distal end of the elongate shaft 732. A stent 742 is disposed over balloon 740. The stent may have a length that matches the working length of the balloon, or the stent length may be shorter than the balloon working length. In preferred embodiments, the stent 742 is shorter than the working length of the balloon 740 so that a proximal portion of the balloon 740 is unconstrained by the stent 742 and this unconstrained portion of the balloon 740 may be slidably advanced or retracted through side hole 720 and under proximal portion 722 of stent 708 as will be discussed below. Stent 742 is crimped to balloon 740 to prevent ejection during delivery. At least a portion of balloon 740, and stent 742 are distally offset relative to balloon 706 and stent 708 so as to minimize profile of the device. In this embodiment the distal stent 742 may be deployed in a main branch of the vessel and the other stent 708 may be deployed in a side branch of the vessel. Alternatively, the distal stent 742 may be deployed in a side branch of a vessel and the other stent 708 may be deployed in the main branch of a vessel. The second catheter 730 is a rapid exchange catheter (RX) having a guidewire lumen 734 extending from the distal guidewire port 738 at the distal end of the elongate shaft 732 to a proximal guidewire port 736 which is closer to the distal port 738 than the proximal end of the catheter shaft 732. The proximal guidewire port 736 is also unobstructed by the capture tube 724 and may be distal thereto. A connector 744, preferably a Luer connector is connected to the proximal end of the elongate shaft 732 and allows an Indeflator or other device to be coupled with an inflation lumen (not shown) in elongate shaft 732 for inflation of balloon 740. A portion of shaft 732 is disposed in the central channel 726 of the capture tube 724 and this helps keep the two catheter shafts 704, 732 parallel and prevents tangling during delivery and as shaft 732 is slidably advanced in the central channel 726. Compression fitting 725 may be used to lock elongate shafts 704, 732 in the capture tube 724 to prevent axial movement. The compression fitting may be a Tuohy-Borst fitting. Also, another portion of shaft 732 is disposed under proximal portion 722 of stent 708. The second catheter 730 may also be slidably advanced or retracted under the proximal portion 722 of stent 708 so that the shaft 732 passes through the side hole 720 in stent 708. Radiopaque markers may be placed at different locations on the shaft 732, often near the balloon 740 or stent 742, to help mark the proximal and distal ends of the stent or balloon, as well to facilitate alignment of the two catheters during stent deployment, as discussed elsewhere in this specification.

Figures 8A, 8B:
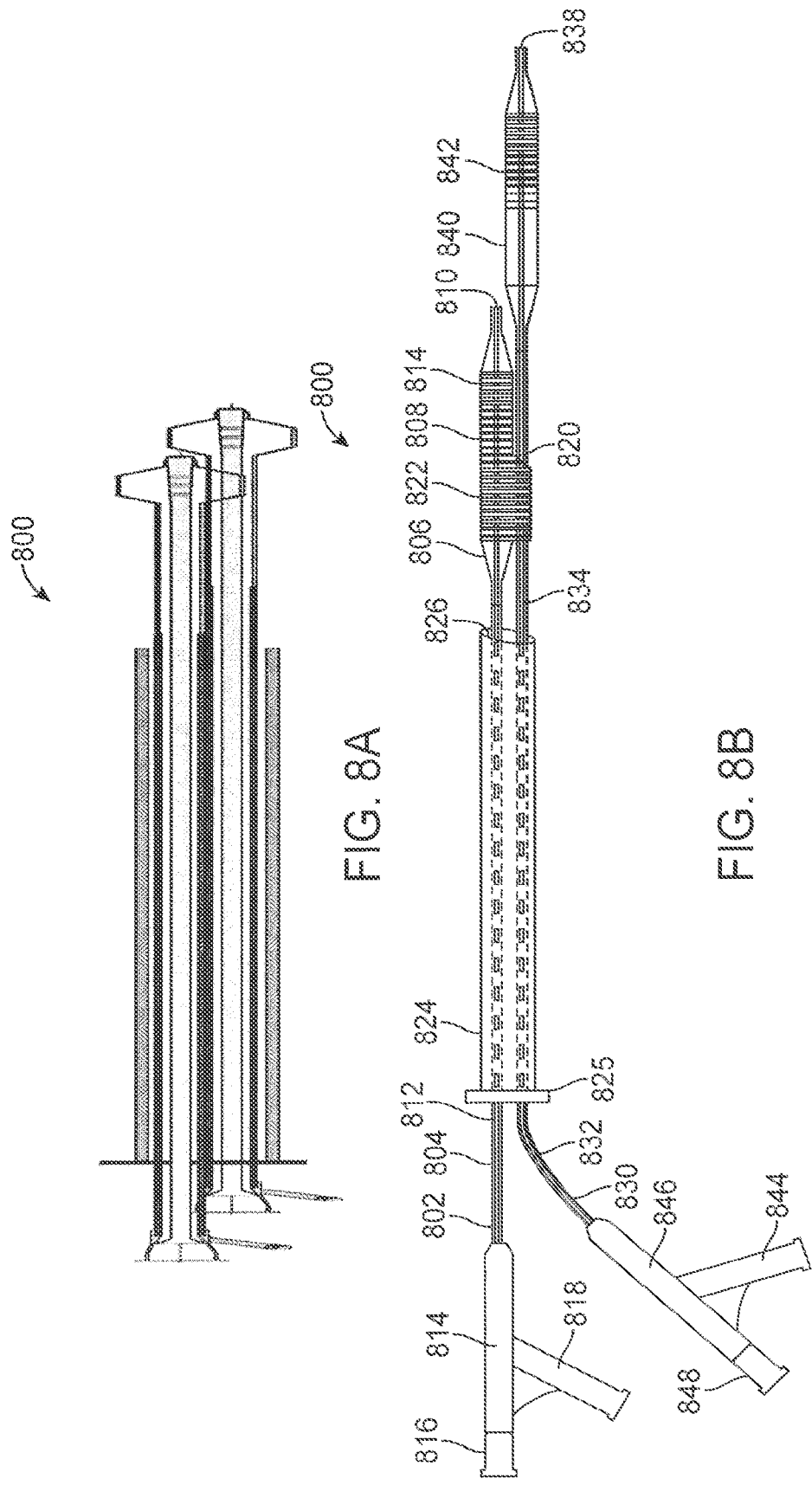
FIGS. 8A-8B illustrate another exemplary embodiment of a system having a capture tube, an over-the-wire mother catheter, and an over-the-wire daughter catheter.

FIG. 8A embodies a catheter system 800 with dual over the wire designs, therefore the capture tube ending point ends preferably about 30 centimeters proximal from the balloon portion of the most distal catheter. FIG. 8B more clearly illustrates the features of the catheter system 800 in FIG. 8A. The stent delivery system 800 includes a first catheter 802, and a second catheter 830. The first catheter 802 includes an elongate shaft 804 with a radially expandable balloon 806 disposed near a distal end of the elongate shaft 804. A stent 808 having a proximal portion 822, a distal portion 814 and a side hole 820 is disposed over the balloon 806. The distal portion 814 is crimped to the balloon 806 to prevent ejection during delivery, while the proximal portion 822 is partially crimped to the balloon 806 so the second catheter 830 may be slidably advanced under the proximal portion 822 of stent 808. The first catheter is an over-the-wire (OTW) catheter having a guidewire lumen 812 extending from the distal guidewire port 810 at the distal end of the elongate shaft 804 to the proximal end of the elongate shaft 804 into Y-adapter 814 having a connector 816. The connector 816 is preferably a Luer connector and this allows easy coupling with a syringe or other device for lumen flushing or injecting contrast media. When unconnected, the guidewire lumen 812 exits via connector 816. A second connector 818, also preferably a Luer connector allows attachment of an Indeflator or other device to the catheter for inflation of the balloon 806 via an inflation lumen (not shown) in the elongate shaft 804. The first catheter 802 is disposed in the central channel 826 of a capture tube 824. Central channel 826 is sized to fit both shafts 804, 832 and allow slidable movement thereof. Shaft 804 is slidable in the central channel 826, or it may be locked with a locking collar 825 such as a Tuohy-Borst compression fitting. Radiopaque markers may be placed at different locations along the shaft 804, often near the balloon 806 and/or stent 808, to help mark the proximal and distal ends of the stent or balloon, as well to facilitate alignment of the two catheters during stent deployment, as discussed elsewhere in this specification.

The second catheter 830 includes an elongate shaft 832 with a radially expandable balloon 840 disposed near a distal end of the elongate shaft 832. A stent 842 is disposed over balloon 840. The stent may have a length that matches the working length of the balloon, or the stent length may be shorter than the balloon working length. In preferred embodiments, the stent 842 is shorter than the working length of the balloon 840 so that a proximal portion of the balloon 840 is unconstrained by the stent 842 and this unconstrained portion of the balloon 840 may be slidably advanced or retracted through side hole 820 and under proximal portion 822 of stent 808 as will be discussed below. Stent 842 is crimped to balloon 840 to prevent ejection during delivery. At least a portion of balloon 840, and stent 842 are distally offset relative to balloon 806 and stent 808 so as to minimize profile of the device. In this embodiment the distal stent 842 may be deployed in a main branch of the vessel and the other stent 808 may be deployed in a side branch of the vessel. Alternatively, the distal stent 842 may be deployed in a side branch of a vessel and the other stent 808 may be deployed in the main branch of a vessel. The second catheter 830 is an over-the-wire (OTW) catheter having a guidewire lumen 834 extending from the distal guidewire port 838 at the distal end of the elongate shaft 832 to the proximal end of the elongate shaft 832 into Y-adapter 846 having a connector 848. The connector 848 is preferably a Luer connector and this allows easy coupling with a syringe or other device for lumen flushing or injecting contrast media. When unconnected, the guidewire lumen 834 exits via connector 848. A second connector 844, also preferably a Luer connector allows attachment of an Indeflator or other device to the catheter for inflation of the balloon 840 via an inflation lumen (not shown) in the elongate shaft 832. A portion of shaft 832 is disposed in the central channel 826 of the capture tube 824 and this helps keep the two catheter shafts 804, 832 parallel and prevents tangling during delivery and as shaft 832 is slidably advanced in the central channel 826. Compression fitting 825 may be used to lock elongate shafts 804, 832 in the capture tube 824 to prevent axial movement. The compression fitting may be a Tuohy-Borst fitting. Also, another portion of shaft 832 is disposed under proximal portion 822 of stent 808. The second catheter 830 may also be slidably advanced or retracted under the proximal portion 822 of stent 808 so that the shaft 832 passes through the side hole 820 in stent 808. Radiopaque markers may be placed at different locations on the shaft 832, often near the balloon 840 or stent 842, to help mark the proximal and distal ends of the stent or balloon, as well to facilitate alignment of the two catheters during stent deployment, as discussed elsewhere in this specification.

FIGS. 9A, 10A, 11A, and 12A illustrate a removable capture tube that is fitted over the dual catheters as described above but the capture tube has a polymer appendage. Once the operator has the catheter system placed near the bifurcation the operator can grab hold of the polymer appendage and pull the capture tube off of the catheters.

FIG. 9A illustrates a catheter system 900 having a distal daughter catheter with a rapid exchange configuration and a proximal mother catheter with an over the wire configuration. FIG. 9B more clearly illustrates the features of the catheter system 900 seen in FIG. 9A. The stent delivery system 900 includes a first catheter 902, and a second catheter 930. The first catheter 902 includes an elongate shaft 904 with a radially expandable balloon 906 disposed near a distal end of the elongate shaft 904. A stent 908 having a proximal portion 922, a distal portion 914 and a side hole 920 is disposed over the balloon 906. The distal portion 914 is crimped to the balloon 906 to prevent ejection during delivery, while the proximal portion 922 is partially crimped to the balloon 906 so the second catheter 930 may be slidably advanced under the proximal portion 922 of stent 908. The first catheter is an over-the-wire (OTW) catheter having a guidewire lumen 912 extending from the distal guidewire port 910 at the distal end of the elongate shaft 904 to the proximal end of the elongate shaft 904 into Y-adapter 914 having a connector 916. The connector 916 is preferably a Luer connector and this allows easy coupling with a syringe or other device for lumen flushing or injecting contrast media. When unconnected, the guidewire lumen 912 exits via connector 916. A second connector 918, also preferably a Luer connector allows attachment of an Indeflator or other device to the catheter for inflation of the balloon 906 via an inflation lumen (not shown) in the elongate shaft 904. The first catheter 902 is disposed in the central channel 926 of a capture tube 924 having a perforated region 945 along its longitudinal length. Central channel 926 is sized to fit both shafts 904, 932 and allow slidable movement thereof. Shaft 904 is slidable in the central channel 926, or it may be locked with a locking collar 925 such as a Tuohy-Borst compression fitting. Radiopaque markers may be placed at different locations along the shaft 904, often near the balloon 906 and/or stent 908, to help mark the proximal and distal ends of the stent or balloon, as well to facilitate alignment of the two catheters during stent deployment, as discussed elsewhere in this specification. The perforated region 945 along the capture tube 924 allows the capture tube to be easily peeled away from both catheter shafts 904, 932 once the catheters have been properly positioned and when no longer needed.

The second catheter 930 includes an elongate shaft 932 with a radially expandable balloon 940 disposed near a distal end of the elongate shaft 932. A stent 942 is disposed over balloon 940. The stent may have a length that matches the working length of the balloon, or the stent length may be shorter than the balloon working length. In preferred embodiments, the stent 942 is shorter than the working length of the balloon 940 so that a proximal portion of the balloon 940 is unconstrained by the stent 942 and this unconstrained portion of the balloon 940 may be slidably advanced or retracted through side hole 920 and under proximal portion 922 of stent 908 as will be discussed below. Stent 942 is crimped to balloon 940 to prevent ejection during delivery. At least a portion of balloon 940, and stent 942 are distally offset relative to balloon 906 and stent 908 so as to minimize profile of the device. In this embodiment the distal stent 942 may be deployed in a main branch of the vessel and the other stent 908 may be deployed in a side branch of the vessel. Alternatively, the distal stent 942 may be deployed in a side branch of a vessel and the other stent 908 may be deployed in the main branch of a vessel. The second catheter 930 is a rapid exchange catheter (RX) having a guidewire lumen 934 extending from the distal guidewire port 938 at the distal end of the elongate shaft 932 to a proximal guidewire port 936 which is closer to the distal port 938 than the proximal end of the catheter shaft 932. The proximal guidewire port 936 is also unobstructed by the capture tube 924 and may be distal thereto. A connector 944, preferably a Luer connector is connected to the proximal end of the elongate shaft 932 and allows an Indeflator or other device to be coupled with an inflation lumen (not shown) in elongate shaft 932 for inflation of balloon 940. A portion of shaft 932 is disposed in the central channel 926 of the capture tube 924 and this helps keep the two catheter shafts 904, 932 parallel and prevents tangling during delivery and as shaft 932 is slidably advanced in the central channel 926. Compression fitting 925 may be used to lock elongate shafts 904, 932 in the capture tube 924 to prevent axial movement. The compression fitting may be a Tuohy-Borst fitting. Also, another portion of shaft 932 is disposed under proximal portion 922 of stent 908. The second catheter 930 may also be slidably advanced or retracted under the proximal portion 922 of stent 908 so that the shaft 932 passes through the side hole 920 in stent 908. Capture tube 924 may be peeled away from shaft 932 by severing the perforated region 945. Radiopaque markers may be placed at different locations on the shaft 932, often near the balloon 940 or stent 942, to help mark the proximal and distal ends of the stent or balloon, as well to facilitate alignment of the two catheters during stent deployment, as discussed elsewhere in this specification.

Figures 10A, 10B:
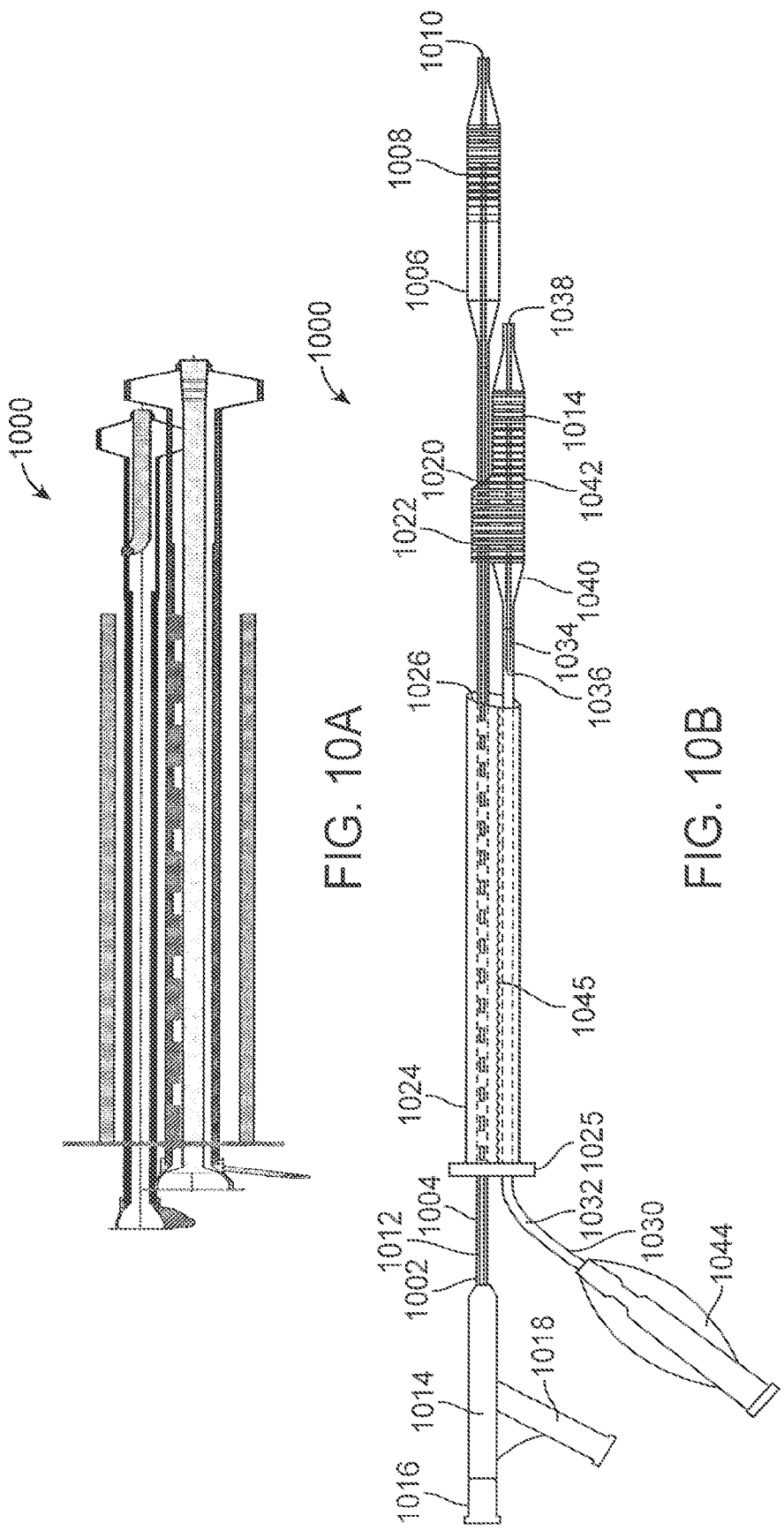
FIGS. 10A-10B illustrate yet other exemplary embodiment of a system having a removable capture tube, an over-the-wire daughter catheter and a rapid exchange mother catheter.

FIG. 10A illustrates a catheter system 1000 having a distal daughter catheter with an over the wire design and a proximal mother catheter with a rapid exchange design. FIG. 10B more clearly illustrates the features of the catheter system 1000 in FIG. 10A. The stent delivery system 1000 includes a first catheter 1002, and a second catheter 1030. The first catheter 1002 includes an elongate shaft 1004 with a radially expandable balloon 1006 disposed near a distal end of the elongate shaft 1004, and a stent 1008 disposed over the balloon 1006. The stent 1008 may be the same length as the working length of the balloon 1008, or it may be shorter. In preferred embodiments, the stent 1008 is shorter than the working length of balloon 1006 such that a proximal portion of balloon 1006 remains unconstrained by stent 1008. The proximal portion of balloon 1006 may be slidably advanced and retracted under stent 1042 via side hole 1020. Stent 1008 is crimped to the balloon 1006 to prevent ejection during delivery. The first catheter is an over-the-wire (OTW) catheter having a guidewire lumen 1012 extending from the distal guidewire port 1010 at the distal end of the elongate shaft 1004 to the proximal end of the elongate shaft 1004 into Y-adapter 1014 having a connector 1016. The connector 1016 is preferably a Luer connector and this allows easy coupling with a syringe or other device for lumen flushing or injecting contrast media. When unconnected, the guidewire lumen 1012 exits via connector 1016. A second connector 1018, also preferably a Luer connector allows attachment of an Indeflator or other device to the catheter for inflation of the balloon 1006 via an inflation lumen (not shown) in the elongate shaft 1004. The first catheter 1002 is disposed in the central channel 1026 of a capture tube 1024 having perforated region 1045. Central channel 1026 is sized to fit both shafts 1004, 1032 and allow slidable movement thereof. Shaft 1004 is slidable in the central channel 1026, or it may be locked with a locking collar 1025 such as a Tuohy-Borst compression fitting. Radiopaque markers may be placed at different locations along the shaft 1004, often near the balloon 1006 and/or stent 1008, to help mark the proximal and distal ends of the stent or balloon, as well to facilitate alignment of the two catheters during stent deployment, as discussed elsewhere in this specification. The perforated region 1045 along the capture tube 1024 allows the capture tube to be easily peeled away from both catheter shafts 1004, 1032 once the catheters have been properly positioned and when no longer needed.

The second catheter 1030 includes an elongate shaft 1032 with a radially expandable balloon 1040 disposed near a distal end of the elongate shaft 1032. A stent 1042 having a proximal portion 1022, a distal portion 1014, and a side hole 1020 is disposed over balloon 1040. The distal portion 1014 is crimped to balloon 1040 to prevent ejection during delivery, while the proximal portion 1022 is partially crimped to balloon 1040 so elongate shaft 1004 may be slidably advanced or retracted under the proximal portion 1022 of stent 1042. The stent may preferably have a length that matches the working length of the balloon, or the stent length may be shorter than the balloon working length. At least a portion of balloon 1006, and stent 1008 are distally offset relative to balloon 1040 and stent 1042 so as to minimize profile of the device. In this embodiment the distal stent 1008 may be deployed in a main branch of the vessel and the other stent 1042 may be deployed in a side branch of the vessel. Alternatively, the distal stent 1008 may be deployed in a side branch of a vessel and the other stent 1042 may be deployed in the main branch of a vessel. The second catheter 1030 is a rapid exchange catheter (RX) having a guidewire lumen 1034 extending from the distal guidewire port 1038 at the distal end of the elongate shaft 1032 to a proximal guidewire port 1036 which is closer to the distal port 1038 than the proximal end of the catheter shaft 1032. The proximal guidewire port 1036 is also unobstructed by the capture tube 1024 and may be distal thereto. A connector 1044, preferably a Luer connector is connected to the proximal end of the elongate shaft 1032 and allows an Indeflator or other device to be coupled with an inflation lumen (not shown) in elongate shaft 1032 for inflation of balloon 1040. A portion of shaft 1032 is disposed in the central channel 1026 of the capture tube 1024 and this helps keep the two catheter shafts 1004, 1032 parallel and prevents tangling during delivery and as shaft 1032 is slidably advanced in the central channel 1026. Compression fitting 1025 may be used to lock elongate shafts 1004, 1032 in the capture tube 1024 to prevent axial movement. The compression fitting may be a Tuohy-Borst fitting. Also, a portion of shaft 1004 is disposed under proximal portion 1022 of stent 1042. The first catheter 1002 may be slidably advanced or retracted under the proximal portion 1022 of stent 1042 so that the shaft 1004 passes through the side hole 1020 in stent 1042. Capture tube 1024 may be peeled away from shaft 1032 by severing the perforated region 1045. Radiopaque markers may be placed at different locations on the shaft 1032, often near the balloon 1040 or stent 1042, to help mark the proximal and distal ends of the stent or balloon, as well to facilitate alignment of the two catheters during stent deployment, as discussed elsewhere in this specification.

Figure 11A:
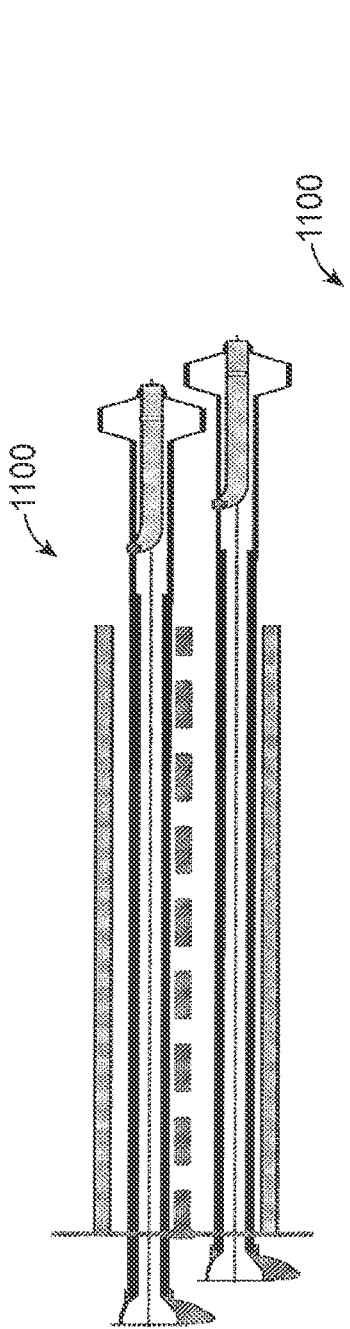
FIGS. 11A-11B illustrate yet another exemplary embodiment of a system having a removable capture tube, a rapid exchange mother catheter and a rapid exchange daughter catheter.
Figure 11B:
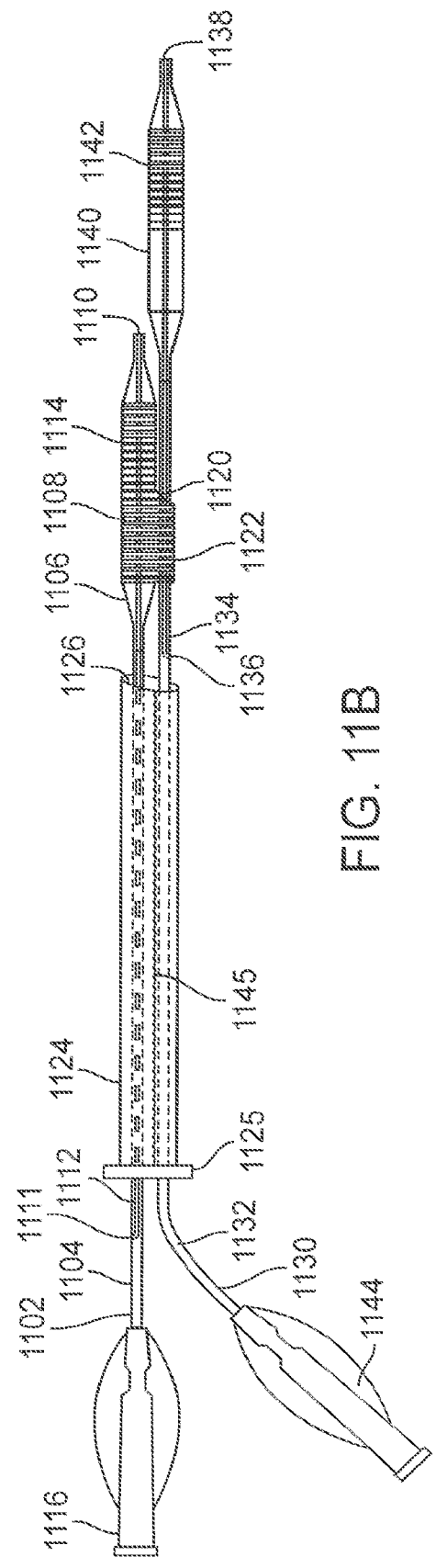

FIG. 11A illustrates a catheter system 1100 having dual rapid exchange design with a removable capture tube. FIG. 11B more clearly illustrates the features of the catheter system 1100 in FIG. 11A. The stent delivery system 1100 includes a first catheter 1102, and a second catheter 1130. The first catheter 1102 includes an elongate shaft 1104 with a radially expandable balloon 1106 disposed near a distal end of the elongate shaft 1104. A stent 1108 having a proximal portion 1122, a distal portion 1114 and a side hole 1120 is disposed over the balloon 1106. The distal portion 1114 is crimped to the balloon 1106 to prevent ejection during delivery, while the proximal portion 1122 is partially crimped to the balloon 1106 so the second catheter 1130 may be slidably advanced under the proximal portion 1122 of stent 1108. The first catheter is a rapid exchange catheter (RX) having a guidewire lumen 1112 extending from the distal guidewire port 1110 at the distal end of the elongate shaft 1104 to a proximal guidewire port 1111 which is closer to the distal port 1110 than the proximal end of the catheter shaft 1104. A connector 1116 is coupled with the proximal end of the elongate shaft 1104. The connector 1116 is preferably a Luer connector and this allows easy coupling with an Indeflator or other device for inflation of the balloon 1106. The first catheter 1102 is disposed in the central channel 1126 of a capture tube 1124 having a perforated region 1145. Central channel 1126 is sized to fit both shafts 1104, 1132 and allow slidable movement thereof. Shaft 1104 is slidable in the central channel 1126, or it may be locked with a locking collar 1125 such as a Tuohy-Borst compression fitting. Radiopaque markers may be placed at different locations along the shaft 1104, often near the balloon 1106 and/or stent 1108, to help mark the proximal and distal ends of the stent or balloon, as well to facilitate alignment of the two catheters during stent deployment, as discussed elsewhere in this specification. The perforated region 1145 along the capture tube 1124 allows the capture tube to be easily peeled away from both catheter shafts 1104, 1132 once the catheters have been properly positioned and when no longer needed.

The second catheter 1130 includes an elongate shaft 1132 with a radially expandable balloon 1140 disposed near a distal end of the elongate shaft 1132. A stent 1142 is disposed over balloon 1140. The stent may have a length that matches the working length of the balloon, or the stent length may be shorter than the balloon working length. In preferred embodiments, the stent 1142 is shorter than the working length of the balloon 1140 so that a proximal portion of the balloon 1140 is unconstrained by the stent 1142 and this unconstrained portion of the balloon 1140 may be slidably advanced or retracted through side hole 1120 and under proximal portion 1122 of stent 1108 as will be discussed below. Stent 1142 is crimped to balloon 1140 to prevent ejection during delivery. At least a portion of balloon 1140, and stent 1142 are distally offset relative to balloon 1106 and stent 1108 so as to minimize profile of the device. In this embodiment the distal stent 1142 may be deployed in a main branch of the vessel and the other stent 1108 may be deployed in a side branch of the vessel. Alternatively, the distal stent 1142 may be deployed in a side branch of a vessel and the other stent 1108 may be deployed in the main branch of a vessel. The second catheter 1130 is a rapid exchange catheter (RX) having a guidewire lumen 1134 extending from the distal guidewire port 1138 at the distal end of the elongate shaft 1132 to a proximal guidewire port 1136 which is closer to the distal port 1138 than the proximal end of the catheter shaft 1132. The proximal guidewire port 1136 is also unobstructed by the capture tube 1124 and may be distal thereto. A connector 1144, preferably a Luer connector is connected to the proximal end of the elongate shaft 1132 and allows an Indeflator or other device to be coupled with an inflation lumen (not shown) in elongate shaft 132 for inflation of balloon 1140. A portion of shaft 1132 is disposed in the central channel 1126 of the capture tube 1124 and this helps keep the two catheter shafts 1104, 1132 parallel and prevents tangling during delivery and as shaft 1132 is slidably advanced in the central channel 1126. Compression fitting 1125 may be used to lock elongate shafts 1104, 1132 in the capture tube 1124 to prevent axial movement. The compression fitting may be a Tuohy-Borst fitting. Also, another portion of shaft 1132 is disposed under proximal portion 1122 of stent 1108. The second catheter 1130 may also be slidably advanced or retracted under the proximal portion 1122 of stent 1108 so that the shaft 1132 passes through the side hole 1120 in stent 1108. Capture tube 1124 may be peeled away from shaft 1132 by severing the perforated region 1145. Radiopaque markers may be placed at different locations on the shaft 1132, often near the balloon 1140 or stent 1142, to help mark the proximal and distal ends of the stent or balloon, as well to facilitate alignment of the two catheters during stent deployment, as discussed elsewhere in this specification.

FIG. 12A illustrates a catheter system 1200 having dual over the wire design with a removable capture tube. FIG. 12B more clearly illustrates the features of the catheter system 1200 in FIG. 12A. The stent delivery system 1200 includes a first catheter 1202, and a second catheter 1230. The first catheter 1202 includes an elongate shaft 1204 with a radially expandable balloon 1206 disposed near a distal end of the elongate shaft 1204. A stent 1208 having a proximal portion 1222, a distal portion 1214 and a side hole 1220 is disposed over the balloon 1206. The distal portion 1214 is crimped to the balloon 1206 to prevent ejection during delivery, while the proximal portion 1222 is partially crimped to the balloon 1206 so the second catheter 1230 may be slidably advanced under the proximal portion 1222 of stent 1208. The first catheter is an over-the-wire (OTW) catheter having a guidewire lumen 1212 extending from the distal guidewire port 1210 at the distal end of the elongate shaft 1204 to the proximal end of the elongate shaft 1204 into Y-adapter 1214 having a connector 1216. The connector 1216 is preferably a Luer connector and this allows easy coupling with a syringe or other device for lumen flushing or injecting contrast media. When unconnected, the guidewire lumen 1212 exits via connector 1216. A second connector 1218, also preferably a Luer connector allows attachment of an Indeflator or other device to the catheter for inflation of the balloon 1206 via an inflation lumen (not shown) in the elongate shaft 1204. The first catheter 1202 is disposed in the central channel 1226 of a capture tube 1224 having a perforated region 1245. Central channel 1226 is sized to fit both shafts 1204, 1232 and allow slidable movement thereof. Shaft 1204 is slidable in the central channel 1226, or it may be locked with a locking collar 1225 such as a Tuohy-Borst compression fitting. Radiopaque markers may be placed at different locations along the shaft 1204, often near the balloon 1206 and/or stent 1208, to help mark the proximal and distal ends of the stent or balloon, as well to facilitate alignment of the two catheters during stent deployment, as discussed elsewhere in this specification. The perforated region 1245 along the capture tube 1224 allows the capture tube to be easily peeled away from both catheter shafts 1204, 1232 once the catheters have been properly positioned and when no longer needed.

The second catheter 1230 includes an elongate shaft 1232 with a radially expandable balloon 1240 disposed near a distal end of the elongate shaft 1232. A stent 1242 is disposed over balloon 1240. The stent may have a length that matches the working length of the balloon, or the stent length may be shorter than the balloon working length. In preferred embodiments, the stent 1242 is shorter than the working length of the balloon 1240 so that a proximal portion of the balloon 1240 is unconstrained by the stent 1242 and this unconstrained portion of the balloon 1240 may be slidably advanced or retracted through side hole 1220 and under proximal portion 1222 of stent 1208 as will be discussed below. Stent 1242 is crimped to balloon 1240 to prevent ejection during delivery. At least a portion of balloon 1240, and stent 1242 are distally offset relative to balloon 1206 and stent 1208 so as to minimize profile of the device. In this embodiment the distal stent 1242 may be deployed in a main branch of the vessel and the other stent 1208 may be deployed in a side branch of the vessel. Alternatively, the distal stent 1242 may be deployed in a side branch of a vessel and the other stent 1208 may be deployed in the main branch of a vessel. The second catheter 1230 is an over-the-wire (OTW) catheter having a guidewire lumen 1234 extending from the distal guidewire port 1238 at the distal end of the elongate shaft 1232 to the proximal end of the elongate shaft 1232 into Y-adapter 1246 having a connector 1248. The connector 1248 is preferably a Luer connector and this allows easy coupling with a syringe or other device for lumen flushing or injecting contrast media. When unconnected, the guidewire lumen 1234 exits via connector 1248. A second connector 1244, also preferably a Luer connector allows attachment of an Indeflator or other device to the catheter for inflation of the balloon 1240 via an inflation lumen (not shown) in the elongate shaft 1232. A portion of shaft 1232 is disposed in the central channel 1226 of the capture tube 1224 and this helps keep the two catheter shafts 1204, 1232 parallel and prevents tangling during delivery and as shaft 1232 is slidably advanced in the central channel 1226. Compression fitting 1225 may be used to lock elongate shafts 1204, 1232 in the capture tube 1224 to prevent axial movement. The compression fitting may be a Tuohy-Borst fitting. Also, another portion of shaft 1232 is disposed under proximal portion 1222 of stent 1208. The second catheter 1230 may also be slidably advanced or retracted under the proximal portion 1222 of stent 1208 so that the shaft 1232 passes through the side hole 1220 in stent 1208. Capture tube 1224 may be peeled away from shaft 1232 by severing the perforated region 1245. Radiopaque markers may be placed at different locations on the shaft 1232, often near the balloon 1240 or stent 1242, to help mark the proximal and distal ends of the stent or balloon, as well to facilitate alignment of the two catheters during stent deployment, as discussed elsewhere in this specification.

FIGS. 13A, 14A, 15A, and 16A illustrates a zipper that allows one catheter to snap in to the other catheter. The zipper is essentially a groove that forms a concave receiving cross section and is carved into a catheter's outer surface in a straight line. The groove can be a single groove over a certain portion of a catheter or it can run from end to end. Alternatively, the catheter can have a series of short grooves of 1 to 10 centimeters in length that run the length of the catheter or only a certain portion. Full length end to end zippers will have reduced profile and reduced friction with the vessel. The resulting groove can receive another catheter and prevent the catheters from dislodging while the operator is advancing the catheters to the bifurcation. Once at the site the operator can still slidably move the catheters forward and back relative to each other. Mother catheters that utilize the groove can have fully crimped stents as described in several of the embodiments above; however, it is possible to allow operators to choose any commercially available catheter with or without a stent and mount the commercially available catheter via the zipper. The mother catheters with an empty zipper would have a mother stent full crimped on the distal balloon portion. After loading the commercially available catheter the operator would have to crimp the proximal portion of the mother stent in situ prior to beginning the clinical procedure. This option may be extremely valuable to operators who can reduce their total inventory of catheters but have more options for treating bifurcated lesions.

FIG. 13A illustrates a catheter system 1300 having a distal daughter catheter with an over the wire design and a proximal mother catheter with a rapid exchange design and a short zipper. FIG. 13B more clearly illustrates the features of the catheter system 1300 in FIG. 13A. The stent delivery system 1300 includes a first catheter 1302, and a second catheter 1330. The first catheter 1302 includes an elongate shaft 1304 with a radially expandable balloon 1306 disposed near a distal end of the elongate shaft 1304. A stent 1308 having a proximal portion 1322, a distal portion 1314 and a side hole 1320 is disposed over the balloon 1306. The distal portion 1314 is crimped to the balloon 1306 to prevent ejection during delivery, while the proximal portion 1322 is partially crimped to the balloon 1306 so the second catheter 1330 may be slidably advanced under the proximal portion 1322 of stent 1308. The first catheter is an over-the-wire (OTW) catheter having a guidewire lumen 1312 extending from the distal guidewire port 1310 at the distal end of the elongate shaft 1304 to the proximal end of the elongate shaft 1304 into Y-adapter 1314 having a connector 1316. The connector 1316 is preferably a Luer connector and this allows easy coupling with a syringe or other device for lumen flushing or injecting contrast media. When unconnected, the guidewire lumen 1312 exits via connector 1316. A second connector 1318, also preferably a Luer connector allows attachment of an Indeflator or other device to the catheter for inflation of the balloon 1306 via an inflation lumen (not shown) in the elongate shaft 1304. The first catheter 1302 also includes a zipper or snap fitting 1324 coupled to the elongate shaft 1304. The snap fit tube 1324 may be coextruded with the first shaft 1304, or it may be bonded or otherwise attached thereto using techniques known to those skilled in the art. The snap fit 1324 may alternatively be coupled with the other shaft 1332. The snap fitting 1324 includes a central channel 1326 extending therethrough and is sized to slidably receive a portion of the second catheter 1330. An elongate slot 1345 extends along the entire length of the snap fitting 1324 and is sized so that shaft 1336 may snapped into the central channel 1326. FIG. 13C illustrates a partial cross-section of FIG. 13B taken along the line C-C and shows shaft 1304 with the snap fitting 1324. Radiopaque markers may be placed at different locations along the shaft 1304, often near the balloon 1306 and/or stent 1308, to help mark the proximal and distal ends of the stent or balloon, as well as to facilitate alignment of the two catheters during stent deployment, as discussed elsewhere in this specification.

The second catheter 1330 includes an elongate shaft 1332 with a radially expandable balloon 1340 disposed near a distal end of the elongate shaft 1332. A stent 1342 is disposed over balloon 1340. The stent may have a length that matches the working length of the balloon, or the stent length may be shorter than the balloon working length. In preferred embodiments, the stent 1342 is shorter than the working length of the balloon 1340 so that a proximal portion of the balloon 1340 is unconstrained by the stent 1342 and this unconstrained portion of the balloon 1340 may be slidably advanced or retracted through side hole 1320 and under proximal portion 1322 of stent 1308 as will be discussed below. Stent 1342 is crimped to balloon 1340 to prevent ejection during delivery. At least a portion of balloon 1340, and stent 1342 are distally offset relative to balloon 1306 and stent 1308 so as to minimize profile of the device. In this embodiment the distal stent 1342 may be deployed in a main branch of the vessel and the other stent 1308 may be deployed in a side branch of the vessel. Alternatively, the distal stent 1342 may be deployed in a side branch of a vessel and the other stent 1308 may be deployed in the main branch of a vessel. The second catheter 1330 is a rapid exchange catheter (RX) having a guidewire lumen 1334 extending from the distal guidewire port 1338 at the distal end of the elongate shaft 1332 to a proximal guidewire port 1336 which is closer to the distal port 1338 than the proximal end of the catheter shaft 1332. The proximal guidewire port 1336 is also unobstructed by the snap fitting 1324 and preferably proximal thereto. A connector 1344, preferably a Luer connector is connected to the proximal end of the elongate shaft 1332 and allows an Indeflator or other device to be coupled with an inflation lumen (not shown) in elongate shaft 1332 for inflation of balloon 1340. A portion of shaft 1332 is snapped into the central channel 1326 of the snap fitting 1324 via slit 1345, and thus shaft 1332 may slide in channel 1326. This helps keep the two catheter shafts 1304, 1332 parallel and prevents tangling during delivery and as shaft 1332 is slidably advanced or retracted relative to shaft 1304. Also, another portion of shaft 1332 is disposed under proximal portion 1322 of stent 1308. The second catheter 1330 may also be slidably advanced or retracted under the proximal portion 1322 of stent 1308 so that the shaft 1332 passes through the side hole 1320 in stent 1308. Radiopaque markers may be placed at different locations on the shaft 1332, often near the balloon 1340 or stent 1342, to help mark the proximal and distal ends of the stent or balloon, as well to facilitate alignment of the two catheters during stent deployment, as discussed elsewhere in this specification.

FIG. 14A illustrates a catheter system 1400 having a proximal mother catheter with a rapid exchange configuration and a distal daughter catheter having an over-the-wire configuration and a short zipper or snap fitting. FIG. 14B more clearly illustrates the features of the catheter system 1400 in FIG. 14A. The stent delivery system 1400 includes a first catheter 1402, and a second catheter 1430. The first catheter 1402 includes an elongate shaft 1404 with a radially expandable balloon 1406 disposed near a distal end of the elongate shaft 1404, and a stent 1408 disposed over the balloon 1406. The stent 1408 may be the same length as the working length of the balloon 1408, or it may be shorter. In preferred embodiments, the stent 1408 is shorter than the working length of balloon 1406 such that a proximal portion of balloon 1406 remains unconstrained by stent 1408. The proximal portion of balloon 1406 may be slidably advanced and retracted under stent 1442 via side hole 1420. Stent 1408 is crimped to the balloon 1406 to prevent ejection during delivery. The first catheter is an over-the-wire (OTW) catheter having a guidewire lumen 1412 extending from the distal guidewire port 1410 at the distal end of the elongate shaft 1404 to the proximal end of the elongate shaft 1404 into Y-adapter 1414 having a connector 1416. The connector 1416 is preferably a Luer connector and this allows easy coupling with a syringe or other device for lumen flushing or injecting contrast media. When unconnected, the guidewire lumen 1412 exits via connector 1416. A second connector 1418, also preferably a Luer connector allows attachment of an Indeflator or other device to the catheter for inflation of the balloon 1406 via an inflation lumen (not shown) in the elongate shaft 1404. The first catheter 1402 also includes a zipper or snap fitting 1424 coupled to the elongate shaft 1404. The snap fit tube 1424 may be coextruded with the first shaft 1404, or it may be bonded or otherwise attached thereto using techniques known to those skilled in the art. The snap fit 1424 may alternatively be coupled with the other shaft 1432. The snap fitting 1424 includes a central channel 1426 extending therethrough and is sized to slidably receive a portion of the second catheter 1430. An elongate slot 1445 extends along the entire length of the snap fitting 1424 and is sized so that shaft 1436 may snapped into the central channel 1426. FIG. 14C illustrates a partial cross-section of FIG. 14B taken along the line C-C and shows shaft 1404 with the snap fitting 1424. Radiopaque markers may be placed at different locations along the shaft 1404, often near the balloon 1406 and/or stent 1408, to help mark the proximal and distal ends of the stent or balloon, as well to facilitate alignment of the two catheters during stent deployment, as discussed elsewhere in this specification.

The second catheter 1430 includes an elongate shaft 1432 with a radially expandable balloon 1440 disposed near a distal end of the elongate shaft 1432. A stent 1442 having a proximal portion 1422, a distal portion 1414, and a side hole 1420 is disposed over balloon 1440. The distal portion 1414 is crimped to balloon 1440 to prevent ejection during delivery, while the proximal portion 1422 is partially crimped to balloon 1440 so elongate shaft 1404 may be slidably advanced or retracted under the proximal portion 1422 of stent 1442. The stent may preferably have a length that matches the working length of the balloon, or the stent length may be shorter than the balloon working length. At least a portion of balloon 1406, and stent 1408 are distally offset relative to balloon 1440 and stent 1442 so as to minimize profile of the device. In this embodiment the distal stent 1408 may be deployed in a main branch of the vessel and the other stent 1442 may be deployed in a side branch of the vessel. Alternatively, the distal stent 1408 may be deployed in a side branch of a vessel and the other stent 1442 may be deployed in the main branch of a vessel. The second catheter 1430 is a rapid exchange catheter (RX) having a guidewire lumen 1434 extending from the distal guidewire port 1438 at the distal end of the elongate shaft 1432 to a proximal guidewire port 1436 which is closer to the distal port 1438 than the proximal end of the catheter shaft 1432. The proximal guidewire port 1436 is also unobstructed by the snap fitting 1424 and preferably proximal thereto. A connector 1444, preferably a Luer connector is connected to the proximal end of the elongate shaft 1432 and allows an Indeflator or other device to be coupled with an inflation lumen (not shown) in elongate shaft 1432 for inflation of balloon 1440. A portion of shaft 1432 is snapped into the central channel 1426 of the snap fitting 1424 via slit 1445, and thus shaft 1432 may slide in channel 1426. This helps keep the two catheter shafts 1404, 1432 parallel and prevents tangling during delivery and as shaft 1432 is slidably advanced or retracted relative to shaft 1404. Also, a portion of shaft 1404 is disposed under proximal portion 1422 of stent 1442. The first catheter 1402 may be slidably advanced or retracted under the proximal portion 1422 of stent 1442 so that the shaft 1404 passes through the side hole 1420 in stent 1442. Radiopaque markers may be placed at different locations on the shaft 1432, often near the balloon 1440 or stent 1442, to help mark the proximal and distal ends of the stent or balloon, as well to facilitate alignment of the two catheters during stent deployment, as discussed elsewhere in this specification.

FIG. 15A illustrates a catheter system 1500 having dual rapid exchange design with a short zipper or snap fitting. FIG. 15B more clearly illustrates the features of the catheter system 1500 in FIG. 15A. The stent delivery system 1500 includes a first catheter 1502, and a second catheter 1530. The first catheter 1502 includes an elongate shaft 1504 with a radially expandable balloon 1506 disposed near a distal end of the elongate shaft 1504. A stent 1508 having a proximal portion 1522, a distal portion 1514 and a side hole 1520 is disposed over the balloon 1506. The distal portion 1514 is crimped to the balloon 1506 to prevent ejection during delivery, while the proximal portion 1522 is partially crimped to the balloon 1506 so the second catheter 1530 may be slidably advanced under the proximal portion 1522 of stent 1508. The first catheter is a rapid exchange catheter (RX) having a guidewire lumen 1512 extending from the distal guidewire port 1510 at the distal end of the elongate shaft 1504 to a proximal guidewire port 1511 which is closer to the distal port 1510 than the proximal end of the catheter shaft 1504. A connector 1516 is coupled with the proximal end of the elongate shaft 1504. The connector 1516 is preferably a Luer connector and this allows easy coupling with an Indeflator or other device for inflation of the balloon 1506. The first catheter 1502 also includes a zipper or snap fitting 1524 coupled to the elongate shaft 1504. The snap fit tube 1524 may be coextruded with the first shaft 1504, or it may be bonded or otherwise attached thereto using techniques known to those skilled in the art. The snap fit 1524 may alternatively be coupled with the other shaft 1532. The snap fitting 1524 includes a central channel 1526 extending therethrough and is sized to slidably receive a portion of the second catheter 1530. An elongate slot 1545 extends along the entire length of the snap fitting 1524 and is sized so that shaft 1536 may snapped into the central channel 1526. FIG. 15C illustrates a partial cross-section of FIG. 15B taken along the line C-C and shows shaft 1504 with the snap fitting 1524. Radiopaque markers may be placed at different locations along the shaft 1504, often near the balloon 1506 and/or stent 1508, to help mark the proximal and distal ends of the stent or balloon, as well to facilitate alignment of the two catheters during stent deployment, as discussed elsewhere in this specification.

The second catheter 1530 includes an elongate shaft 1532 with a radially expandable balloon 1540 disposed near a distal end of the elongate shaft 1532. A stent 1542 is disposed over balloon 1540. The stent may have a length that matches the working length of the balloon, or the stent length may be shorter than the balloon working length. In preferred embodiments, the stent 1542 is shorter than the working length of the balloon 1540 so that a proximal portion of the balloon 1540 is unconstrained by the stent 1542 and this unconstrained portion of the balloon 1540 may be slidably advanced or retracted through side hole 1520 and under proximal portion 1522 of stent 1508 as will be discussed below. Stent 1542 is crimped to balloon 1540 to prevent ejection during delivery. At least a portion of balloon 1540, and stent 1542 are distally offset relative to balloon 1506 and stent 1508 so as to minimize profile of the device. In this embodiment the distal stent 1542 may be deployed in a main branch of the vessel and the other stent 1508 may be deployed in a side branch of the vessel. Alternatively, the distal stent 1542 may be deployed in a side branch of a vessel and the other stent 1508 may be deployed in the main branch of a vessel. The second catheter 1530 is a rapid exchange catheter (RX) having a guidewire lumen 1534 extending from the distal guidewire port 1538 at the distal end of the elongate shaft 1532 to a proximal guidewire port 1536 which is closer to the distal port 1538 than the proximal end of the catheter shaft 1532. The proximal guidewire port 1536 is also unobstructed by the snap fitting 1524 and may be distal thereto. A connector 1544, preferably a Luer connector is connected to the proximal end of the elongate shaft 1532 and allows an Indeflator or other device to be coupled with an inflation lumen (not shown) in elongate shaft 1532 for inflation of balloon 1540. A portion of shaft 1532 is snapped into the central channel 1526 of the snap fitting 1524 via slit 1545, and thus shaft 1532 may slide in channel 1526. This helps keep the two catheter shafts 1504, 1532 parallel and prevents tangling during delivery and as shaft 1532 is slidably advanced or retracted relative to shaft 1504. Also, another portion of shaft 1532 is disposed under proximal portion 1522 of stent 1508. The second catheter 1530 may also be slidably advanced or retracted under the proximal portion 1522 of stent 1508 so that the shaft 1532 passes through the side hole 1520 in stent 1508. Radiopaque markers may be placed at different locations on the shaft 1532, often near the balloon 1540 or stent 1542, to help mark the proximal and distal ends of the stent or balloon, as well as to facilitate alignment of the two catheters during stent deployment, as discussed elsewhere in this specification.

FIG. 16A illustrates a catheter system 1600 having a dual over the wire design with a short zipper or snap fitting. FIG. 16B more clearly illustrates the features of the catheter system 1600 in FIG. 16A. The stent delivery system 1600 includes a first catheter 1602, and a second catheter 1630. The first catheter 1602 includes an elongate shaft 1604 with a radially expandable balloon 1606 disposed near a distal end of the elongate shaft 1604. A stent 1608 having a proximal portion 1622, a distal portion 1614 and a side hole 1620 is disposed over the balloon 1606. The distal portion 1614 is crimped to the balloon 1606 to prevent ejection during delivery, while the proximal portion 1622 is partially crimped to the balloon 1606 so the second catheter 1630 may be slidably advanced under the proximal portion 1622 of stent 1608. The first catheter is an over-the-wire (OTW) catheter having a guidewire lumen 1612 extending from the distal guidewire port 1610 at the distal end of the elongate shaft 1604 to the proximal end of the elongate shaft 1604 into Y-adapter 1614 having a connector 1616. The connector 1616 is preferably a Luer connector and this allows easy coupling with a syringe or other device for lumen flushing or injecting contrast media. When unconnected, the guidewire lumen 1612 exits via connector 1616. A second connector 1618, also preferably a Luer connector allows attachment of an Indeflator or other device to the catheter for inflation of the balloon 1606 via an inflation lumen (not shown) in the elongate shaft 1604. The first catheter 1602 also includes a zipper or snap fitting 1624 coupled to the elongate shaft 1604. The snap fit tube 1624 may be coextruded with the first shaft 1604, or it may be bonded or otherwise attached thereto using techniques known to those skilled in the art. The snap fit 1624 may alternatively be coupled with the other shaft 1632. The snap fitting 1624 includes a central channel 1626 extending therethrough and is sized to slidably receive a portion of the second catheter 1630. An elongate slot 1645 extends along the entire length of the snap fitting 1624 and is sized so that shaft 1636 may snapped into the central channel 1626. FIG. 16C illustrates a partial cross-section of FIG. 16B taken along the line C-C and shows shaft 1604 with the snap fitting 1624. Radiopaque markers may be placed at different locations along the shaft 1604, often near the balloon 1606 and/or stent 1608, to help mark the proximal and distal ends of the stent or balloon, as well to facilitate alignment of the two catheters during stent deployment, as discussed elsewhere in this specification.

The second catheter 1630 includes an elongate shaft 1632 with a radially expandable balloon 1640 disposed near a distal end of the elongate shaft 1632. A stent 1642 is disposed over balloon 1640. The stent may have a length that matches the working length of the balloon, or the stent length may be shorter than the balloon working length. In preferred embodiments, the stent 1642 is shorter than the working length of the balloon 1640 so that a proximal portion of the balloon 1640 is unconstrained by the stent 1642 and this unconstrained portion of the balloon 1640 may be slidably advanced or retracted through side hole 1620 and under proximal portion 1622 of stent 1608 as will be discussed below. Stent 1642 is crimped to balloon 1640 to prevent ejection during delivery. At least a portion of balloon 1640, and stent 1642 are distally offset relative to balloon 1606 and stent 1608 so as to minimize profile of the device. In this embodiment the distal stent 1642 may be deployed in a main branch of the vessel and the other stent 1608 may be deployed in a side branch of the vessel. Alternatively, the distal stent 1642 may be deployed in a side branch of a vessel and the other stent 1608 may be deployed in the main branch of a vessel. The second catheter 1630 is an over-the-wire (OTW) catheter having a guidewire lumen 1634 extending from the distal guidewire port 1638 at the distal end of the elongate shaft 1632 to the proximal end of the elongate shaft 1632 into Y-adapter 1646 having a connector 1648. The connector 1648 is preferably a Luer connector and this allows easy coupling with a syringe or other device for lumen flushing or injecting contrast media. When unconnected, the guidewire lumen 1634 exits via connector 1648. A second connector 1644, also preferably a Luer connector allows attachment of an Indeflator or other device to the catheter for inflation of the balloon 1640 via an inflation lumen (not shown) in the elongate shaft 1632. A portion of shaft 1632 is snapped into the central channel 1626 of the snap fitting 1624 via slit 1645, and thus shaft 1632 may slide in channel 1626. This helps keep the two catheter shafts 1604, 1632 parallel and prevents tangling during delivery and as shaft 1632 is slidably advanced or retracted relative to shaft 1604. Also, another portion of shaft 1632 is disposed under proximal portion 1622 of stent 1608. The second catheter 1630 may also be slidably advanced or retracted under the proximal portion 1622 of stent 1608 so that the shaft 1632 passes through the side hole 1620 in stent 1608. Radiopaque markers may be placed at different locations on the shaft 1632, often near the balloon 1640 or stent 1642, to help mark the proximal and distal ends of the stent or balloon, as well as to facilitate alignment of the two catheters during stent deployment, as discussed elsewhere in this specification.

FIG. 17A illustrates a catheter system 1700 having a distal daughter catheter with a rapid exchange configuration a proximal mother catheter with an over-the-wire configuration and an end to end zipper, or snap fitting. This embodiment is similar to that shown in FIG. 13A-13B, with the major difference being the length of the snap fitting and the location of one of the guidewire ports. FIG. 17B more clearly illustrates the features of the catheter system 1700 in FIG. 17A. The stent delivery system 1700 includes a first catheter 1702, and a second catheter 1730. The first catheter 1702 includes an elongate shaft 1704 with a radially expandable balloon 1706 disposed near a distal end of the elongate shaft 1704. A stent 1708 having a proximal portion 1722, a distal portion 1714 and a side hole 1720 is disposed over the balloon 1706. The distal portion 1714 is crimped to the balloon 1706 to prevent ejection during delivery, while the proximal portion 1722 is partially crimped to the balloon 1706 so the second catheter 1730 may be slidably advanced under the proximal portion 1722 of stent 1708. The first catheter is an over-the-wire (OTW) catheter having a guidewire lumen 1712 extending from the distal guidewire port 1710 at the distal end of the elongate shaft 1704 to the proximal end of the elongate shaft 1704 into Y-adapter 1714 having a connector 1716. The connector 1716 is preferably a Luer connector and this allows easy coupling with a syringe or other device for lumen flushing or injecting contrast media. When unconnected, the guidewire lumen 1712 exits via connector 1716. A second connector 1718, also preferably a Luer connector allows attachment of an Indeflator or other device to the catheter for inflation of the balloon 1706 via an inflation lumen (not shown) in the elongate shaft 1704. The first catheter 1702 also includes a zipper or snap fitting 1724 coupled to the elongate shaft 1704. The snap fit tube 1724 may be coextruded with the first shaft 1704, or it may be bonded or otherwise attached thereto using techniques known to those skilled in the art. The snap fit 1724 may alternatively be coupled with the other shaft 1732. The snap fitting 1724 includes a central channel 1726 extending therethrough and is sized to slidably receive a portion of the second catheter 1730. An elongate slot 1745 extends along the entire length of the snap fitting 1724 and is sized so that shaft 1736 may snapped into the central channel 1726. The snap fitting 1724 may extend from the distal end of connectors 1714, 1744 to the proximal end of balloon 1706, or it may be shorter, extending only partially between the connectors 1714, 1744 and the balloon 1706. FIG. 17C illustrates a partial cross-section of FIG. 17B taken along the line C-C and shows shaft 1704 with the snap fitting 1724. Radiopaque markers may be placed at different locations along the shaft 1704, often near the balloon 1706 and/or stent 1708, to help mark the proximal and distal ends of the stent or balloon, as well to facilitate alignment of the two catheters during stent deployment, as discussed elsewhere in this specification.

The second catheter 1730 includes an elongate shaft 1732 with a radially expandable balloon 1740 disposed near a distal end of the elongate shaft 1732. A stent 1742 is disposed over balloon 1740. The stent may have a length that matches the working length of the balloon, or the stent length may be shorter than the balloon working length. In preferred embodiments, the stent 1742 is shorter than the working length of the balloon 1740 so that a proximal portion of the balloon 1740 is unconstrained by the stent 1742 and this unconstrained portion of the balloon 1740 may be slidably advanced or retracted through side hole 1720 and under proximal portion 1722 of stent 1708 as will be discussed below. Stent 1742 is crimped to balloon 1740 to prevent ejection during delivery. At least a portion of balloon 1740, and stent 1742 are distally offset relative to balloon 1706 and stent 1708 so as to minimize profile of the device. In this embodiment the distal stent 1742 may be deployed in a main branch of the vessel and the other stent 1708 may be deployed in a side branch of the vessel. Alternatively, the distal stent 1742 may be deployed in a side branch of a vessel and the other stent 1708 may be deployed in the main branch of a vessel. The second catheter 1730 is a rapid exchange catheter (RX) having a guidewire lumen 1734 extending from the distal guidewire port 1738 at the distal end of the elongate shaft 1732 to a proximal guidewire port 1736 which is closer to the distal port 1738 than the proximal end of the catheter shaft 1732. The proximal guidewire port 1736 is also unobstructed by the snap fitting 1724 and preferably distal thereto. A connector 1744, preferably a Luer connector is connected to the proximal end of the elongate shaft 1732 and allows an Indeflator or other device to be coupled with an inflation lumen (not shown) in elongate shaft 1732 for inflation of balloon 1740. A portion of shaft 1732 is snapped into the central channel 1726 of the snap fitting 1724 via slit 1745, and thus shaft 1732 may slide in channel 1726. This helps keep the two catheter shafts 1704, 1732 parallel and prevents tangling during delivery and as shaft 1732 is slidably advanced or retracted relative to shaft 1704. Also, another portion of shaft 1732 is disposed under proximal portion 1722 of stent 1708. The second catheter 1730 may also be slidably advanced or retracted under the proximal portion 1722 of stent 1708 so that the shaft 1732 passes through the side hole 1720 in stent 1708. Radiopaque markers may be placed at different locations on the shaft 1732, often near the balloon 1740 or stent 1742, to help mark the proximal and distal ends of the stent or balloon, as well to facilitate alignment of the two catheters during stent deployment, as discussed elsewhere in this specification.

Figure 18A:
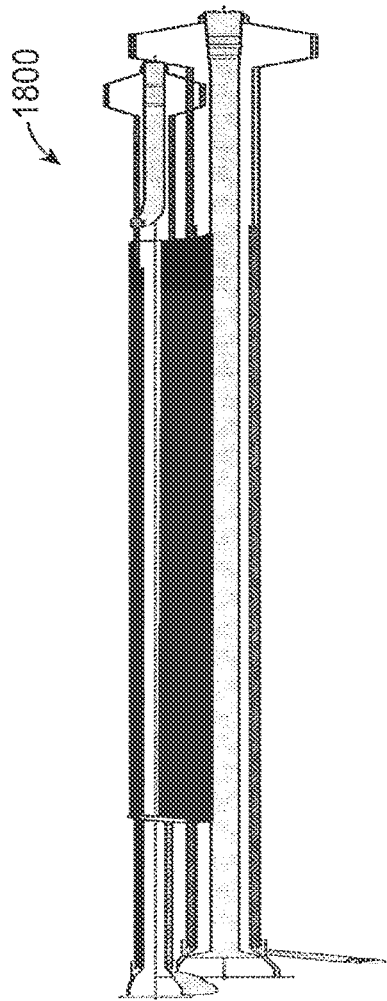
FIGS. 18A-18C illustrate another exemplary embodiment of a system having a snap fitting, an over-the-wire daughter catheter and a rapid exchange mother catheter.
Figure 18B:
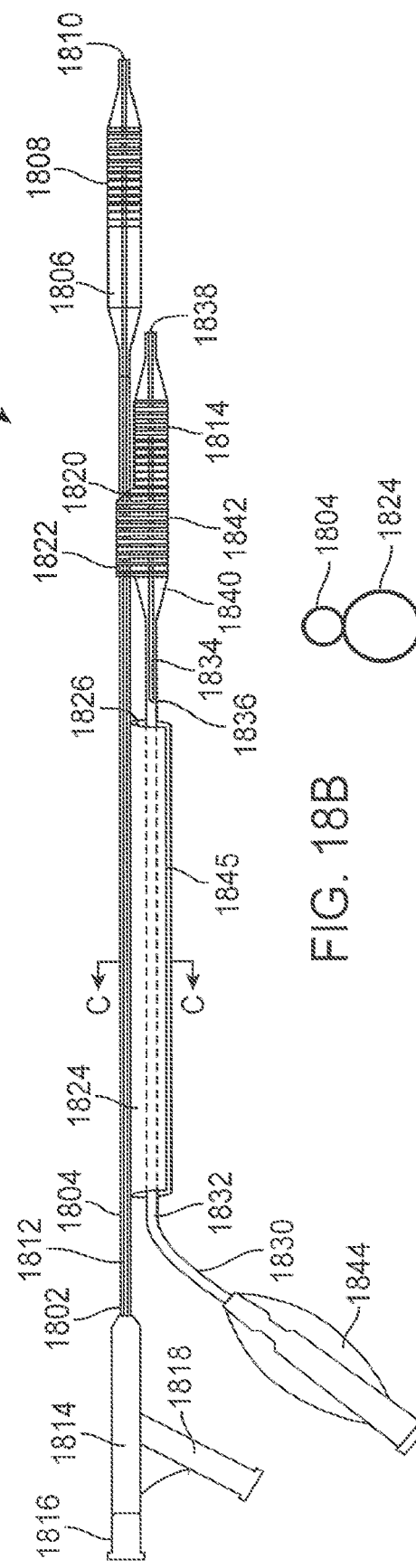
Figure 18C:
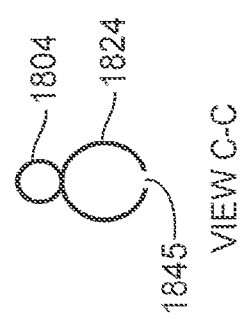

FIG. 18A illustrates a catheter system 1800 having a proximal mother catheter with a rapid exchange configuration and a distal daughter catheter with an end to end zipper or snap fitting. FIG. 18A is similar to the embodiment of FIG. 14A-14B, with the major difference being the length of the snap fitting and the location of one of the guidewire ports. FIG. 18B more clearly illustrates the features of the catheter system 1800 in FIG. 18A. The stent delivery system 1800 includes a first catheter 1802, and a second catheter 1830. The first catheter 1802 includes an elongate shaft 1804 with a radially expandable balloon 1806 disposed near a distal end of the elongate shaft 1804, and a stent 1808 disposed over the balloon 1806. The stent 1808 may be the same length as the working length of the balloon 1808, or it may be shorter. In preferred embodiments, the stent 1808 is shorter than the working length of balloon 1806 such that a proximal portion of balloon 1806 remains unconstrained by stent 1808. The proximal portion of balloon 1806 may be slidably advanced and retracted under stent 1842 via side hole 1820. Stent 1808 is crimped to the balloon 1806 to prevent ejection during delivery. The first catheter is an over-the-wire (OTW) catheter having a guidewire lumen 1812 extending from the distal guidewire port 1810 at the distal end of the elongate shaft 1804 to the proximal end of the elongate shaft 1804 into Y-adapter 1814 having a connector 1816. The connector 1816 is preferably a Luer connector and this allows easy coupling with a syringe or other device for lumen flushing or injecting contrast media. When unconnected, the guidewire lumen 1812 exits via connector 1816. A second connector 1818, also preferably a Luer connector allows attachment of an Indeflator or other device to the catheter for inflation of the balloon 1806 via an inflation lumen (not shown) in the elongate shaft 1804. The first catheter 1802 also includes a zipper or snap fitting 1824 coupled to the elongate shaft 1804. The snap fit tube 1824 may be coextruded with the first shaft 1804, or it may be bonded or otherwise attached thereto using techniques known to those skilled in the art. The snap fit 1824 may alternatively be coupled with the other shaft 1832. The snap fitting 1824 includes a central channel 1826 extending therethrough and is sized to slidably receive a portion of the second catheter 1830. An elongate slot 1845 extends along the entire length of the snap fitting 1824 and is sized so that shaft 1836 may snapped into the central channel 1826. FIG. 18C illustrates a partial cross-section of FIG. 18B taken along the line C-C and shows shaft 1804 with the snap fitting 1824. The snap fitting 1824 may extend from the distal end of connectors 1814, 1844 to the proximal end of balloon 1840, or it may be shorter, extending only partially between the connectors 1814, 1844 and the balloon 1806. Radiopaque markers may be placed at different locations along the shaft 1804, often near the balloon 1806 and/or stent 1808, to help mark the proximal and distal ends of the stent or balloon, as well to facilitate alignment of the two catheters during stent deployment, as discussed elsewhere in this specification.

The second catheter 1830 includes an elongate shaft 1832 with a radially expandable balloon 1840 disposed near a distal end of the elongate shaft 1832. A stent 1842 having a proximal portion 1822, a distal portion 1814, and a side hole 1820 is disposed over balloon 1840. The distal portion 1814 is crimped to balloon 1840 to prevent ejection during delivery, while the proximal portion 1822 is partially crimped to balloon 1840 so elongate shaft 1804 may be slidably advanced or retracted under the proximal portion 1822 of stent 1842. The stent may preferably have a length that matches the working length of the balloon, or the stent length may be shorter than the balloon working length. At least a portion of balloon 1806, and stent 1808 are distally offset relative to balloon 1840 and stent 1842 so as to minimize profile of the device. In this embodiment the distal stent 1808 may be deployed in a main branch of the vessel and the other stent 1842 may be deployed in a side branch of the vessel. Alternatively, the distal stent 1808 may be deployed in a side branch of a vessel and the other stent 1842 may be deployed in the main branch of a vessel. The second catheter 1830 is a rapid exchange catheter (RX) having a guidewire lumen 1834 extending from the distal guidewire port 1838 at the distal end of the elongate shaft 1832 to a proximal guidewire port 1836 which is closer to the distal port 1838 than the proximal end of the catheter shaft 1832. The proximal guidewire port 1836 is also unobstructed by the snap fitting 1824 and preferably distal thereto. A connector 1844, preferably a Luer connector is connected to the proximal end of the elongate shaft 1832 and allows an Indeflator or other device to be coupled with an inflation lumen (not shown) in elongate shaft 1832 for inflation of balloon 1840. A portion of shaft 1832 is snapped into the central channel 1826 of the snap fitting 1824 via slit 1845, and thus shaft 1832 may slide in channel 1826. This helps keep the two catheter shafts 1804, 1832 parallel and prevents tangling during delivery and as shaft 1832 is slidably advanced or retracted relative to shaft 1804. Also, a portion of shaft 1804 is disposed under proximal portion 1822 of stent 1842. The first catheter 1802 may be slidably advanced or retracted under the proximal portion 1822 of stent 1842 so that the shaft 1804 passes through the side hole 1820 in stent 1842. Radiopaque markers may be placed at different locations on the shaft 1832, often near the balloon 1840 or stent 1842, to help mark the proximal and distal ends of the stent or balloon, as well to facilitate alignment of the two catheters during stent deployment, as discussed elsewhere in this specification.

Figure 19A:
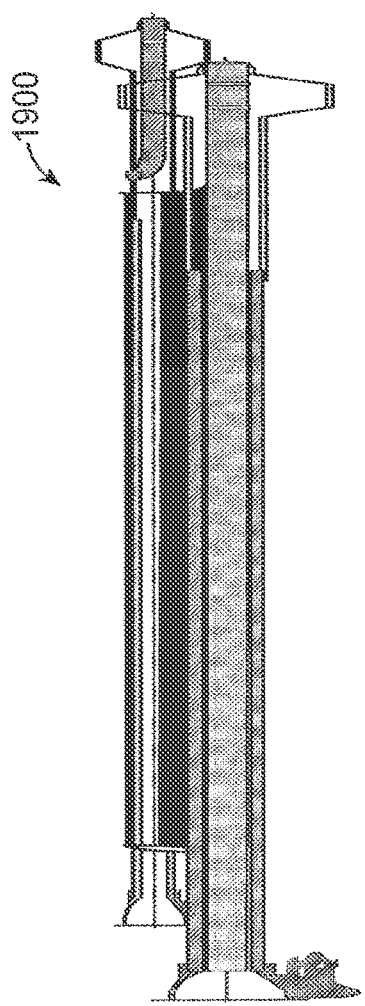
FIGS. 19A-19C illustrate another exemplary embodiment of a system having a snap fitting, a rapid exchange mother catheter and a rapid exchange daughter catheter.
Figure 19B:
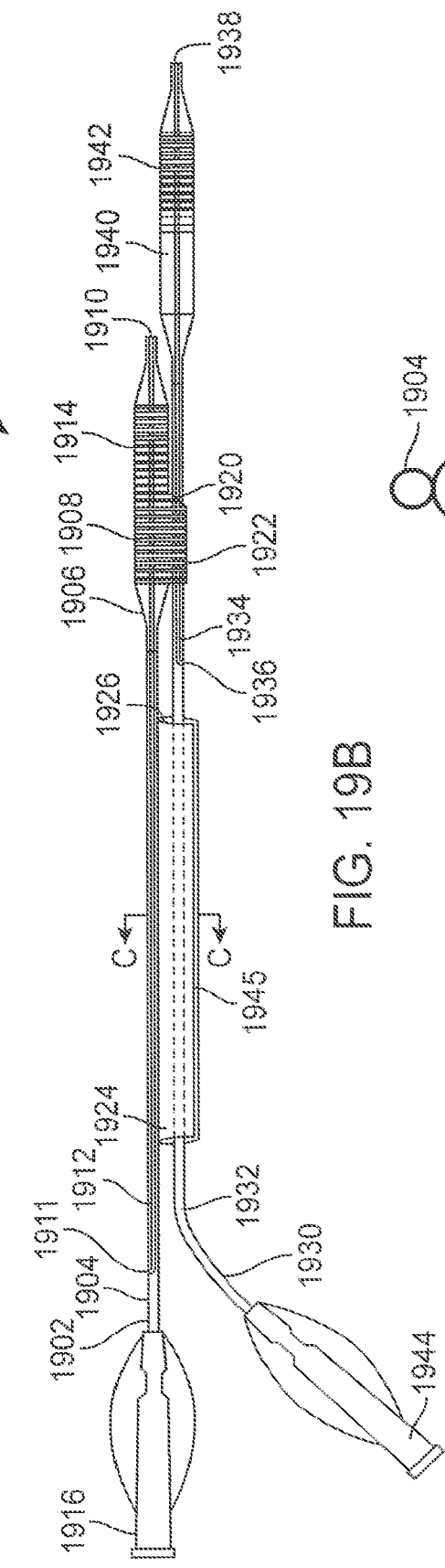
Figure 19C:
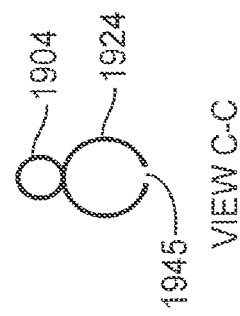

FIG. 19A illustrates a catheter system 1900 having a dual rapid exchange design with an end to end zipper or snap fitting. FIG. 19A is similar to the embodiment of FIG. 15A-15B, with the major difference being the length of the snap fitting. FIG. 19B more clearly illustrates the features of the catheter system 1900 in FIG. 19A. The stent delivery system 1900 includes a first catheter 1902, and a second catheter 1930. The first catheter 1902 includes an elongate shaft 1904 with a radially expandable balloon 1906 disposed near a distal end of the elongate shaft 1904. A stent 1908 having a proximal portion 1922, a distal portion 1914 and a side hole 1920 is disposed over the balloon 19. The distal portion 1914 is crimped to the balloon 1906 to prevent ejection during delivery, while the proximal portion 1922 is partially crimped to the balloon 1906 so the second catheter 1930 may be slidably advanced under the proximal portion 1922 of stent 1908. The first catheter is a rapid exchange catheter (RX) having a guidewire lumen 1912 extending from the distal guidewire port 1910 at the distal end of the elongate shaft 1904 to a proximal guidewire port 1911 which is closer to the distal port 1910 than the proximal end of the catheter shaft 1904. A connector 1916 is coupled with the proximal end of the elongate shaft 1904. The connector 1916 is preferably a Luer connector and this allows easy coupling with an Indeflator or other device for inflation of the balloon 1906. The first catheter 1902 also includes a zipper or snap fitting 1924 coupled to the elongate shaft 1904. The snap fit tube 1924 may be coextruded with the first shaft 1904, or it may be bonded or otherwise attached thereto using techniques known to those skilled in the art. The snap fit 1924 may alternatively be coupled with the other shaft 1932. The snap fitting 1924 includes a central channel 1926 extending therethrough and is sized to slidably receive a portion of the second catheter 1930. An elongate slot 1945 extends along the entire length of the snap fitting 1924 and is sized so that shaft 1932 may snapped into the central channel 1926. FIG. 19C illustrates a partial cross-section of FIG. 19B taken along the line C-C and shows shaft 1904 with the snap fitting 1924. Radiopaque markers may be placed at different locations along the shaft 1904, often near the balloon 1906 and/or stent 1908, to help mark the proximal and distal ends of the stent or balloon, as well to facilitate alignment of the two catheters during stent deployment, as discussed elsewhere in this specification.

The second catheter 1930 includes an elongate shaft 1932 with a radially expandable balloon 1940 disposed near a distal end of the elongate shaft 1932. A stent 1942 is disposed over balloon 1940. The stent may have a length that matches the working length of the balloon, or the stent length may be shorter than the balloon working length. In preferred embodiments, the stent 1942 is shorter than the working length of the balloon 1940 so that a proximal portion of the balloon 1940 is unconstrained by the stent 1942 and this unconstrained portion of the balloon 1940 may be slidably advanced or retracted through side hole 1920 and under proximal portion 1922 of stent 1908 as will be discussed below. Stent 1942 is crimped to balloon 1940 to prevent ejection during delivery. At least a portion of balloon 1940, and stent 1942 are distally offset relative to balloon 1906 and stent 1908 so as to minimize profile of the device. In this embodiment the distal stent 1942 may be deployed in a main branch of the vessel and the other stent 1908 may be deployed in a side branch of the vessel. Alternatively, the distal stent 1942 may be deployed in a side branch of a vessel and the other stent 1908 may be deployed in the main branch of a vessel. The second catheter 1930 is a rapid exchange catheter (RX) having a guidewire lumen 1934 extending from the distal guidewire port 1938 at the distal end of the elongate shaft 1932 to a proximal guidewire port 1936 which is closer to the distal port 1938 than the proximal end of the catheter shaft 1932. The proximal guidewire port 1936 is also unobstructed by the snap fitting 1924 and may be distal thereto. A connector 1944, preferably a Luer connector is connected to the proximal end of the elongate shaft 1932 and allows an Indeflator or other device to be coupled with an inflation lumen (not shown) in elongate shaft 1932 for inflation of balloon 1940. A portion of shaft 1932 is snapped into the central channel 1926 of the snap fitting 1924 via slit 1945, and thus shaft 1932 may slide in channel 1926. This helps keep the two catheter shafts 1904, 1932 parallel and prevents tangling during delivery and as shaft 1932 is slidably advanced or retracted relative to shaft 1904. Also, another portion of shaft 1932 is disposed under proximal portion 1922 of stent 1908. The second catheter 1930 may also be slidably advanced or retracted under the proximal portion 1922 of stent 1908 so that the shaft 1932 passes through the side hole 1920 in stent 1908. Radiopaque markers may be placed at different locations on the shaft 1932, often near the balloon 1940 or stent 1942, to help mark the proximal and distal ends of the stent or balloon, as well to facilitate alignment of the two catheters during stent deployment, as discussed elsewhere in this specification.

FIG. 20A illustrates a catheter system 2000 having a dual over the wire design with an end to end zipper or snap fitting. FIG. 20A is similar to the embodiment of FIG. 16A-16B, with the major difference being the length of the snap fitting. FIG. 20B more clearly illustrates the features of the catheter system 2000 in FIG. 20A. The stent delivery system 2000 includes a first catheter 2002, and a second catheter 2030. The first catheter 2002 includes an elongate shaft 2004 with a radially expandable balloon 2006 disposed near a distal end of the elongate shaft 2004. A stent 2008 having a proximal portion 2022, a distal portion 2014 and a side hole 2020 is disposed over the balloon 2006. The distal portion 2014 is crimped to the balloon 2006 to prevent ejection during delivery, while the proximal portion 2022 is partially crimped to the balloon 2006 so the second catheter 2030 may be slidably advanced under the proximal portion 2022 of stent 2008. The first catheter is an over-the-wire (OTW) catheter having a guidewire lumen 2012 extending from the distal guidewire port 2010 at the distal end of the elongate shaft 2004 to the proximal end of the elongate shaft 2004 into Y-adapter 2014 having a connector 2016. The connector 2016 is preferably a Luer connector and this allows easy coupling with a syringe or other device for lumen flushing or injecting contrast media. When unconnected, the guidewire lumen 2012 exits via connector 2016. A second connector 2018, also preferably a Luer connector allows attachment of an Indeflator or other device to the catheter for inflation of the balloon 2006 via an inflation lumen (not shown) in the elongate shaft 2004. The first catheter 2002 also includes a zipper or snap fitting 2024 coupled to the elongate shaft 2004. The snap fit tube 2024 may be coextruded with the first shaft 2004, or it may be bonded or otherwise attached thereto using techniques known to those skilled in the art. The snap fit 2024 may alternatively be coupled with the other shaft 2032. The snap fitting 2024 includes a central channel 2026 extending therethrough and is sized to slidably receive a portion of the second catheter 2030. An elongate slot 2045 extends along the entire length of the snap fitting 2024 and is sized so that shaft 2036 may snapped into the central channel 2026. FIG. 20C illustrates a partial cross-section of FIG. 20B taken along the line C-C and shows shaft 2004 with the snap fitting 2024. Radiopaque markers may be placed at different locations along the shaft 2004, often near the balloon 2006 and/or stent 2008, to help mark the proximal and distal ends of the stent or balloon, as well to facilitate alignment of the two catheters during stent deployment, as discussed elsewhere in this specification.

The second catheter 2030 includes an elongate shaft 2032 with a radially expandable balloon 2040 disposed near a distal end of the elongate shaft 2032. A stent 2042 is disposed over balloon 2040. The stent may have a length that matches the working length of the balloon, or the stent length may be shorter than the balloon working length. In preferred embodiments, the stent 2042 is shorter than the working length of the balloon 2040 so that a proximal portion of the balloon 2040 is unconstrained by the stent 2042 and this unconstrained portion of the balloon 2040 may be slidably advanced or retracted through side hole 2020 and under proximal portion 2022 of stent 2008 as will be discussed below. Stent 2042 is crimped to balloon 2040 to prevent ejection during delivery. At least a portion of balloon 2040, and stent 2042 are distally offset relative to balloon 2006 and stent 2008 so as to minimize profile of the device. In this embodiment the distal stent 2042 may be deployed in a main branch of the vessel and the other stent 2008 may be deployed in a side branch of the vessel. Alternatively, the distal stent 2042 may be deployed in a side branch of a vessel and the other stent 2008 may be deployed in the main branch of a vessel. The second catheter 2030 is an over-the-wire (OTW) catheter having a guidewire lumen 2034 extending from the distal guidewire port 2038 at the distal end of the elongate shaft 2032 to the proximal end of the elongate shaft 2032 into Y-adapter 2046 having a connector 2048. The connector 2048 is preferably a Luer connector and this allows easy coupling with a syringe or other device for lumen flushing or injecting contrast media. When unconnected, the guidewire lumen 2034 exits via connector 2048. A second connector 2044, also preferably a Luer connector allows attachment of an Indeflator or other device to the catheter for inflation of the balloon 204 (via an inflation lumen (not shown) in the elongate shaft 2032. A portion of shaft 2032 is snapped into the central channel 2026 of the snap fitting 2024 via slit 2045, and thus shaft 2032 may slide in channel 2026. This helps keep the two catheter shafts 2004, 2032 parallel and prevents tangling during delivery and as shaft 2032 is slidably advanced or retracted relative to shaft 2004. Also, another portion of shaft 2032 is disposed under proximal portion 2022 of stent 2008. The second catheter 2030 may also be slidably advanced or retracted under the proximal portion 2022 of stent 2008 so that the shaft 2032 passes through the side hole 2020 in stent 2008. Radiopaque markers may be placed at different locations on the shaft 2032, often near the balloon 2040 or stent 2042, to help mark the proximal and distal ends of the stent or balloon, as well to facilitate alignment of the two catheters during stent deployment, as discussed elsewhere in this specification.

FIGS. 21A, 22A, 23A, and 24A illustrate catheters that can be used with an alternative embodiment where the mother catheter is provided to the operator with a mother stent that is crimped on the distal portion of the mother catheter balloon. The proximal portion of the mother stent is uncrimped or partially crimped. The operator can mount any commercially available catheter or balloon on a wire through the mother stent proximal end and exit out the side hole of the mother stent. The operator can align the catheters to suit the patient's anatomy and crimp the proximal portion of the mother stent. The operator can crimp the stent tightly so that the catheters do not move relative to each other. It is possible for the operator to place the catheters at the bifurcation and if necessary pullback on the commercially available catheter to adjust the alignment if necessary. Then the operator can gently push the system distally to ensure complete apposition.

Figure 21A:
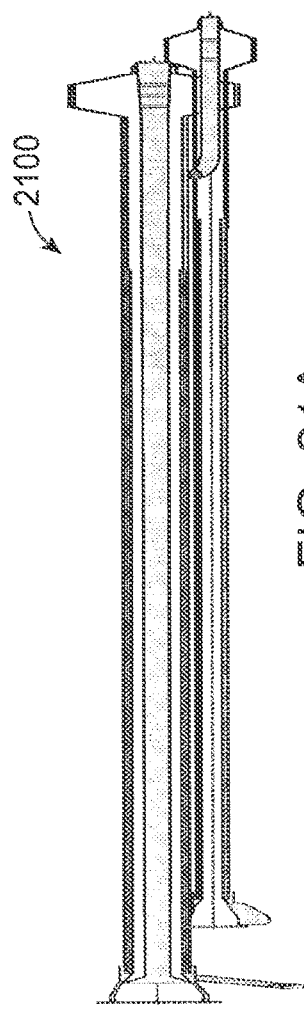
FIGS. 21A-21B illustrate yet another exemplary embodiment of a system having an over-the-wire mother catheter and a rapid exchange daughter catheter.
Figure 21B:
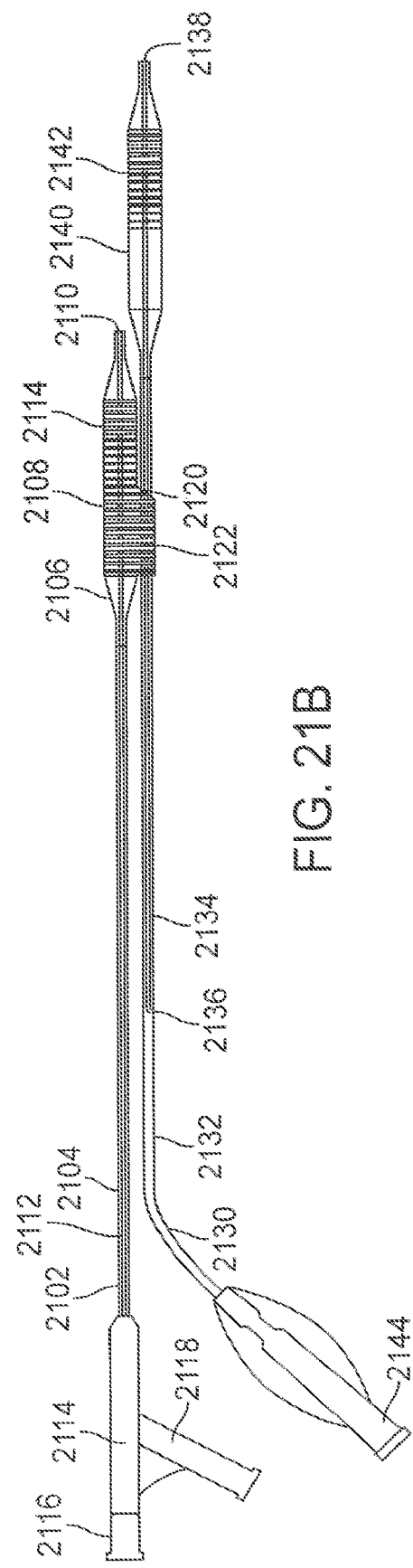

FIG. 21A illustrates a catheter system 2100 having a distal daughter catheter with a rapid exchange configuration and a proximal mother catheter with an over-the-wire configuration. FIG. 21B more clearly illustrates the features of the catheter system 2100 in FIG. 21A. The stent delivery system 2100 includes a first catheter 2102, and a second catheter 2130. The first catheter 2102 includes an elongate shaft 2104 with a radially expandable balloon 2106 disposed near a distal end of the elongate shaft 2104. A stent 2108 having a proximal portion 2122, a distal portion 2114 and a side hole 2120 is disposed over the balloon 2106. The distal portion 2114 is crimped to the balloon 2106 to prevent ejection during delivery, while the proximal portion 2122 is partially crimped to the balloon 2106 so the second catheter 2130 may be slidably advanced under the proximal portion 2122 of stent 2108. The first catheter is an over-the-wire (OTW) catheter having a guidewire lumen 2112 extending from the distal guidewire port 2110 at the distal end of the elongate shaft 2104 to the proximal end of the elongate shaft 2104 into Y-adapter 2114 having a connector 2116. The connector 2116 is preferably a Luer connector and this allows easy coupling with a syringe or other device for lumen flushing or injecting contrast media. When unconnected, the guidewire lumen 2112 exits via connector 2116. A second connector 2118, also preferably a Luer connector allows attachment of an Indeflator or other device to the catheter for inflation of the balloon 2106 via an inflation lumen (not shown) in the elongate shaft 2104. Radiopaque markers may be placed at different locations along the shaft 2104, often near the balloon 2106 and/or stent 2108, to help mark the proximal and distal ends of the stent or balloon, as well to facilitate alignment of the two catheters during stent deployment, as discussed elsewhere in this specification.

The second catheter 2130 includes an elongate shaft 2132 with a radially expandable balloon 2140 disposed near a distal end of the elongate shaft 2132. A stent 2142 is disposed over balloon 2140. The stent may have a length that matches the working length of the balloon, or the stent length may be shorter than the balloon working length. In preferred embodiments, the stent 2142 is shorter than the working length of the balloon 2140 so that a proximal portion of the balloon 2140 is unconstrained by the stent 2142 and this unconstrained portion of the balloon 2140 may be slidably advanced or retracted through side hole 2120 and under proximal portion 2122 of stent 2108 as will be discussed below. Stent 2142 is crimped to balloon 2140 to prevent ejection during delivery. At least a portion of balloon 2140, and stent 2142 are distally offset relative to balloon 2106 and stent 2108 so as to minimize profile of the device. In this embodiment the distal stent 2142 may be deployed in a main branch of the vessel and the other stent 2108 may be deployed in a side branch of the vessel. Alternatively, the distal stent 2142 may be deployed in a side branch of a vessel and the other stent 2108 may be deployed in the main branch of a vessel. The second catheter 2130 is a rapid exchange catheter (RX) having a guidewire lumen 2134 extending from the distal guidewire port 2138 at the distal end of the elongate shaft 2132 to a proximal guidewire port 2136 which is closer to the distal port 2138 than the proximal end of the catheter shaft 2132. A connector 2144, preferably a Luer connector is connected to the proximal end of the elongate shaft 2132 and allows an Indeflator or other device to be coupled with an inflation lumen (not shown) in elongate shaft 2132 for inflation of balloon 2140. Having a portion of shaft 2132 disposed under proximal portion 2122 of stent 2108 helps keep catheter 2104, 2132 parallel and prevents tangling during delivery and as shaft 2132 is slidably advanced or retracted relative to shaft 2104. Also, another portion of shaft 2132 is disposed under proximal portion 2122 of stent 2108. The second catheter 2130 may also be slidably advanced or retracted under the proximal portion 2122 of stent 2108 so that the shaft 2132 passes through the side hole 2120 in stent 2108. Radiopaque markers may be placed at different locations on the shaft 2132, often near the balloon 2140 or stent 2142, to help mark the proximal and distal ends of the stent or balloon, as well to facilitate alignment of the two catheters during stent deployment, as discussed elsewhere in this specification.

Figure 22A:
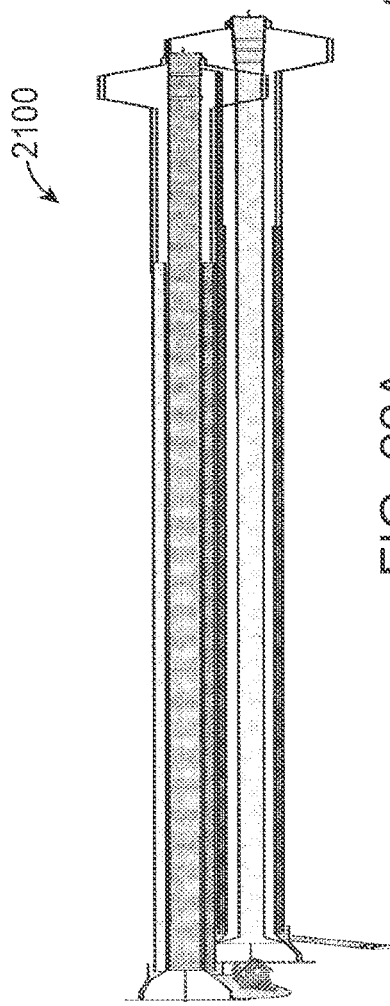
FIGS. 22A-22B illustrate yet another exemplary embodiment of a system having an over-the-wire daughter catheter and a rapid exchange mother catheter.
Figure 22B:
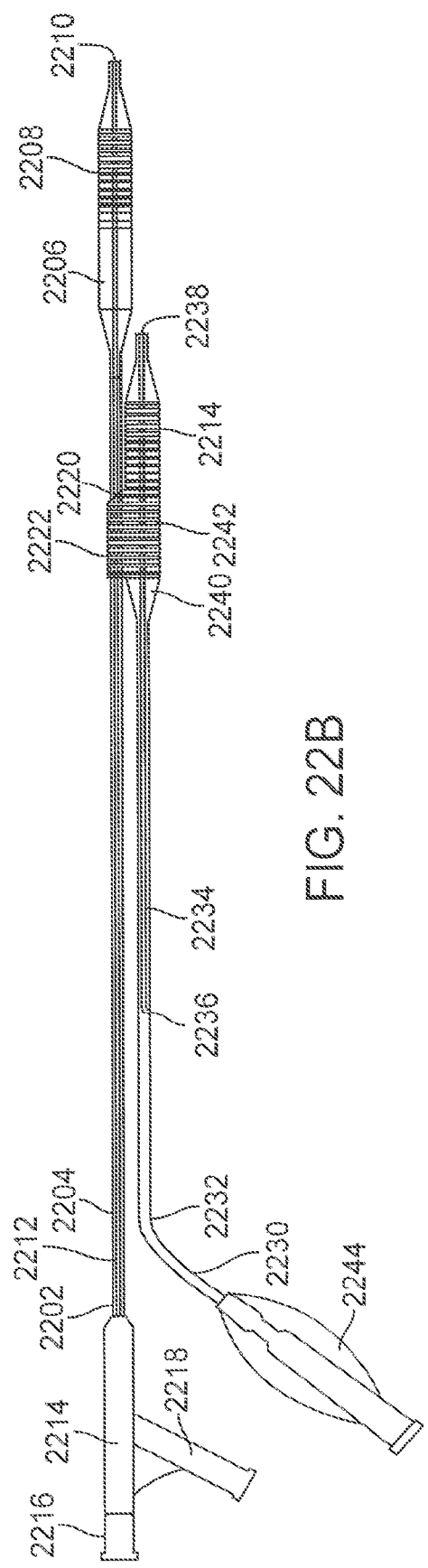

FIG. 22A illustrates a catheter system 2200 having a proximal mother catheter with an over the wire design and a distal daughter catheter with an over-the-wire configuration. FIG. 22B more clearly illustrates the features of the catheter system 2200 in FIG. 22A. The stent delivery system 2200 includes a first catheter 2202, and a second catheter 2230. The first catheter 2202 includes an elongate shaft 2204 with a radially expandable balloon 2206 disposed near a distal end of the elongate shaft 2204, and a stent 2208 disposed over the balloon 2206. The stent 2208 may be the same length as the working length of the balloon 2208, or it may be shorter. In preferred embodiments, the stent 2208 is shorter than the working length of balloon 2206 such that a proximal portion of balloon 2206 remains unconstrained by stent 2208. The proximal portion of balloon 2206 may be slidably advanced and retracted under stent 2242 via side hole 2220. Stent 2208 is crimped to the balloon 2206 to prevent ejection during delivery. The first catheter is an over-the-wire (OTW) catheter having a guidewire lumen 2212 extending from the distal guidewire port 2210 at the distal end of the elongate shaft 2204 to the proximal end of the elongate shaft 2204 into Y-adapter 2214 having a connector 2216. The connector 2216 is preferably a Luer connector and this allows easy coupling with a syringe or other device for lumen flushing or injecting contrast media. When unconnected, the guidewire lumen 2212 exits via connector 2216. A second connector 2218, also preferably a Luer connector allows attachment of an Indeflator or other device to the catheter for inflation of the balloon 2206 via an inflation lumen (not shown) in the elongate shaft 2204. Radiopaque markers may be placed at different locations along the shaft 2204, often near the balloon 2206 and/or stent 2208, to help mark the proximal and distal ends of the stent or balloon, as well as to facilitate alignment of the two catheters during stent deployment, as discussed elsewhere in this specification.

The second catheter 2230 includes an elongate shaft 2232 with a radially expandable balloon 2240 disposed near a distal end of the elongate shaft 2232. A stent 2242 having a proximal portion 2222, a distal portion 2214, and a side hole 2220 is disposed over balloon 2240. The distal portion 2214 is crimped to balloon 2240 to prevent ejection during delivery, while the proximal portion 2222 is partially crimped to balloon 2240 so elongate shaft 2204 may be slidably advanced or retracted under the proximal portion 2222 of stent 2242. The stent may preferably have a length that matches the working length of the balloon, or the stent length may be shorter than the balloon working length. At least a portion of balloon 2206, and stent 2208 are distally offset relative to balloon 2240 and stent 2242 so as to minimize profile of the device. In this embodiment the distal stent 2208 may be deployed in a main branch of the vessel and the other stent 2242 may be deployed in a side branch of the vessel. Alternatively, the distal stent 2208 may be deployed in a side branch of a vessel and the other stent 2242 may be deployed in the main branch of a vessel. The second catheter 2230 is a rapid exchange catheter (RX) having a guidewire lumen 2234 extending from the distal guidewire port 2238 at the distal end of the elongate shaft 2232 to a proximal guidewire port 2236 which is closer to the distal port 2238 than the proximal end of the catheter shaft 2232. A connector 2244, preferably a Luer connector is connected to the proximal end of the elongate shaft 2232 and allows an Indeflator or other device to be coupled with an inflation lumen (not shown) in elongate shaft 2232 for inflation of balloon 2240. Having a portion of shaft 2204 disposed under proximal portion 2222 of stent 2208 helps keep catheter 2202, 2232 parallel and prevents tangling during delivery and as shaft 2204 is slidably advanced or retracted relative to shaft 2232. The first catheter 2202 may be slidably advanced or retracted under the proximal portion 2222 of stent 2242 so that the shaft 2204 passes through the side hole 2220 in stent 2242. Radiopaque markers may be placed at different locations on the shaft 2232, often near the balloon 2240 or stent 2242, to help mark the proximal and distal ends of the stent or balloon, as well to facilitate alignment of the two catheters during stent deployment, as discussed elsewhere in this specification.

Figure 23A:
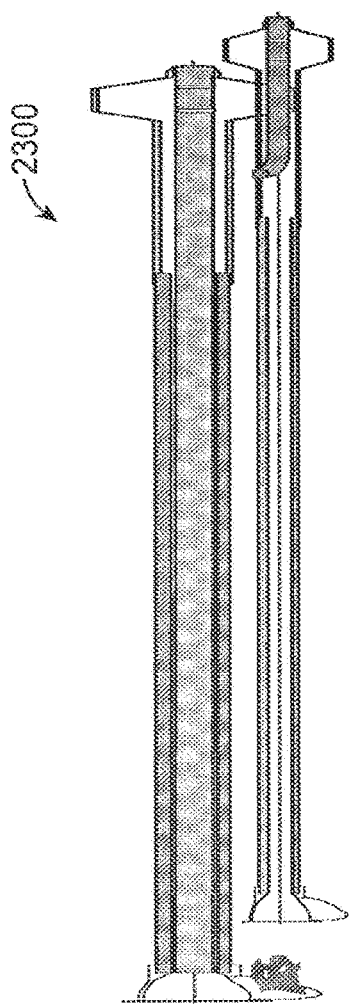
FIGS. 23A-23B illustrate yet another exemplary embodiment of a system having a rapid exchange mother catheter and a rapid exchange daughter catheter.
Figure 23B:
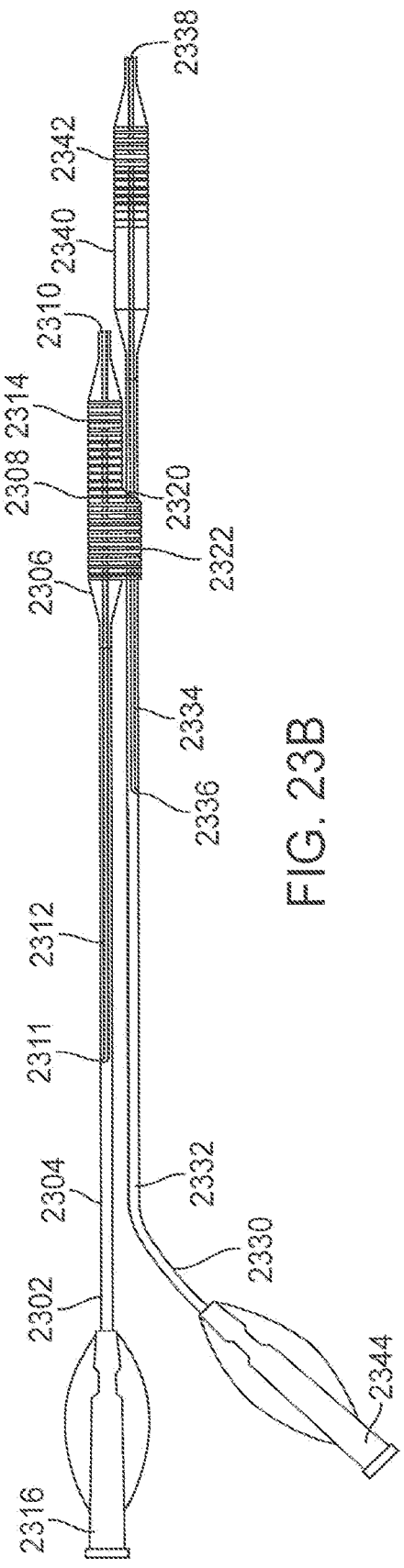
Figure 25A:
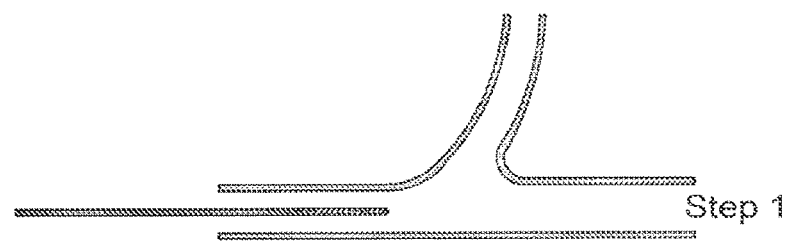
FIGS. 25A-25B, 26A-26B, 27A-27B, 28A-28B, 29A-29B, and 30A-30B illustrate an exemplary method of treating a bifurcation.
Figure 25B:
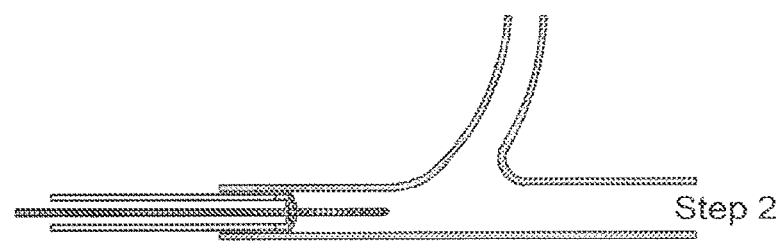
Figure 26A:
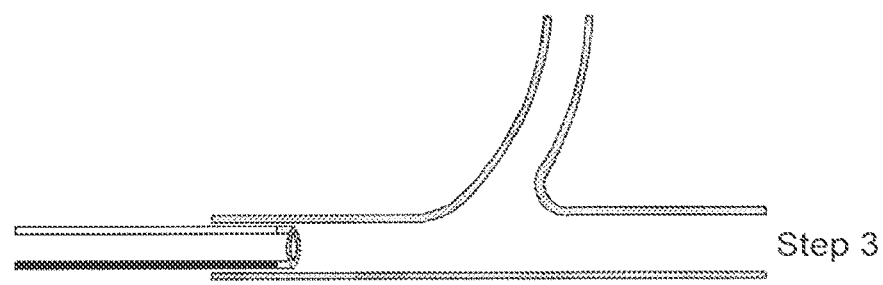
Figure 26B:
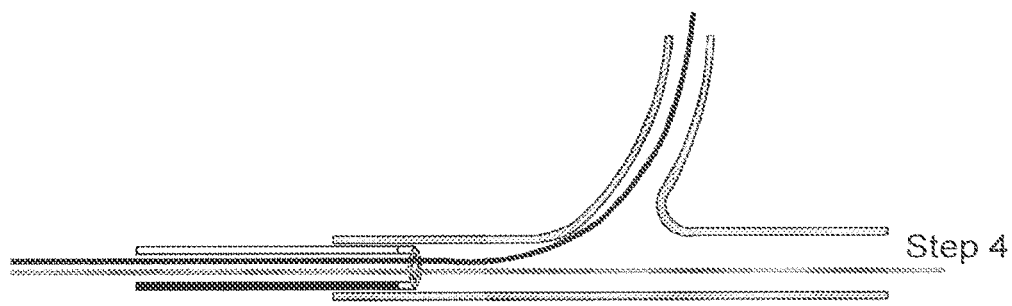
Figure 27A:
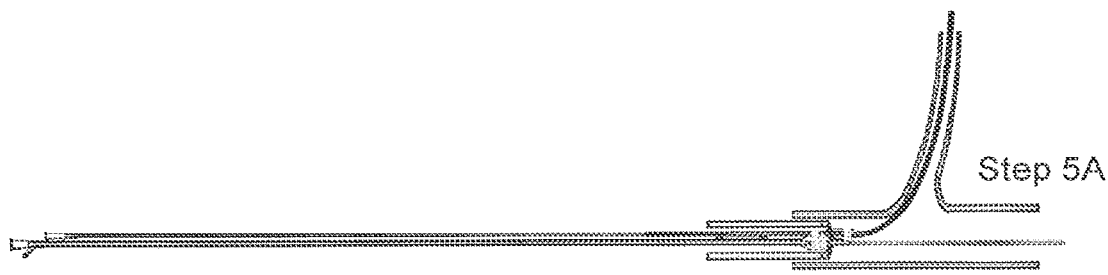
Figure 27B:
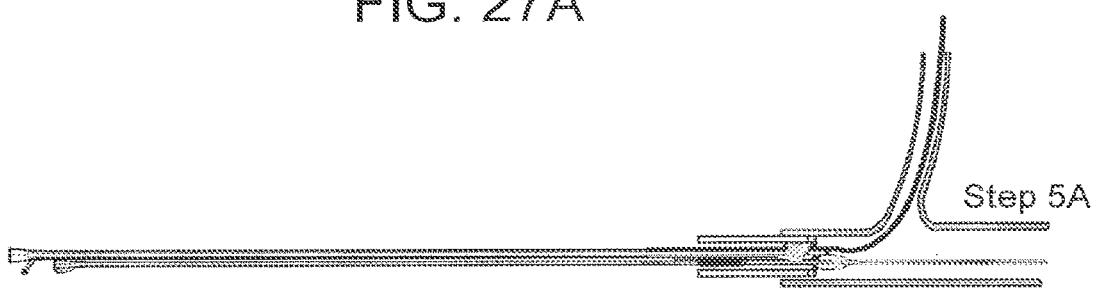
Figure 28A:
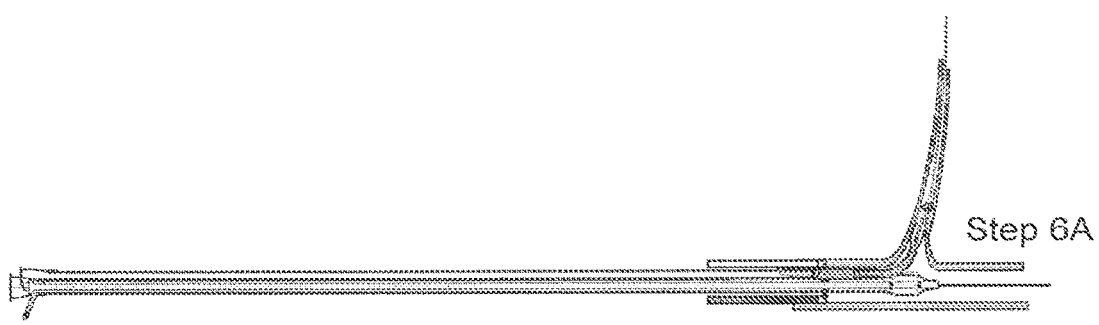
Figure 28B:
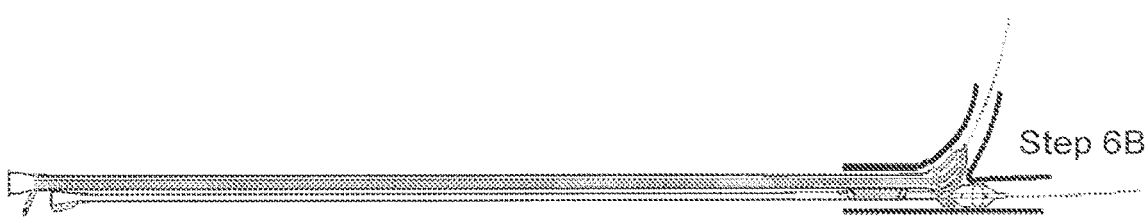
Figure 29A:
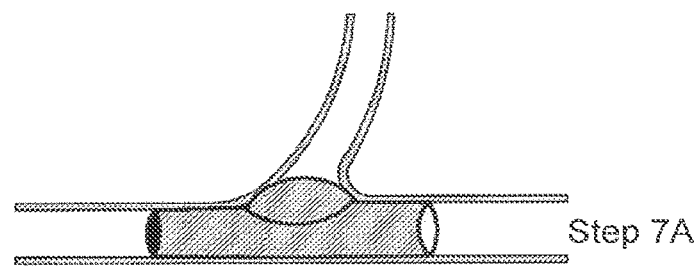
Figure 29B:
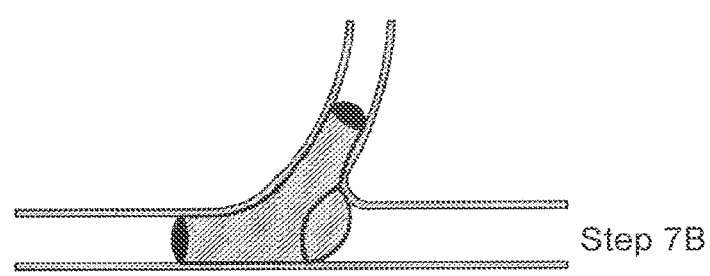
Figure 30A:
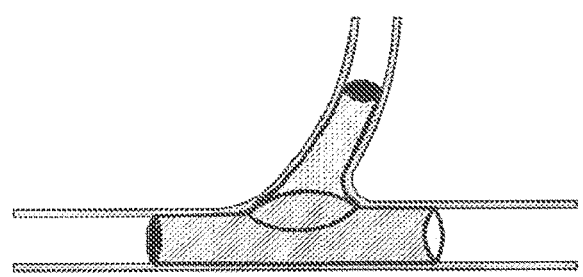
Figure 30B:
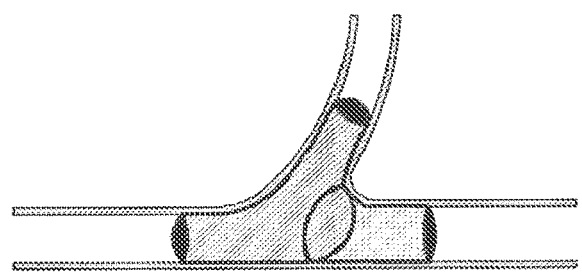

FIG. 23A illustrates a catheter system 2300 having a dual rapid exchange design. FIG. 23B more clearly illustrates the features of the catheter system 2300 in FIG. 23A. The stent delivery system 2300 includes a first catheter 2302, and a second catheter 2330. The first catheter 2302 includes an elongate shaft 2304 with a radially expandable balloon 2306 disposed near a distal end of the elongate shaft 2304. A stent 2308 having a proximal portion 2322, a distal portion 2314 and a side hole 2320 is disposed over the balloon 2306. The distal portion 2314 is crimped to the balloon 2306 to prevent ejection during delivery, while the proximal portion 2322 is partially crimped to the balloon 2306 so the second catheter 2330 may be slidably advanced under the proximal portion 2322 of stent 2308. The first catheter is a rapid exchange catheter (RX) having a guidewire lumen 2312 extending from the distal guidewire port 2310 at the distal end of the elongate shaft 2304 to a proximal guidewire port 2311 which is closer to the distal port 2310 than the proximal end of the catheter shaft 2304. A connector 2316 is coupled with the proximal end of the elongate shaft 2304. The connector 2116 is preferably a Luer connector and this allows easy coupling with an Indeflator or other device for inflation of the balloon 2306. Radiopaque markers may be placed at different locations along the shaft 2304, often near the balloon 2306 and/or stent 2308, to help mark the proximal and distal ends of the stent or balloon, as well to facilitate alignment of the two catheters during stent deployment, as discussed elsewhere in this specification.

The second catheter 2330 includes an elongate shaft 2332 with a radially expandable balloon 2340 disposed near a distal end of the elongate shaft 2332. A stent 2342 is disposed over balloon 2340. The stent may have a length that matches the working length of the balloon, or the stent length may be shorter than the balloon working length. In preferred embodiments, the stent 2342 is shorter than the working length of the balloon 2340 so that a proximal portion of the balloon 2340 is unconstrained by the stent 2342 and this unconstrained portion of the balloon 2340 may be slidably advanced or retracted through side hole 2320 and under proximal portion 2322 of stent 2308 as will be discussed below. Stent 2342 is crimped to balloon 2340 to prevent ejection during delivery. At least a portion of balloon 2340, and stent 2342 are distally offset relative to balloon 2306 and stent 2308 so as to minimize profile of the device. In this embodiment the distal stent 2342 may be deployed in a main branch of the vessel and the other stent 2308 may be deployed in a side branch of the vessel. Alternatively, the distal stent 2342 may be deployed in a side branch of a vessel and the other stent 2308 may be deployed in the main branch of a vessel. The second catheter 2330 is a rapid exchange catheter (RX) having a guidewire lumen 2334 extending from the distal guidewire port 2338 at the distal end of the elongate shaft 2332 to a proximal guidewire port 2336 which is closer to the distal port 2338 than the proximal end of the catheter shaft 2332. A connector 2344, preferably a Luer connector is connected to the proximal end of the elongate shaft 2332 and allows an Indeflator or other device to be coupled with an inflation lumen (not shown) in elongate shaft 2332 for inflation of balloon 2340. Having a portion of shaft 2332 disposed under proximal portion 2322 of stent 2208 helps keep catheters 2302, 2332 parallel and prevents tangling during delivery and as shaft 2332 is slidably advanced or retracted relative to shaft 2304. The second catheter 2330 may also be slidably advanced or retracted under the proximal portion 2322 of stent 2308 so that the shaft 2332 passes through the side hole 2320 in stent 2308. Radiopaque markers may be placed at different locations on the shaft 2332, often near the balloon 2340 or stent 2342, to help mark the proximal and distal ends of the stent or balloon, as well to facilitate alignment of the two catheters during stent deployment, as discussed elsewhere in this specification.

FIG. 24A illustrates a catheter system 2400 having a dual over the wire design. FIG. 24B more clearly illustrates the features of the catheter system 2400 in FIG. 24A. The stent delivery system 2400 includes a first catheter 2402, and a second catheter 2430. The first catheter 2402 includes an elongate shaft 2404 with a radially expandable balloon 2406 disposed near a distal end of the elongate shaft 2404. A stent 2408 having a proximal portion 2422, a distal portion 2414 and a side hole 2420 is disposed over the balloon 2406. The distal portion 2414 is crimped to the balloon 2406 to prevent ejection during delivery, while the proximal portion 2422 is partially crimped to the balloon 2406 so the second catheter 2430 may be slidably advanced under the proximal portion 2422 of stent 2408. The first catheter is an over-the-wire (OTW) catheter having a guidewire lumen 2412 extending from the distal guidewire port 2410 at the distal end of the elongate shaft 2404 to the proximal end of the elongate shaft 2404 into Y-adapter 2414 having a connector 2416. The connector 2416 is preferably a Luer connector and this allows easy coupling with a syringe or other device for lumen flushing or injecting contrast media. When unconnected, the guidewire lumen 2412 exits via connector 2416. A second connector 2418, also preferably a Luer connector allows attachment of an Indeflator or other device to the catheter for inflation of the balloon 2406 via an inflation lumen (not shown) in the elongate shaft 2404. Radiopaque markers may be placed at different locations along the shaft 2404, often near the balloon 2406 and/or stent 2408, to help mark the proximal and distal ends of the stent or balloon, as well to facilitate alignment of the two catheters during stent deployment, as discussed elsewhere in this specification.

The second catheter 2430 includes an elongate shaft 2432 with a radially expandable balloon 2440 disposed near a distal end of the elongate shaft 2432. A stent 2442 is disposed over balloon 2440. The stent may have a length that matches the working length of the balloon, or the stent length may be shorter than the balloon working length. In preferred embodiments, the stent 2442 is shorter than the working length of the balloon 2440 so that a proximal portion of the balloon 2440 is unconstrained by the stent 2442 and this unconstrained portion of the balloon 2440 may be slidably advanced or retracted through side hole 2420 and under proximal portion 2422 of stent 2408 as will be discussed below. Stent 2442 is crimped to balloon 2440 to prevent ejection during delivery. At least a portion of balloon 2440, and stent 2442 are distally offset relative to balloon 2406 and stent 2408 so as to minimize profile of the device. In this embodiment the distal stent 2442 may be deployed in a main branch of the vessel and the other stent 2408 may be deployed in a side branch of the vessel. Alternatively, the distal stent 2442 may be deployed in a side branch of a vessel and the other stent 2408 may be deployed in the main branch of a vessel. The second catheter 2430 is an over-the-wire (OTW) catheter having a guidewire lumen 2434 extending from the distal guidewire port 2438 at the distal end of the elongate shaft 2432 to the proximal end of the elongate shaft 2432 into Y-adapter 2446 having a connector 2448. The connector 2448 is preferably a Luer connector and this allows easy coupling with a syringe or other device for lumen flushing or injecting contrast media. When unconnected, the guidewire lumen 2434 exits via connector 2448. A second connector 2444, also preferably a Luer connector allows attachment of an Indeflator or other device to the catheter for inflation of the balloon 2440 via an inflation lumen (not shown) in the elongate shaft 2432. Having a portion of shaft 2432 disposed under proximal portion 2422 of stent 2408 helps keep catheters 2402, 2430 parallel and prevents tangling during delivery and as shaft 2432 is slidably advanced or retracted relative to shaft 2404. The second catheter 2430 may also be slidably advanced or retracted under the proximal portion 2422 of stent 2408 so that the shaft 2432 passes through the side hole 2420 in stent 2408. Radiopaque markers may be placed at different locations on the shaft 2432, often near the balloon 2440 or stent 2442, to help mark the proximal and distal ends of the stent or balloon, as well to facilitate alignment of the two catheters during stent deployment, as discussed elsewhere in this specification.

In any of the embodiments disclosed herein, commercially available catheters and commercially available stents may be matched up to form the systems illustrated. In still other embodiments, commercially available catheters that are single use devices for treating a single vessel may be mated together in various combinations and coupled together with a polymer sleeve. The operator chooses the two catheters for the patient's anatomy then slides a sized polymer sleeve over both catheters from the distal ends. Once the operator has the catheters aligned the polymer sleeve can be treated with a heat or light source to shrink and bond the two catheters together with friction. The polymer sleeve is made of typical polymers that can act as shrink wrap when treated with a heat or light source. The polymer of the polymer sleeve for example could be manufactured with polyolefin, a chemical used in manufacturing shrink wrap. The polymer sleeve would not crosslink or covalently attach to the catheters, several types of polymers are commercially available and have the requisite properties, thin, strong, not adhesive, and reaction times to their source of ten minutes or less. The polymer sleeves are typically 15 centimeters in length and have various diameters to suit typical catheter diameters 4 French to 20 French. The operator can test that the bond is holding by applying slight pressure prior to the procedure. If the polymer sleeve does not hold tightly the operator may elect to use a smaller diameter polymer sleeve or use more than one polymer sleeve by placing the polymer sleeves adjacent to each other. Alternatively, several smaller sleeves from 1 to 10 centimeters in length could be placed over several different portions of the catheters.

In any of the embodiments discussed herein, a therapeutic agent may be disposed on the stent or balloon and eluted therefrom in a controlled manner into the target treatment area such as a stenotic lesion. Exemplary therapeutic agents help inhibit restenosis, hyperplasia or have other therapeutic benefits. Exemplary anti-hyperplasia agents include anti-neoplastic drugs, such as paclitaxel, methotrexate, and batimastal; antibiotics such as doxycycline, tetracycline, rapamycin, everolimus, biolimus A9, novolimus, myolimus, zotarolimus, and other analogs and derivatives of rapamycin, and actinomycin; amino suppressants such as dexamethasone and methyl prednisolone; nitric oxide sources such as nitroprussides; estrogen; estradiols; and the like. Methods for applying the therapeutic agent to the stent or balloon are well known to those skilled in the art, and have been described in the patent and scientific literature.

Stent Delivery:

FIGS. 25A-30B illustrate an exemplary delivery sequence of a preferred embodiment in eight steps. Step 1 illustrates the introduction of a 0.035 inch guidewire up to the bifurcation. Step 2 illustrates the tracking of a guide catheter over the guidewire. Step 3 illustrates the removal of the guidewire and placement position of the guide catheter. Step 4 illustrates the tracking and placement of a rapid exchange compatible wire in the daughter vessel and an over the wire compatible wire in the mother vessel. Step 5A & 5B illustrate tracking of the catheter system distally over both the guidewires. Step 6A illustrates the inflation of the daughter balloon and placement of the daughter stent and partial deployment of the mother stent. Step 6B illustrates the inflation of the mother balloon to place the distal portion of the mother stent in the mother vessel. Step 7A illustrates mother stent in the main branch with side hole facing the daughter vessel. Step 7B illustrates the bifurcated stent partially in the daughter vessel and daughter ostium completely opened and continuing on to the mother vessel.

In an alternative embodiment the delivery catheter mother balloons having tapered ends to accommodate balloons and stents with non-uniform profiles. For example, the proximal end of the daughter vessel stent may be designed to have a larger circumference than the distal end to compensate for the natural bifurcation anatomy. The daughter vessel balloon would likewise have a taper to properly expand the stent and ensure complete apposition. Additionally, it is possible to design the mother stent to expand differentially along its profile to compensate for a larger arterial diameter at the carina or ostium. In other words, the proximal and distal ends of the mother vessel balloon and mother vessel stent would be smaller in circumference while the center portion of the mother vessel stent would have a larger circumference. In an alternative embodiment the mother vessel balloon has tapered ends to accommodate the distal balloon catheter portion and guidewire lumen. Further, the mother vessel balloon may be designed for differential expansion to accommodate natural vessel anatomy.

In a preferred embodiment the distal (daughter) balloon catheter portion is crimped with a half stent on a rapid exchange catheter. The daughter vessel stent is about 4-20 millimeters long and the daughter vessel balloon is approximately twice as long in length. The mother vessel stent is about 10-30 millimeters long, and is differentially crimped to allow independent operation of the daughter balloon catheter portion. The distal portion of the mother vessel stent is crimped tightly enough to keep the entire stent from unintentionally dislodging during the procedure. The proximal portion of the mother vessel stent is crimped just tightly enough to reduce the crossing profile and to allow the daughter balloon catheter portion to be moved distal or proximal relative to the mother balloon catheter portion. The proximal (mother) balloon catheter portion is an over the wire type design with the mother vessel balloon preferably about 3 centimeters proximal to the daughter vessel balloon. In an alternative embodiment a stent is designed to allow differential expansion of the middle portion of the stent relative to the proximal and distal ends. In particular, the design facilitates the placement of the stent across a bifurcation lesion in the mother vessel because it has a larger circumference in the middle portion relative to the ends than a stent with a constant profile. Further, the profile can be adjusted so that the largest circumference can be placed proximal or distal to the midpoint of the stent. In the particular embodiment the largest circumference is distal to the midpoint of the stent, but could be easily reversed for variable patient anatomy. Partial crimping has the following features that make it possible to maintain sufficient stent retention during delivery and placement and still allows the secondary system adjustability and deliverability.

Figure 31:
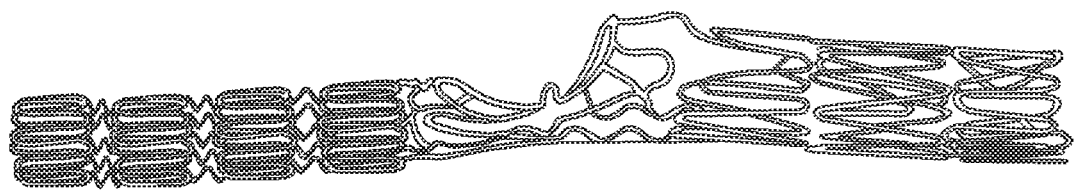
FIG. 31 illustrates an exemplary embodiment of a stent.
Figure 32:
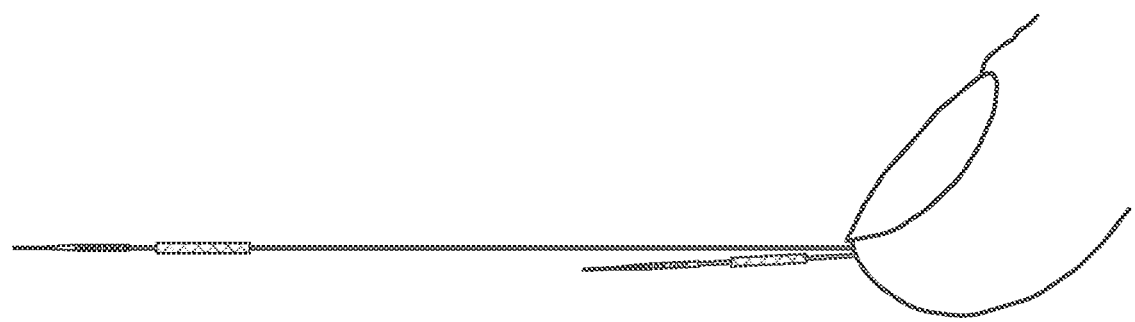
FIG. 32 illustrates an exemplary embodiment of a system having a mother catheter and a daughter catheter.
Figure 33:
FIG. 33 highlights the distal portion of the system illustrated in FIG. 32.
Figure 34:
FIG. 34 illustrates alignment of the stents in FIGS. 32-33.

FIG. 31 shows a partially crimped bifurcation stent prior to placement on any balloon catheter. FIG. 32-34 illustrate an embodiment of the present invention in three steps. First, the bifurcation stent is partially crimped over approximately one-third its distal portion onto the mother catheter balloon and the daughter catheter is loaded through the mother catheter and mother stent where the daughter stent can be crimped separately. Second, the daughter stent is crimped and pulled back proximally to align the daughter stent proximal end near the mother stent distal end. Third and final the proximal portion of the mother stent can be crimped to reduce the outer diameter; yet still allow independent movement of the two catheters relative to each other.

Figure 35:
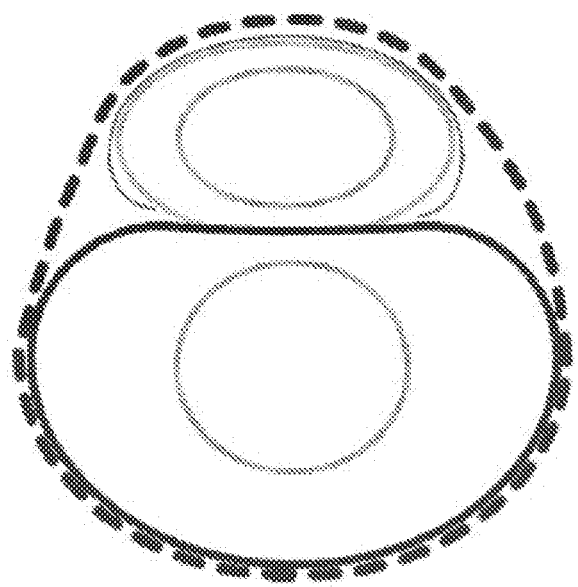
FIG. 35 illustrates a cross-section of a stent crimped over a mother catheter and a daughter catheter.

FIG. 35 illustrates a cross section of a mother and daughter balloon catheter system without a daughter stent. The daughter catheter is on top of the mother catheter. The mother stent is differentially crimped around the mother catheter balloon and daughter catheter because the daughter catheter profile is smaller than the mother catheter. The differential crimping is non-uniform and can create various cross sectional shapes to accommodate different catheter designs, balloon designs, and stent designs. For example, pear shaped or a figure eight are possible configurations. The current embodiment is designed to reduce the profile as much as possible. In one preferred method of manufacturing a protective sheet is placed between the two catheters. The protective sheet only needs to cover the portions that will come in contact during the crimping process, then the protective sheet can be removed.

Figure 36:
FIG. 36 illustrates a stent disposed over a mother catheter and a daughter catheter.

FIG. 36 Illustrates a side view of the mother stent mounted on the mother catheter balloon and the daughter catheter mounted on the mother catheter through the mother stent. The distal portion of the mother stent will be crimped under standard conditions to hold stent firmly to the mother balloon and mother catheter. The proximal portion of the mother stent is the partially crimped to reduce the profile; but still allows the daughter catheter freedom to move proximal or distal relative to the mother catheter. This embodiment illustrates that the stent is differentially crimped in both the circumferential and longitudinal direction. The amount of crimping will be determined by the stent design and size, catheter dimensions, and balloon dimensions; thus the crimping is differential along the longitudinal axis.

Figure 37:
FIG. 37 illustrates a stent disposed over a mother catheter and a daughter catheter, and a stent disposed over the daughter catheter.

FIG. 37 illustrates a side view of the mother stent mounted on the mother catheter balloon and the daughter catheter mounted on the mother catheter through the mother stent. The daughter catheter also includes a stent that can be crimped under standard conditions. The distal portion of the mother stent will be crimped under standard conditions to hold stent firmly to the mother balloon and mother catheter. In one experiment, this arrangement was tested to determine the strength of the distal crimping of the mother stent by pulling the daughter catheter and stent proximally; the results were that the daughter catheter successfully passed through the crimped mother stent and still retained the daughter stent as well. Additional features may be utilized during the crimping process such as adding a slight positive internal pressure to the balloon so that the final balloon surface pillows about 0.002 inch beyond the outer diameter of the stent. This process can yield a design that protects the stent from engaging with the vessel thus reducing friction and improving stent retention at the same time.

Further, this process improves safety and reduces trauma to the vessel. While the above embodiment discloses a bifurcation stent that is crimped at or about its distal half; this is not a limitation. The stent could be differentially crimped along its axis depending upon stent design, for example; if a hole in the side of a stent was not centered along the axis. It may be preferential to have the distal crimped portion of the bifurcation stent extend just distal of the hole that the daughter catheter to pass through. Alternatively, the distal crimped portion could extend partially or entirely over the hole that the daughter catheter passes through.

Figure 38A:
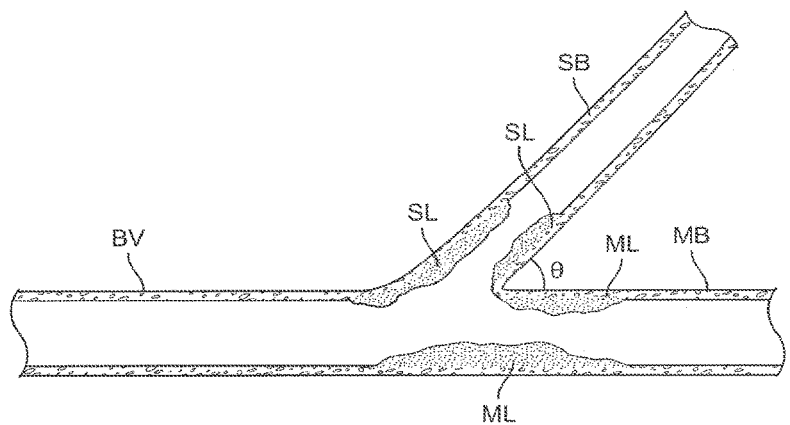
FIGS. 38A-38M illustrate an exemplary method of treating a bifurcation.
Figure 38B:
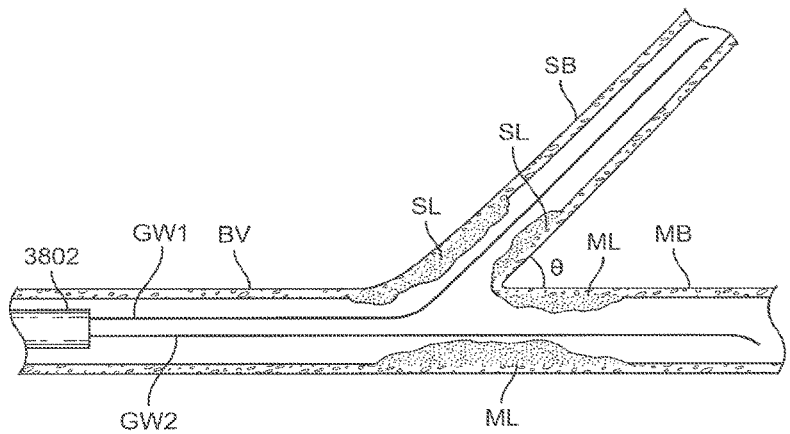
Figure 38C:
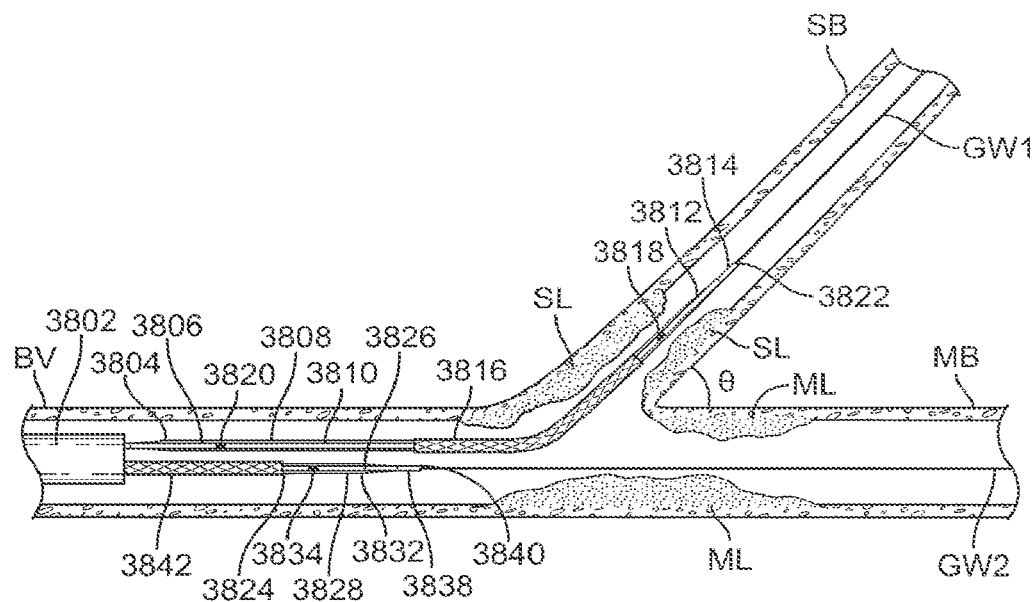

FIGS. 38A-38M more clearly illustrate an exemplary method of treating a bifurcated vessel such as a bifurcated coronary artery. In FIG. 38A the bifurcated vessel BV includes a side branch vessel SB and a main branch vessel MB. The main branch has a main branch lesion ML, and the side branch has a side branch lesion SL. The angle between the side branch and the main branch is referred to as the bifurcation angle, and is indicated by θ. When the bifurcation angle θ is less than about 60 to 70 degrees, the distal most stent of the system can be effectively positioned in the side branch. However, when the bifurcation angle is greater than or equal to about 60 to 70 degrees, it becomes more challenging to position the distal most stent in the side branch. Moreover, when the distal stent is retracted proximally toward the stent having the side hole (discussed below), the catheter shaft may bind against the side hole resulting in damage to the catheter shaft and/or stent. Therefore, in preferred embodiments, when the bifurcation angle is less than about 60 to 70 degrees, the distal most stent is preferably positioned in the side branch and the proximal most stent is advanced into the main branch. When the bifurcation angle is greater than or equal to about 60 to 70 degrees, the distal most stent is positioned in the main branch and the other stent is positioned partially in the main branch and partially in the side branch. This is not intended to limit the use of the catheter system, and either stent may be placed in either side branch or main branch depending on operator preference. In FIG. 38B, a guidecatheter 3802 is advanced distally until its distal end is adjacent the bifurcation. A pair of guidewires GW1, GW2 are then advanced from the guidecatheter 3802 distally toward the bifurcation such that the first guidewire GW1 is advanced into the side branch SB and so that the distal tip of the first guidewire GW1 is distal of the side branch lesion SL. Similarly, the second guidewire GW2 is also advanced distally in the main branch MB until the distal tip of the second guidewire GW2 is distal of the main branch lesion ML. In FIG. 38C, a stent delivery system having a first catheter 3804 and a second catheter 3824 are advanced distally from the guidecatheter 3802 toward the bifurcation. The first delivery catheter 3804 includes an elongate catheter shaft 3806 and a radially expandable balloon 3808 disposed over a distal portion of elongate shaft 3806. A balloon expandable stent 3816 is disposed over the balloon 3808. In this exemplary embodiment, the stent is shorter than the working length of the balloon 3808, therefore a proximal portion 3810 of the balloon 3808 and a distal portion 3812 are unconstrained by the stent 3816. The proximal portion 3810 may be retracted under a portion of the second stent 3842 and thus when balloon 3808 is inflated, it will radially expand stent 3816 and a portion of stent 3842. However, this is not intended to be limiting, and the stent length may be substantially equal to the working length of the balloon, or it may a shorter length as previously discussed. Proximal radiopaque marker 3820 and distal radiopaque marker 3818 help define proximal and distal ends of the stent 3816 as well as proximal and distal ends of the balloon 3808. The radiopaque markers will also be used to help align the two catheters during treatment of the bifurcation, as will be discussed below. The distal tip 3814 may be a soft durometer polymer thereby minimizing trauma to the vessel during delivery. A distal guidewire port 3822 extends from the distal tip 3814 and allows guidewire GW1 to exit or enter a guidewire lumen (not shown) in the elongate shaft 3806. The first catheter 3804 may be a rapid exchange catheter or an over-the-wire catheter, examples of which have been disclosed above. The second catheter 3824 (best seen in FIG. 38D) includes an elongate catheter shaft 3826 with a radially expandable balloon 3828 disposed over a distal region of the elongate shaft 3826. A stent 3842 having a side hole 3844 is disposed over the balloon 3828. The length of the stent 3842 may be substantially the same as the working length of the balloon 3828 or it may be less than the working length. In this exemplary embodiment, the stent 3842 has a length shorter than the working length of the balloon 3828 thus a proximal portion 3830 and a distal portion 3832 remain unconstrained by the stent 3842. Proximal radiopaque marker 3836 and distal radiopaque marker 3834 help define the proximal and distal ends of the stent 3842 as well as the proximal and distal ends of the balloon 3828. The radiopaque markers will also be used to help align the two catheters during treatment of the bifurcation, as will be discussed below. The distal tip 3838 may be a soft durometer polymer thereby minimizing trauma to the vessel during delivery. A distal guidewire port 3840 extends from the distal tip 3838 and allows guidewire GW2 to exit or enter a guidewire lumen (not shown) in the elongate shaft 3826. The second catheter 3824 may be a rapid exchange catheter or an over-the-wire catheter, examples of which have previously been disclosed above.

Referring back to FIG. 38C, the bifurcation angle is less than about 60 to 70 degrees, and the first catheter 3804 and the second catheter 3824 are further advanced distally so that the first catheter tracks over the first guidewire GW1 into the side branch SB while the second catheter 3824 tracks over the second guidewire GW2 in the main branch MB toward the main branch lesion ML. Because the first catheter 3804 is coupled with the second catheter 3824 via stent 3842, both catheters are advanced distally simultaneously thereby reducing procedure time, although this is not meant to be limiting, as each catheter may be advanced independently of the other. In this embodiment the first balloon 3808 and first stent 3816 are distal to the second balloon 3828 and second stent 3842. This axial offset minimizes the system profile.

Figure 38D:
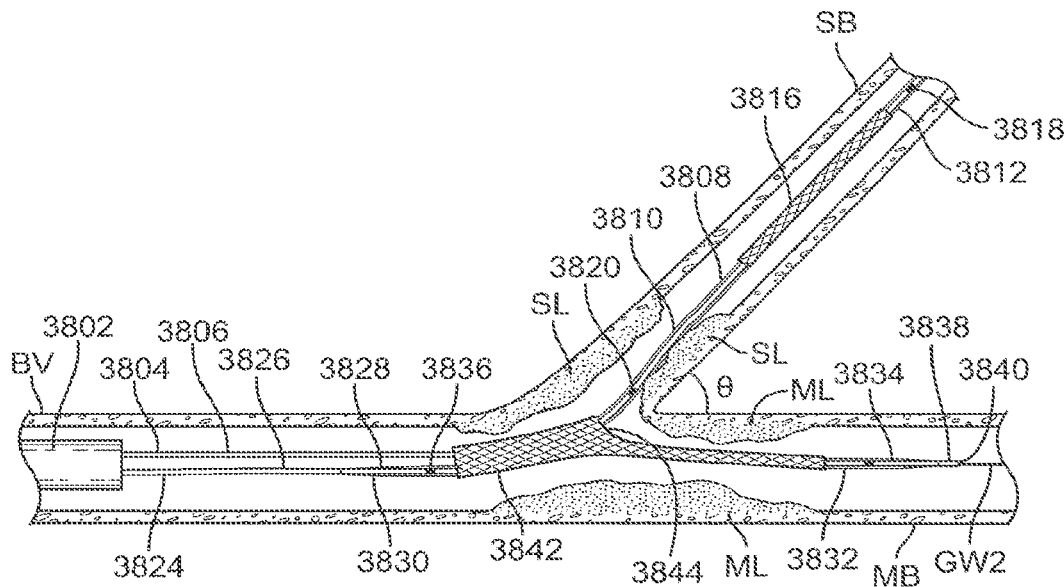

In FIG. 38D, both catheters 3804, 3824 are advanced further distally toward the bifurcation until the first stent 3816 is distal to the side branch lesion SL and the second stent 3842 traverses the main branch lesion ML and the side hole 3844 is adjacent the ostium of the side branch SB. Advancement of both catheters 3804, 3824 is again performed simultaneously, although they could also be advanced independently of one another. The operator will feel resistance against further advancement of the catheters 3804, 3824 because as the catheters are advanced further distally, the two catheter shafts 3806, 3826 will spread apart relative to one another as they are forced against the carina of the bifurcation. However, a portion of the first elongate shaft 3806 is disposed under a portion of the second stent 3842, therefore the two shafts 3806, 3826 can only spread apart so far. Thus, when an operator feels resistance against further advancement of the catheter shafts, the operator knows that both catheters 3804, 3824 and their associated stents and balloons are properly positioned relative to the bifurcation.

Figure 38E:
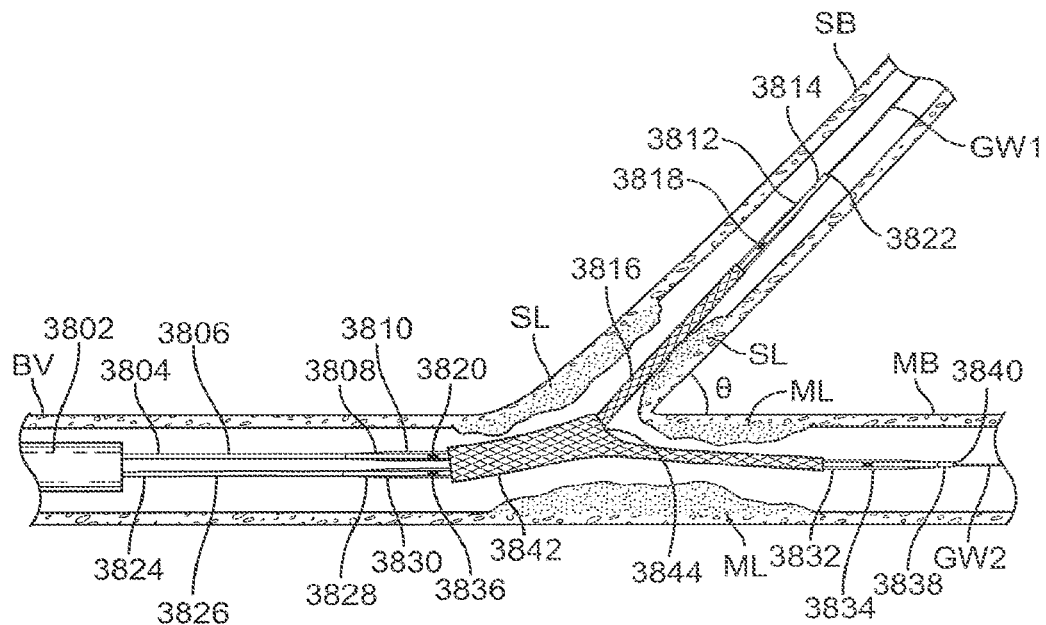

In FIG. 38E, the first catheter 3804 is retracted proximally relative to the second catheter 3824. Because a portion of the first catheter shaft 3806 is disposed under a portion of the second stent 3842, the first shaft 3806 is slidably retracted into side hole 3844 and the first shaft 3806 and proximal portion 3810 of balloon 3808 are slidably retracted under a portion of second stent 3842. The first shaft is proximally retracted until proximal radiopaque marker 3820 lines up with proximal radiopaque marker 3836 so that a proximal end of the first stent 3816 will be aligned with the side hole 3844 in the second stent 3842. An operator may feel resistance during retraction of the first elongate shaft 3806 relative to the second elongate shaft 3826 when the ends of the stents 3816, 3842 engage one another. Stent 3842 has a distal portion crimped to balloon 3828 to prevent ejection during delivery, and a proximal portion is partially crimped thereto or uncrimped to allow catheter 3804 to slide thereunder. Crimping of the stent is disclosed in greater detail in U.S. Provisional Patent Application No. 61/317,198, previously incorporated by reference. The ends of the stents may butt up against one another, overlap with one another, interleave with one another, or combinations thereof. Additional details related to the engagement of the stents is disclosed in U.S. Provisional Patent Application No. 61/317, 121 also previously incorporated herein by reference. Both stents 3816, 3842 are disposed adjacent their respective lesions SL, ML, and the side hole 3844 is in rough alignment with the ostium to the side branch SB and the side branch stent 3816.

Figure 38F:
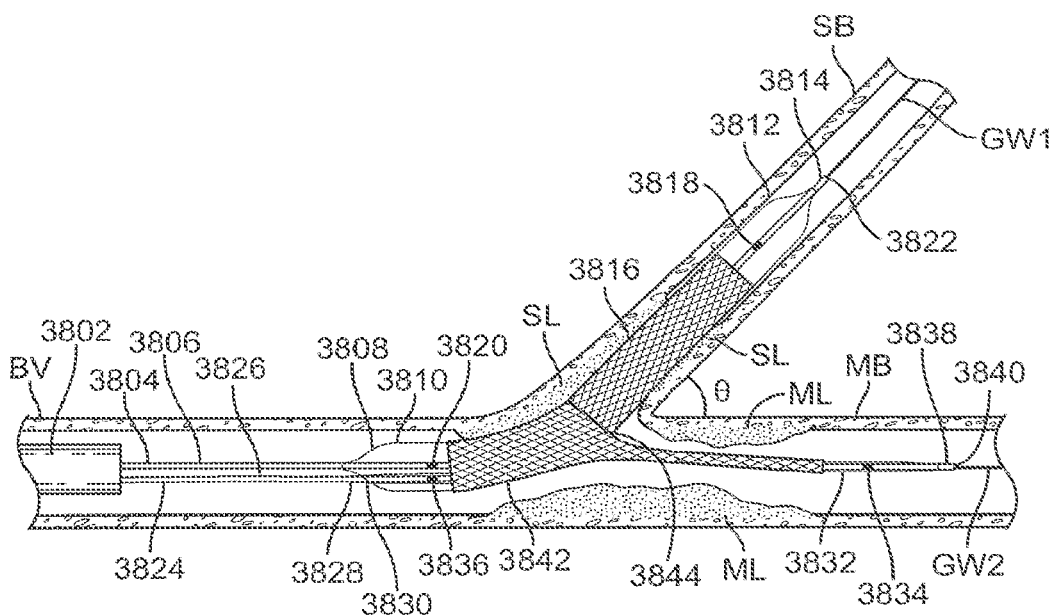

In FIG. 38F, the balloon 3808 is radially expanded, often with contrast medium, saline, or a combination thereof thereby radially expanding the first stent 3816 into engagement with the side branch lesion SL and the walls of the side branch. A proximal portion 3810 and a distal portion 3812 of the balloon 3808 will also expand, thus a proximal portion of the second stent 3842 will also be radially expanded. Expansion of the stents occurs simultaneously. Since a portion of balloon 3808 also passes through side hole 3844, expansion of balloon 3808 also partially expands the side hole 3844 and also aligns the side hole 3844 with the ostium of the side branch.

Figure 38G:
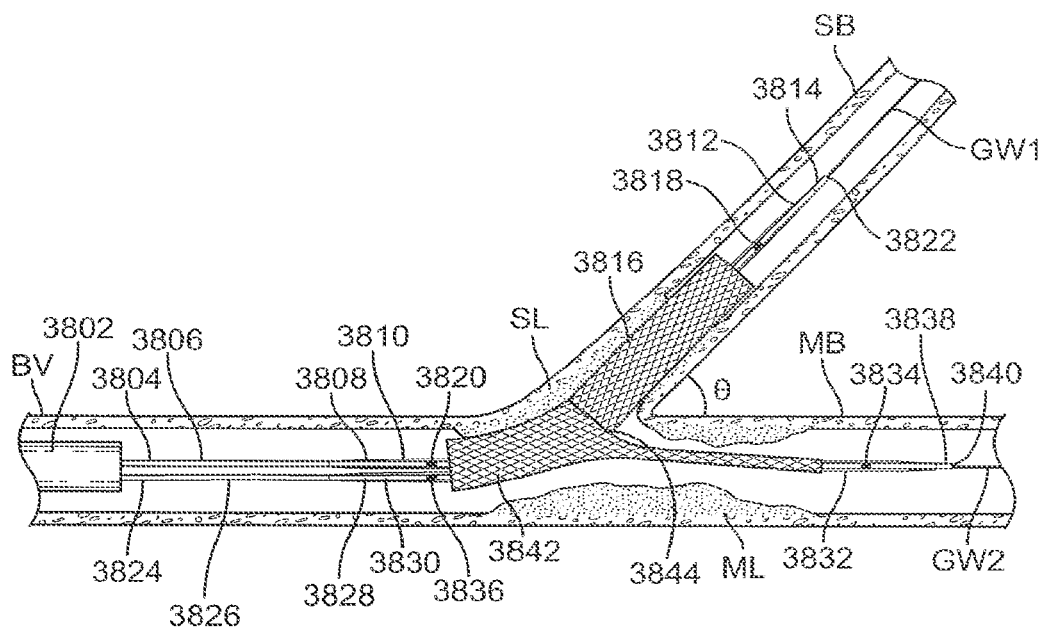
Figure 38H:
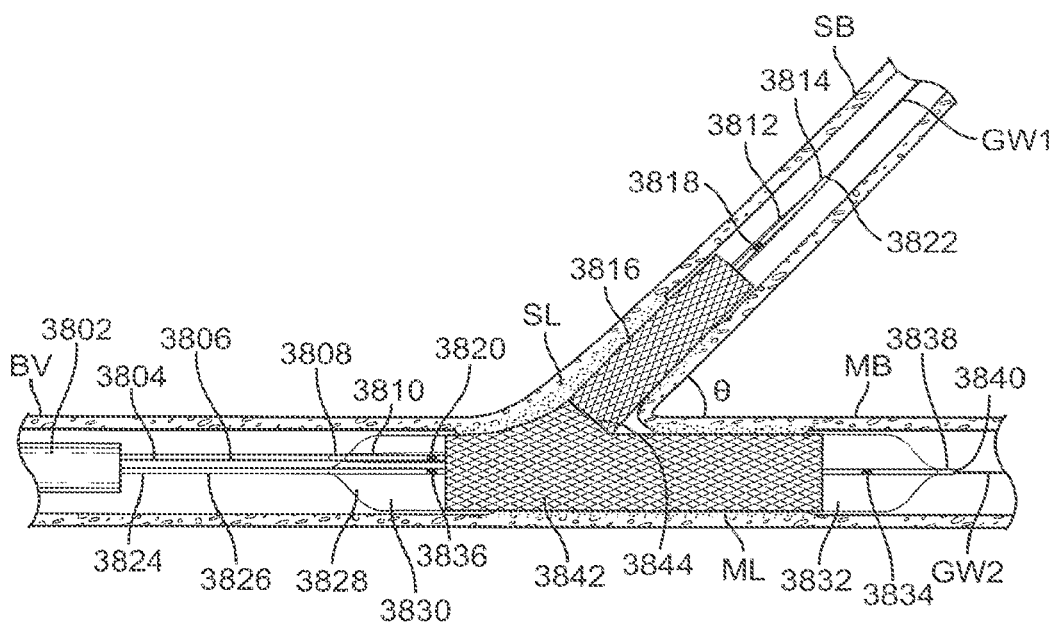

In FIG. 38G the balloon 3808 is contracted, and then in FIG. 38H the other balloon 3828 is radially expanded, with contrast medium, saline, or a combination thereof, thereby further radially expanding the second stent 3842. Expansion of balloon 3828 expands the proximal portion of the stent 3842 into engagement with the main branch vessel wall and main branch lesion ML, and the distal portion of the stent 3842 is also radially expanded into the main branch vessel wall as well as the main branch lesion ML. The side hole 3844 is also further aligned with the ostium of the side branch SB.

Figure 38I:
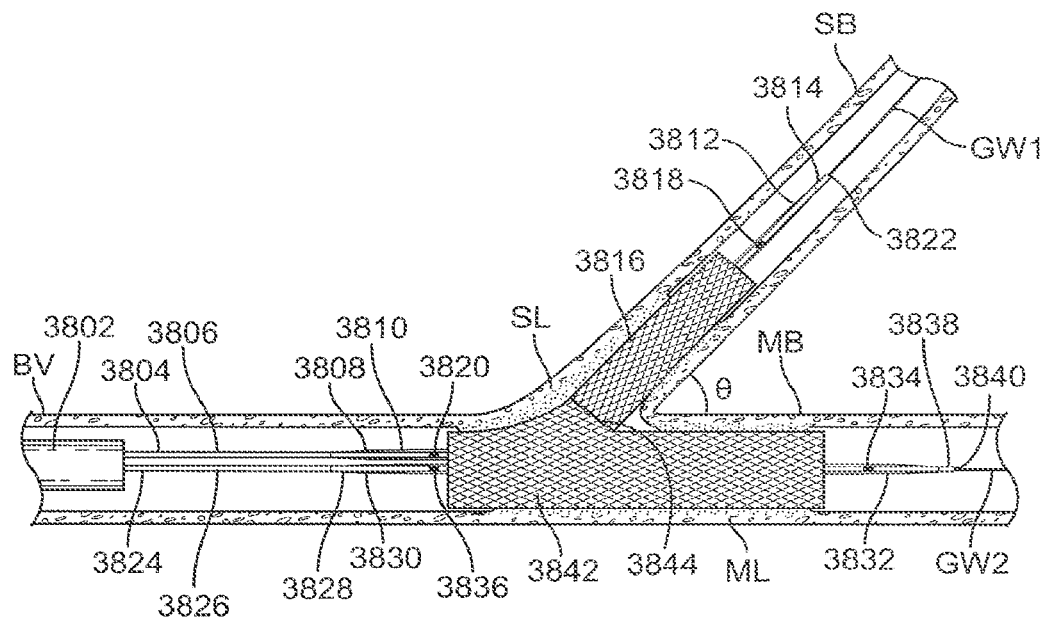
Figure 38J:
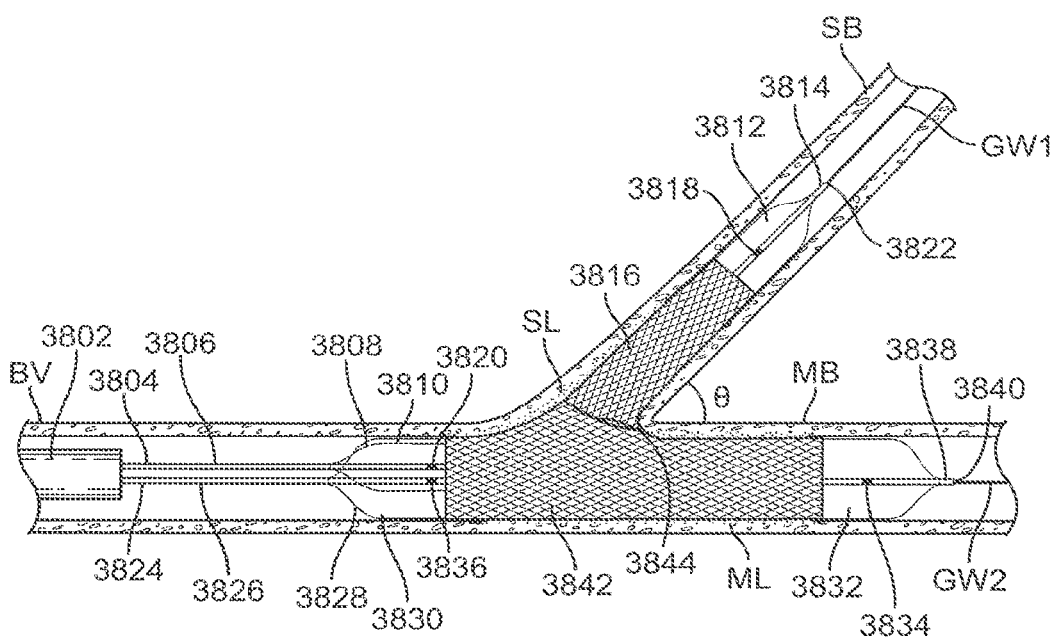

Referring now to FIG. 38I, balloon 3828 is contracted and then both balloons are simultaneously inflated in a "kissing balloon" technique as seen in FIG. 38J. Both balloons 3808, 3828 are inflated with contrast medium, saline, or combinations thereof until they engage one another and are fully expanded in the main branch MB and side branch SB. The kissing balloon technique ensures that both stents 3816, 3842 are fully expanded and in full apposition with their respective vessel wall and lesion. Additionally, the kissing balloon technique lines up the proximal end of the first sent 3816 with the side hole 3844 in the second stent 3842, thereby ensuring that continuous and smooth scaffolding from the main branch MB into the side branch SB. Also, the kissing balloons technique ensures that the side hole does not block the ostium to the side branch thereby avoiding "stent jailing," or disrupting blood flow into the side branch.

Figure 38K:
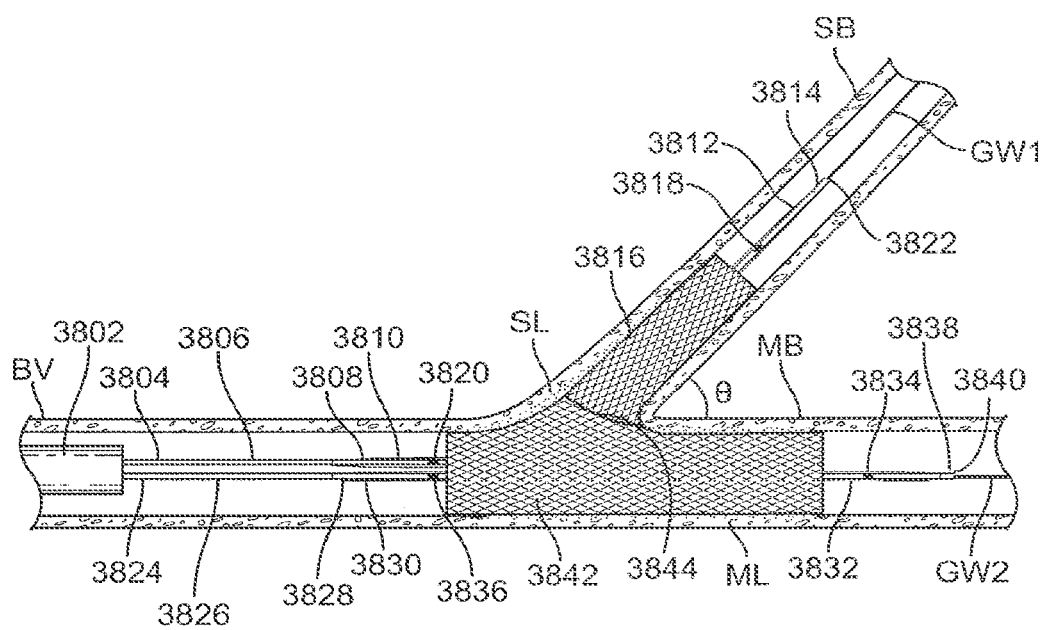
Figure 38L:
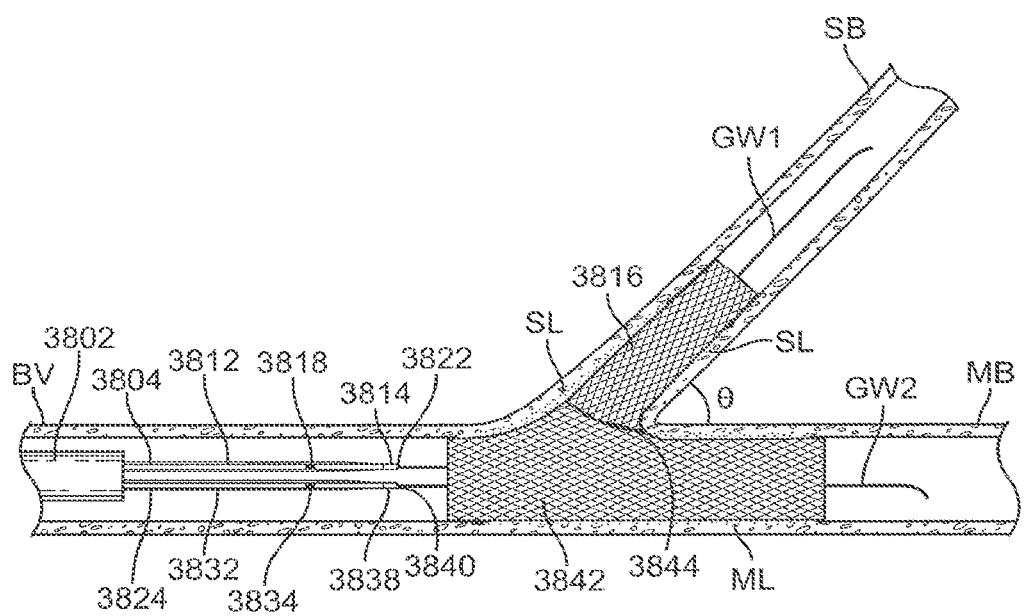
Figure 38M:
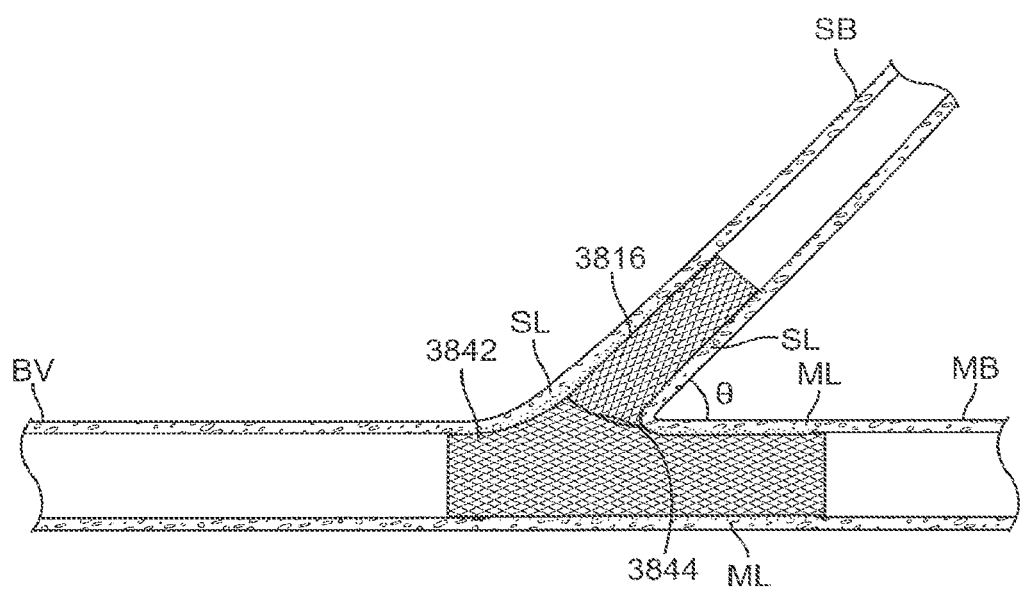

In FIG. 38K, both balloons 3808, 3828 are contracted, and in FIG. 38L both catheters 3804, 3824 are retracted proximally. The catheters may be retracted simultaneously or independently of one another. The first catheter 3804 is retracted through both stents 3816, 3842 and also passes through the side hole 3844. The second catheter 3824 is retracted through the second stent 3842. In FIG. 38M, both catheters 3804, 3828 have been removed, as well as the guidecatheter 3802 and both guidewires GW1, GW2. Stents 3816, 3842 remain implanted in at the bifurcation. Optionally, the stents or balloons may contain therapeutic agents such as those previously discussed, and these may elute out into the lesion at a controlled rate in order to help prevent restenosis.

FIGS. 39A-39M more clearly illustrate another exemplary embodiment of a method for treating a bifurcated vessel. This method is similar to that previously disclosed, with the major difference being that the distal-most catheter is used to treat the main branch vessel, and the proximal-most catheter is used to treat the side branch vessel. In the previous embodiment, the distal-most catheter is used to treat the side branch vessel and the proximal-most catheter is used to treat the main branch.

Figure 39A:
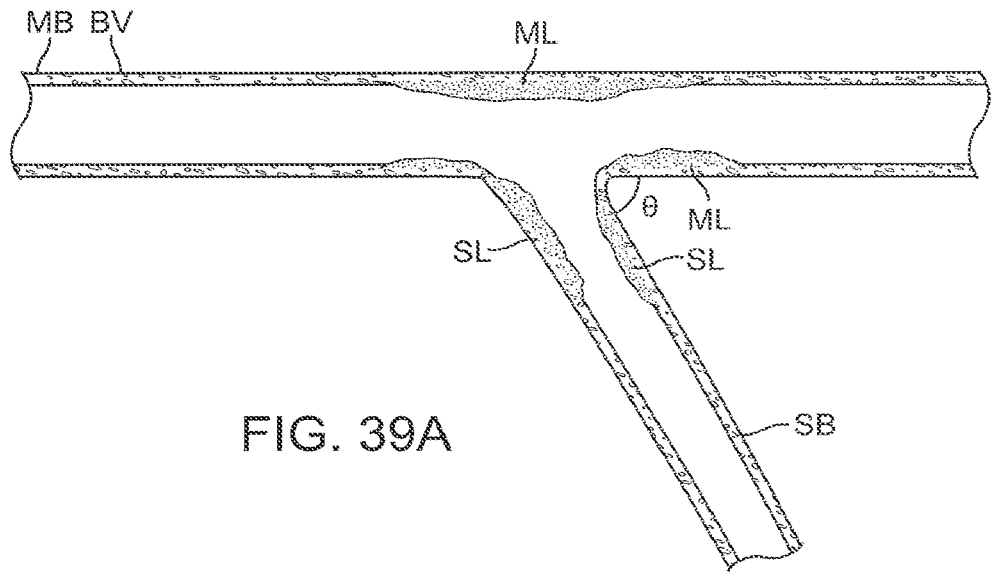
FIGS. 39A-39M illustrate another exemplary method of treating a bifurcation.
Figure 39B:
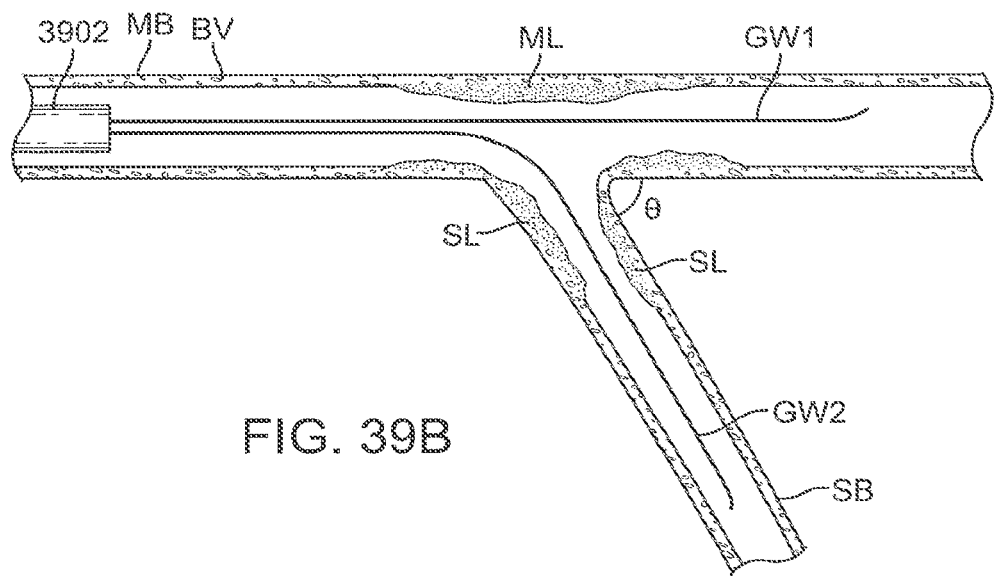

In FIG. 39A, the bifurcated vessel BV includes a side branch vessel SB and a main branch vessel MB. The main branch has a main branch lesion ML, and the side branch has a side branch lesion SL. The angle between the side branch and the main branch is referred to as the bifurcation angle, and is indicated by θ. When the bifurcation angle θ is less than about 60 to 70 degrees, the distal most stent of the system can be effectively positioned in the side branch. However, when the bifurcation angle is greater than or equal to about 60 to 70 degrees, it becomes more challenging to position the distal most stent in the side branch. Moreover, when the distal stent is retracted proximally toward the stent having the side hole (discussed below), the catheter shaft may bind against the side hole resulting in damage to the catheter shaft and/or stent. Therefore, in preferred embodiments, when the bifurcation angle is less than about 60 to 70 degrees, the distal most stent is preferably positioned in the side branch and the proximal most stent is advanced into the main branch. When the bifurcation angle is greater than or equal to about 60 to 70 degrees, the distal most stent is positioned in the main branch and the other stent is positioned partially in the main branch and partially in the side branch. This is not intended to limit the use of the catheter system, and either stent may be placed in either side branch or main branch depending on operator preference. In FIG. 39B, a guidecatheter 3902 is advanced distally into the vessel until it is adjacent the bifurcation and the lesions ML, SL. A first guidewire GW1 is advanced distally in the main branch MB until it is distal of the main branch lesion ML. A second guidewire is also advanced distally until it enters the side branch SB and it is distal of the side branch lesion SL.

Figure 39C:
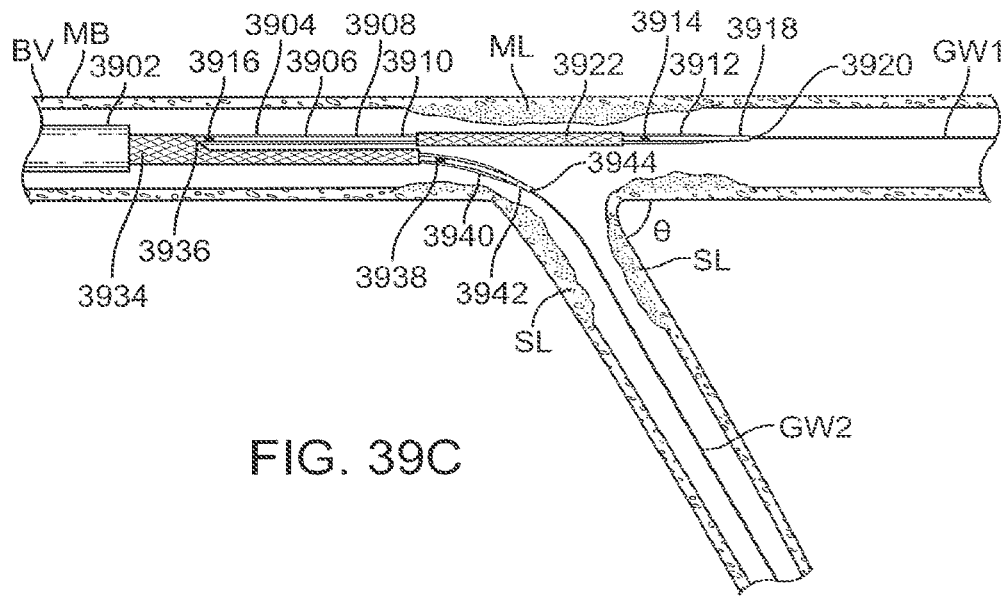

In FIG. 39C, a treatment system having a first catheter 3904, and a second catheter 3924 are advanced distally through the guidecatheter 3902 toward the bifurcation. The two catheters 3904, 3924 may be advanced independently of one another, or the two catheters may preferably be advanced simultaneously. The first catheter 3904 includes an elongate shaft 3906 with a radially expandable balloon 3908 on a distal portion of the elongate shaft 3906. A stent 3922 is disposed over the balloon 3908. The length of the stent 3922 may substantially match the working length of the balloon 3908, or it the length of the stent 3922 may be less than the working length of the balloon 3908 such that a proximal portion 3910 and a distal portion 3912 of the balloon remains unconstrained by the stent 3922. A proximal radiopaque marker 3916 and a distal radiopaque marker 3914 may be used to help determine the proximal and distal ends of the balloon 3908 as well as the proximal and distal ends of the stent 3922. A soft durometer polymer tip may be used on the distal portion of the catheter shaft 3906 so as to prevent trauma to the vessel during delivery, and the catheter shaft 3906 has a distal guidewire port 3920 to allow a guidewire GW1 to enter or exit a guidewire lumen (not shown) in the catheter shaft 3906. The first catheter 3904 may be a rapid exchange catheter or it may be an over-the-wire catheter. The second catheter 3924 (best seen in FIG. 39D) includes an elongate shaft 3926 having a radially expandable balloon 3928 on a distal portion thereof. A second stent 3934 is disposed over the second balloon 3928. The stent length may substantially match the working length of the balloon, or it may be less. In this embodiment, the length of stent 3934 is less than the working length of balloon 3928, thus a proximal portion 3930 and a distal portion 3940 of the balloon remain unconstrained by the stent 3934. A portion of the first elongate shaft 3906 is disposed under a proximal portion of the second stent 3934, and the stent 3934 also has a side hole 3936 so that the first elongate shaft 3906 may exit therefrom. The first elongate shaft 3906 may slide under the stent 3934 relative to the second elongate shaft 3926, thus a proximal portion 3910 of balloon 3908 is also disposed under stent 3934. When balloon 3908 is expanded, a proximal portion of stent 3934 will also be expanded. The second catheter shaft 3926 also includes a proximal radiopaque marker 3932 and a distal radiopaque marker 3938 that help identify the proximal and distal ends of the balloon 3928 and the proximal and distal ends of the stent 3934. The second catheter 3924 also has a soft durometer polymer tip 3942 that helps minimize trauma to the vessel during delivery, and a distal guidewire port 3944 allows a guidewire to be inserted or to exit from a guidewire lumen (not shown) in the elongate shaft 3926. The second catheter 3924 may be an over-the-wire catheter or it may be rapid exchange. The first stent 3922 and balloon 3908 are distal to the second stent 3939 and second balloon 3928.

Figure 39D:
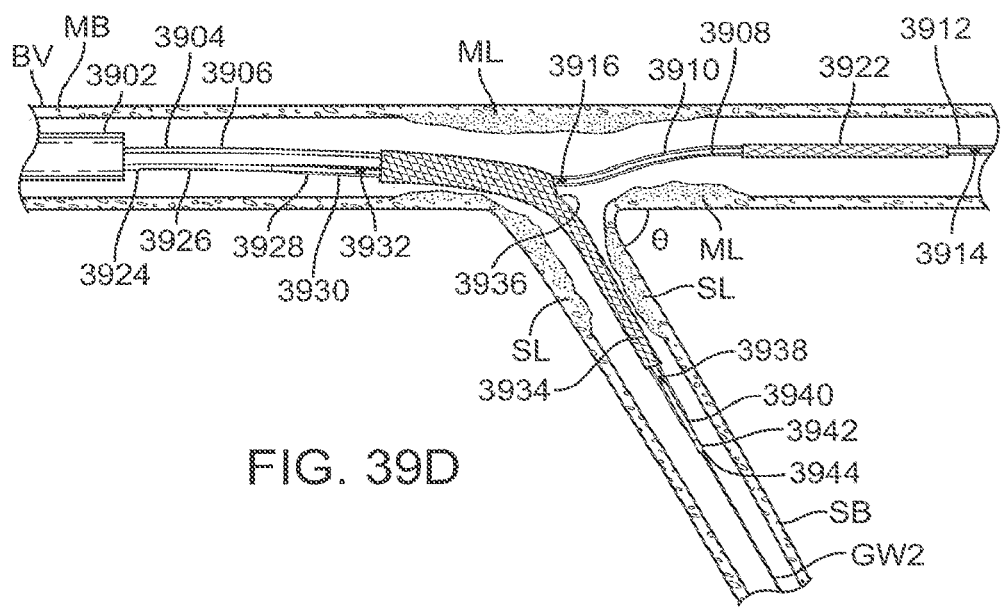

In FIG. 39D, the bifurcation angle θ is greater than about 60 to 70 degrees. Both catheters 3904, 3924 are further advanced distally toward the bifurcation until the first stent 3922 is distal to the main branch lesion ML, and the second stent 3934 is partially disposed in the side branch SB adjacent the side branch lesion SL, and the stent 3934 is also disposed in the main branch MB adjacent the main branch lesion ML. The side hole 3936 also faces generally in the direction of the main branch vessel MB. Advancement of both catheters is preferably performed simultaneously, although they could also be advanced independently of one another. The operator will feel resistance against further advancement of the catheters 3904, 3924 because as the catheters are advanced further distally, the two catheter shafts 3906, 3926 will spread apart relative to one another as they are forced against the carina of the bifurcation. However, a portion of the first elongate shaft 3906 is disposed under a portion of the second stent 3934, therefore the two shafts 3906, 3926 can only spread apart so far. Thus, when an operator feels resistance against further advancement of the catheter shafts, the operator knows that both catheters 3904, 3924 and their associated stents and balloons are properly positioned relative to the bifurcation.

Figure 39E:
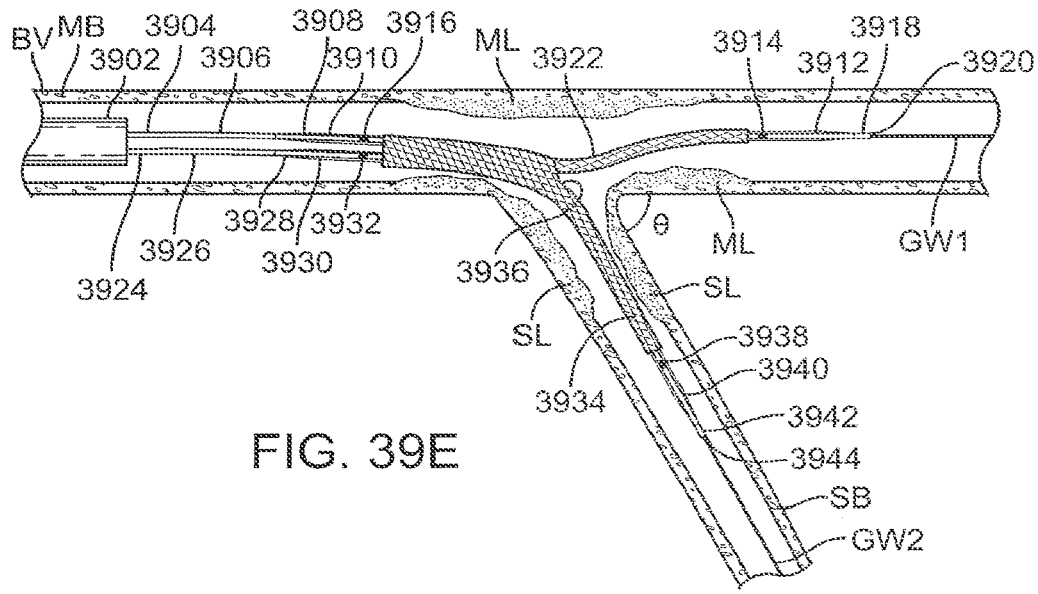

In FIG. 39E the first catheter 3904 is retracted proximally relative to the second catheter 3924 so a proximal portion 3910 of balloon 3908 is disposed under stent 3934. Stent 3934 has a distal portion crimped to balloon 3928 so that it will not be ejected during delivery, and a proximal portion is partially crimped or uncrimped over balloon 3928 to allow shaft 3906 to slidably pass thereunder. Stent crimping is described in greater detail in U.S. Provisional Patent Application No. 61/317,198, previously incorporated herein by reference. Because a portion of the first catheter shaft 3906 is disposed under a portion of the second stent 3934, the first shaft 3906 is slidably retracted into side hole 3936 and the first shaft 3906 is also slidably retracted under a portion of second stent 3934. The first shaft is proximally retracted until proximal radiopaque marker 3916 lines up with proximal radiopaque marker 3932 so that a proximal end of the first stent 3922 will be aligned with the side hole 3936 in the second stent 3934. An operator may feel resistance during retraction of the first elongate shaft 3906 relative to the second elongate shaft 3926 when the ends of the stents 3922, 3934 engage one another. The ends of the stents may butt up against one another, overlap with one another, interleave with one another, or combinations thereof. Additional details related to the engagement of the stents is disclosed in U.S. Provisional Patent Application No. 61/317,121 previously incorporated herein by reference. Both stents 3922, 3934 are disposed adjacent their respective lesions SL, ML, and the side hole 3936 is in rough alignment with the main branch vessel MB.

Figure 39F:
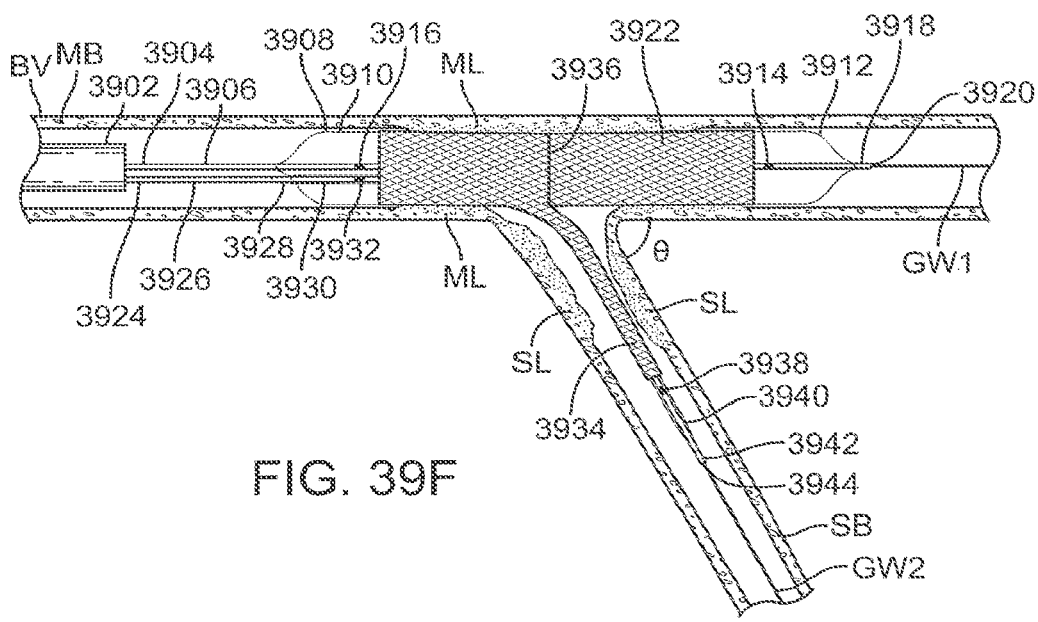

In FIG. 39F, the balloon 3908 is radially expanded, often with contrast medium, saline, or a combination thereof thereby radially expanding the first stent 3922 into engagement with the main branch lesion ML and the walls of the main branch. A proximal portion of the second stent 3934 is also expanded into engagement with the main branch lesion ML and the walls of the main branch, while a distal portion of the second stent 3934 remains unexpanded in the side branch SB. The first stent 3922 and the proximal portion of the second stent 3934 are radially expanded simultaneously. The inner surfaces of both stents form a smooth lumen for blood flow through the main branch. Since a portion of balloon 3908 also passes through side hole 3936, expansion of balloon 3908 also partially expands the side hole 3936 and also aligns the side hole 3936 with the main branch lumen.

Figure 39G:
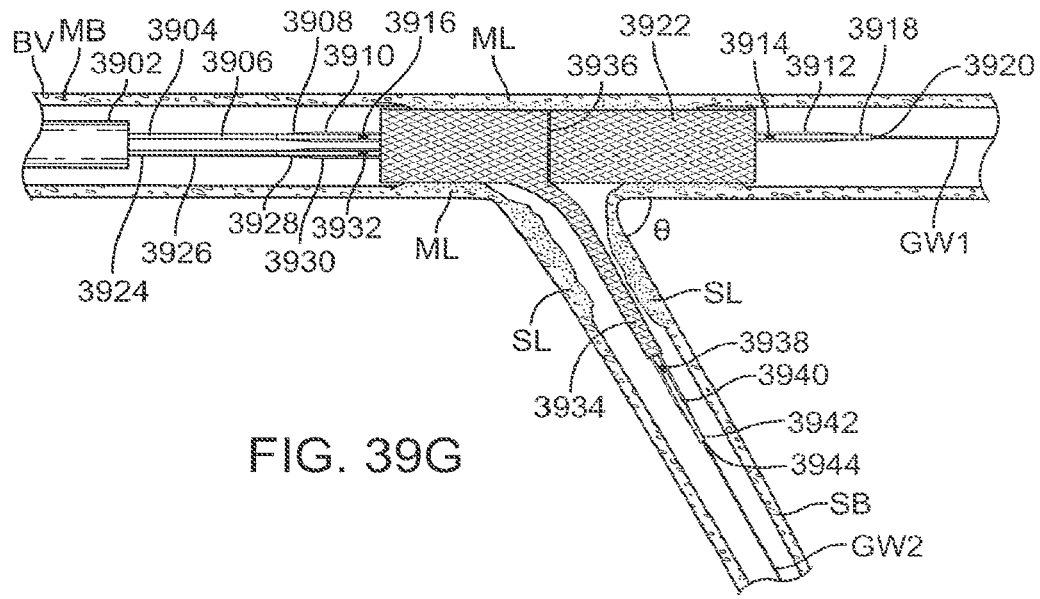
Figure 39H:
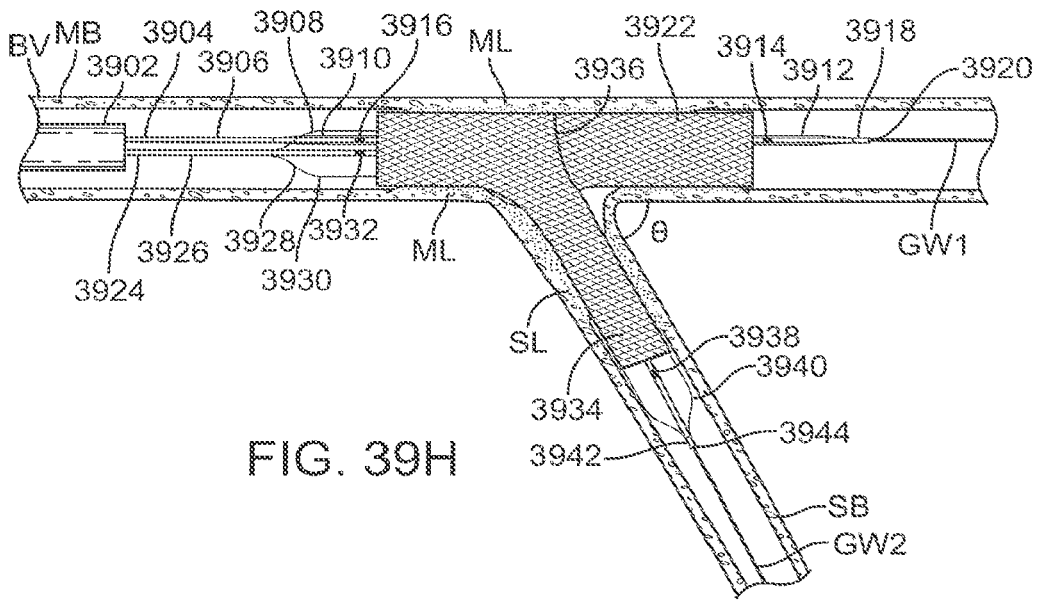

In FIG. 39G the balloon 3908 is contracted, and then in FIG. 39H the other balloon 3928 is radially expanded, with contrast medium, saline, or a combination thereof, thereby further radially expanding the second stent 3934. Expansion of balloon 3928 expands a distal portion of stent 3934 into engagement with the side branch vessel wall and side branch lesion SL. The proximal portion of stent 3934 and side hole 3936 may also be further expanded and aligned with the first stent 3922. The side hole is also further aligned with the lumen of the main branch.

Figure 39I:
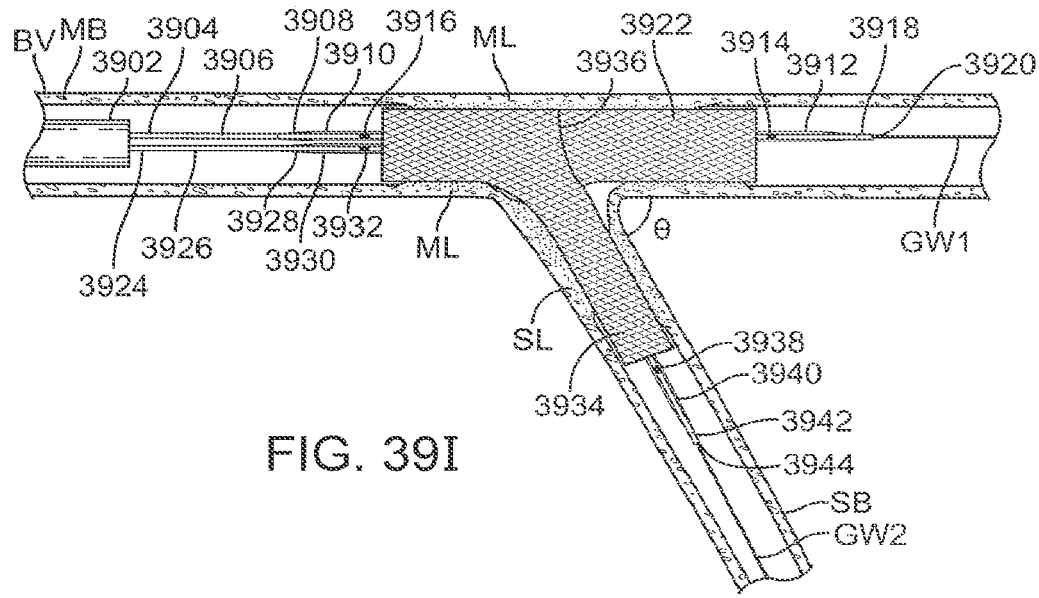
Figure 39J:
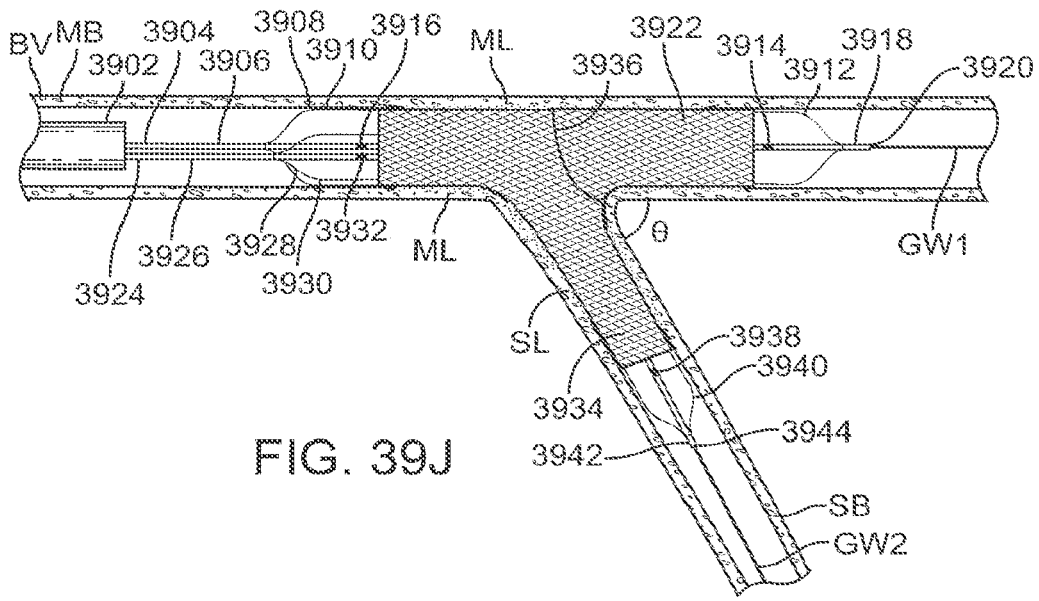

Referring now to FIG. 39I, balloon 3928 is contracted and then both balloons are simultaneously inflated in a "kissing balloon" technique as seen in FIG. 39J. Both balloons 3908, 3928 are inflated with contrast medium, saline, or combinations thereof until they engage one another and are fully expanded in the main branch MB and side branch SB. The kissing balloon technique ensures that both stents 3922, 3934 are fully expanded and in full apposition with their respective vessel wall and lesion. Additionally, the kissing balloon technique lines up the proximal end of the first sent 3922 with the side hole 3936 in the second stent 3934, thereby ensuring that continuous and smooth scaffolding from the main branch MB into the side branch SB. Alignment of the two stents is disclosed in greater detail in U.S. Provisional Patent Application No. 61/317,121, previously incorporated herein by reference. Also, the kissing balloons technique ensures that the side hole does not block the main branch or disrupting blood flow across the bifurcation.

Figure 39K:
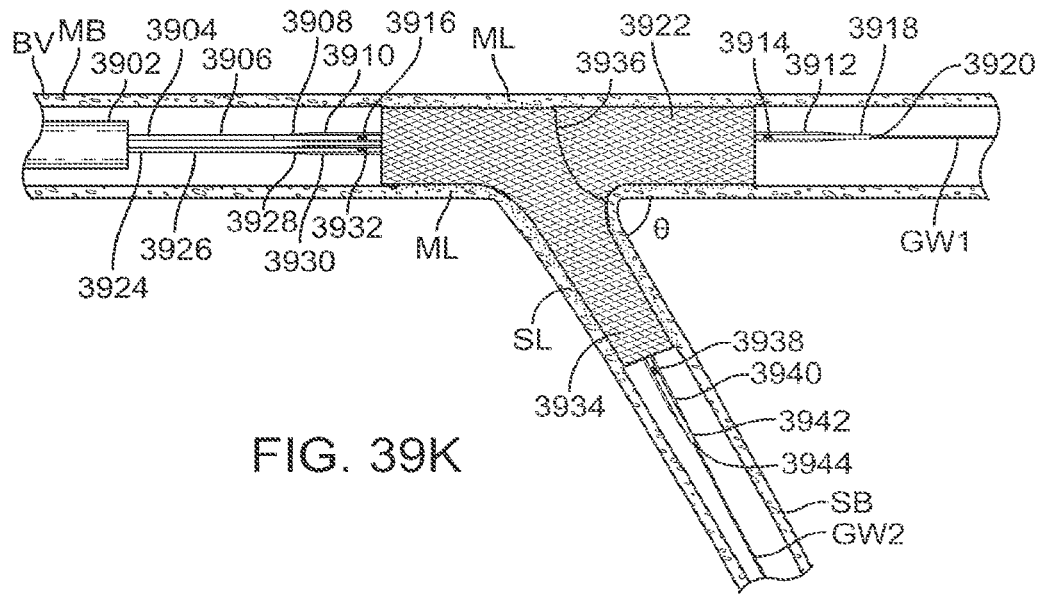
Figure 39L:
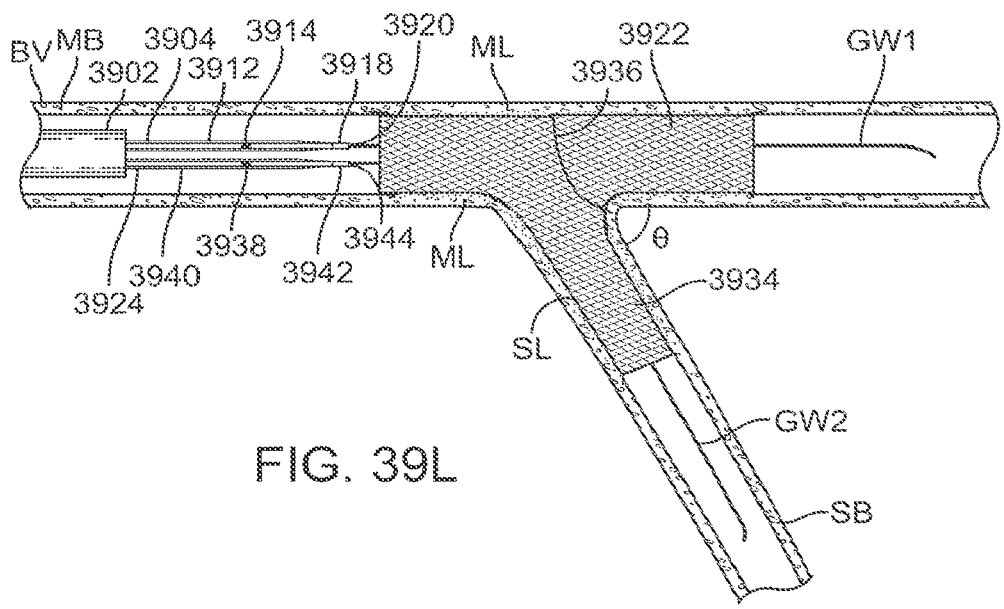
Figure 39M:
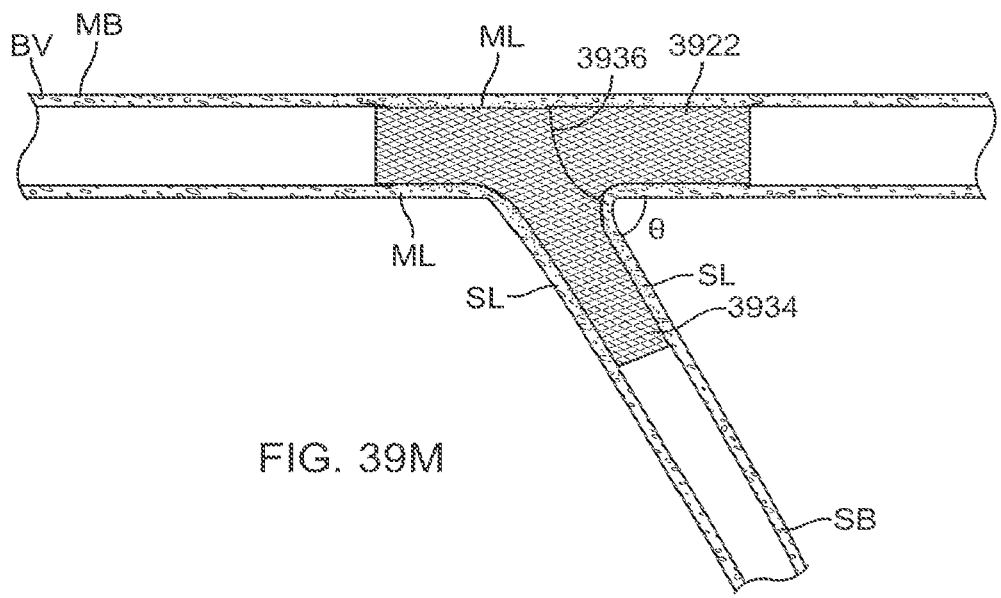

In FIG. 39K, both balloons 3908, 3928 are contracted, and in FIG. 39L both catheters 3904, 3924 are retracted proximally. The catheters may be retracted simultaneously or independently of one another. The first catheter 3904 is retracted through both stents 3922, 3934 and also passes through the side hole 3936. The second catheter 3924 is retracted through the second stent 3934. In FIG. 39M, both catheters 3904, 3924 have been removed, as well as the guidecatheter 3802 and both guidewires GW1, GW2. Stents 3922, 3934 remain implanted in at the bifurcation. Optionally, the stents or balloons may contain therapeutic agents such as those previously discussed, and these may elute out into the lesion at a controlled rate in order to help prevent restenosis.

Any of the methods described above may use any of the stents disclosed herein in any of the system configurations described. Additionally, any of the features previously described above may also be used. Therefore, one of skill in the art will appreciate that any number of combinations may made. For example, catheter systems may have any combination of rapid exchange or over-the-wire configurations, with any of the stents disclosed herein, with or without a therapeutic agent on a stent or a balloon, and with or without any of the hollow exchange port, capture tube, removable capture tube, or snap fittings described above.

Figure 40A:
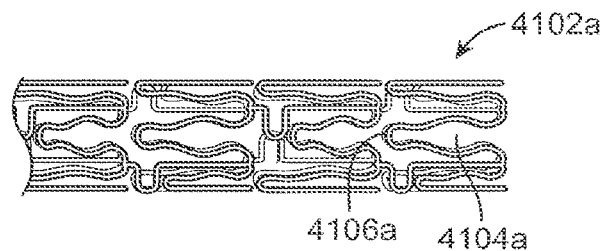
FIGS. 40A-40H illustrate various stents that may be used with the systems and methods disclosed herein to treat bifurcations.
Figure 40B:
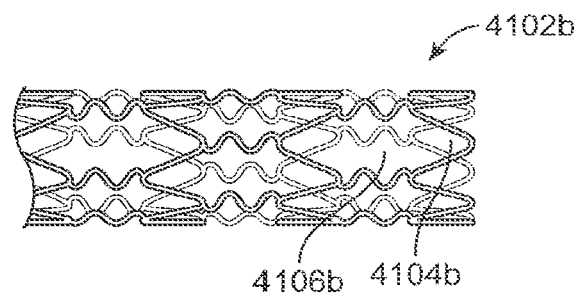
Figure 40C:
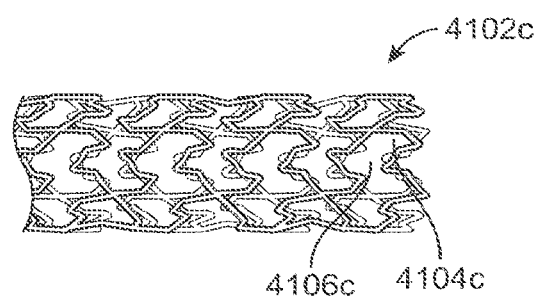
Figure 40D:
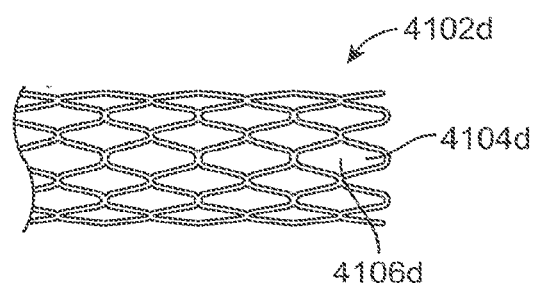
Figure 40E:
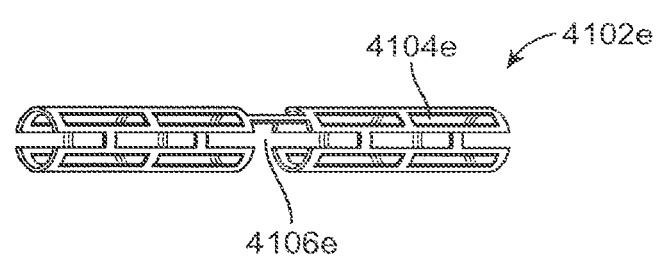
Figure 40F:
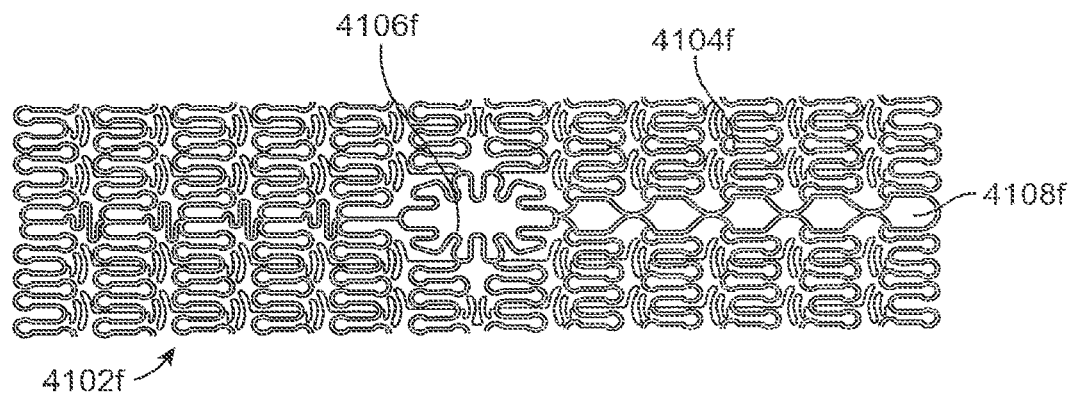
Figure 40G:
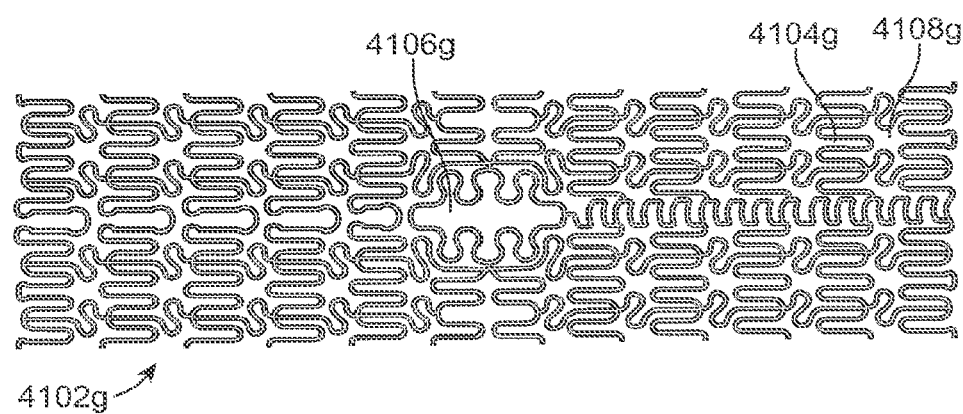
Figure 40H:
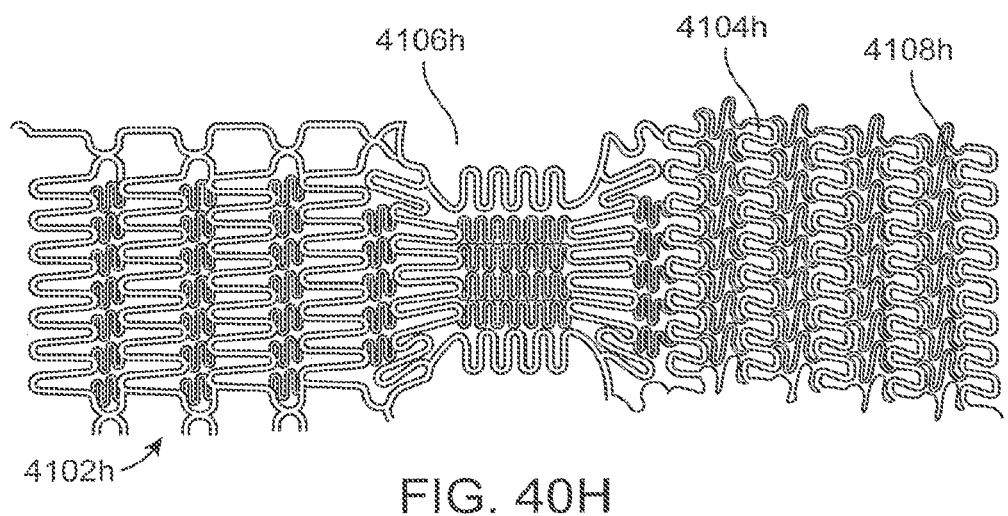

Stents:

The catheter systems and methods described above may use a commercially available stent for either the proximal or distal stent in the system. When a commercially available stent is used for the distal stent, it need only be crimped to the distal balloon catheter. When the commercially available stent is used for the proximal stent it may be partially crimped to the proximal balloon such that a portion of a second catheter shaft is slidably disposed under the stent and a portion of the second catheter shaft slidably passes through a side hole in the stent. The stent is crimped to the proximal balloon so that it is not displaced from the balloon during delivery, and also so the second catheter shaft can slide thereunder. FIGS. 40A-40E illustrate several examples of commercially available stents that may be used in catheter system configurations and methods described above, either as is, or with slight modification. For example, FIG. 40A illustrates the Abbott Vascular Xience® drug eluting stent 4102a. A portion of a catheter shaft may be disposed under the stent through its central channel and the catheter may exit a side hole in the stent. A side hole may be the gap 4104a created between adjacent struts in a cell, or the gap 4106a between axially adjacent cells. FIG. 40B illustrates the Cordis Cypher® stent 4102b. Again a portion of a catheter shaft may be disposed under the stent through its central channel and the catheter may exit a side hole in the stent. A side hole may be the gap 4104b created between adjacent struts in a cell, or the gap 4106b between axially adjacent cells. FIG. 40C illustrates the Boston Scientific Taxus® Liberté® stent 4102c. A portion of a catheter shaft may be disposed under the stent through its central channel and the catheter may exit a side hole in the stent. A side hole may be the gap 4104c created between adjacent struts in a cell, or the gap 4106c between axially adjacent cells. FIG. 40D illustrates the Medtronic Endeavor® stent 4102d. A portion of a catheter shaft may be disposed under the stent through its central channel and the catheter may exit a side hole in the stent. A side hole may be the gap 4104d created between adjacent struts in a cell, or the gap 4106d between axially adjacent cells. FIG. 40E illustrates a Palmaz-Schatz® stent 4104e. A portion of a catheter shaft may be disposed under the stent through its central channel and the catheter may exit a side hole in the stent. A side hole may be the gap 4104e created between adjacent struts in a cell, or the gap 4106e between axially adjacent segments. Other stents have been designed with side holes that are specifically intended to treat bifurcations. These stents may also be used with the systems and method disclosed herein. For example, FIGS. 40F-40H illustrate several embodiments of stents from Boston Scientific and are disclosed in detail in U.S. Pat. No. 7,678,142. FIG. 40F shows a stent 4102f after it has been unrolled and flattened having a side hole 4106f. 40F illustrates a stent geometry (unrolled, plan view) where the struts create a side hole 4106f that allows access to a side branch, and that can accommodate a catheter shaft as described herein. The side hole may be formed by the spaces 4104f, 4108f between struts. FIG. 40G illustrates another stent geometry (unrolled, plan view) having a side hole 4106g. Alternatively, the side hole may be formed by the spaces 4104g, 4108g between struts or axial connectors. FIG. 40H illustrates still another stent geometry (unrolled, plan view) having a side hole 4106h. The side hole may also be formed by the space between struts 4104h or axial connectors 4108h. In any of these embodiments, a catheter shaft may be slidably disposed under a portion of the stent, and the catheter shaft may exit the side hole. Additionally, any of the stents or balloons disclosed herein may carry a therapeutic agent such as those described above for local drug delivery. Also, while the stents disclosed herein are preferably balloon expandable, one of skill in the art will appreciate that self-expanding, and hybrid balloon expandable/self-expanding stents may also be used.

Figure 42A:
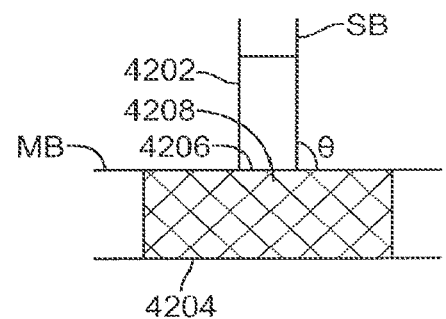
FIGS. 42A-42C illustrate engagement of a side branch stent with a main branch stent.
Figure 42B:
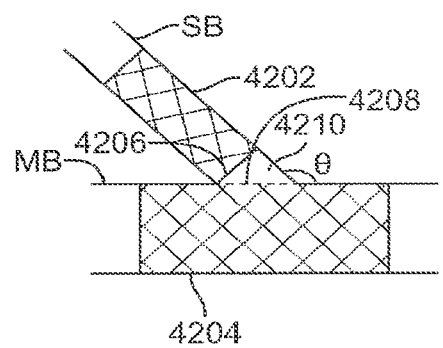
Figure 42C:
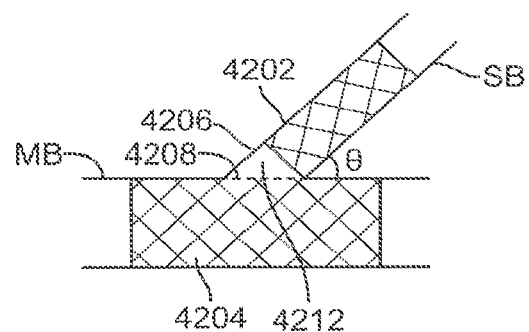

Stent Alignment:

FIGS. 42A-42C illustrate various ways a side branch stent can line up with a main branch stent. In FIG. 42A, the side branch SB is substantially perpendicular to the main branch MB, therefore the bifurcation angle θ is about 90 degrees. In this situation, the proximal end 4206 of the side branch stent 4202 will be substantially flush with the side hole 4208 in the main branch stent 4204 (assuming proper deployment of both stents). This is desirable since there are no gaps and hence no unscaffolded regions between the two stents 4202, 4204. However, when the bifurcation angle θ increases (FIG. 42B) or decreases (FIG. 42C), a portion of the side branch will remain unstented. For example, in FIG. 42B the bifurcation angle increases and because of the right cylindrical shape of the stent, in which the end is perpendicular to the sidewalls of the stent, a gap 4210 exits between the proximal end 4206 of the side branch stent 4202 and the side hole 4208 of the main branch stent 4204. Similarly, in FIG. 42C, when the bifurcation angle decreases, there is also a gap 4212 between the proximal end 4206 of stent 4202 and the side hole 4208 of stent 4204. FIG. 42C is typical of human anatomy, therefore the gap 4212 often is upstream of the bifurcation. Gaps are undesirable since they are unscaffolded and recoil and restenosis may occur in this region. Additionally, in the case where a stent is used for drug elution, the gap region may not receive any of the drug.

Figure 43A:
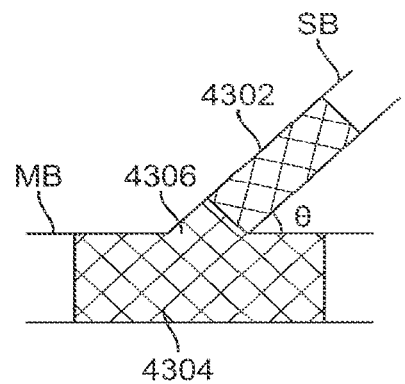
FIGS. 43A-43B illustrate other configurations of a side branch stent engaging a main branch stent.
Figure 43B:
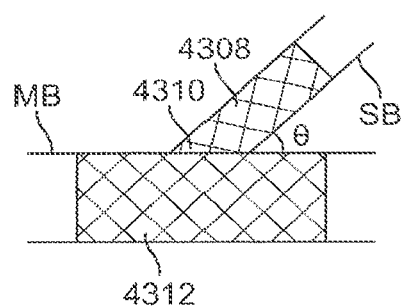

One possible solution for ensuring that the gap between a side branch stent and a main branch stent is eliminated or reduced is shown in FIG. 43A. The side branch stent 4302 is a right cylindrical sent. The main branch stent 4304 has aside hole 4306 with struts that expand outwardly into the gap region, thereby ensuring continuous scaffolding. An alternative solution in FIG. 43B is to fabricate the proximal end 4310 of the side branch stent 4308 with its proximal end non-perpendicular to the central axis of the stent so that the proximal end of the side branch stent lines up with the side hole in the main branch stent 4312. Even using the geometries illustrated in FIG. 43A-43B still requires careful alignment of the side branch stent with the main branch side hole. Therefore, it would be desirable to provide a stent geometry that facilitates alignment.

Figure 44:
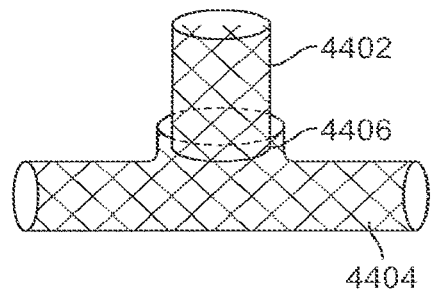
FIGS. 44-46 illustrate still other configurations of engagement of a side branch stent with a main branch stent.
Figure 45:
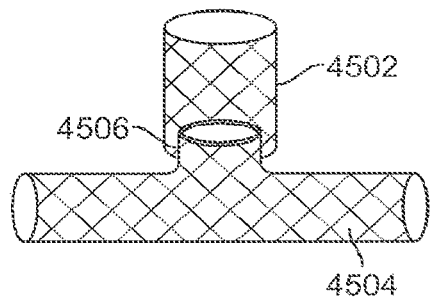
Figure 46:
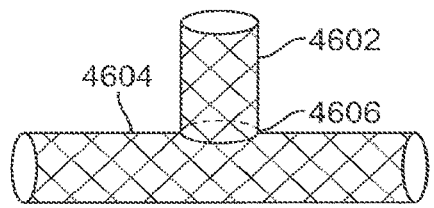

The ends of the side branch stent and the main branch stent may intersect in several different ways thereby providing continuous and uniform coverage of the bifurcation. For example, in FIG. 44, a portion 4406 of side branch stent 4402 may be disposed inside main branch stent 4404. FIG. 45 shows a portion 4506 of the main branch stent 4504 disposed inside the side branch stent 4502. Neither situation in FIG. 44 or 45 are ideal as overlapping of stents may result in metal rubbing on metal as well as possibly disrupting blood flow or causing stagnation points. A more desirable interface between stents is shown in FIG. 46 where the end of the side branch stent 4602 butts up against the side hole in main branch stent 4604. The interface region 4606 is desirable since it provides continuous scaffolding of the vessel without gaps between ends of the stents. However, depending on the stent geometry, gaps may still exist between stents. Therefore, in preferred embodiments, the ends of the stents will interleave or interdigitate with one another.

Figure 47A:
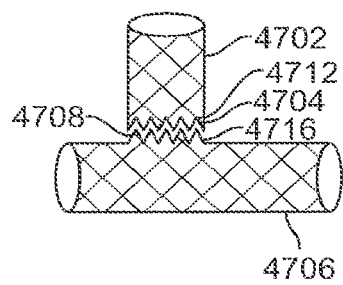
FIGS. 47A-47D illustrate interdigitation of a side branch stent and a main branch stent.
Figure 47B:
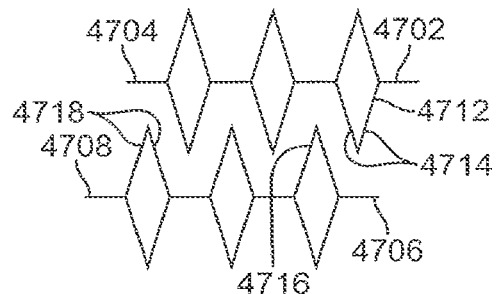

FIGS. 47A-47D illustrate several exemplary embodiments where the ends of the side branch stent and the side hole of the main branch stent interleave with one another or interdigitate. For example, in FIG. 47A, a proximal end 4704 of side branch stent 4702 has a series of axially extending elements or fingers 4712 which interdigitate or interleave with the laterally extending elements or fingers 4716 that extend laterally from the side hole 4708 of main branch stent 4706. FIG. 47B illustrates an exemplary embodiment of interdigitating axial and lateral elements. A proximal end 4704 of side branch stent 4702 has a plurality of axially extending elements 4712. The axially extending elements 4712 are formed from a plurality of interconnected stent struts 4714, in this case forming a triangular shape. Similarly, the side hole 4708 of the main branch stent 4706 has a plurality of laterally extending elements 4716 that are formed from a plurality of interconnected stent struts 4718. In this case the laterally extending elements 4716 are formed into a triangular shape. Thus the apex of one triangular shaped element fits in between adjacent elements on the adjacent stent. Or alternatively, the peaks fit in the valleys, and the valleys receive the peaks.

Figure 47C:
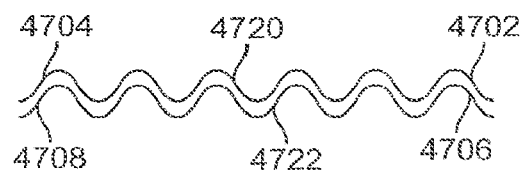
Figure 47D:
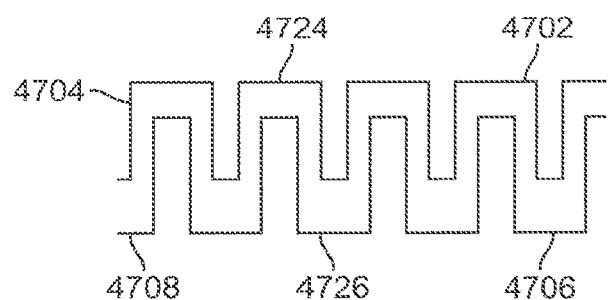

FIG. 47C illustrates still another exemplary embodiment of interleaving or interdigitating elements. The proximal end 4704 of the side branch stent 4702 includes a strut 4720 formed into a series of peaks and valleys. Similarly, the side hole 4708 of the main branch stent 4706 will also have a strut 4722 that has been formed into a series of peaks and valleys. Therefore, the peaks of the side branch stent will fit into the valleys of the adjacent main branch stent side hole, and similarly the valleys of the side branch stent receive the peaks of the side hole. FIG. 47D illustrates yet another exemplary embodiment of interleaving or interdigitation of stent ends. The proximal end 4704 of side branch stent 4702 includes a strut 4724 formed into a series of rectangular peaks and valleys. The side hole 4708 of the main branch stent 4706 also has a strut 4726 formed into a series of rectangular peaks and valleys. The peaks and valleys interleave and interdigitate with one another.

Figure 41A:
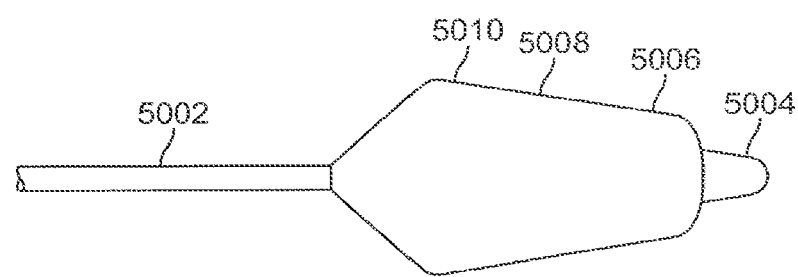
FIGS. 41A-41B illustrate exemplary embodiments of balloon configurations.
Figure 41B:
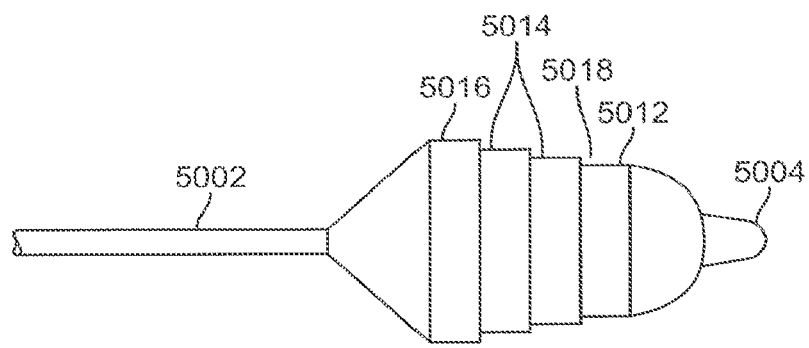

Balloon Configurations:

The balloons used to radially expand the stents described herein may be cylindrical balloons having a constant diameter along the working length, or diameter may vary. When stenting a tapered vessel, it may be advantageous to use a balloon which has a variable diameter balloon that more closely matches the vessel anatomy. For example, in FIG. 41A, a tapered balloon 5006 is attached to the distal portion of shaft 5002. A soft durometer tip 5004 prevents vessel trauma during delivery. The balloon is tapered such that a proximal portion 5010 of the balloon has a larger diameter than a distal portion 5006. Any taper may be used. FIG. 41B illustrates another embodiment of a balloon 5012 having a plurality of stepped regions 5014. The stepped regions may be incremented in any amount, and in preferred embodiments, a proximal portion 5016 of the balloon has a larger diameter than a distal portion 5018. Any of these embodiments, or combinations thereof may be used in the systems and methods described herein to treat a bifurcation. Use of a tapered or stepped balloon allows a stent to be expanded to more closely match the vessel walls, where a proximal portion of the expanded stent has a larger diameter than a distal portion of the stent.

Figure 48:
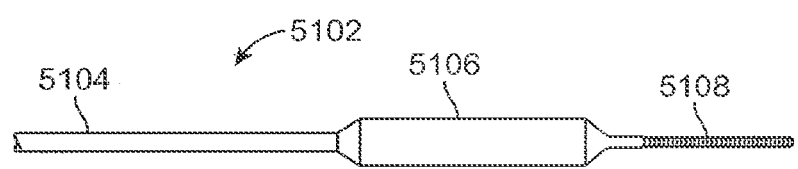
FIG. 48 illustrates another exemplary balloon catheter.

In addition to using catheters having rapid exchange or over-the-wire guidewire lumens, and tapered or stepped balloons, the balloon catheters may not always employ a guidewire lumen. Instead, a fixed wire may be attached to a distal end of the catheter. For example, FIG. 48 illustrates an exemplary embodiment of a fixed wire catheter 5102 having a balloon 5106 attached to a distal portion of the shaft 5104. A section of guidewire 5108 is fixedly attached to the distal end of the catheter and this fixed wire helps the catheter track through the vessels. The fixed wire may have any number of shapes including straight, curved, J-tip, etc. This embodiment may be used with any of the systems and methods disclosed herein, and it may or may not have a stent crimped to the balloon. The fixed wire catheter may be used in main branch, or more preferably it may be used in the side branch.

Fully Crimped Stent Embodiments:

In the embodiments previously described, a first catheter (often the side branch catheter) is partially disposed under a stent on a second catheter (often the main branch catheter). A portion of the stent is fully crimped to the second catheter in order to prevent the stent from moving during delivery and deployment, while a second portion of the stent is partially crimped in order to allow the first catheter to slide under the stent and move relative to the second catheter. While this embodiment is promising, it would also be desirable to provide delivery catheter systems that do not rely on partial crimping.

Figure 49A:
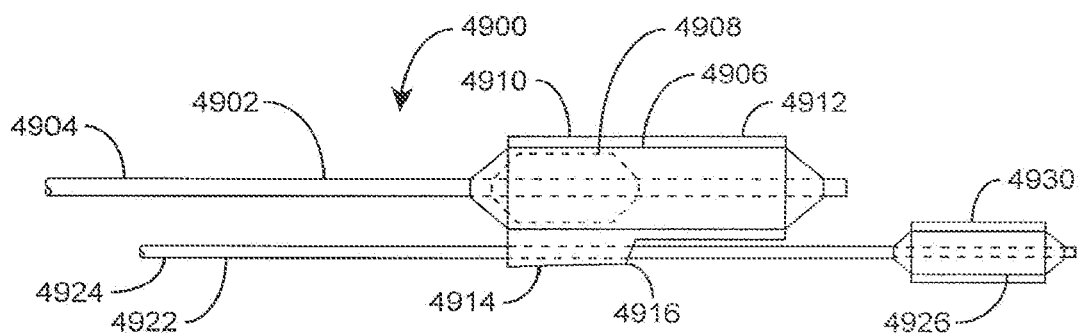
FIGS. 49A-49C illustrate another exemplary embodiment of a stent delivery system that may be used to treat bifurcated vessels.
Figure 49B:
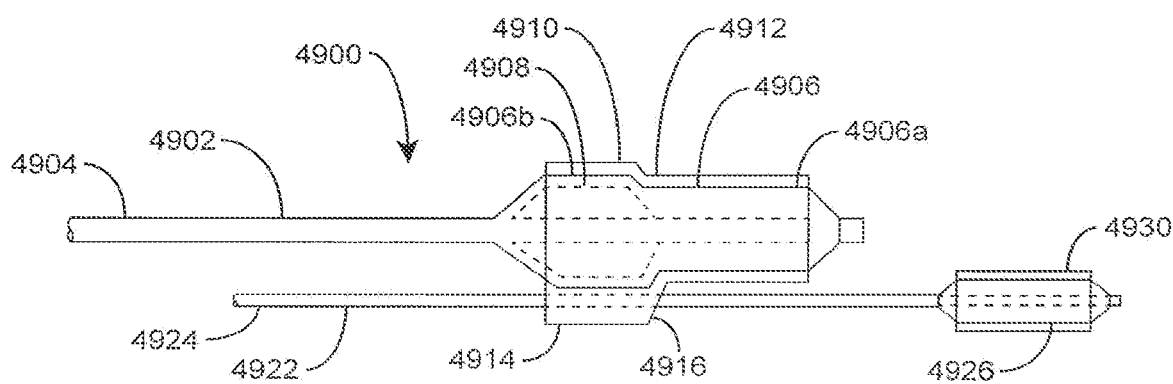
Figure 49C:
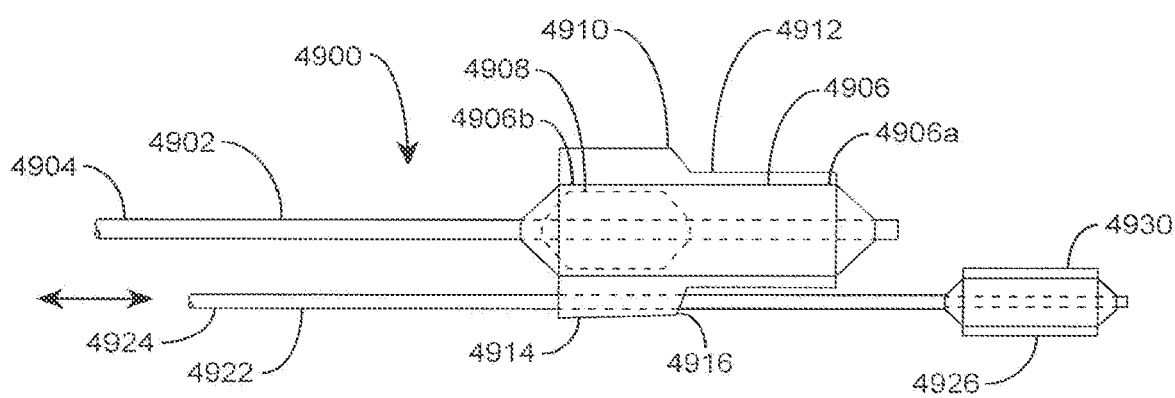

FIGS. 49A-49C illustrate an alternative embodiment of a stent delivery catheter that may be used for treating bifurcated vessels without the partial crimping previously described above. Stent delivery system 4900 includes two delivery catheters 4902 and 4922. The first delivery catheter 4902 includes an elongate flexible shaft 4904 having proximal and distal ends. A first expandable member, such as a balloon 4906 is disposed adjacent the distal end of the elongate flexible shaft 4904. A second auxiliary expandable member, here a balloon 4908 is disposed under the first balloon 4906. The auxiliary balloon 4908 has a shorter working length than the working length of the first balloon 4906. A stent 4910 is disposed over the first balloon 4906 and also over the auxiliary balloon 4908. The working length of the first balloon preferably is substantially the same as the length of the stent 4910. However, because the auxiliary balloon 4908 is shorter than the first balloon 4906, a proximal portion 4914 of the stent 4910 is disposed over both balloons 4906, 4908, and a distal portion 4912 of the stent 4910 is disposed only over balloon 4906. Stent 4910 includes a side hole 4916.

The second delivery catheter 4922 includes a second elongate shaft 4924 and an expandable member, here a balloon 4926 near the distal end of the elongate shaft 4924. Optionally, a second stent 4930 is disposed over the second delivery catheter balloon 4926. A portion of the second elongate shaft is disposed under a proximal portion 4914 of stent 4910, and shaft 4924 extends through the side hole 4916 in stent 4910. Stent 4910 is crimped onto both delivery catheters 4902, 4922 so that the stent 4910 will not move relative to the first balloon 4906 during delivery through the vasculature, and also so that the second elongate shaft 4924 will not move relative to stent 4910 or the first elongate shaft 4904 during delivery through the vasculature. In this embodiment, stent 4910 is crimped over both shafts 4904, 4924. Other aspects of delivery system 4900 may take the same form as previously described above in other exemplary embodiments. For example, either delivery catheter 4902, 4922 may have over-the-wire or rapid exchange guidewire features such as those previously described. Additionally, the stent 4910 may be any of the stents previously described, with or without the therapeutic agents previously described above. Other features described above may be used in combination with or as a substitute with the features described in this embodiment. The delivery system may be used to treat bifurcated vessels in a similar manner as described above.

Because the stent 4910 is crimped sufficiently to prevent axial movement of the first delivery catheter 4902 relative to the second delivery catheter 4922, a portion of the crimped stent will have to be loosened or released in order to allow movement of the catheters for proper alignment when treating a bifurcated vessel. FIG. 49B illustrates how the auxiliary balloon 4908 is used. Once the catheter has been advanced to the bifurcation as previously described in this specification, the auxiliary balloon 4908 may be expanded.

As auxiliary balloon 4908 expands, it also expands a proximal portion 4906b of balloon 4906 into engagement with a proximal portion 4914 of stent 4910. This expands the proximal portion 4914 of stent 4910 slightly, while the distal portion 4912 of stent 4910 and the distal portion 4906a of balloon 4906 remain unexpanded because the auxiliary balloon 4908 does not extend thereunder. After auxiliary balloon 4908 has been expanded, it is deflated as shown in FIG. 49C. Expansion of the auxiliary balloon 4908 permanently deforms and enlarges the proximal portion 4914 of stent 4910 while the distal portion 4912 of stent 4910 maintains its original crimped diameter. Also, balloon 4906 returns substantially to its original unexpanded diameter. This results in an annular gap 4928 being created on a proximal portion 4914 of stent 4910. This gap 4928 allows enough clearance between the second elongate shaft 4924, stent 4910, and balloon 4906 such that the second elongate shaft 4924 may then be slidably advanced and retracted under stent 4910 with a portion of the second shaft 4924 extending from or exiting the side hole 4916 of stent 4910. Once the second elongate shaft 4924 may be moved under stent 4910, the two catheter shafts may be positioned at the bifurcation using similar methods as previously described above. Stent 4910 and optional stent 4930 may then also be expanded using similar methods as described above to treat the bifurcated vessel. This exemplary embodiment is advantageous because is avoids the need for a partially crimped stent. Additionally, because the entire stent is crimped in this embodiment, the stent may have higher retention forces than a partially crimped stent, and thus the likelihood of stent ejection is reduced.

Figure 50A:
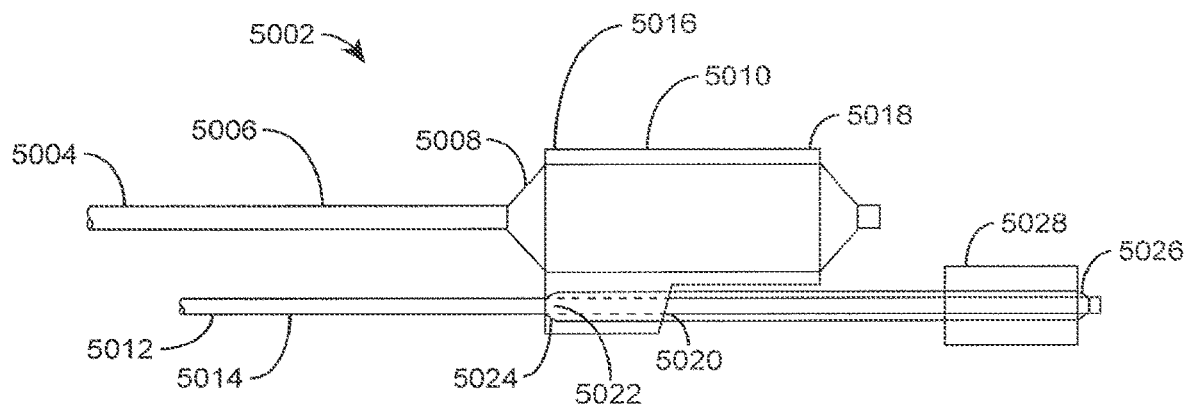
FIGS. 50A-50C illustrate another exemplary embodiment of a stent delivery system that may be used to treat bifurcated vessels.
Figure 50B:
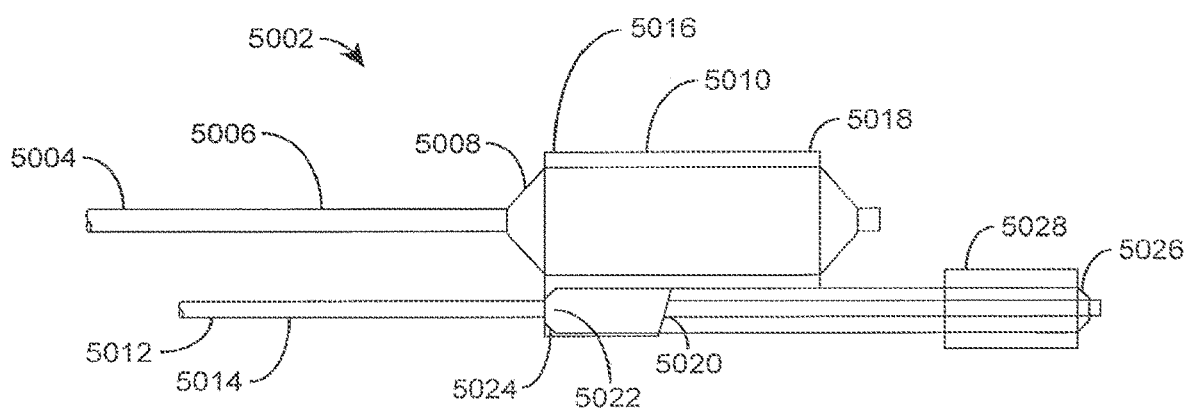
Figure 50C:
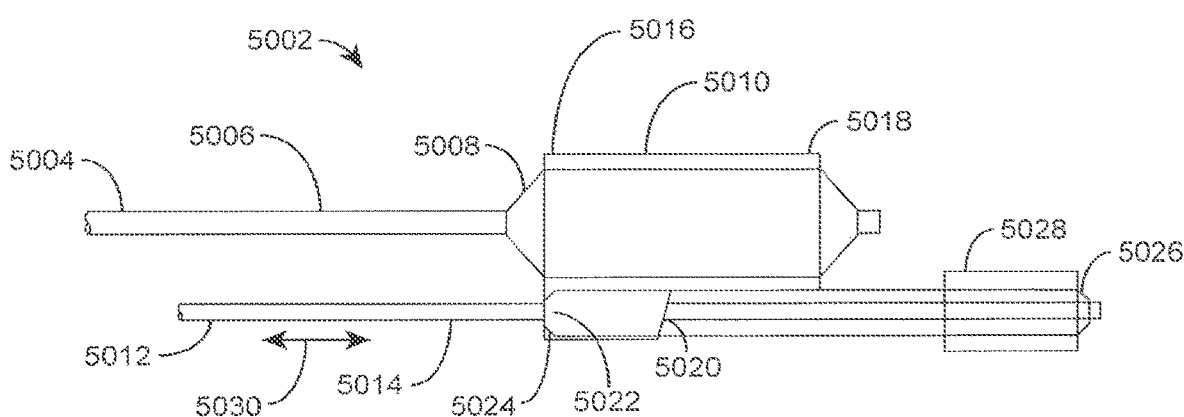

FIGS. 50A-50C illustrate another exemplary embodiment of stent delivery system used to treat a bifurcated vessel where the stents may be fully crimped to the balloon catheters, thereby avoiding some of the challenges of partial crimping as discussed above. The stent delivery system 5002 is similar to the system 4900 previously described, with the main difference being that instead of a balloon under the balloon, this embodiment has a long side branch balloon that is disposed under the main branch stent and also under the side branch stent. The long balloon may be used to partially expand the main branch stent without dislodging the side branch stent, thereby creating enough space between the stent and the side branch catheter to allow slidable movement therebetween. Stent delivery system 5002 includes a first stent delivery catheter 5004 and a second stent delivery catheter 5012.

The first stent delivery catheter 5004 has a first catheter shaft 5006 with a radially expandable balloon 5008 disposed near the distal end of shaft 5006. A stent 5010 having a proximal end 5016, a distal end 5018, and a side hole 5020 therebetween is disposed over the balloon 5008. The stent is fully crimped to the balloon 5008 such that the stent does not dislodge from the first delivery catheter 5004 during advancement through the vasculature. The second stent delivery catheter 5012 has a second catheter shaft 5014, a balloon 5022 with a proximal end 5024, a distal end 5026, and a stent 5028 disposed over a distal portion of the balloon 5022. The balloon 5022 is long enough so that a proximal portion of the balloon is disposed under a proximal portion of stent 5010 in the first delivery catheter 5004 and a distal portion of the balloon is also disposed under the second stent 5028. The second stent 5028 is fully crimped to balloon 5028 to prevent axial motion. The first stent 5010 is also crimped such that the second delivery catheter 5012 cannot move relative to the first delivery catheter.

In use, once both delivery catheters are advanced to a target treatment site, the balloon 5022 on the second delivery catheter 5012 may be partially inflated in order to slightly expand stent 5010 without expanding stent 5028. Balloon 5022 is then deflated, thereby creating sufficient space between balloon 5008, stent 5010, and shaft 5014 to allow proximal or distal axial movement shown by arrow 5030 of shaft 5014 relative to the first delivery catheter 5004. This allows the second delivery catheter to be positioned in the main branch, or more preferably in the side branch. Once positioned in a desired location, the stent 5028 may be expanded and the other stent 5008 may also be expanded, preferably in the main branch with the side hole 5020 aligned with the ostium to the side branch.

In an alternative embodiment, instead of one long side branch balloon 5022, this balloon may be substituted with two independently inflatable balloons. One balloon may be disposed under stent 5010 and the other balloon may be disposed under stent 5028. Inflation of the proximal-most balloon would loosen the crimp on stent 5010 thereby allowing axial movement of the catheters relative to one another, and inflation of the distal-most balloon would allow radial expansion of stent 5028.

Figure 51A:
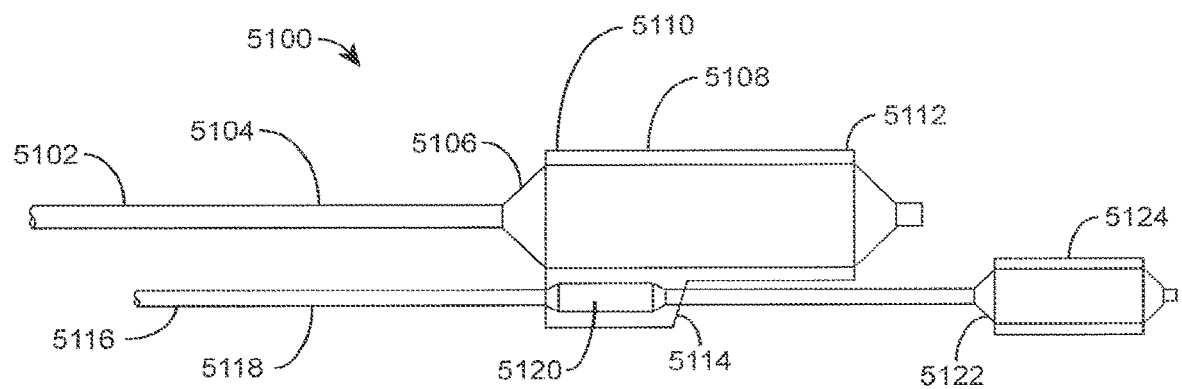
FIGS. 51A-51C illustrate another exemplary embodiment of a stent delivery system that may be used to treat bifurcated vessels.
Figure 51B:
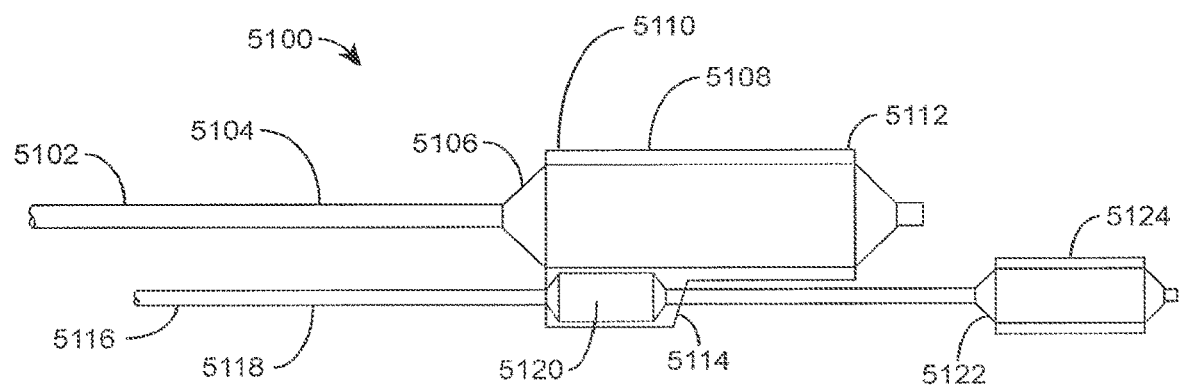
Figure 51C:
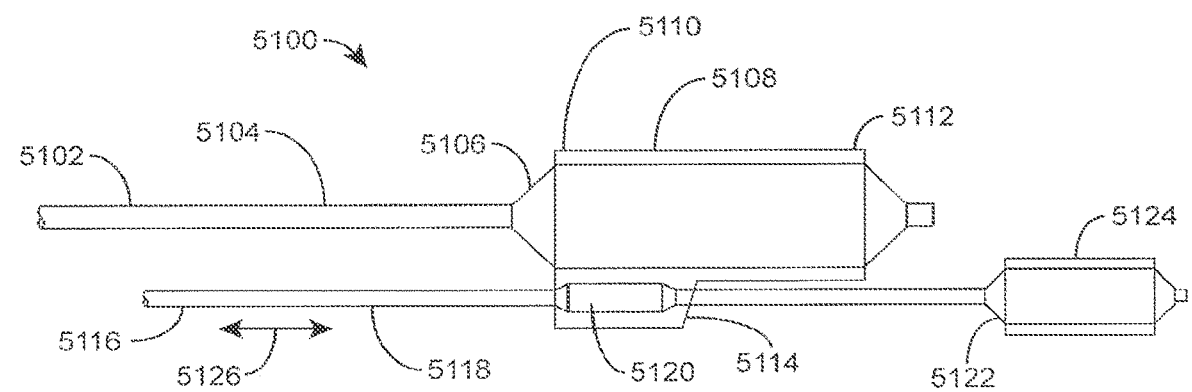

FIGS. 51A-51C illustrate still another exemplary embodiment of a stent delivery system that may be used to treat bifurcated vessels, with stents that are fully crimped to their respective balloons. Stent delivery system 5100 includes a first delivery catheter 5102 and a second delivery catheter 5116. The first stent delivery catheter has a first elongate shaft 5104 and a radially expandable balloon 5106 disposed near the distal end of the first elongate shaft 5104. A stent 5108 is fully crimped to the balloon 5106 to prevent dislodgement during delivery. The stent 5108 has a proximal portion 5110, a distal portion 5112 and a side hole 5114 therebetween. The second stent delivery catheter 5116 includes a second elongate shaft 5118, a proximal expandable balloon 5120, a distal expandable balloon 5122 and a stent 5124 disposed over the distal expandable member 5122. The two balloons 5120, 5122 may be independently inflatable of one another, or the two may be fluidly coupled together so that they are inflated simultaneously. The proximal balloon 5120 is disposed under a proximal portion of stent 5108 and a portion of second shaft 5118 passes through the side hole 5114. The proximal portion of stent 5110 is crimped over balloon 5106 and balloon 5120 to prevent dislodgement during delivery. The crimp is sufficient to prevent axial movement of the first catheter relative to the second catheter. After the catheter has been advanced toward the bifurcation, the second balloon 5120 may be radially expanded, thereby expanding the proximal portion 5110 of stent 5108, as seen in FIG. 51B. Once the proximal balloon is deflated in FIG. 51C, the second delivery catheter 5116 may be slidably advanced and retracted under the proximal portion of stent 5108 as indicated by arrow 5126. This allows the stent 5124 to be positioned in a desired location for stenting, preferably in the side branch. Use of the system for stent deployment generally takes the same form as previously discussed above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for treating a bifurcated vessel, the system comprising:
a first delivery catheter comprising a first elongate shaft with a proximal end and a distal end, a first expandable member adjacent the distal end of the first elongate shaft, and a first radially expandable stent disposed over the first expandable member;
wherein the first stent comprises a sidewall having a side hole therethrough, and
wherein the first stent has a crimped configuration and an expanded configuration, in the crimped configuration the first stent is coupled with the first expandable member, and in the expanded configuration the first stent supports a vessel wall; and
a second delivery catheter comprising:
a second elongate shaft with a proximal end and a distal end,
a second expandable member having a proximal portion and a distal portion, the distal portion of the second expandable member adjacent the distal end of the second elongate shaft, and
a second radially expandable stent, wherein the second expandable member has a longitudinal length such that the proximal portion of the second expandable member is disposed under a proximal portion of the first stent, and the distal portion of the second expandable member is disposed under the second stent,
wherein a portion of the second delivery catheter passes through the side hole in the first radially expandable stent,
wherein in the crimped configuration, the first stent is crimped over the first and second delivery catheters such that the first stent remains attached to the first and the second delivery catheters during advancement of the delivery catheters through a blood vessel, and
wherein a partial radial expansion of the second expandable member radially expands only the proximal portion of the first stent without radially expanding the second stent, while a distal portion of the first stent remains crimped to the first expandable member, and
wherein the partial radial expansion of the second expandable member forms a gap between an inside surface of the proximal portion of the first stent and an outer surface of the second elongate shaft thereby permitting slidable movement of the second elongate shaft under the first stent and relative to the first elongate shaft, and
wherein the second elongate shaft is slidably disposable through the side hole in the first stent when the second expandable member is partially expanded.

2. The system of claim 1, wherein the second expandable member is distal to the first expandable member during delivery of the first and second delivery catheters to the bifurcated vessel.

3. The system of claim 1, wherein in the crimped configuration, the first stent is crimped to the first and the second delivery catheters thereby preventing axial movement of the first elongate shaft relative to the second elongate shaft during advancement through the blood vessel.

4. The system of claim 1, wherein the second expandable member has a collapsed configuration and a fully radially expanded configuration, and
wherein in the collapsed configuration of the second expandable member, the first delivery catheter is sized to be advanced through the blood vessel, and
wherein in the fully radially expanded configuration of the second expandable member, the second expandable member engages and partially expands the proximal portion of the first stent.

5. The system of claim 1, wherein the first stent comprises a balloon expandable stent.

6. The system of claim 1, wherein the second stent has a collapsed configuration and an expanded configuration, in the collapsed configuration the second stent is coupled with the second expandable member, and in the expanded configuration the second stent supports a vessel wall.

7. The system of claim 6, wherein the second stent comprises a balloon expandable stent.

8. The system of claim 1, wherein the first expandable member and the second expandable member are independently expandable of one another.

9. The system of claim 1, wherein the first expandable member or the second expandable member comprises a balloon.

10. The system of claim 1, wherein each of the first delivery catheter and the second delivery catheter comprise a guidewire lumen.

11. The system of claim 10, wherein the first delivery catheter comprises a distal guidewire opening in the distal end of the first elongate shaft, and a proximal guidewire opening, the proximal guidewire opening spaced closer to the distal guidewire opening than the proximal end of the first elongate shaft, and
wherein the guidewire lumen in the first delivery catheter is configured to slidably receive a guidewire, and wherein the guidewire lumen extends from the distal guidewire opening to the proximal guidewire opening.

12. The system of claim 11, wherein the second delivery catheter comprises a distal guidewire opening in the distal end of the second elongate shaft, and a proximal guidewire opening, the proximal guidewire opening spaced closer to the distal guidewire opening than the proximal end of the second elongate shaft, and
wherein the guidewire lumen in the second delivery catheter is configured to slidably receive a guidewire, and wherein the guidewire lumen extends from the distal guidewire opening to the proximal guidewire opening.

13. The system of claim 10, wherein the first delivery catheter comprises a distal guidewire opening in the distal end of the first elongate shaft, and a proximal guidewire opening in the proximal end of the first elongate shaft such that the proximal guidewire opening is closer to the proximal end of the first elongate shaft than the distal guidewire opening, and
wherein the guidewire lumen in the first delivery catheter is configured to slidably receive a guidewire, and wherein the guidewire lumen extends from the distal guidewire opening to the proximal guidewire opening.

14. The system of claim 10, wherein the second delivery catheter comprises a distal guidewire opening in the distal end of the second elongate shaft, and a proximal guidewire opening in the proximal end of the second elongate shaft such that the proximal guidewire opening is closer to the proximal end of the second elongate shaft than the distal guidewire opening, and
wherein the guidewire lumen in the second delivery catheter is configured to slidably receive a guidewire, and wherein the guidewire lumen extends from the distal guidewire opening to the proximal guidewire opening.

15. The system of claim 1, further comprising a therapeutic agent disposed on the first radially expandable stent, or one of the expandable members, the therapeutic agent adapted to being eluted therefrom.

16. The system of claim 15, wherein the therapeutic agent comprises an anti-restenosis agent.

* * * * *

UNITED STATES PATENT AND TRADEMARK OFFICE
CERTIFICATE OF CORRECTION

PATENT NO. : 11,717,428 B2
APPLICATION NO. : 17/225354
DATED : August 8, 2023
INVENTOR(S) : Henry Bourang It is certified that error appears in the above-identified patent and that said Letters Patent is hereby corrected as shown below:

On the Title Page

In Column 1, under "Related U.S. Application Data", Line 1, delete "(60)" and insert --(63)-- therefor In the Specification In Column 1, Line 29, after "situ", insert --,--

In Column 2, Line 12, delete "inventors" and insert --inventor's-- therefor

In Column 2, Line 49, delete "6,258,121:6,231,600; 5,837,008," and insert --6,258,121; 6,231,600; 5,837,008;-- therefor In Column 15, Line 46, delete "20" and insert --200-- therefor In Column 15, Line 52, delete "208," and insert --206,-- therefor In Column 20, Line 50, delete "aside" and insert --a side-- therefor In Column 21, Line 24, delete "608," and insert --606,-- therefor In Column 26, Line 51, delete "1008," and insert --1006,-- therefor In Column 29, Line 6, delete "132" and insert --1132-- therefor In Column 32, Line 57, delete "1408," and insert --1406,-- therefor In Column 38, Line 42, delete "1808," and insert --1806,-- therefor Signed and Sealed this
Nineteenth Day of December, 2023

*Katherine Kelly Vidal*

Katherine Kelly Vidal
*Director of the United States Patent and Trademark Office*

CERTIFICATE OF CORRECTION (continued)
U.S. Pat. No. 11,717,428 B2

In Column 40, Line 9, delete "19." and insert --1906.-- therefor

In Column 42, Line 36, delete "204 (via" and insert --2040 via-- therefor

In Column 44, Line 25, delete "2208," and insert --2206,-- therefor

In Column 54, Line 66, delete "3939" and insert --3934-- therefor

In Column 57, Line 30, delete "4104*e*." and insert --4102*e*.-- therefor

In Column 58, Line 25, delete "aside" and insert --a side-- therefor

In Column 62, Line 12, delete "5008" and insert --5010-- therefor